United States Patent [19]

Tatsuki et al.

[11] Patent Number: 5,776,365

[45] Date of Patent: *Jul. 7, 1998

[54] CARBOXYLATE COMPOUNDS, LIQUID CRYSTAL MATERIALS, LIQUID CRYSTAL COMPOSITIONS AND LIQUID CRYSTAL ELEMENTS

[75] Inventors: Yuuichirou Tatsuki; Shinichi Nishiyama; Junichi Kawabata; Tooru Yamanaka; Chiho Tanaka, all of Sodegaura, Japan

[73] Assignee: Mitsui Chemicals, Inc., Tokyo, Japa

[*] Notice: The term of this patent shall not extend beyond the expiration date of Pat. No. 5,422,039.n

[21] Appl. No.: 479,213

[22] Filed: Jun. 7, 1995

Related U.S. Application Data

[63] Continuation of Ser. No. 438,036, May 8, 1995, Pat. No. 5,725,798, which is a continuation of Ser. No. 180,452, Jan. 12, 1994, abandoned, which is a continuation-in-part of Ser. No. 995,208, Dec. 23, 1992, abandoned.

[30] Foreign Application Priority Data

| Dec. 27, 1991 | [JP] | Japan | 3-347122 |
| Mar. 13, 1992 | [JP] | Japan | 4-55209 |
| Mar. 13, 1992 | [JP] | Japan | 4-55210 |

[51] Int. Cl.$^6$ ............ C09K 19/32; C09K 19/34; C07C 69/76
[52] U.S. Cl. .......... 252/299.62; 252/299.61; 252/299.63; 252/299.66; 252/299.67; 560/56; 560/80
[58] Field of Search ........ 252/299.01, 299.62, 252/299.61, 299.63, 299.66, 299.67; 560/56, 80, 127

[56] References Cited

U.S. PATENT DOCUMENTS

| 4,386,007 | 5/1983 | Krause et al. | |
| 4,391,731 | 7/1983 | Boller et al. | 252/299.62 |
| 4,613,209 | 9/1986 | Goodby et al. | 252/299.62 |
| 4,680,137 | 7/1987 | Isoyama et al. | 252/299.62 |
| 4,886,620 | 12/1989 | Hopf et al. | |
| 4,921,632 | 5/1990 | Nakamura et al. | 252/299.1 |
| 5,246,622 | 9/1993 | Shimizu et al. | 252/299.62 |
| 5,352,379 | 10/1994 | Nishiyama et al. | 252/299.62 |
| 5,356,561 | 10/1994 | Shimizu et al. | 252/299.62 |
| 5,389,287 | 2/1995 | Nishiyama et al. | 252/299.62 |

FOREIGN PATENT DOCUMENTS

| 2045325 | 6/1991 | Canada . |
| 2047377 | 7/1991 | Canada . |
| 0332456 | 9/1989 | European Pat. Off. . |
| 0341922 | 11/1989 | European Pat. Off. . |
| 0401961 | 12/1990 | European Pat. Off. . |
| 0413585 | 2/1991 | European Pat. Off. . |
| 0431929 | 6/1991 | European Pat. Off. . |
| 0440134 | 8/1991 | European Pat. Off. . |
| 0467662 | 1/1992 | European Pat. Off. . |
| 56-46855 | 4/1981 | Japan . |
| 56-108740 | 8/1981 | Japan . |
| 249092 | 2/1990 | Japan . |

*Primary Examiner*—Shean C. Wu
*Attorney, Agent, or Firm*—Sherman and Shalloway

[57] ABSTRACT

There is provided a carboxylic acid compound represented by the following formulae (I) to (IV):

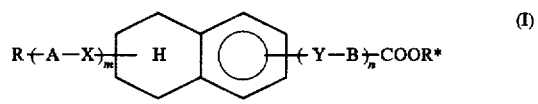

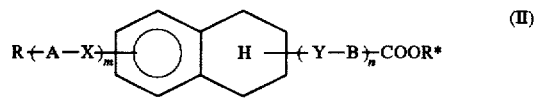

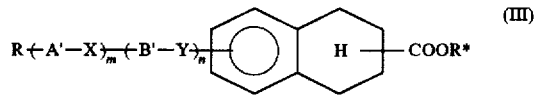

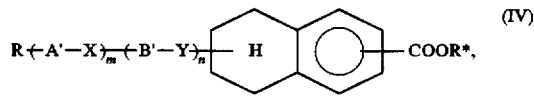

a liquid crystal material consisting of the carboxylic acid ester compound, a liquid crystal composition comprising the carboxylic acid ester compound, and a liquid crystal element using the carboxylic acid ester compound. There can be obtained advantages such as low operating temperature, high speed switching, very small electric power consumption, and high-stable contrast.

65 Claims, 70 Drawing Sheets

CARBOXYLATE COMPOUNDS, LIQUID CRYSTAL MATERIALS, LIQUID CRYSTAL COMPOSITIONS AND LIQUID CRYSTAL ELEMENTS

A continuation of application Ser. No. 08/438,036 now U.S. Pat. No. 5,725,798, filed on May 8, 1995, which in turn is a continuation of application Ser. No. 08/180,452 now abandoned, filed Jan. 12, 1994, which in turn is which application is a continuation-in-part of an application Ser. No. 07/995,208, filed Dec. 23, 1992, now abandoned.

FIELD OF THE INVENTION

This invention relates to novel carboxylate (carboxylic acid ester) compounds, liquid crystal materials consisting of said carboxylate compounds, liquid crystal compositions comprising said carboxylate compounds and liquid crystal elements filled with said liquid crystal marerials or said liquid crystal compositions.

BACKGROUND OF THE INVENTION

Display devices using liquid crystal compounds, which are used widely at present, are driven by means of a TN (twisted nematic) mode.

Such driving display devices, however have problems that since the position of the molecule of the liquid crystal compound present in the element must be changed in order to change displayed images, the driving time necessary therefor becomes longer, and also the voltage necessary for changing the position of the molecule of the liquid crystal compound, that is, the electric power consumption becomes larger.

Differing from switching elements utilizing the TN ode or an STN mode, those using ferroelectric liquid crystal compounds are able to function as switching elements only by changing the direction of molecular orientation of the liquid crystal compounds, hence the switching time required for operating the switching elements is shortened remarkably. Further, because a Ps×E value obtained from a spontaneous polarization (Ps) of the ferroelectric liquid crystal compound and an intensity of the electric field (E) applied thereto is an effective energy output for changing the direction of molecular orientation of said liquid crystal compound, the power consumption required therefor can also be minimized. Such ferroelectric liquid crystal compounds are suitable particularly for use in display devices for moving picture, because they have two steady states depending upon the direction of applied electric field, i.e. bistability, and also have very favorable switching threshold value characteristics.

Such ferroelectric liquid crystal compounds or anti-ferroelectric liquid crystal compounds are used in optical switching elements or the like, these compounds are required to have many characteristics such that their operating temperature is in the vicinity of or below ordinary temperature, operating temperature range is broad, switching speed is high (fast) and switching threshold value voltage is within an appropriate range. In particular, of these characteristics, the operating temperature range is especially important when the ferroelectric crystal compounds or anti-ferroelectric crystal compounds are put to practical use.

However, in ferroelectric liquid crystal compounds known hitherto, the operating temperature range are generally narrow, and even in the case of ferroelectric liquid crystal compounds having a wide operating temperature range, said operating temperature range is in a high temperature region excluding room temperature, as disclosed, for example, in a paper by R. B. Meyer et al., J. de Phys., Vol. 36, 169 (1975) or in a paper by M. Taguchi and T. Harada, "Proceedings of Eleventh Conference on Liquid Crystal," 168 (1985). Thus, no ferroelectric liquid crystal compounds satisfactory from the standpoint of practical use are obtainable yet.

Further, anti-ferroelectric liquid crystal compounds have the same tendency as observed in the ferroelectric liquid crystal compounds, and no anti-ferroelectric liquid crystal compounds satisfactory from the standpoint of practical use are obtainable yet.

OBJECT OF THE INVENTION

The present invention has made to solve the above-mentioned problems associated with the prior art. An object of the invention is to provide novel carboxylate compounds and liquid crystal materials consisting the same. Another object of the invention is to provide liquid crystal compositions comprising the carboxylate compounds and liquid crystal elements filled with the liquid crystal materials or the liquid crystal compositions comprising the carboxylate compounds. More particularly, the novel carboxylate compounds are usable for forming liquid crystal elements which are low in operating temperature, high (fast) in switching speed, very small in electric power consumption and, moreover, capable of giving stabilized contrast, and applications thereof.

SUMMARY OF THE INVENTION

The first carboxylate compound of the invention includes those represented by the following formula [I] or [II]

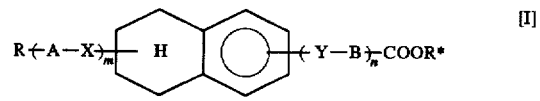

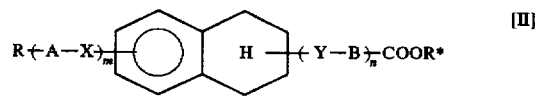

wherein

R is a group selected from the group consisting of an alkyl of 3–20 carbon atoms, an alkoxy of 3–20 carbon atoms and a halogenated alkyl of 3–20 carbon atoms, X and Y are independently a group selected from the group consisting of —COO—, —OCO—, —CH$_2$CH$_2$—, —CH$_2$O—, —OCH$_2$—, —S—S—, —CO—CH$_2$— and —CH$_2$—CO—, or a single bond, A is a group selected from the group consisting of

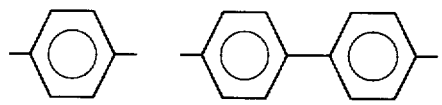

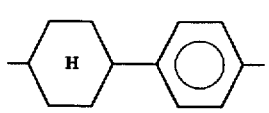

-continued

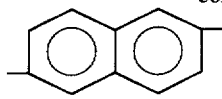

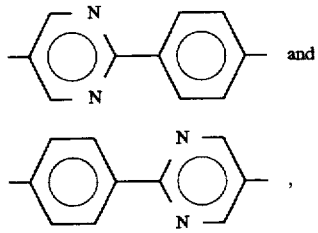

B is a group selected from the group consisting of

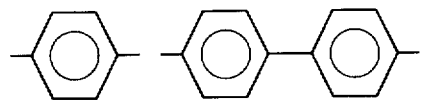

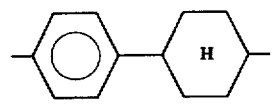

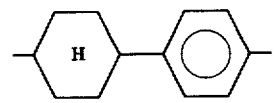

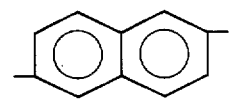

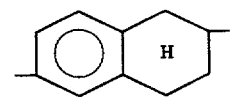

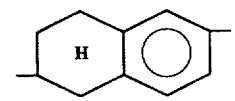

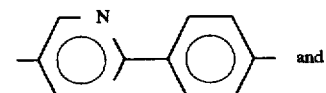

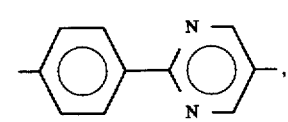

R* is an optically active group of 4–20 carbon atoms containing at least one asymmetric (or chiral) carbon atom where hydrogen atoms attached to the carbon atoms constituting said optically active group may be substituted with a halogen atom, m is 1 or 2, and n is an integer of 0–2.

The second carboxylate compound of the invention includes those represented by the following formula [III] or [IV]

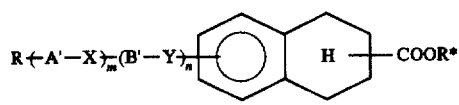

[III]

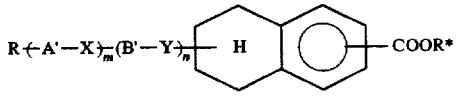

[IV]

wherein R, R*, X and Y are as defined in the formula [I] or [II], provided that R may be a hydrocarbon group having —OCO— group where at least a part of hydrogen atoms constituting said hydrocarbon group may be substituted with halogen atoms, and R may have at least one asymmetric carbon atom, A' and B' are independently a group selected from the group consisting of

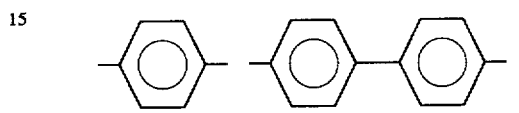

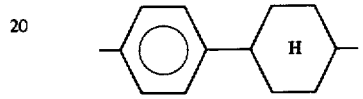

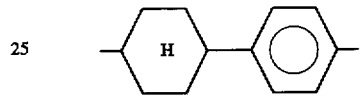

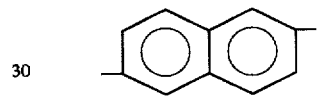

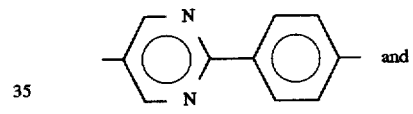

m is 1 or 2, n is 0–2, and m+n≧2.

The liquid crystal materials of the invention are characterized by consisting of a carboxylate compound represented by the above-mentioned formula [I], [II], [III] or [IV].

The liquid crystal compositions of the invention are characterized by comprising a carboxylate compound represented by the above-mentioned formula [I], [II], [III] or [IV].

The liquid crystal elements of the invention are characterized in that said crystal elements comprise a cell composed of two substrate facing each other and a gap formed by said substrates, and a liquid crystal substance filled in the gap of said cell, said liquid crystal substance containing a carboxylate compound represented by the above-mentioned formula [I], [II], [III] or [IV].

Thus, the present invention provides novel carboxylate compounds which are of high usefulness as liquid crystal materials. Accordingly, liquid crystal elements of the invention which is composed of two substrates, a gap formed therebetween is filled with a liquid crystal composition comprising the novel carboxylate compound or a liquid crystal material consisting of this compound, possess excellent liquid crystal characteristics.

By the use of the carboxylate compounds of the invention as liquid crystal materials, there can be obtained various kinds of devices having excellent characteristics such as a broad operating temperature range, a fast switching speed, a very small electric power consumption and a stabilized contrast.

Figure 1:
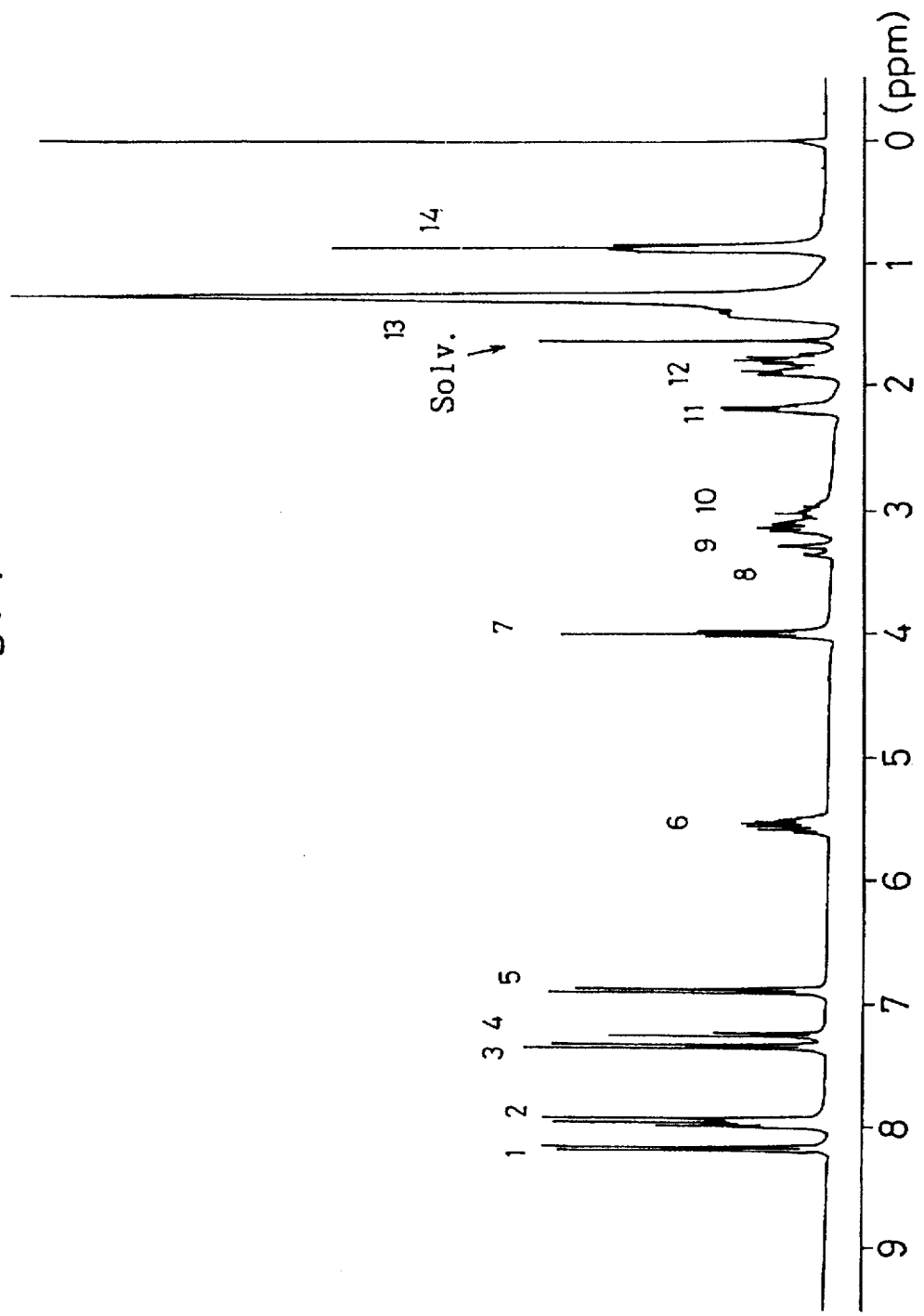
FIG. 1 shows $^1$H-NMR spectrum of 4-[6-(4-decyloxybenzoyloxy)-5,6,7,8-tetrahydro-2-naphthoyloxy]benzoic acid (R)-1-trifluoromethylheptyl ester [Exemplified compound (4)].

Numerals used in the drawings have the following meanings:

11a,11b,27a,27b,37,47,57 . . . Transparent substrate
12,23,33,43,53 . . . Liquid crystal substance
13,58 . . . Cell
14 . . . Gap
15a,15b,25a,25b,35,45,55 . . . Transparent electrode
26 . . . Concentric spacer
36 . . . Comb-shaped spacer
46 . . . Fiber
56 . . . Polarizing plate

DETAILED DESCRIPTION OF THE INVENTION

The present invention is illustrated below in detail.

First, the carboxylate compounds and liquid crystal materials of the invention are illustrated.

The first carboxylate compound of the invention may be represented by the following formula [I] or [II].

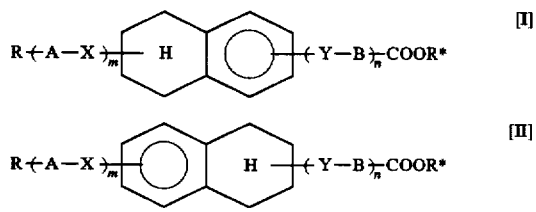

In the formula [I] or [III], R is a group selected from the group consisting of an alkyl of 3–20 carbon atoms, an alkoxy of 3–20 carbon atoms, a halogenated alkyl of 3–20 carbon atoms and halogenated alkoxy of 3–20 carbon atoms.

When R in the above formula [I] or [II] is an alkyl of 3–20 carbon atoms, the alkyl may be straight, branched and alicyclic. In particular, the carboxylate compounds having a straight chain alkyl R exhibit excellent liquid crystal properties because the molecules have a rigid linear structure. The straight chain alkyl may include hexyl, heptyl, octyl, nonyl, decyl, undecyl, dodecyl, tetradecyl, hexadecyl and octadecyl.

When R is an alkoxy of 3–20 carbon atoms, the alkoxy may include those having such alkyls as mentioned above. Thus, the alkoxy may include hexoxy, heptoxy, octyloxy, nonyloxy, decyloxy, undecyloxy, dodecyloxy, tetradecyloxy, heptadecyloxy, hexadecyloxy and octadecyloxy.

When R is a halogenated alkyl or alkoxy of 3–20 carbon atoms, the halogenated alkyl or alkoxy includes those in which at least a part of hydrogen atoms of such alkyl or a alkoxy such as mentioned above is substituted with a halogen atom such as F, Cl, Br or I.

When R is a branched alkyl, alkoxy, halogenated alkyl or halogenated alkoxy of 3–20 carbon atoms, R may have at least one asymmetric carbon atom. R having an asymmetric carbon atom may be a (R)-body, a (S)-body or a racemic mixture thereof.

Among the above groups having an asymmetric carbon atom, the branched alkoxy and the branched halogenated alkoxy are preferred as R and may include 2-methylbutyloxy, 1-metylhexyloxy, 4-methylhexyloxy, 1-ethylhexyloxy, 1-methylheptyloxy, 2-methylheptyloxy, 5-methylheptyloxy, 1-ethylheplyloxy, 1-methylheptyloxy, 2-methyloctyloxy, 6-methyloctyloxy and those, of which a part of hydrogen atoms in each of the above groups is substituted with a halogen atom, including 1-trifluoromethylheptyloxy.

Further, when R is the alkoxy or halogenated alkoxy, at least one —$CH_2$— constituting the alkoxy or halogenated alkoxy may be replaced by a group selected from the group consisting of —O—, —S—, —CO—, —CHCN—, —O—CO—, —O—COO—, —CO—O— and —CH=CH—. In this case, however, these replacing groups are introduced into one of the above-mentioned groups so that the hetero atoms contained in R are not directly bonded together. Such alkoxy and halogenated alkoxy may include $C_2H_5$—OCO—$CH_2$—C*H($CF_3$)O—.

The carboxylate compounds having alkoxy group R exhibit particularly excellent liquid crystal properties.

In the formula [I] or [II], X and Y are each independently a group selected from the group consisting of —COO—, —OCO—, —$CH_2CH_2$—, —$CH_2O$—, —$OCH_2$—, —S—S—, —CO—$CH_2$— and —$CH_2$—CO—, or a single bond. In the case where the carboxylate compounds of the formula [I] or [II] of the invention are used as liquid crystal materials, it is preferable that X and Y are each independently a group selected from the group consisting of —COO—, —OCO—, —$CH_2CH_2$—, —$CH_2O$—, and —$OCH_2$—, or a single bond. Particularly preferred X and Y are each independently —COO—, —OCO— or a single bond. It is especially preferred that at least one of X and Y, preferably both are —COO—.

In the above formula [I] or [II], A is a group selected from the group consisting of

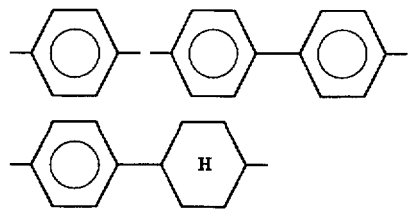

In the above formula [I] or [II], B is a group selected from the group consisting of

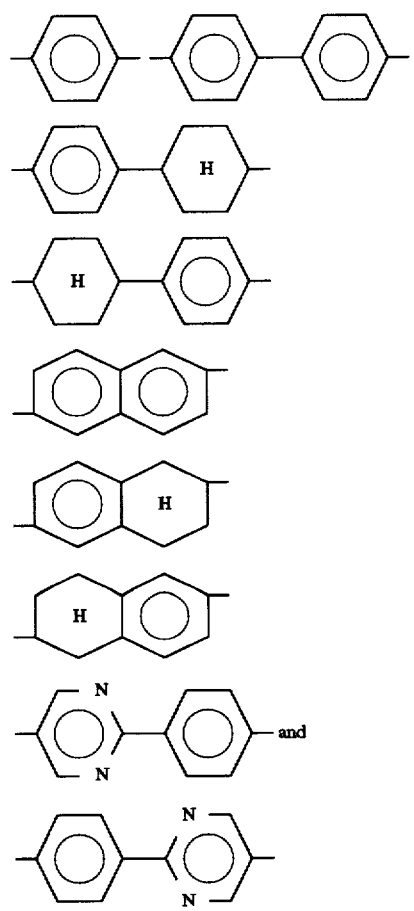

In the above formula [I] or [II], R* is an optically active group of 4–20 carbon atoms having at least one asymmetric (or chiral) carbon atom. R* may be a (R)-body or a (S)-body. In this case, hydrogen atoms attached to the carbon atoms constituting this optically active group may be substituted with a halogen atom such as F, Cl, Br or I.

It is particularly preferred that R* is a group represented by the following formula [V]

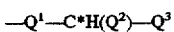

wherein $Q^1$ is —$(CH_2)_q$ in which q is an integer of 0–6, and $Q^2$ and $Q^3$ are different from each other, and are each independently an alkyl of 1–10 carbon atoms, a fluoroalkyl of 1–10 carbon atoms or a halogen atom. Examples of the alkyl of 1–10 carbon atoms include methyl, ethyl, propyl, butyl, pentyl, hexyl, heptyl, octyl, nonyl and decyl. Examples of the fluoroalkyl include those in which at least a part of the hydrogen atoms attached to the carbon atoms of the above-mentioned alkyl is substituted with a fluorine atom. Example of the halogen atom includes F, Cl, Br or I.

In the above formula [V], the groups or atoms $Q^2$ and $Q^3$ should be different always from each other, namely, should not be identical with each other. Further, when one of $Q^2$ and $Q^3$ is a halogen atom, the other is usually alkyl or fluoroalkyl.

When $Q^1$, $Q^2$ and $Q^3$ in the above formula [V] have $CH_2$ group (—$CH_2$— structure) or $CF_2$ group (—$CF_2$— structure) in their structure, at least a part of these groups may be replaced by at least one group selected from the group consisting of —O—, —S—, —CO—, —CHX— (X is a halogen atom), —CHCN—, —O—CO—, —O—COO—, —CO—O— and —CH=CH—. In this case, however, these replacing groups are introduced into the above-mentioned structures so that the hetero atoms (N, O, etc.) constituting said groups are not directly bonded together. Accordingly, the replacement by these groups does not formed afresh a bond such as —O—O— or —N—O—.

In the formula [I] or [II], R* is preferably selected from the group consisting of —C*H(CF₃)—C₆H₁₃, —C*H(CH₃)—C₆H₁₃, —C*H(CH₃)—C₅H₁₁, —C*H(C₂H₅)—C₅H₁₁, —C*H(C₂H₅)—C₆H₁₃, —CH₂—C*H(CH₃)—C₂H₅, —(CH₂)₃—C*H(CH₃)—C₂H₅, —C*H(CF₃)—CH₂—COO—C₂H₅, —C*H(CF₃)—C₄H₉, —C*H(CF₃)—C₅H₁₁ and —C*H(CF₃)—C₈H₁₇. Thus, R* is an optically active group having at least one asymmetric carbon. As shown in the specified groups, the hydrogen atoms attached to the carbon atoms constituting the optically active group may be substituted with a halogen atom such as fluorine atom.

Of these groups of the formula [V] illustrated above, preferred is either of the following groups in view of characteristics of the carboxylate compound used as a liquid crystal material into account.

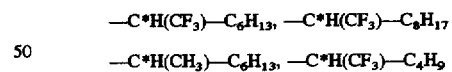

In the formula [I] or [II], m is 1 or 2, and n is an integer of 0–2. Particularly, when the carboxylate compounds of the formula [I] or [II] are used as a liquid crystal material, n is preferably 0 or 1.

The 5,6,7,8-tetrahydronaphthyl group constituting a main skeleton of the above formula [I] or [II] includes 5,6,7,8-tetrahydro-1,5-naphthyl, 5,6,7,8-tetrahydro-1,6-naphthyl, 5,6,7,8-tetrahydro-2,6-naphthyl and 5,6,7,8-tetrahydro-1,7-naphthyl.

For the use of the carboxylate compounds of the invention represented by the formula [I] or [II] as liquid crystal materials, it is preferable that the molecule is linear as a whole. On that account, the 5,6,7,8-tetrahydro-2,6-naphthyl is particularly preferred.

Examples of the carboxylate compounds represented by the formula [I] are shown in the following Tables 1-1 to 1-7.

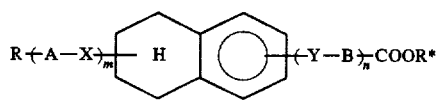

[I]

TABLE 1-1

| Compound Number | R | A | X | m | Y | B | n | R* | Exam. No. |
|---|---|---|---|---|---|---|---|---|---|
| 1 | $C_7H_{15}O-$ | ⌬ | $-COO-$ | 1 | $-COO-$ | ⌬ | 1 | $-C^*H(CF_3)-C_6H_{13}$ | |
| 2 | $C_8H_{17}O-$ | " | " | 1 | " | " | 1 | " | |
| 3 | $C_9H_{19}O-$ | " | " | 1 | " | " | 1 | " | |
| 4 | $C_{10}H_{21}O-$ | " | " | 1 | " | " | 1 | " | 1 |
| 5 | $C_{11}H_{23}O-$ | " | " | 1 | " | " | 1 | " | |
| 6 | $C_{12}H_{25}O-$ | " | " | 1 | " | " | 1 | " | |
| 7 | $C_{14}H_{29}O-$ | " | " | 1 | " | " | 1 | " | |
| 8 | $C_{16}H_{33}O-$ | " | " | 1 | " | " | 1 | " | |
| 9 | $C_7H_{15}-$ | ⌬ | $-COO-$ | 1 | $-COO-$ | ⌬ | 1 | $-C^*H(CF_3)-C_6H_{13}$ | |
| 10 | $C_8H_{17}-$ | " | " | 1 | " | " | 1 | " | |
| 11 | $C_9H_{19}-$ | " | " | 1 | " | " | 1 | " | |
| 12 | $C_{10}H_{21}-$ | " | " | 1 | " | " | 1 | " | |
| 13 | $C_{11}H_{23}-$ | " | " | 1 | " | " | 1 | " | |
| 14 | $C_{12}H_{25}-$ | " | " | 1 | " | " | 1 | " | |
| 15 | $C_{14}H_{29}-$ | " | " | 1 | " | " | 1 | " | |
| 16 | $C_{16}H_{33}-$ | " | " | 1 | " | " | 1 | " | |

Note) In the compounds listed in the table, a tetrahydronaphthyl group is 2,6—linked. The same shall apply hereinafter.

TABLE 1-2

| Compound Number | R | A | X | m | Y | B | n | R* | Exam. No. |
|---|---|---|---|---|---|---|---|---|---|
| 17 | $C_{10}H_{21}O-$ | ⬡ | $-COO-$ | 1 | $-COO-$ | ⬡-⬡ | 1 | $-C^*H(CF_3)-C_6H_{13}$ | |
| 18 | " | " | " | 1 | " | ⬡-⬡(H) | 1 | " | |
| 19 | " | " | " | 1 | " | ⬡-⬡ | 1 | " | |
| 20 | " | " | " | 1 | " | ⬡⬡ | 1 | " | |
| 21 | " | " | " | 1 | " | ⬡⬡(H) | 1 | " | 2 |
| 22 | " | " | " | 1 | " | ⬡⬡(H,H) | 1 | " | 3 |
| 23 | " | " | " | 1 | " | pyridine-⬡ | 1 | " | |
| 24 | $C_{10}H_{21}O-$ | ⬡ | $-COO-$ | 1 | $-COO-$ | ⬡ | 1 | $-C^*H(CH_3)-C_6H_{13}$ | |
| 25 | " | " | " | 1 | " | " | 1 | $-C^*H(CH_3)-C_5H_{11}$ | |
| 26 | " | " | " | 1 | " | " | 1 | $-C^*H(C_2H_5)-C_5H_{11}$ | |
| 27 | " | " | " | 1 | " | " | 1 | $-C^*H(C_2H_5)-C_6H_{13}$ | |
| 28 | " | " | " | 1 | " | " | 1 | $-CH_2-C^*H(CH_3)-C_2H_5$ | |
| 29 | " | " | " | 1 | " | " | 1 | $-(CH_2)_3-C^*H(CH_3)-C_2H_5$ | |
| 30 | " | " | " | 1 | " | " | 1 | $-C^*H(CF_3)-CH_2-COO-C_2H_5$ | |

TABLE 1-3

| Compound Number | R | A | X | m | Y | B | n | R* | Exam. No. |
|---|---|---|---|---|---|---|---|---|---|
| 31 | $C_7H_{15}O-$ | –⌬– | –COO– | 1 | — | — | 0 | $-C^*H(CF_3)-C_6H_{13}$ | |
| 32 | $C_8H_{17}O-$ | " | " | 1 | — | — | 0 | " | |
| 33 | $C_9H_{19}O-$ | " | " | 1 | — | — | 0 | " | |
| 34 | $C_{10}H_{21}O-$ | " | " | 1 | — | — | 0 | " | |
| 35 | $C_{11}H_{23}O-$ | " | " | 1 | — | — | 0 | " | |
| 36 | $C_{12}H_{25}O-$ | " | " | 1 | — | — | 0 | " | |
| 37 | $C_{14}H_{29}O-$ | " | " | 1 | — | — | 0 | " | |
| 38 | $C_{16}H_{33}O-$ | " | " | 1 | — | — | 0 | " | |
| 39 | $C_7H_{15}O-$ | –⌬–⌬– | " | 1 | — | –⌬– | 1 | " | |
| 40 | $C_8H_{17}O-$ | " | " | 1 | " | " | 1 | " | |
| 41 | $C_9H_{19}O-$ | " | " | 1 | " | " | 1 | " | |
| 42 | $C_{10}H_{21}O-$ | " | " | 1 | " | " | 1 | " | |
| 43 | $C_{11}H_{23}O-$ | " | " | 1 | " | " | 1 | " | |
| 44 | $C_{12}H_{25}O-$ | " | " | 1 | " | " | 1 | " | |
| 45 | $C_{14}H_{29}O-$ | " | " | 1 | " | " | 1 | " | |
| 46 | $C_{16}H_{33}O-$ | " | " | 1 | " | " | 1 | " | |
| 47 | $C_7H_{15}O-$ | " | " | 1 | — | — | 0 | " | |
| 48 | $C_8H_{17}O-$ | " | " | 1 | — | — | 0 | " | |
| 49 | $C_9H_{19}O-$ | " | " | 1 | — | — | 0 | " | |
| 50 | $C_{10}H_{21}O-$ | " | " | 1 | — | — | 0 | " | |
| 51 | $C_{11}H_{23}O-$ | " | " | 1 | — | — | 0 | " | |
| 52 | $C_{12}H_{25}O-$ | " | " | 1 | — | — | 0 | " | |
| 53 | $C_{14}H_{29}O-$ | " | " | 1 | — | — | 0 | " | |
| 54 | $C_{16}H_{33}O-$ | " | " | 1 | — | — | 0 | " | |

TABLE 1-4

| Compound Number | R | A | X | m | Y | B | n | R* | Exam. No. |
|---|---|---|---|---|---|---|---|---|---|
| 55 | $C_7H_{15}O-$ | –⌬–H– | –COO– | 1 | –COO– | –⌬– | 1 | $C^*H(CF_3)-C_6H_{13}$ | |
| 56 | $C_8H_{17}O-$ | " | " | 1 | " | " | 1 | " | |
| 57 | $C_9H_{19}O-$ | " | " | 1 | " | " | 1 | " | |
| 58 | $C_{10}H_{21}O-$ | " | " | 1 | " | " | 1 | " | |
| 59 | $C_{11}H_{23}O-$ | " | " | 1 | " | " | 1 | " | |
| 60 | $C_{12}H_{25}O-$ | " | " | 1 | " | " | 1 | " | |
| 61 | $C_{14}H_{29}O-$ | " | " | 1 | " | " | 1 | " | |
| 62 | $C_{16}H_{33}O-$ | " | " | 1 | " | " | 1 | " | |
| 63 | $C_7H_{15}O-$ | –⌬–H– | –COO– | 1 | — | — | 0 | $-C^*H(CF_3)-C_6H_{13}$ | |
| 64 | $C_8H_{17}O-$ | " | " | 1 | — | — | 0 | " | |
| 65 | $C_9H_{19}O-$ | " | " | 1 | — | — | 0 | " | |
| 66 | $C_{10}H_{21}O-$ | " | " | 1 | — | — | 0 | " | |
| 67 | $C_{11}H_{23}O-$ | " | " | 1 | — | — | 0 | " | |
| 68 | $C_{12}H_{25}O-$ | " | " | 1 | — | — | 0 | " | |
| 69 | $C_{14}H_{29}O-$ | " | " | 1 | — | — | 0 | " | |
| 70 | $C_{16}H_{33}O-$ | " | " | 1 | — | — | 0 | " | |
| 71 | $C_7H_{15}O-$ | –H–⌬– | –COO– | 1 | –COO– | –⌬– | 1 | $-C^*H(CF_3)-C_6H_{13}$ | |

TABLE 1-4-continued

| Compound Number | R | A | X | m | Y | B | n | R* | Exam. No. |
|---|---|---|---|---|---|---|---|---|---|
| 72 | $C_8H_{17}O-$ | " | " | 1 | " | " | 1 | " | |
| 73 | $C_9H_{19}O-$ | " | " | 1 | " | " | 1 | " | |
| 74 | $C_{10}H_{21}O-$ | " | " | 1 | " | " | 1 | " | |
| 75 | $C_{11}H_{23}O-$ | " | " | 1 | " | " | 1 | " | |
| 76 | $C_{12}H_{25}O-$ | " | " | 1 | " | " | 1 | " | |
| 77 | $C_{14}H_{29}O-$ | " | " | 1 | " | " | 1 | " | |
| 78 | $C_{16}H_{33}O-$ | " | " | 1 | " | " | 1 | " | |

TABLE 1-5

| Compound Number | R | A | X | m | Y | B | n | R* | Exam. No. |
|---|---|---|---|---|---|---|---|---|---|
| 79 | $C_7H_{15}O-$ | cyclohexyl-phenyl | $-COO-$ | 1 | — | — | 0 | $C*H(CF_3)-C_6H_{13}$ | |
| 80 | $C_8H_{17}O-$ | " | " | 1 | — | — | 0 | " | |
| 81 | $C_9H_{19}O-$ | " | " | 1 | — | — | 0 | " | |
| 82 | $C_{10}H_{21}O-$ | " | " | 1 | — | — | 0 | " | |
| 83 | $C_{11}H_{23}O-$ | " | " | 1 | — | — | 0 | " | |
| 84 | $C_{12}H_{25}O-$ | " | " | 1 | — | — | 0 | " | |
| 85 | $C_{14}H_{29}O-$ | " | " | 1 | — | — | 0 | " | |
| 86 | $C_{16}H_{33}O-$ | " | " | 1 | — | — | 0 | " | |
| 87 | $C_7H_{15}O-$ | naphthyl | $-COO-$ | 1 | $-COO-$ | phenyl | 1 | $-C*H(CF_3)-C_6H_{13}$ | |
| 88 | $C_8H_{17}O-$ | " | " | 1 | " | " | 1 | " | |
| 89 | $C_9H_{19}O-$ | " | " | 1 | " | " | 1 | " | |
| 90 | $C_{10}H_{21}O-$ | " | " | 1 | " | " | 1 | " | |
| 91 | $C_{11}H_{23}O-$ | " | " | 1 | " | " | 1 | " | |
| 92 | $C_{12}H_{25}O-$ | " | " | 1 | " | " | 1 | " | |
| 93 | $C_{14}H_{29}O-$ | " | " | 1 | " | " | 1 | " | |
| 94 | $C_{16}H_{33}O-$ | " | " | 1 | " | " | 1 | " | |
| 95 | $C_7H_{15}O-$ | naphthyl | $-COO-$ | 1 | — | — | 0 | $-C*H(CF_3)-C_6H_{13}$ | |
| 96 | $C_8H_{17}O-$ | " | " | 1 | — | — | 0 | " | |
| 97 | $C_9H_{19}O-$ | " | " | 1 | — | — | 0 | " | |
| 98 | $C_{10}H_{21}O-$ | " | " | 1 | — | — | 0 | " | |
| 99 | $C_{11}H_{23}O-$ | " | " | 1 | — | — | 0 | " | |
| 100 | $C_{12}H_{25}O-$ | " | " | 1 | — | — | 0 | " | |
| 101 | $C_{14}H_{29}O-$ | " | " | 1 | — | — | 0 | " | |
| 102 | $C_{16}H_{33}O-$ | " | " | 1 | — | — | 0 | " | |

TABLE 1-6

| Compound Number | R | A | X | m | Y | B | n | R* | Exam. No. |
|---|---|---|---|---|---|---|---|---|---|
| 103 | $C_7H_{15}O-$ | pyrazine-phenyl | $-COO-$ | 1 | $-COO-$ | phenyl | 1 | $-C*H(CF_3)-C_6H_{13}$ | |

TABLE 1-6-continued

| Compound Number | R | A | X | m | Y | B | n | R* | Exam. No. |
|---|---|---|---|---|---|---|---|---|---|
| 104 | $C_8H_{17}O-$ | " | " | 1 | " | " | 1 | " | |
| 105 | $C_9H_{19}O-$ | " | " | 1 | " | " | 1 | " | |
| 106 | $C_{10}H_{21}O-$ | " | " | 1 | " | " | 1 | " | |
| 107 | $C_{11}H_{23}O-$ | " | " | 1 | " | " | 1 | " | |
| 108 | $C_{12}H_{25}O-$ | " | " | 1 | " | " | 1 | " | |
| 109 | $C_{14}H_{29}O-$ | " | " | 1 | " | " | 1 | " | |
| 110 | $C_{16}H_{33}O-$ | " | " | 1 | " | " | 1 | " | |
| 111 | $C_7H_{15}O-$ | 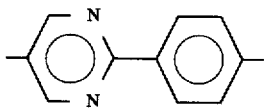 | $-COO-$ | 1 | — | — | 0 | $-C^*H(CF_3)-C_6H_{13}$ | |
| 112 | $C_8H_{17}O-$ | " | " | 1 | — | — | 0 | " | |
| 113 | $C_9H_{19}O-$ | " | " | 1 | — | — | 0 | " | |
| 114 | $C_{10}H_{21}O-$ | " | " | 1 | — | — | 0 | " | |
| 115 | $C_{11}H_{23}O-$ | " | " | 1 | — | — | 0 | " | |
| 116 | $C_{12}H_{25}O-$ | " | " | 1 | — | — | 0 | " | |
| 117 | $C_{14}H_{29}O-$ | " | " | 1 | — | — | 0 | " | |
| 118 | $C_{16}H_{33}O-$ | " | " | 1 | — | — | 0 | " | |
| 119 | $C_7H_{15}-$ | 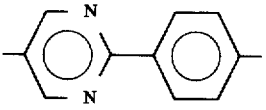 | $-COO-$ | 1 | $-COO-$ | 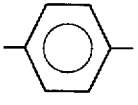 | 1 | $-C^*H(CF_3)-C_6H_{13}$ | |
| 120 | $C_8H_{17}-$ | " | " | 1 | " | " | 1 | " | |
| 121 | $C_9H_{19}-$ | " | " | 1 | " | " | 1 | " | |
| 122 | $C_{10}H_{21}-$ | " | " | 1 | " | " | 1 | " | |
| 123 | $C_{11}H_{23}-$ | " | " | 1 | " | " | 1 | " | |
| 124 | $C_{12}H_{25}-$ | " | " | 1 | " | " | 1 | " | |
| 125 | $C_{14}H_{29}-$ | " | " | 1 | " | " | 1 | " | |
| 126 | $C_{16}H_{33}-$ | " | " | 1 | " | " | 1 | " | |

TABLE 1-7

| Compound Number | R | A | X | m | Y | B | n | R* | Exam. No. |
|---|---|---|---|---|---|---|---|---|---|
| 127 | $C_7H_{15}-$ | 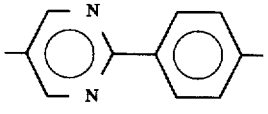 | $-COO-$ | 1 | — | — | 0 | $-C^*H(CF_3)-C_6H_{13}$ | |
| 128 | $C_8H_{17}-$ | " | " | 1 | — | — | 0 | " | |
| 129 | $C_9H_{19}-$ | " | " | 1 | — | — | 0 | " | |
| 130 | $C_{10}H_{21}-$ | " | " | 1 | — | — | 0 | " | 4 |
| 131 | $C_{11}H_{23}-$ | " | " | 1 | — | — | 0 | " | |
| 132 | $C_{12}H_{25}-$ | " | " | 1 | — | — | 0 | " | |
| 133 | $C_{14}H_{29}-$ | " | " | 1 | — | — | 0 | " | |
| 134 | $C_{16}H_{33}-$ | " | " | 1 | — | — | 0 | " | |
| 135 | $C_7H_{15}O-$ | 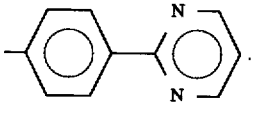 | $-COO-$ | 1 | $-COO-$ | 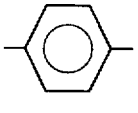 | 1 | $-C^*H(CF_3)-C_6H_{13}$ | |
| 136 | $C_8H_{17}O-$ | " | " | 1 | " | " | 1 | " | |
| 137 | $C_9H_{19}O-$ | " | " | 1 | " | " | 1 | " | |
| 138 | $C_{10}H_{21}O-$ | " | " | 1 | " | " | 1 | " | |
| 139 | $C_{11}H_{23}O-$ | " | " | 1 | " | " | 1 | " | |
| 140 | $C_{12}H_{25}O-$ | " | " | 1 | " | " | 1 | " | |
| 141 | $C_{14}H_{29}O-$ | " | " | 1 | " | " | 1 | " | |
| 142 | $C_{16}H_{33}O-$ | " | " | 1 | " | " | 1 | " | |

TABLE 1-7-continued

| Compound Number | R | A | X | m | Y | B | n | R* | Exam. No. |
|---|---|---|---|---|---|---|---|---|---|
| 143 | C₇H₁₅O— | 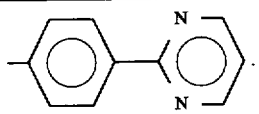 | —COO— | 1 | — | — | 0 | —C*H(CF₃)—C₆H₁₃ | |
| 144 | C₈H₁₇O— | " | " | 1 | — | — | 0 | " | |
| 145 | C₉H₁₉O— | " | " | 1 | — | — | 0 | " | |
| 146 | C₁₀H₂₁O— | " | " | 1 | — | — | 0 | " | |
| 147 | C₁₁H₂₃O— | " | " | 1 | — | — | 0 | " | |
| 148 | C₁₂H₂₅O— | " | " | 1 | — | — | 0 | " | |
| 149 | C₁₄H₂₉O— | " | " | 1 | — | — | 0 | " | |
| 150 | C₁₆H₃₃O— | " | " | 1 | — | — | 0 | " | |

TABLE 1-8

| Compound Number | R | A | X | m | Y | B | n | R* | Exam. No. |
|---|---|---|---|---|---|---|---|---|---|
| 151 | C₇H₁₅O— | —⌬— | —OCO— | 1 | —OCO— | —⌬— | 1 | —C*H(CF₃)—C₆H₁₃ | |
| 152 | C₈H₁₇O— | " | " | 1 | " | " | 1 | " | |
| 153 | C₉H₁₉O— | " | " | 1 | " | " | 1 | " | |
| 154 | C₁₀H₂₁O— | " | " | 1 | " | " | 1 | " | 45 |
| 155 | C₁₁H₂₃O— | " | " | 1 | " | " | 1 | " | |
| 156 | C₁₂H₂₅O— | " | " | 1 | " | " | 1 | " | |
| 157 | C₁₄H₂₉O— | " | " | 1 | " | " | 1 | " | |
| 158 | C₁₆H₃₃O— | " | " | 1 | " | " | 1 | " | |
| 159 | C₇H₁₅O— | —⌬— | —OCO— | 1 | —OCO— | —⌬— | 1 | —C*H(CH₃)—C₆H₁₃ | |
| 160 | C₈H₁₇O— | " | " | 1 | " | " | 1 | " | |
| 161 | C₉H₁₉O— | " | " | 1 | " | " | 1 | " | |
| 162 | C₁₀H₂₁O— | " | " | 1 | " | " | 1 | " | 46 |
| 163 | C₁₁H₂₃O— | " | " | 1 | " | " | 1 | " | |
| 164 | C₁₂H₂₅O— | " | " | 1 | " | " | 1 | " | |
| 165 | C₁₄H₂₉O— | " | " | 1 | " | " | 1 | " | |
| 166 | C₁₆H₃₃O— | " | " | 1 | " | " | 1 | " | |

Examples of the carboxylate compounds represented by the formula [II] are shown in the following Tables 2-1 to 2-7.

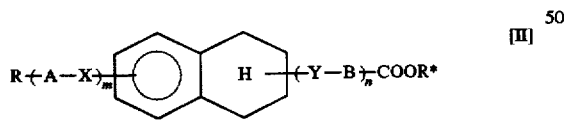

[II]

TABLE 2-1

| Compound Number | R | A | X | m | Y | B | n | R* | Exam. No. |
|---|---|---|---|---|---|---|---|---|---|
| 201 | C₇H₁₅O— | —⌬— | —COO— | 1 | —COO— | —⌬— | 1 | —C*H(CF₃)—C₆H₁₃ | |
| 202 | C₈H₁₇O— | " | " | 1 | " | " | 1 | " | |
| 203 | C₉H₁₉O— | " | " | 1 | " | " | 1 | " | |

TABLE 2-1-continued
| Compound Number | R | A | X | m | Y | B | n | R* | Exam. No. |
|---|---|---|---|---|---|---|---|---|---|
| 204 | $C_{10}H_{21}O-$ | " | " | 1 | " | " | 1 | " | 8 |
| 205 | $C_{11}H_{23}O-$ | " | " | 1 | " | " | 1 | " | |
| 206 | $C_{12}H_{25}O-$ | " | " | 1 | " | " | 1 | " | |
| 207 | $C_{14}H_{29}O-$ | " | " | 1 | " | " | 1 | " | |
| 208 | $C_{16}H_{33}O-$ | " | " | 1 | " | " | 1 | " | |
| 209 | $C_7H_{15}-$ |  | $-COO-$ | 1 | $-COO-$ | 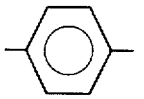 | 1 | $-C*H(CF_3)-C_6H_{13}$ | |
| 210 | $C_8H_{17}-$ | " | " | 1 | " | " | 1 | " | |
| 211 | $C_9H_{19}-$ | " | " | 1 | " | " | 1 | " | |
| 212 | $C_{10}H_{21}-$ | " | " | 1 | " | " | 1 | " | 42 |
| 213 | $C_{11}H_{23}-$ | " | " | 1 | " | " | 1 | " | |
| 214 | $C_{12}H_{25}-$ | " | " | 1 | " | " | 1 | " | |
| 215 | $C_{14}H_{29}-$ | " | " | 1 | " | " | 1 | " | |
| 216 | $C_{16}H_{33}-$ | " | " | 1 | " | " | 1 | " | |
Note) In the compounds listed in the table, a tetrahydronaphthyl group is 2,6-linked. The same shall apply hereinafter.

TABLE 2-2
| Compound Number | R | A | X | m | Y | B | n | R* | Ex. No. |
|---|---|---|---|---|---|---|---|---|---|
| 217 | $C_{10}H_{21}O-$ | 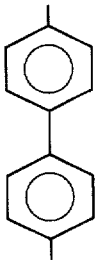 | -COO- | 1 | -COO- | 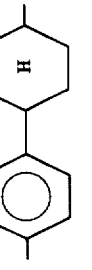 | 1 | $-C^*H(CF_3)-C_6H_{13}$ | |
| 218 | " | " | " | 1 | " | 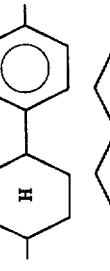 | 1 | " | |
| 219 | " | " | " | 1 | " |  | 1 | " | |
| 220 | " | " | " | 1 | " | 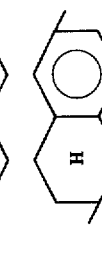 | 1 | " | |
| 221 | " | " | " | 1 | " | 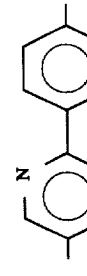 | 1 | " | |
| 222 | " | " | " | 1 | " | 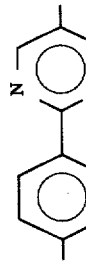 | 1 | " | |
| 223 | " | " | " | 1 | " | | 1 | " | 9 |
| 224 | " | " | " | 1 | " | | 1 | " | 10 |
| 225 | $C_{10}H_{21}O-$ | | -COO- | 1 | -COO- | | 1 | $-C^*H(CH_3)-C_6H_{13}$ | |

TABLE 2-2-continued
| Compound Number | R | A | X | m | Y | B | n | R* | Ex. No. |
|---|---|---|---|---|---|---|---|---|---|
| 226 | " | " | " | 1 | " | " | 1 | $-C^*H(CH_3)-C_5H_{11}$ | |
| 227 | " | " | " | 1 | " | " | 1 | $-C^*H(C_2H_5)-C_5H_{11}$ | |
| 228 | " | " | " | 1 | " | " | 1 | $-C^*H(C_2H_5)-C_6H_{13}$ | |
| 229 | " | " | " | 1 | " | " | 1 | $-CH_2-C^*H(CH_3)-C_2H_5$ | |
| 230 | " | " | " | 1 | " | " | 1 | $-(CH_2)_3-C^*H(CH_3)-C_2H_5$ | |
| 231 | " | " | " | 1 | " | " | 1 | $-C^*H(CF_3)-CH_2-COO-C_2H_5$ | |
| 232 | $C_7H_{15}O-$ | 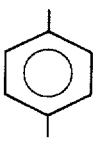 | $-COO-$ | 1 | — | — | 0 | $-C^*H(CF_3)-C_6H_{13}$ | 17 |
| 233 | $C_8H_{17}O-$ | " | " | 1 | — | — | 0 | " | |
| 234 | $C_9H_{19}O-$ | " | " | 1 | — | — | 0 | " | |
| 235 | $C_{10}H_{21}O-$ | " | " | 1 | — | — | 0 | " | |
| 236 | $C_{11}H_{23}O-$ | " | " | 1 | — | — | 0 | " | |
| 237 | $C_{12}H_{25}O-$ | " | " | 1 | — | — | 0 | " | |
| 238 | $C_{14}H_{29}O-$ | " | " | 1 | — | — | 0 | " | |
| 239 | $C_{16}H_{33}O-$ | " | " | 1 | — | — | 0 | " | |

TABLE 2-3

| Compound Number | R | A | X | m | Y | B | n | R* | Exam. No. |
|---|---|---|---|---|---|---|---|---|---|
| 240 | $C_7H_{15}O-$ | 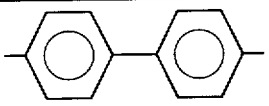 | $-COO-$ | 1 | $-COO-$ | 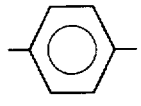 | 1 | $-C*H(CF_3)-C_6H_{13}$ | |
| 241 | $C_8H_{17}O-$ | " | " | 1 | " | " | 1 | " | |
| 242 | $C_9H_{19}O-$ | " | " | 1 | " | " | 1 | " | |
| 243 | $C_{10}H_{21}O-$ | " | " | 1 | " | " | 1 | " | |
| 244 | $C_{11}H_{23}O-$ | " | " | 1 | " | " | 1 | " | |
| 245 | $C_{12}H_{25}O-$ | " | " | 1 | " | " | 1 | " | |
| 246 | $C_{14}H_{29}O-$ | " | " | 1 | " | " | 1 | " | |
| 247 | $C_{16}H_{33}O-$ | " | " | 1 | " | " | 1 | " | |
| 248 | $C_7H_{15}O-$ | 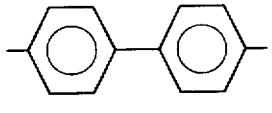 | $-COO-$ | 1 | — | — | 0 | $-C*H(CF_3)-C_6H_{13}$ | |
| 249 | $C_8H_{17}O-$ | " | " | 1 | — | — | 0 | " | 48 |
| 250 | $C_9H_{19}O-$ | " | " | 1 | — | — | 0 | " | 49 |
| 251 | $C_{10}H_{21}O-$ | " | " | 1 | — | — | 0 | " | 11 |
| 252 | $C_{11}H_{23}O-$ | " | " | 1 | — | — | 0 | " | 31 |
| 253 | $C_{12}H_{25}O-$ | " | " | 1 | — | — | 0 | " | 32 |
| 254 | $C_{14}H_{29}O-$ | " | " | 1 | — | — | 0 | " | 50 |
| 255 | $C_{16}H_{33}O-$ | " | " | 1 | — | — | 0 | " | |
| 256 | $C_7H_{15}O-$ | 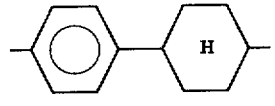 | $-COO-$ | 1 | $-COO-$ | 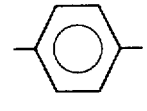 | 1 | $-C*H(CF_3)-C_6H_{13}$ | |
| 257 | $C_8H_{17}O-$ | " | " | 1 | " | " | 1 | " | |
| 258 | $C_9H_{19}O-$ | " | " | 1 | " | " | 1 | " | |
| 259 | $C_{10}H_{21}O-$ | " | " | 1 | " | " | 1 | " | |
| 260 | $C_{11}H_{23}O-$ | " | " | 1 | " | " | 1 | " | |
| 261 | $C_{12}H_{25}O-$ | " | " | 1 | " | " | 1 | " | |
| 262 | $C_{14}H_{29}O-$ | " | " | 1 | " | " | 1 | " | |
| 263 | $C_{16}H_{33}O-$ | " | " | 1 | " | " | 1 | " | |

TABLE 2-4

| Compound Number | R | A | X | m | Y | B | n | R* | Exam. No. |
|---|---|---|---|---|---|---|---|---|---|
| 264 | $C_7H_{15}O-$ | 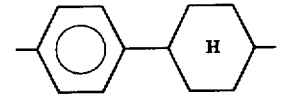 | $-COO-$ | 1 | — | — | 0 | $-C*H(CF_3)-C_6H_{13}$ | |
| 265 | $C_8H_{17}O-$ | " | " | 1 | — | — | 0 | " | 39 |
| 266 | $C_9H_{19}O-$ | " | " | 1 | — | — | 0 | " | |
| 267 | $C_{10}H_{21}O-$ | " | " | 1 | — | — | 0 | " | 12 |
| 268 | $C_{11}H_{23}O-$ | " | " | 1 | — | — | 0 | " | |
| 269 | $C_{12}H_{25}O-$ | " | " | 1 | — | — | 0 | " | 40 |
| 270 | $C_{14}H_{29}O-$ | " | " | 1 | — | — | 0 | " | |
| 271 | $C_{16}H_{33}O-$ | " | " | 1 | — | — | 0 | " | |
| 272 | $C_7H_{15}O-$ | 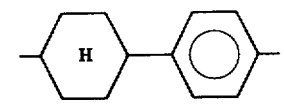 | $-COO-$ | 1 | $-COO-$ | 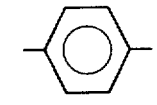 | 1 | $-C*H(CF_3)-C_6H_{13}$ | |
| 273 | $C_8H_{17}O-$ | " | " | 1 | " | " | 1 | " | |
| 274 | $C_9H_{19}O-$ | " | " | 1 | " | " | 1 | " | |
| 275 | $C_{10}H_{21}O-$ | " | " | 1 | " | " | 1 | " | |
| 276 | $C_{11}H_{23}O-$ | " | " | 1 | " | " | 1 | " | |
| 277 | $C_{12}H_{25}O-$ | " | " | 1 | " | " | 1 | " | |
| 278 | $C_{14}H_{29}O-$ | " | " | 1 | " | " | 1 | " | |

TABLE 2-4-continued

| Compound Number | R | A | X | m | Y | B | n | R* | Exam. No. |
|---|---|---|---|---|---|---|---|---|---|
| 279 | $C_{16}H_{33}O-$ | " | " | 1 | " | " | 1 | " | |
| 280 | $C_7H_{15}O-$ | cyclohexyl-phenyl | $-COO-$ | 1 | — | — | 0 | $-C*H(CF_3)-C_6H_{13}$ | |
| 281 | $C_8H_{17}O-$ | " | " | 1 | — | — | 0 | " | |
| 282 | $C_9H_{19}O-$ | " | " | 1 | — | — | 0 | " | |
| 283 | $C_{10}H_{21}O-$ | " | " | 1 | — | — | 0 | " | |
| 284 | $C_{11}H_{23}O-$ | " | " | 1 | — | — | 0 | " | |
| 285 | $C_{12}H_{25}O-$ | " | " | 1 | — | — | 0 | " | |
| 286 | $C_{14}H_{29}O-$ | " | " | 1 | — | — | 0 | " | |
| 287 | $C_{16}H_{33}O-$ | " | " | 1 | — | — | 0 | " | |

TABLE 2-5

| Compound Number | R | A | X | m | Y | B | n | R* | Exam. No. |
|---|---|---|---|---|---|---|---|---|---|
| 288 | $C_7H_{15}O-$ | naphthyl | $-COO-$ | 1 | $-COO-$ | phenyl | 1 | $-C*H(CF_3)-C_6H_{13}$ | 13 |
| 289 | $C_8H_{17}O-$ | " | " | 1 | " | " | 1 | " | |
| 290 | $C_9H_{19}O-$ | " | " | 1 | " | " | 1 | " | |
| 291 | $C_{10}H_{21}O-$ | " | " | 1 | " | " | 1 | " | |
| 292 | $C_{11}H_{23}O-$ | " | " | 1 | " | " | 1 | " | |
| 293 | $C_{12}H_{25}O-$ | " | " | 1 | " | " | 1 | " | |
| 294 | $C_{14}H_{29}O-$ | " | " | 1 | " | " | 1 | " | |
| 295 | $C_{16}H_{33}O-$ | " | " | 1 | " | " | 1 | " | |
| 296 | $C_7H_{15}O-$ | naphthyl | $-COO-$ | 1 | — | — | 0 | $-C*H(CF_3)-C_6H_{13}$ | 14 |
| 297 | $C_8H_{17}O-$ | " | " | 1 | — | — | 0 | " | |
| 298 | $C_9H_{19}O-$ | " | " | 1 | — | — | 0 | " | |
| 299 | $C_{10}H_{21}O-$ | " | " | 1 | — | — | 0 | " | 15 |
| 300 | $C_{11}H_{23}O-$ | " | " | 1 | — | — | 0 | " | |
| 301 | $C_{12}H_{25}O-$ | " | " | 1 | — | — | 0 | " | |
| 302 | $C_{14}H_{29}O-$ | " | " | 1 | — | — | 0 | " | |
| 303 | $C_{16}H_{33}O-$ | " | " | 1 | — | — | 0 | " | |
| 304 | $C_7H_{15}O-$ | pyrimidinyl-phenyl | $-COO-$ | 1 | $-COO-$ | phenyl | 1 | $-C*H(CF_3)-C_6H_{13}$ | |
| 305 | $C_8H_{17}O-$ | " | " | 1 | " | " | 1 | " | |
| 306 | $C_9H_{19}O-$ | " | " | 1 | " | " | 1 | " | |
| 307 | $C_{10}H_{21}O-$ | " | " | 1 | " | " | 1 | " | |
| 308 | $C_{11}H_{23}O-$ | " | " | 1 | " | " | 1 | " | |
| 309 | $C_{12}H_{25}O-$ | " | " | 1 | " | " | 1 | " | |
| 310 | $C_{14}H_{29}O-$ | " | " | 1 | " | " | 1 | " | |
| 311 | $C_{16}H_{33}O-$ | " | " | 1 | " | " | 1 | " | |

TABLE 2-6

| Compound Number | R | A | X | m | Y | B | n | R* | Exam. No. |
|---|---|---|---|---|---|---|---|---|---|
| 312 | $C_7H_{15}O-$ | 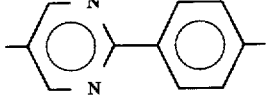 | $-COO-$ | 1 | — | — | 0 | $-C*H(CF_3)-C_6H_{13}$ | |
| 313 | $C_8H_{17}O-$ | " | " | 1 | — | — | 0 | " | 65 |
| 314 | $C_9H_{19}O-$ | " | " | 1 | — | — | 0 | " | |
| 315 | $C_{10}H_{21}O-$ | " | " | 1 | — | — | 0 | " | |
| 316 | $C_{11}H_{23}O-$ | " | " | 1 | — | — | 0 | " | |
| 317 | $C_{12}H_{25}O-$ | " | " | 1 | — | — | 0 | " | |
| 318 | $C_{14}H_{29}O-$ | " | " | 1 | — | — | 0 | " | |
| 319 | $C_{16}H_{33}O-$ | " | " | 1 | — | — | 0 | " | |
| 320 | $C_7H_{15}-$ | 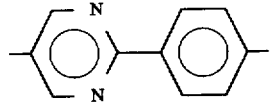 | $-COO-$ | 1 | $-COO-$ |  | 1 | $-C*H(CF_3)-C_6H_{13}$ | |
| 321 | $C_8H_{17}-$ | " | " | 1 | " | " | 1 | " | |
| 322 | $C_9H_{19}-$ | " | " | 1 | " | " | 1 | " | |
| 323 | $C_{10}H_{21}-$ | " | " | 1 | " | " | 1 | " | |
| 324 | $C_{11}H_{23}-$ | " | " | 1 | " | " | 1 | " | |
| 325 | $C_{12}H_{25}-$ | " | " | 1 | " | " | 1 | " | |
| 326 | $C_{14}H_{29}-$ | " | " | 1 | " | " | 1 | " | |
| 327 | $C_{16}H_{33}-$ | " | " | 1 | " | " | 1 | " | |
| 328 | $C_7H_{15}-$ | 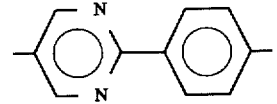 | $-COO-$ | 1 | — | — | 0 | $-C*H(CF_3)-C_6H_{13}$ | |
| 329 | $C_8H_{17}-$ | " | " | 1 | — | — | 0 | " | |
| 330 | $C_9H_{19}-$ | " | " | 1 | — | — | 0 | " | |
| 331 | $C_{10}H_{21}-$ | " | " | 1 | — | — | 0 | " | 16 |
| 332 | $C_{11}H_{23}-$ | " | " | 1 | — | — | 0 | " | |
| 333 | $C_{12}H_{25}-$ | " | " | 1 | — | — | 0 | " | |
| 334 | $C_{14}H_{29}-$ | " | " | 1 | — | — | 0 | " | |
| 335 | $C_{16}H_{33}-$ | " | " | 1 | — | — | 0 | " | |

TABLE 2-7

| Compound Number | R | A | X | m | Y | B | n | R* | Exam. No. |
|---|---|---|---|---|---|---|---|---|---|
| 336 | $C_7H_{15}O-$ | 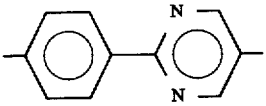 | $-COO-$ | 1 | $-COO-$ |  | 1 | $-C*H(CF_3)-C_6H_{13}$ | |
| 337 | $C_8H_{17}O-$ | " | " | 1 | " | " | 1 | " | |
| 338 | $C_9H_{19}O-$ | " | " | 1 | " | " | 1 | " | |
| 339 | $C_{10}H_{21}O-$ | " | " | 1 | " | " | 1 | " | |
| 340 | $C_{11}H_{23}O-$ | " | " | 1 | " | " | 1 | " | |
| 341 | $C_{12}H_{25}O-$ | " | " | 1 | " | " | 1 | " | |
| 342 | $C_{14}H_{29}O-$ | " | " | 1 | " | " | 1 | " | |
| 343 | $C_{16}H_{33}O-$ | " | " | 1 | " | " | 1 | " | |
| 344 | $C_7H_{15}O-$ | 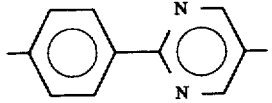 | $-COO-$ | 1 | — | — | 0 | $-C*H(CF_3)-C_6H_{13}$ | |
| 345 | $C_8H_{17}O-$ | " | " | 1 | — | — | 0 | " | |
| 346 | $C_9H_{19}O-$ | " | " | 1 | — | — | 0 | " | |
| 347 | $C_{10}H_{21}O-$ | " | " | 1 | — | — | 0 | " | |

TABLE 2-7-continued

| Compound Number | R | A | X | m | Y | B | n | R* | Exam. No. |
|---|---|---|---|---|---|---|---|---|---|
| 348 | $C_{11}H_{23}O-$ | " | " | 1 | — | — | 0 | " | |
| 349 | $C_{12}H_{25}O-$ | " | " | 1 | — | — | 0 | " | |
| 350 | $C_{14}H_{29}O-$ | " | " | 1 | — | — | 0 | " | |
| 351 | $C_{16}H_{33}O-$ | " | " | 1 | — | — | 0 | " | |
| 352 | $C_7H_{15}-$ | —⟨phenyl⟩—⟨phenyl⟩— | —COO— | 1 | — | — | 0 | $-C^*H(CF_3)-C_6H_{13}$ | |
| 353 | $C_8H_{17}-$ | " | " | 1 | — | — | 0 | " | 33 |
| 354 | $C_9H_{19}-$ | " | " | 1 | — | — | 0 | " | 51 |
| 355 | $C_{10}H_{21}-$ | " | " | 1 | — | — | 0 | " | 34 |
| 356 | $C_{11}H_{23}-$ | " | " | 1 | — | — | 0 | " | 52 |
| 357 | $C_{12}H_{25}-$ | " | " | 1 | — | — | 0 | " | 35 |
| 358 | $C_{14}H_{29}-$ | " | " | 1 | — | — | 0 | " | 53 |
| 359 | $C_{16}H_{33}-$ | " | " | 1 | — | — | 0 | " | |

TABLE 2-8

| Compound Number | R | A | X | m | Y | B | n | R* | Exam. No |
|---|---|---|---|---|---|---|---|---|---|
| 360 | $C_7H_{15}-$ | —⟨phenyl⟩—⟨cyclohexyl H⟩— | —COO— | 1 | — | — | 0 | $-C^*H(CF_3)-C_6H_{13}$ | |
| 361 | $C_8H_{17}-$ | " | " | 1 | — | — | 0 | " | |
| 362 | $C_9H_{19}-$ | " | " | 1 | — | — | 0 | " | |
| 363 | $C_{10}H_{21}-$ | " | " | 1 | — | — | 0 | " | |
| 364 | $C_{11}H_{23}-$ | " | " | 1 | — | — | 0 | " | 41 |
| 365 | $C_{12}H_{25}-$ | " | " | 1 | — | — | 0 | " | |
| 366 | $C_{14}H_{29}-$ | " | " | 1 | — | — | 0 | " | 47 |
| 367 | $C_{16}H_{33}-$ | " | " | 1 | — | — | 0 | " | |
| 368 | $C_7H_{15}O-$ | —⟨phenyl⟩—⟨phenyl⟩— | —COO— | 1 | — | — | 0 | $-C^*H(CF_3)-C_8H_{17}$ | |
| 369 | $C_8H_{17}O-$ | " | " | 1 | — | — | 0 | " | |
| 370 | $C_9H_{19}O-$ | " | " | 1 | — | — | 0 | " | |
| 371 | $C_{10}H_{21}O-$ | " | " | 1 | — | — | 0 | " | |
| 372 | $C_{11}H_{23}O-$ | " | " | 1 | — | — | 0 | " | 54 |
| 373 | $C_{12}H_{25}O-$ | " | " | 1 | — | — | 0 | " | |
| 374 | $C_{14}H_{29}O-$ | " | " | 1 | — | — | 0 | " | |
| 375 | $C_{16}H_{33}O-$ | " | " | 1 | — | — | 0 | " | |
| 376 | $C_7H_{15}-$ | —⟨phenyl⟩—⟨phenyl⟩— | —COO— | 1 | — | — | 0 | $-C^*H(CF_3)-C_8H_{17}$ | |
| 377 | $C_8H_{17}-$ | " | " | 1 | — | — | 0 | " | |
| 378 | $C_9H_{19}-$ | " | " | 1 | — | — | 0 | " | |
| 379 | $C_{10}H_{21}-$ | " | " | 1 | — | — | 0 | " | |
| 380 | $C_{11}H_{23}-$ | " | " | 1 | — | — | 0 | " | |
| 381 | $C_{12}H_{25}-$ | " | " | 1 | — | — | 0 | " | |
| 382 | $C_{14}H_{29}-$ | " | " | 1 | — | — | 0 | " | |
| 383 | $C_{16}H_{33}-$ | " | " | 1 | — | — | 0 | " | |

TABLE 2-9

| Compound Number | R | A | X | m | Y | B | n | R* | Exam. No |
|---|---|---|---|---|---|---|---|---|---|
| 384 | $C_7H_{15}O-$ | 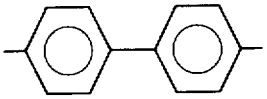 | $-COO-$ | 1 | — | — | 0 | $-C^*H(CF_3)-C_5H_{11}$ | |
| 385 | $C_8H_{17}O-$ | " | " | 1 | — | — | 0 | " | |
| 386 | $C_9H_{19}O-$ | " | " | 1 | — | — | 0 | " | 66 |
| 387 | $C_{10}H_{21}O-$ | " | " | 1 | — | — | 0 | " | 67 |
| 388 | $C_{11}H_{23}O-$ | " | " | 1 | — | — | 0 | " | 68 |
| 389 | $C_{12}H_{25}O-$ | " | " | 1 | — | — | 0 | " | |
| 390 | $C_{14}H_{29}O-$ | " | " | 1 | — | — | 0 | " | |
| 391 | $C_{16}H_{33}O-$ | " | " | 1 | — | — | 0 | " | |
| 392 | $C_7H_{15}-$ | 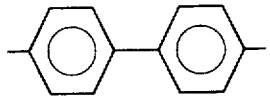 | $-COO-$ | 1 | — | — | 0 | $-C^*H(CF_3)-C_5H_{11}$ | |
| 393 | $C_8H_{17}-$ | " | " | 1 | — | — | 0 | " | |
| 394 | $C_9H_{19}-$ | " | " | 1 | — | — | 0 | " | |
| 395 | $C_{10}H_{21}-$ | " | " | 1 | — | — | 0 | " | |
| 396 | $C_{11}H_{23}-$ | " | " | 1 | — | — | 0 | " | |
| 397 | $C_{12}H_{25}-$ | " | " | 1 | — | — | 0 | " | 69 |
| 398 | $C_{14}H_{29}-$ | " | " | 1 | — | — | 0 | " | |
| 399 | $C_{16}H_{33}-$ | " | " | 1 | — | — | 0 | " | |
| 400 | $C_7H_{15}O-$ | 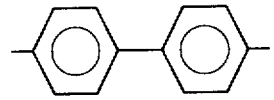 | $-COO-$ | 1 | — | — | 0 | $-C^*H(CF_3)-C_4H_9$ | |
| 401 | $C_8H_{17}O-$ | " | " | 1 | — | — | 0 | " | |
| 402 | $C_9H_{19}O-$ | " | " | 1 | — | — | 0 | " | |
| 403 | $C_{10}H_{21}O-$ | " | " | 1 | — | — | 0 | " | 70 |
| 404 | $C_{11}H_{23}O-$ | " | " | 1 | — | — | 0 | " | |
| 405 | $C_{12}H_{25}O-$ | " | " | 1 | — | — | 0 | " | 71 |
| 406 | $C_{14}H_{29}O-$ | " | " | 1 | — | — | 0 | " | |
| 407 | $C_{16}H_{33}O-$ | " | " | 1 | — | — | 0 | " | |

TABLE 2-10

| Compound Number | R | A | X | m | Y | B | n | R* | Exam. No |
|---|---|---|---|---|---|---|---|---|---|
| 408 | $C_7H_{15}-$ | 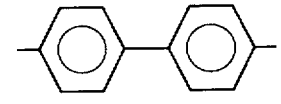 | $-COO-$ | 1 | — | — | 0 | $-C^*H(CF_3)-C_4H_9$ | |
| 409 | $C_8H_{17}-$ | " | " | 1 | — | — | 0 | " | |
| 410 | $C_9H_{19}-$ | " | " | 1 | — | — | 0 | " | |
| 411 | $C_{10}H_{21}-$ | " | " | 1 | — | — | 0 | " | |
| 412 | $C_{11}H_{23}-$ | " | " | 1 | — | — | 0 | " | |
| 413 | $C_{12}H_{25}-$ | " | " | 1 | — | — | 0 | " | 72 |
| 414 | $C_{14}H_{29}-$ | " | " | 1 | — | — | 0 | " | 73 |
| 415 | $C_{16}H_{33}-$ | " | " | 1 | — | — | 0 | " | |
| 416 | $C_7H_{15}O-$ | 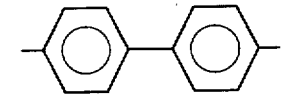 | $-CH_2O-$ | 1 | — | — | 0 | $-C^*H(CF_3)-C_6H_{13}$ | |
| 417 | $C_8H_{17}O-$ | " | " | 1 | — | — | 0 | " | |
| 418 | $C_9H_{19}O-$ | " | " | 1 | — | — | 0 | " | |
| 419 | $C_{10}H_{21}O-$ | " | " | 1 | — | — | 0 | " | 58 |
| 420 | $C_{11}H_{23}O-$ | " | " | 1 | — | — | 0 | " | |
| 421 | $C_{12}H_{25}O-$ | " | " | 1 | — | — | 0 | " | 59 |
| 422 | $C_{14}H_{29}O-$ | " | " | 1 | — | — | 0 | " | |
| 423 | $C_{16}H_{33}O-$ | " | " | 1 | — | — | 0 | " | |

TABLE 2-10-continued

| Compound Number | R | A | X | m | Y | B | n | R* | Exam. No |
|---|---|---|---|---|---|---|---|---|---|
| 424 | $C_7H_{15}-$ |  | $-CH_2O-$ | 1 | — | — | 0 | $-C^*H(CF_3)-C_6H_{13}$ | |
| 425 | $C_8H_{17}-$ | " | " | 1 | — | — | 0 | " | |
| 426 | $C_9H_{19}-$ | " | " | 1 | — | — | 0 | " | |
| 427 | $C_{10}H_{21}-$ | " | " | 1 | — | — | 0 | " | 60 |
| 428 | $C_{11}H_{23}-$ | " | " | 1 | — | — | 0 | " | |
| 429 | $C_{12}H_{25}-$ | " | " | 1 | — | — | 0 | " | 61 |
| 430 | $C_{14}H_{29}-$ | " | " | 1 | — | — | 0 | " | |
| 431 | $C_{16}H_{33}-$ | " | " | 1 | — | — | 0 | " | |

TABLE 2-11

| Compound Number | R | A | X | m | Y | B | n | R* | Exam. No |
|---|---|---|---|---|---|---|---|---|---|
| 432 | $C_7H_{15}O-$ | phenyl-cyclohexyl (H) | $-CH_2O-$ | 1 | — | — | 0 | $-C^*H(CF_3)-C_6H_{13}$ | |
| 433 | $C_8H_{17}O-$ | " | " | 1 | — | — | 0 | " | |
| 434 | $C_9H_{19}O-$ | " | " | 1 | — | — | 0 | " | |
| 435 | $C_{10}H_{21}O-$ | " | " | 1 | — | — | 0 | " | |
| 436 | $C_{11}H_{23}O-$ | " | " | 1 | — | — | 0 | " | |
| 437 | $C_{12}H_{25}O-$ | " | " | 1 | — | — | 0 | " | |
| 438 | $C_{14}H_{29}O-$ | " | " | 1 | — | — | 0 | " | 62 |
| 439 | $C_{16}H_{33}O-$ | " | " | 1 | — | — | 0 | " | |
| 440 | $C_7H_{15}-$ | phenyl-cyclohexyl (H) | $-CH_2O-$ | 1 | — | — | 0 | $-C^*H(CF_3)-C_6H_{13}$ | |
| 441 | $C_8H_{17}-$ | " | " | 1 | — | — | 0 | " | |
| 442 | $C_9H_{19}-$ | " | " | 1 | — | — | 0 | " | |
| 443 | $C_{10}H_{21}-$ | " | " | 1 | — | — | 0 | " | |
| 444 | $C_{11}H_{23}-$ | " | " | 1 | — | — | 0 | " | |
| 445 | $C_{12}H_{25}-$ | " | " | 1 | — | — | 0 | " | |
| 446 | $C_{14}H_{29}-$ | " | " | 1 | — | — | 0 | " | |
| 447 | $C_{16}H_{33}-$ | " | " | 1 | — | — | 0 | " | |
| 448 | $C_7H_{15}O-$ | biphenyl | $-CH_2CH_2-$ | 1 | — | — | 0 | $-C^*H(CF_3)-C_6H_{13}$ | |
| 449 | $C_8H_{17}O-$ | " | " | 1 | — | — | 0 | " | |
| 450 | $C_9H_{19}O-$ | " | " | 1 | — | — | 0 | " | |
| 451 | $C_{10}H_{21}O-$ | " | " | 1 | — | — | 0 | " | |
| 452 | $C_{11}H_{23}O-$ | " | " | 1 | — | — | 0 | " | 63 |
| 453 | $C_{12}H_{25}O-$ | " | " | 1 | — | — | 0 | " | |
| 454 | $C_{14}H_{29}O-$ | " | " | 1 | — | — | 0 | " | |
| 455 | $C_{16}H_{33}O-$ | " | " | 1 | — | — | 0 | " | |

TABLE 2-12

| Compound Number | R | A | X | m | Y | B | n | R* | Exam. No |
|---|---|---|---|---|---|---|---|---|---|
| 456 | $C_7H_{15}-$ |  | $-CH_2CH_2-$ | 1 | — | — | 0 | $-C^*H(CF_3)-C_6H_{13}$ | |
| 457 | $C_8H_{17}-$ | " | " | 1 | — | — | 0 | " | |
| 458 | $C_9H_{19}-$ | " | " | 1 | — | — | 0 | " | |
| 459 | $C_{10}H_{21}-$ | " | " | 1 | — | — | 0 | " | |

TABLE 2-12-continued

| Compound Number | R | A | X | m | Y | B | n | R* | Exam. No |
|---|---|---|---|---|---|---|---|---|---|
| 460 | $C_{11}H_{23}-$ | " | " | 1 | — | — | 0 | " | |
| 461 | $C_{12}H_{25}-$ | " | " | 1 | — | — | 0 | " | |
| 462 | $C_{14}H_{29}-$ | " | " | 1 | — | — | 0 | " | |
| 463 | $C_{16}H_{33}-$ | " | " | 1 | — | — | 0 | " | |
| 464 | $C_7H_{15}O-$ | 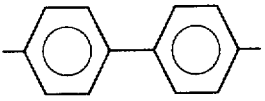 | $-COO-$ | 1 | — | — | 0 | $-C^*H(CH_3)-C_6H_{13}$ | |
| 465 | $C_8H_{17}O-$ | " | " | 1 | — | — | 0 | " | |
| 466 | $C_9H_{19}O-$ | " | " | 1 | — | — | 0 | " | |
| 467 | $C_{10}H_{21}O-$ | " | " | 1 | — | — | 0 | " | 55 |
| 468 | $C_{11}H_{23}O-$ | " | " | 1 | — | — | 0 | " | |
| 469 | $C_{12}H_{25}O-$ | " | " | 1 | — | — | 0 | " | |
| 470 | $C_{14}H_{29}O-$ | " | " | 1 | — | — | 0 | " | |
| 471 | $C_{16}H_{33}O-$ | " | " | 1 | — | — | 0 | " | |
| 472 | $C_7H_{15}-$ | 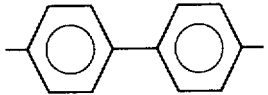 | $-COO-$ | 1 | — | — | 0 | $-C^*H(CH_3)-C_6H_{13}$ | |
| 473 | $C_8H_{17}-$ | " | " | 1 | — | — | 0 | " | 36 |
| 474 | $C_9H_{19}-$ | " | " | 1 | — | — | 0 | " | |
| 475 | $C_{10}H_{21}-$ | " | " | 1 | — | — | 0 | " | 37 |
| 476 | $C_{11}H_{23}-$ | " | " | 1 | — | — | 0 | " | |
| 477 | $C_{12}H_{25}-$ | " | " | 1 | — | — | 0 | " | |
| 478 | $C_{14}H_{29}-$ | " | " | 1 | — | — | 0 | " | |
| 479 | $C_{16}H_{33}-$ | " | " | 1 | — | — | 0 | " | |

TABLE 2-13

| Compound Number | R | A | X | m | Y | B | n | R* | Exam. No |
|---|---|---|---|---|---|---|---|---|---|
| 480 | $C_7H_{15}O-$ | 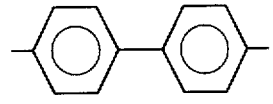 | $-COO-$ | 1 | — | — | 0 | $-C^*H(CF_3)-CH_2COOC_2H_5$ | |
| 481 | $C_8H_{17}O-$ | " | " | 1 | — | — | 0 | " | |
| 482 | $C_9H_{19}O-$ | " | " | 1 | — | — | 0 | " | |
| 483 | $C_{10}H_{21}O-$ | " | " | 1 | — | — | 0 | " | 56 |
| 484 | $C_{11}H_{23}O-$ | " | " | 1 | — | — | 0 | " | |
| 485 | $C_{12}H_{25}O-$ | " | " | 1 | — | — | 0 | " | |
| 486 | $C_{14}H_{29}O-$ | " | " | 1 | — | — | 0 | " | |
| 487 | $C_{16}H_{33}O-$ | " | " | 1 | — | — | 0 | " | |
| 488 | $C_7H_{15}-$ | 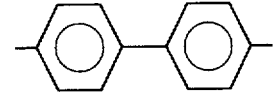 | $-COO-$ | 1 | — | — | 0 | $-C^*H(CF_3)-CH_2COOC_2H_5$ | |
| 489 | $C_8H_{17}-$ | " | " | 1 | — | — | 0 | " | |
| 490 | $C_9H_{19}-$ | " | " | 1 | — | — | 0 | " | |
| 491 | $C_{10}H_{21}-$ | " | " | 1 | — | — | 0 | " | 57 |
| 492 | $C_{11}H_{23}-$ | " | " | 1 | — | — | 0 | " | |
| 493 | $C_{12}H_{25}-$ | " | " | 1 | — | — | 0 | " | |
| 494 | $C_{14}H_{29}-$ | " | " | 1 | — | — | 0 | " | |
| 495 | $C_{16}H_{33}-$ | " | " | 1 | — | — | 0 | " | |
| 496 | $C_7H_{15}O-$ | 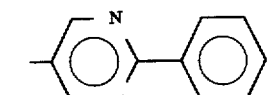 | $-CH_2O-$ | 1 | — | — | 0 | $-C^*H(CF_3)-C_6H_{13}$ | |
| 497 | $C_8H_{17}O-$ | " | " | 1 | — | — | 0 | " | |
| 498 | $C_9H_{19}O-$ | " | " | 1 | — | — | 0 | " | |
| 499 | $C_{10}H_{21}O-$ | " | " | 1 | — | — | 0 | " | |
| 500 | $C_{11}H_{23}O-$ | " | " | 1 | — | — | 0 | " | |

TABLE 2-13-continued

| Compound Number | R | A | X | m | Y | B | n | R* | Exam. No |
|---|---|---|---|---|---|---|---|---|---|
| 501 | $C_{12}H_{25}O-$ | " | " | 1 | — | — | 0 | " | |
| 502 | $C_{14}H_{29}O-$ | " | " | 1 | — | — | 0 | " | |
| 503 | $C_{16}H_{33}O-$ | " | " | 1 | — | — | 0 | " | |

TABLE 2-14

| Compound Number | R | A | X | m | Y | B | n | R* | Exam. No |
|---|---|---|---|---|---|---|---|---|---|
| 504 | $C_7H_{15}-$ | 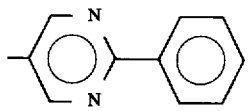 | $-CH_2O-$ | 1 | — | — | 0 | $-C*H(CF_3)-C_6H_{13}$ | |
| 505 | $C_8H_{17}-$ | " | " | 1 | — | — | 0 | " | |
| 506 | $C_9H_{19}-$ | " | " | 1 | — | — | 0 | " | |
| 507 | $C_{10}H_{21}-$ | " | " | 1 | — | — | 0 | " | 64 |
| 508 | $C_{11}H_{23}-$ | " | " | 1 | — | — | 0 | " | |
| 509 | $C_{12}H_{25}-$ | " | " | 1 | — | — | 0 | " | |
| 510 | $C_{14}H_{29}-$ | " | " | 1 | — | — | 0 | " | |
| 511 | $C_{16}H_{33}-$ | " | " | 1 | — | — | 0 | " | |

The carboxylate compounds exemplified above may be prepared by means of a combination of known synthesis techniques.

For instance, the carboxylate compound of the above formula [I] may be synthesized in accordance with the following synthesis route.

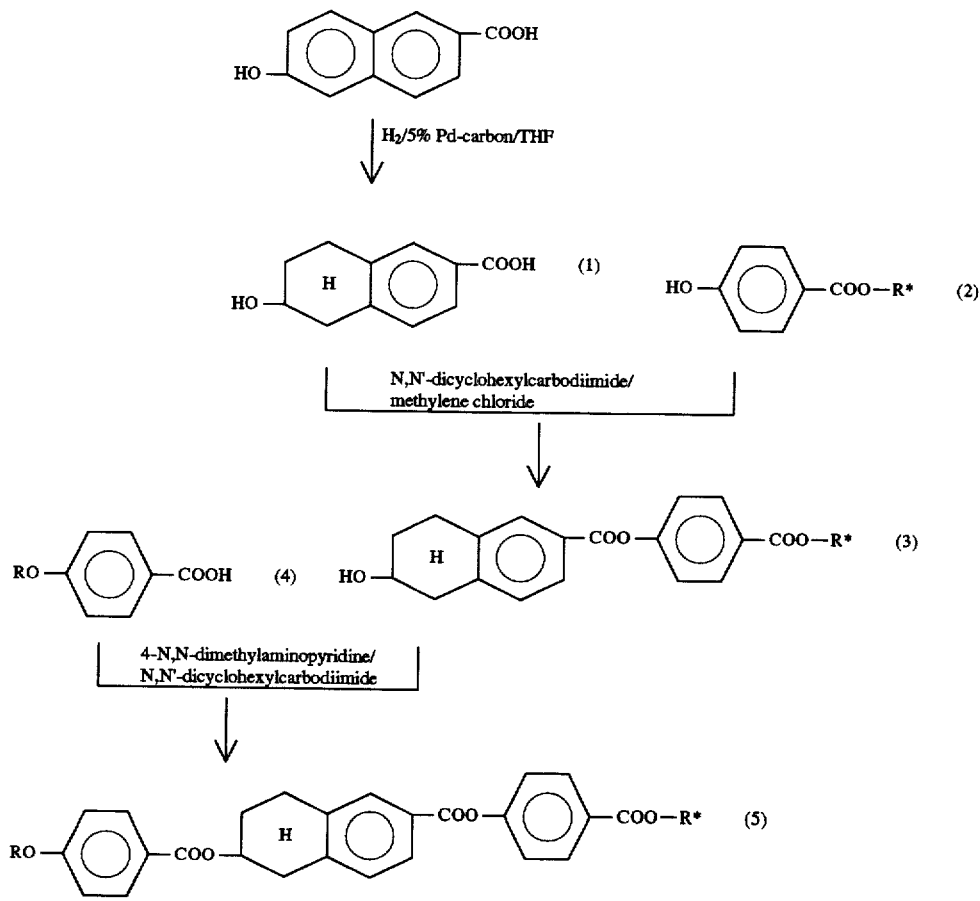

For example, 6-hydroxynaphthalene-2-carboxylic acid in a solvent such as tetrahydrofuran is reduced with hydrogen gas in the presence of a reducing catalyst such as a palladium/carbon under elevated pressure to obtain 5,6,7,8-tetrahydro-6-hydroxynaphthalene-2-carboxylic acid (1).

Subsequently, an ester compound (2) obtained from hydroxybenzoic acid and an alcohol having an asymmetric carbon is reacted with the 5,6,7,8-tetrahydro-6-hydroxynaphthalene-carboxylic acid (1) obtained by the above step in the presence of 4-N,N-dimethylaminopyridine and a solvent such as methylene chloride while adding dropwise a solution of N,N'-dicyclohexylcarbodiimide, whereby 4-(5', 6',7',8'-tetrahydro-6'-hydroxy-2'-naphthoyloxy)benzoate (3) is obtained.

Furthermore, 4-alkoxybenzoic acid (4) prepared separately in conventional means is reacted with the 4-(5',6',7', 8'-tetrahydro-6'-hydroxy-2'-naphthoyloxy)benzoate (3) obtained by the above step in the presence of 4-N,N-dimethylaminopyridine and a solvent such as methylene chloride while adding dropwise a solution of N,N'-dicyclohexylcarbodiimide, whereby the carboxylate compound (5) represented by the formula [I] is obtained.

In the above synthesis route, the 4-alkoxybenzoic acid (4) can be replaced with the carboxylic acid compound represented by the formula: R—A$^1$—COOH, wherein A$^1$ is the same group as described as A in the formula (I) but other than p-phenylene group, to replace the p-phenylene group in the carboxylic acid ester compound (5) with the group othr than the p-phenylene group. Such carboxylic acid compound may includes 4-alkoxybiphenyl carboxylic acid and 4-(5'-alkyl-2'-pyrimidinyl)benzoic acid.

The 4-alkoxybenzoic acid (4) can be also replaced with the carboxylic acid compound represented by the formula: R$^1$—A—COOH, wherein R$^1$ is the same alkyl or the alkoxy as described as R in the formula (I), provided that R$^1$ contains at least one asymmetric carbon atom and/or, in R$^1$, a part of hydrogen atoms therein is substituted with a halogen atom.

The carboxylic acid compound: R$^1$—A—COOH is sold at a market, for example, those, in which R$^1$ has at least one asymmetric atom, such as 4-((R)-1'-methylheptyloxy)benzoic acid (manufactured by Arakawa Kagaku Kogyo K.K.).

Further, the carboxylic acid compound: R$^1$—A—COOH, in which R$^1$ has at least one asymmetric carbon atom, may be synthesized in accordance with the following synthesis route.

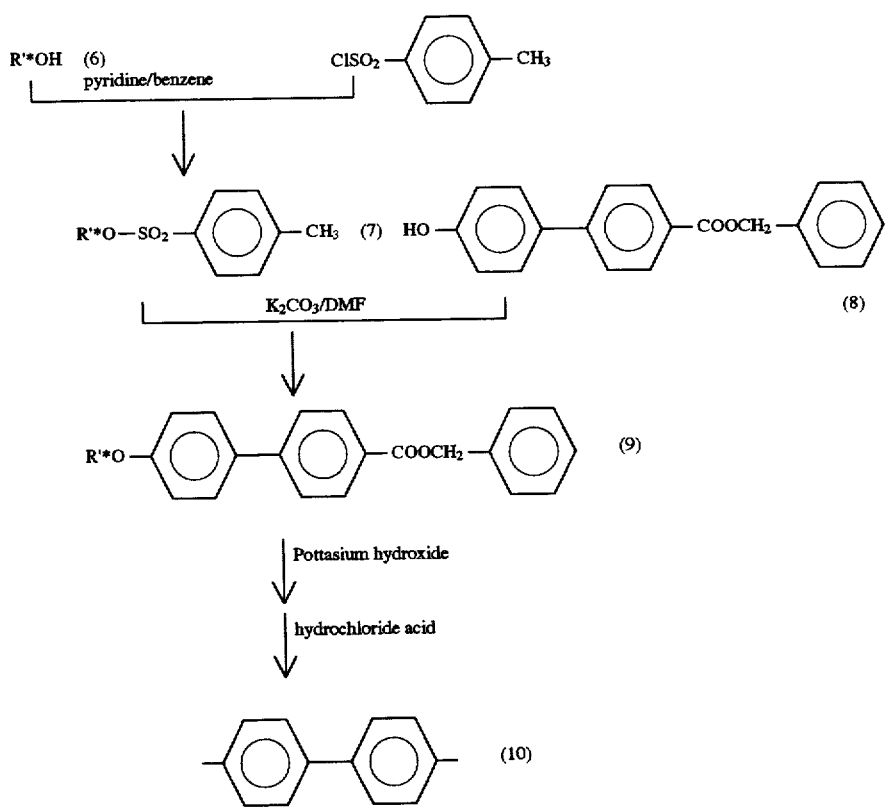

For example, an alchohol having a group R'* containing an asymmetric atom (6) is reacted with p-toluenesulfonyl chloride in the presence of pyridine in a solvent such as benzene and the reaction mixture to obtain p-toluenesulfonic acid R'*-oxy ester (7). A mixture of the obtained p-toluenesulfonic acid R'*-oxy ester (7) and 4'-hydroxy-4-biphenylcarboxylic acid benzyl ester (8) are refluxed with N,N-dimethylformamide (DMF) and potassium carbonate to obtain R'*-oxy-4-biphenylcarboxylic acid benzyl ester (9). A mixture of the thus obtained ester (9), pottasium hydroxide, ethanol and water is heated under reflux and the resulting mixture was acidified by an acidifying catalyst such as hydrochloric acid to obtain R'*-oxy-4-biphenylcarboxylic acid (10).

The carboxylate compounds represented by the above formula [II] may be synthesized in accordance with the following synthesis route.

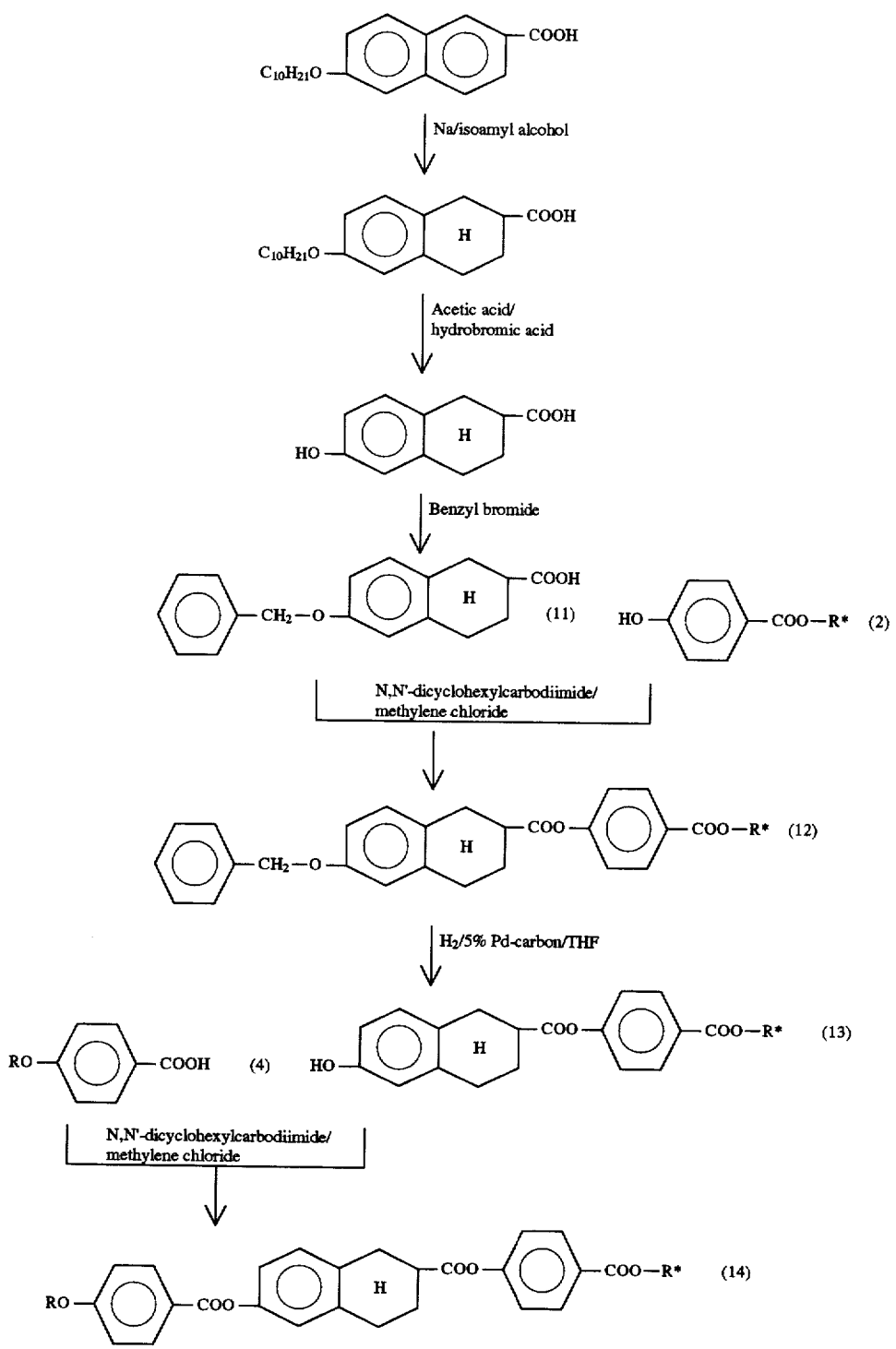

For example, a mixture of 6-n-alkoxynaphthalene-2-carboxylic acid and 1,2-ethoxyethane is refluxed in the presence of metallic sodium while adding dropwise thereto isoamyl alcohol to obtain 1,2,3,4-tetrahydro-6-n-alkoxynaphthalene-2-carboxylic acid.

The thus obtained 1,2,3,4-tetrahydro-6-n-alkoxynaphthalene-2-carboxylic acid is reacted with acetic acid and hydrobromic acid to obtain 1,2,3,4-tetrahydro-6-hydroxynaphthalene-2-carboxylic acid.

The 1,2,3,4-tetrahydro-6-hydroxynaphthalene-2-carboxylic acid obtained in the above manner is reacted with benzyl bromide in the presence of potassium hydroxide to obtain 1,2,3,4-tetrahydro-6-benzyloxynaphthalene-2-carboxylic acid (11).

Subsequently, an ester compound (2) obtained from hydroxybenzoic acid and an alcohol having an asymmetric carbon are reacted with the 1,2,3,4-tetrahydro-6-benzyloxynaphthalene-2-carboxylic acid (11) obtained by the above step in the presence of 4-N,N-dimethylaminopyridine and a solvent such as methylene chloride while adding dropwise thereto a solution of N,N'-dicyclohexylcarbodiimide, whereby 4-(1',2',3',4'-tetrahydro-6'-benzyloxy-2'-naphthoyloxy)benzoate (12) is obtained.

The thus obtained 4-(1',2',3',4'-tetrahydro-6'-benzyloxy-2'-naphthoyloxy)benzoate (12) in a solvent such as tetrahydrofuran is reduced with hydrogen gas in the presence of a reducing catalyst such as palladium/carbon to obtain 4-(1',2'3',4'-tetrahydro-6'-hydroxy-2'-naphthoyloxy)benzoate (13).

Subsequently, 4-alkoxybenzoic acid (4) prepared separately in conventional means is reacted with the 4-(1',2',3',4'-tetrahydro-6'-hydroxy-2'-naphthoyloxy)benzoate (13) obtained by the above step in the presence of 4-N,N-dimethylaminopyridine and a solvent such as methylene chloride while adding dropwise thereto N,N'-dicyclohexylcarbodiimide, whereby the carboxylate compound (14) represented by the formula [II] is obtained.

In the above synthesis route, the 4-alkoxybenzoic acid (4) can be replaced with the other carboxylic acid: R—A$^1$—COOH or R$^1$—A—COOH, both of which are described in the synthesis of the carboxylate compound (5) represented by the formula [I].

The other carboxylate compound represented by the formula (II), in which x is —CH$_2$O—, may be obtained by the following thynsesis route.

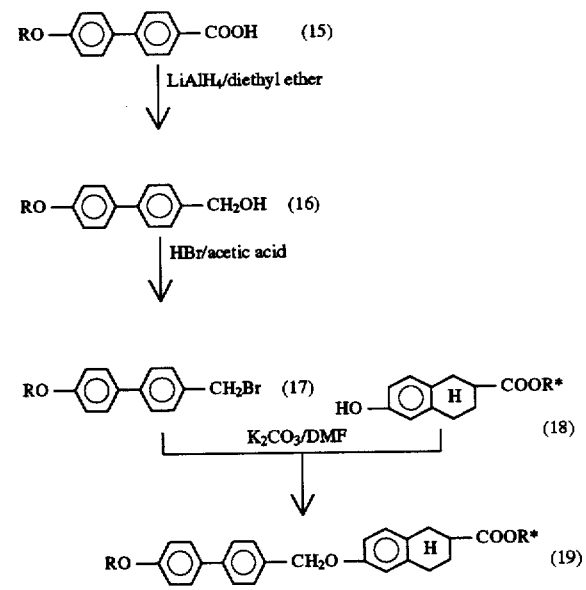

For example, to a diethyl ether solution of LiAlH$_4$, 4-alkoxybiphenylcarboxylic acid (15) is added to reduce the carboxylic acid (15), whereby 4'-alkoxy-4-hydroxymethylbiphenyl (16) is obtained. The thus obtained 4'-alkoxy-4-hydroxymethylbiphenyl (6) is heated in the acetic acid solution of HBr to obtain 4'-alkoxy-4'-bromomethylbiphenyl (17). The resulting 4'-alkoxy-4'-bromomethylbiphenyl (17) is heated with 6-hydroxy-1,2,3,4-tetrahydro-2-naphthalenecarboxylic acid ester (18) in the dimethylformamide (DMF) solution of K$_2$CO$_3$, whereby the methyloxy carboxylate compound (19) represented by the formula [I], in which x is —CH$_2$O—, may be obtained.

Further, the other carboxy acid ester compound represented by the formula (II), in which x is —CH$_2$CH$_2$—, may be obtained by the following synthsis route.

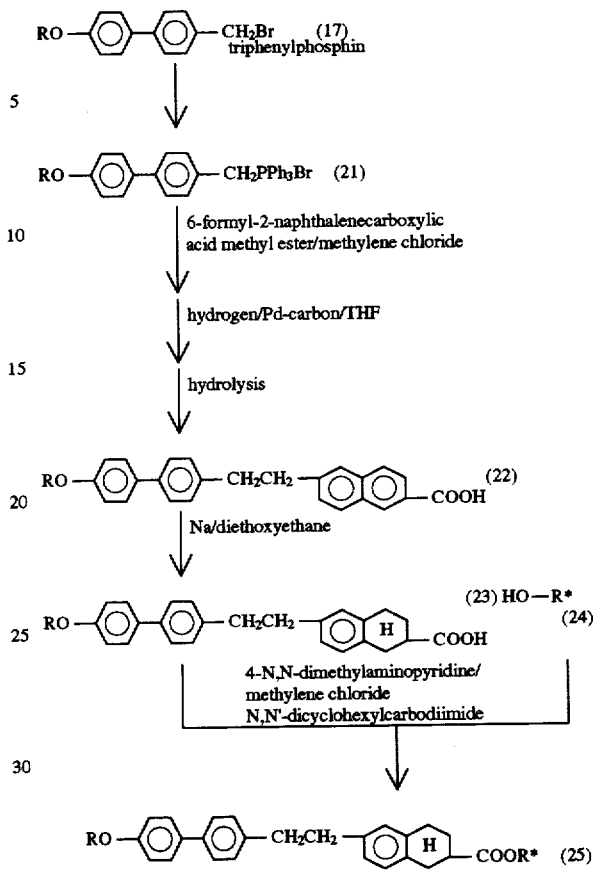

For example, 4'-alkoxy-4-bromobiphenyl (17) is reacted with triphenylphosphin to obtain triphenylphosphonium salt of 4'-alkoxybiphenyl (21). The thus obtained triphenylphosphonium salt of 4$^1$-alkoxybiphenyl (21) is reacted with 6-formyl-2-naphthalenecarboxylic acid methyl ester as a solution in such as methylene chrolide and then the resulting compound is reacted with hydrogen in the presence of the reducing catalyst such as paradium carbon in a solvent such as tetrahydrofuran (THF) to obtain 6-[4'-alkoxy-4-biphenyl-)ethyl]-2-naphthalenecarboxylic acid methyl ester. The resulting 6-[4'-alkoxy-4-biphenyl)ethyl]-2-naphthalenecarboxylic acid methyl ester is hydrolysised to obtain 6-[4'-alkoxy-4-biphenyl)ethyl]-2-naphthalenecarboxylic acid (22).

The thus obtained 6-[4'-alkoxy-4-biphenyl)ethyl]-2-naphthalenecarboxylic acid (22) is hydrogenated in the presence of metal sodium in a solvent such as 1,2-diethoxyethane to obtain 6-[4'-alkoxy-4-biphenyl)ethyl]-1,2,3,4-tetrahydro-2-naphthalenecarboxylic acid (23). Finally, the resulting 6-[4'-alkoxy-4-biphenyl)ethyl]-1,2,3,4-tetrahydro-2-naphthalenecarboxylic acid (23) is reacted with an alcohol (24) having an asymmetric carbon in the presence of 4-N,N-dimethylaminoprydine, whereby the above-mentioned carboxylate compound (25) represented by the formula (II), in which x is —CH$_2$CH$_2$—, may be obtained.

These processes for the preparation of the carboxylate compounds of the invention are provided only by way of non-limiting illustration.

For instance, among the carboxylate compounds of the invention prepared by the above-mentioned processes, $^1$H-NMR of $^4$-($^6$-($^4$-decyloxybenzoyloxy)-5,6,7,8-tetrahydro-2-naphthoyloxy]benzoic acid (R)-1-trifluoromethylheptyl ester [Exemplified compound (4)] represented by the following formula is shown in FIG. 1.

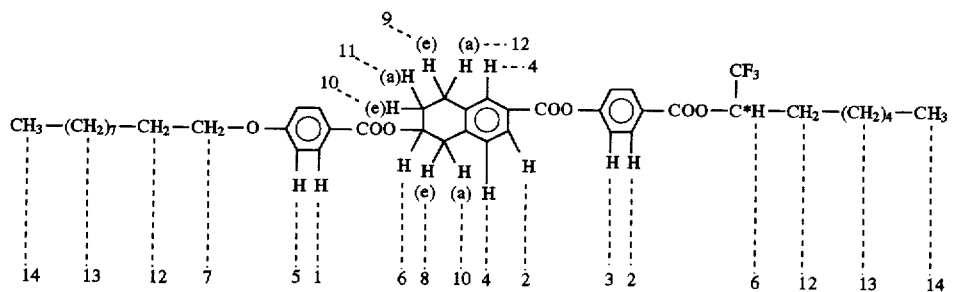

In this formula, (e) represents an equatorial steric conformation, (a) represents an axial steric conformation, and the numbers 1 to 14 showing hydrogen atoms correspond to the peaks in FIG. 1.

Figure 2:
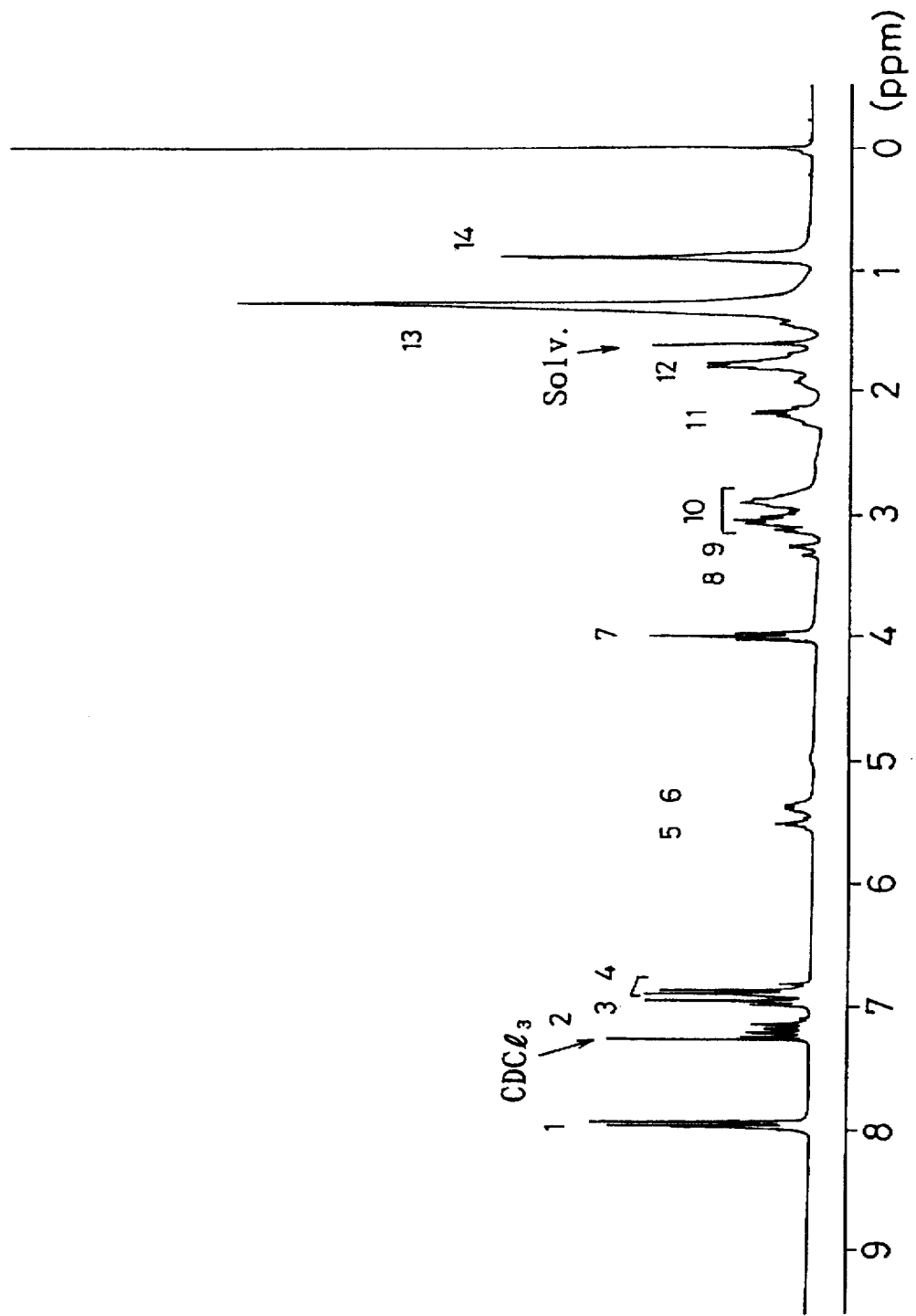
FIG. 2 shows $^1$H-NMR spectrum of 6-[6-(4-decyloxybenzoyloxy)-5,6,7,8-tetrahydro-2-naphthoyloxy]-1,2,3,4-tetrahydro-2-naphthalenecarboxylic acid (R)-1-trifluoromethylheptyl ester [Exemplified compound (21)].

Further, $^1$H-NMR of 6-[6-(4-decyloxybenzoyloxy)-5,6,7,8-tetrahydro-2-naphthoyloxy]-1,2,3,4-tetrahydro-2-naphthalenecarboxylic acid (R)-1-trifluoromethylheptyl ester [Exemplified compound (21)] represented by the following formula is shown in FIG. 2.

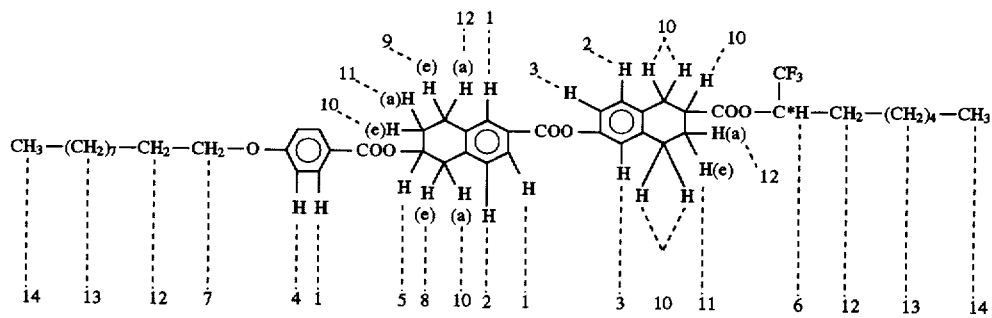

In this formula, the numbers 1 to 14 showing hydrogen atoms correspond to the peaks in FIG. 2.

Figure 3:
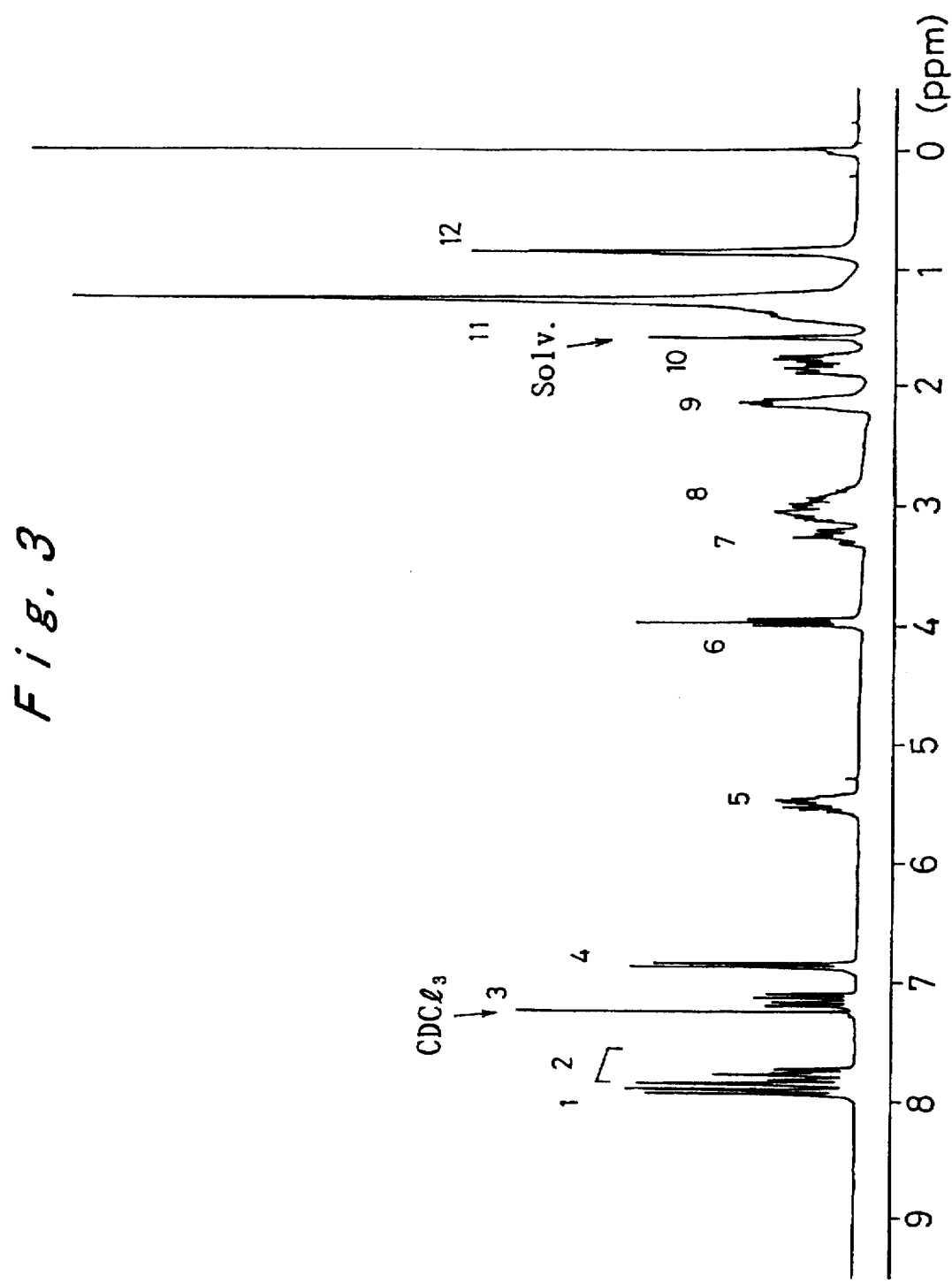
FIG. 3 shows $^1$H-NMR spectrum of 6-[6-(4-decyloxybenzoyloxy)-5,6,7,8-tetrahydro-2-naphthoyloxy]-5,6,7,8-tetrahydro-2-naphthalenecarboxylic acid (R)-1-trifluoromethylheptyl ester [Exemplified compound (22)].

Furthermore, $^1$H-NMR of 6-[6-(4-decyloxybenzoyloxy)-5,6,7,8-tetrahydro-2-naphthoyloxy]-5,6,7,8-tetrahydro-2-naphthalenecarboxylic acid (R)-1-trifluoromethylheptyl ester [Exemplified compound (22)] represented by the following formula is shown in FIG. 3.

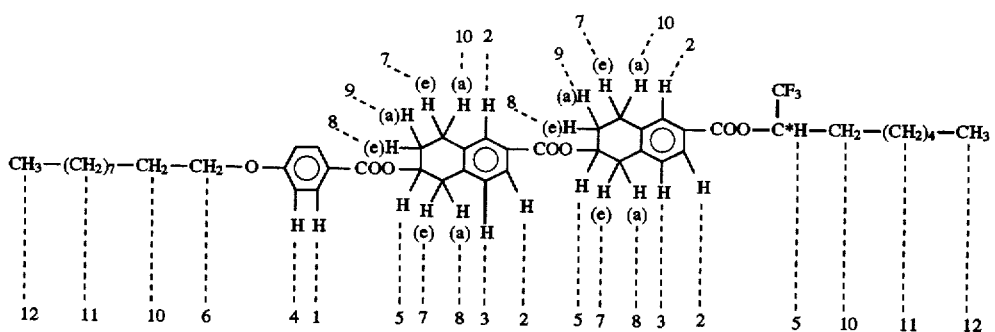

In this formula, the numbers 1 to 12 showing hydrogen atoms correspond to the peaks in FIG. 3.

Figure 4:
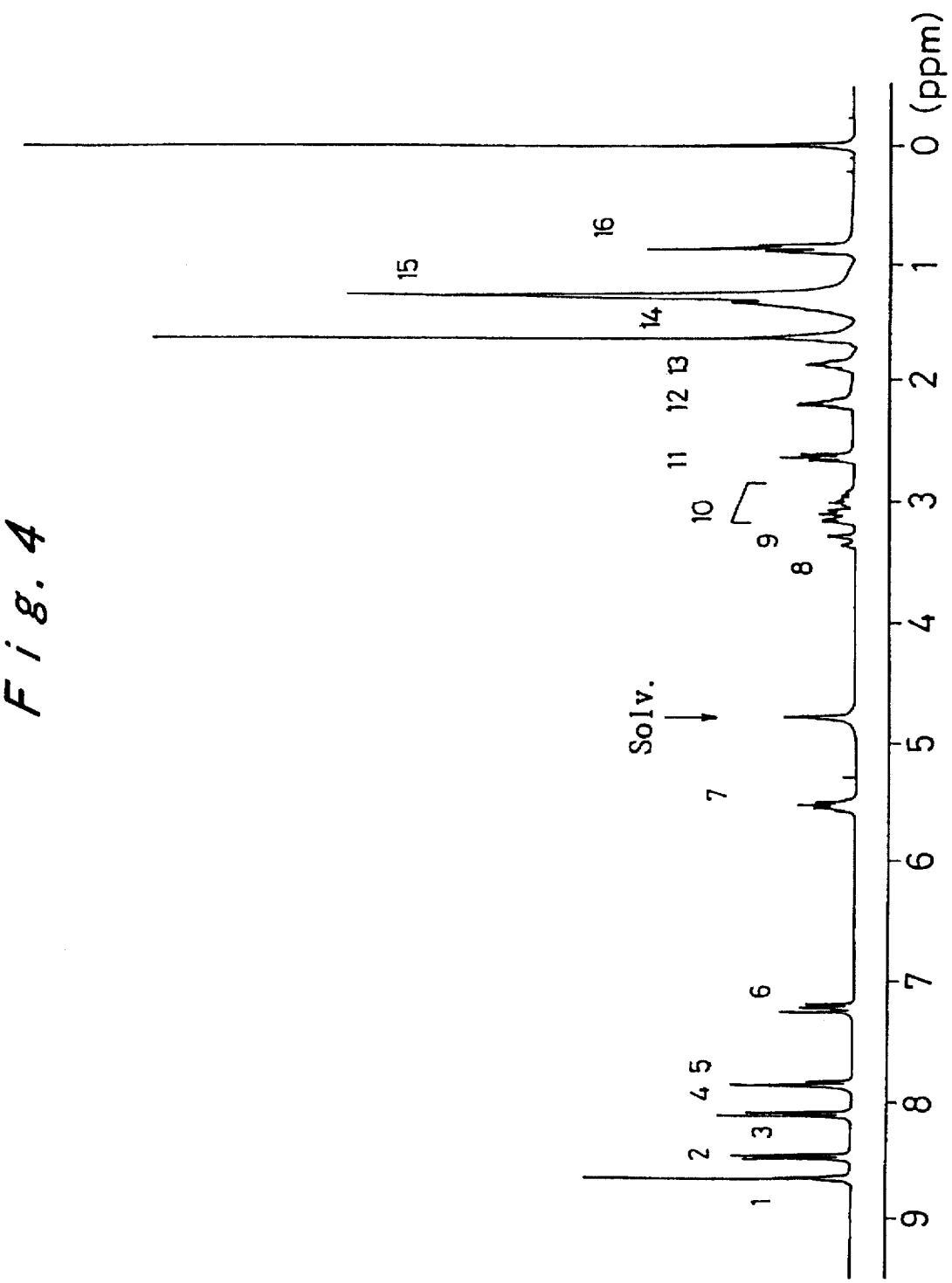
FIG. 4 shows $^1$H-NMR spectrum of 6-[4-(5-decyl-2-pyrimidinyl)benzoyloxy]-5,6,7,8-tetrahydro-2-naphthalenecarboxylic acid (R)-1-trifluoromethylheptyl ester [Exemplified compound (130)].

Still further, $^1$H-NMR of 6-[4-(5-decyl-2-pyrimidinyl)benzoyloxy]-5,6,7,8-tetrahydro-2-naphthalenecarboxylic acid (R)-1-trifluoromethylheptyl ester [Exemplified compound (130)] represented by the following formula is shown in FIG. 4.

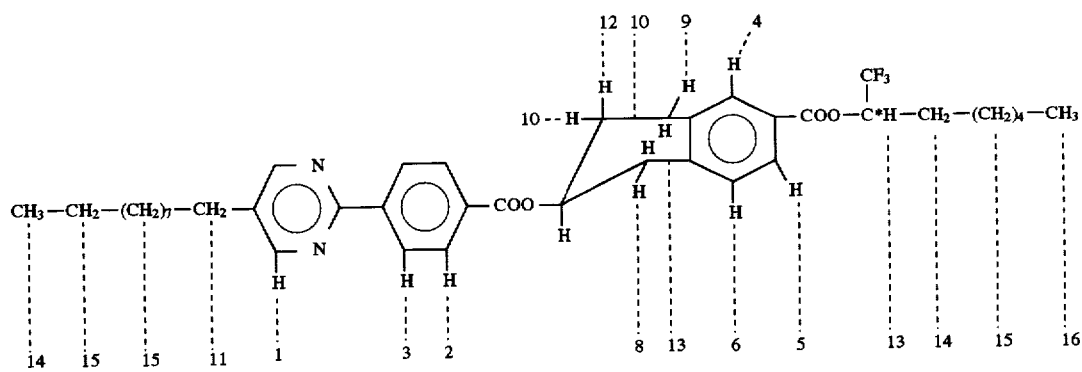

In this formula, the numbers 1 to 16 showing hydrogen atoms correspond to the peak in FIG. 4.

Figure 5:
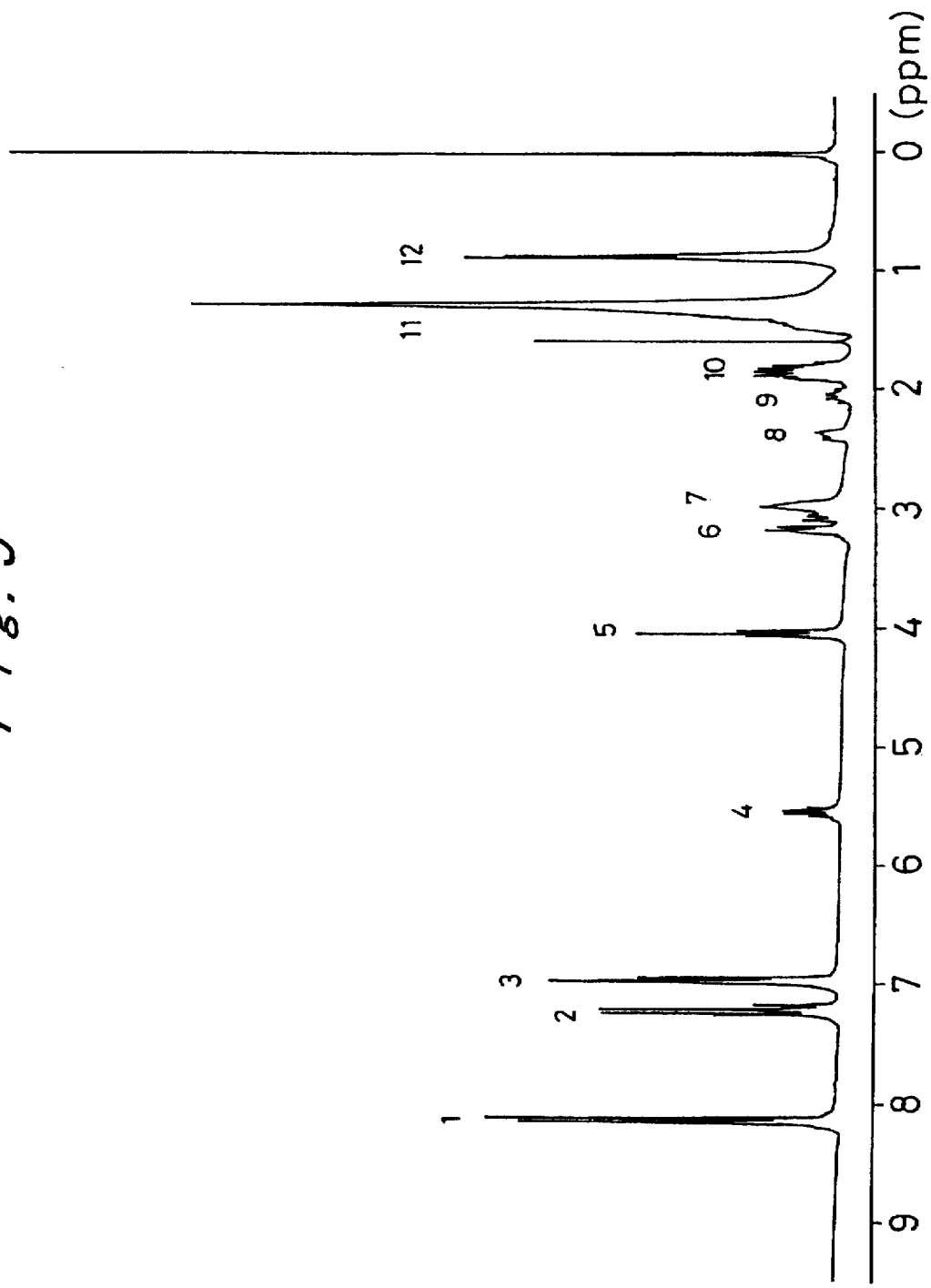
FIG. 5 shows $^1$H-NMR spectrum of 4-[6-(4-decyloxybenzoyloxy)-1,2,3,4-tetrahydro-2-naphthoyloxy]benzoic acid (R)-1-trifluoromethylheptyl ester [Exemplified compound (204)].

Similarly, among the carboxylate compounds of the invention prepared in the manner as mentioned above, $^1$H-NMR of 4-[6-(4-decyloxybenzoyloxy)-1,2,3,4-tetrahydro-2-naphthoyloxy]benzoic acid (R)-1-trifluoromethylheptyl ester [Exemplified compound (204)] represented by the following formula is shown in FIG. 5.

Figure 6:
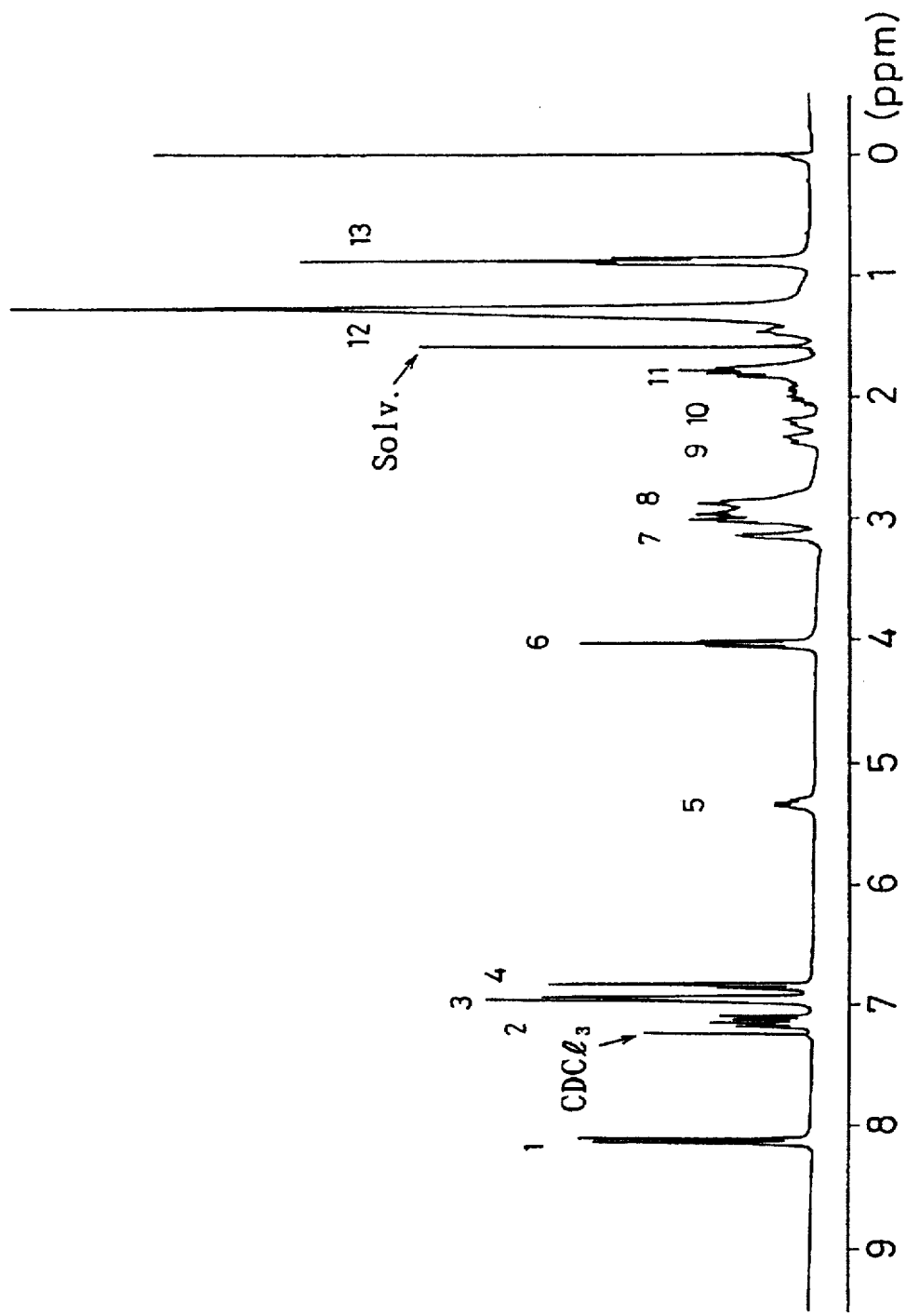
FIG. 6 shows $^1$H-NMR spectrum of 6-[6-(4-decyloxybenzoyloxy)-1,2,3,4-tetrahydro-2-naphthoyloxy]-1,2,3,4-tetrahydro-2-naphthalenecarboxylic acid (R)-1-trifluoromethylheptyl ester [Exemplified compound (221)].

In this formula, the numbers 1 to 13 showing hydrogen atoms correspond to the peaks in FIG. 6.

Figure 7:
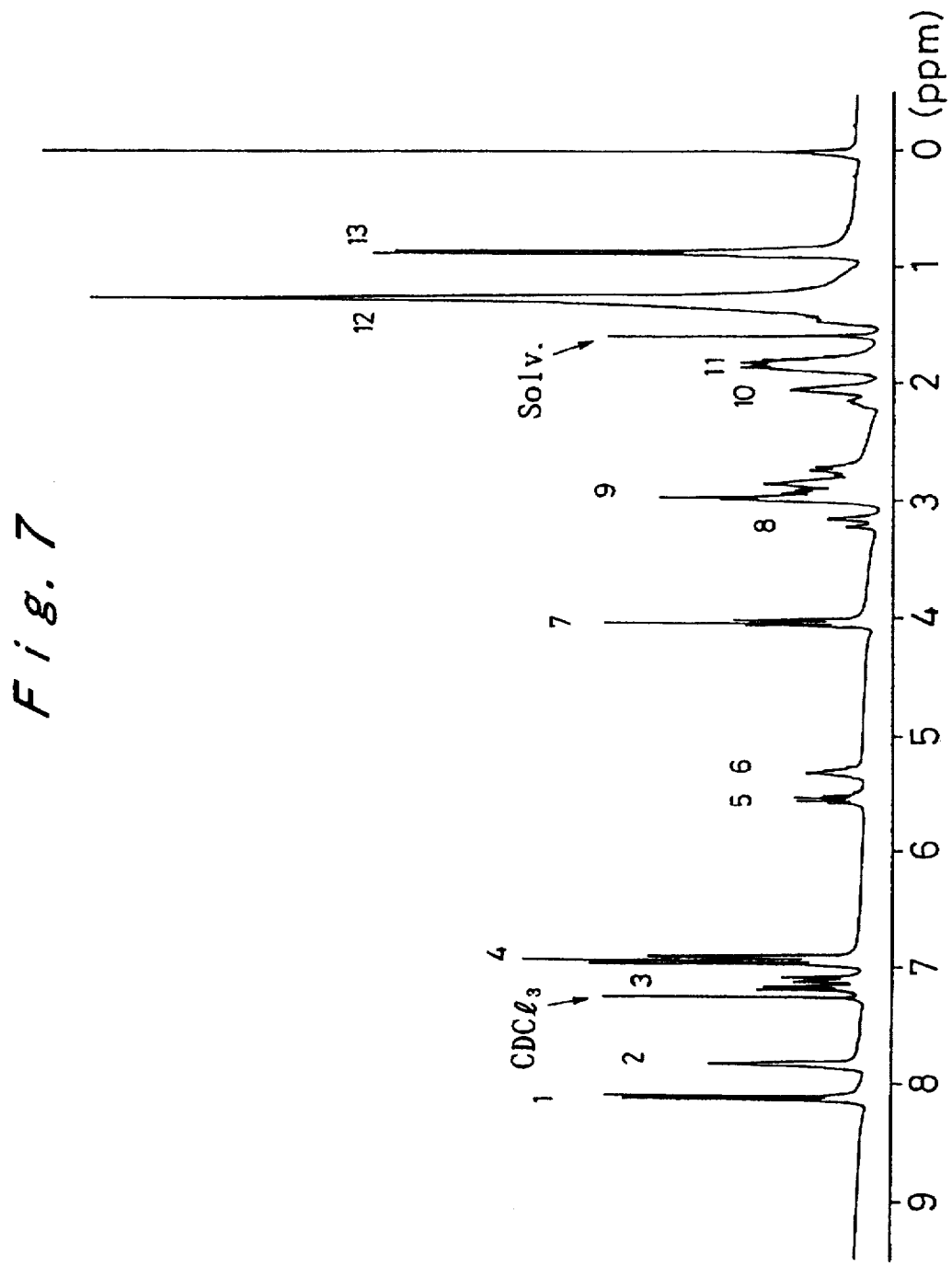
FIG. 7 shows $^1$H-NMR spectrum of 6-[6-(4-decyloxybenzoyloxy)-1,2,3,4-tetrahydro-2-naphthoyloxy]-5,6,7,8-tetrahydro-2-naphthalenecarboxylic acid (R)-1-trifluoromethylheptyl ester [Exemplified compound (222)].

Furthermore, $^1$H-NMR of 6-[6-(4-decyloxybenzoyloxy)-1,2,3,4-tetrahydro-2-naphthoyloxy]-5,6,7,8-tetrahydro-2-naphthalenecarboxylic acid (R)-1-trifluoromethylheptyl ester [Exemplified compound (222)] represented by the following formula is shown in FIG. 7.

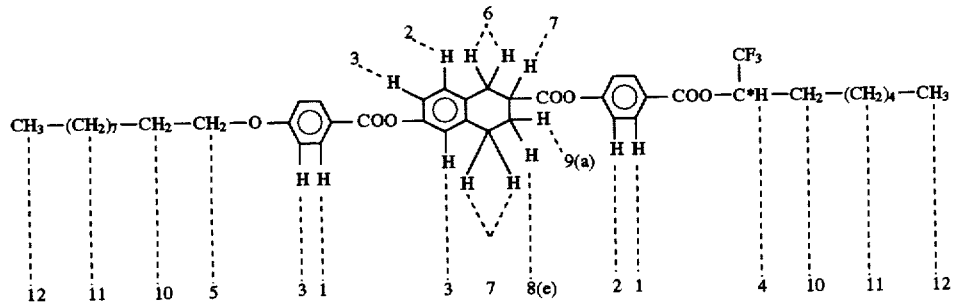

In this formula, (e) represents an equatorial steric conformation, and (a) represents an axial steric conformation, and the numbers 1 to 12 showing hydrogen atoms correspond to the peaks in FIG. 5.

Further, $^1$H-NMR of 6-[6-(4-decyloxybenzoyloxy)-1,2,3,4-tetrahydro-2-naphthoyloxy]-1,2,3,4-tetrahydro-2-naphthalenecarboxylic acid (R)-1-trifluoromethylheptyl ester [Exemplified compound (221)] represented by the following formula is shown in FIG. 6.

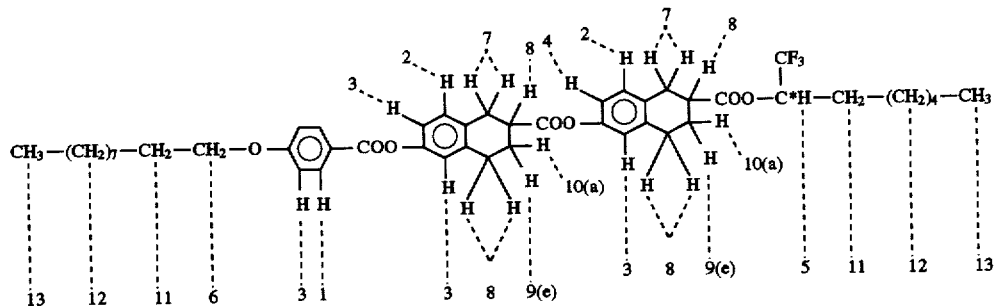

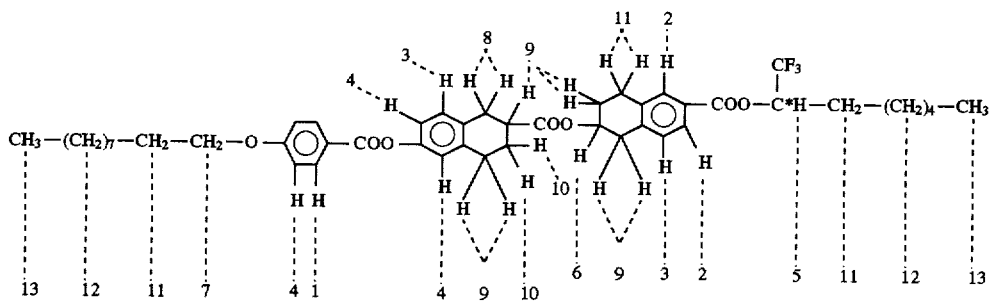

In this formula, the numbers 1 to 13 showing hydrogen atoms correspond to the peaks in FIG. 7.

Figure 8:
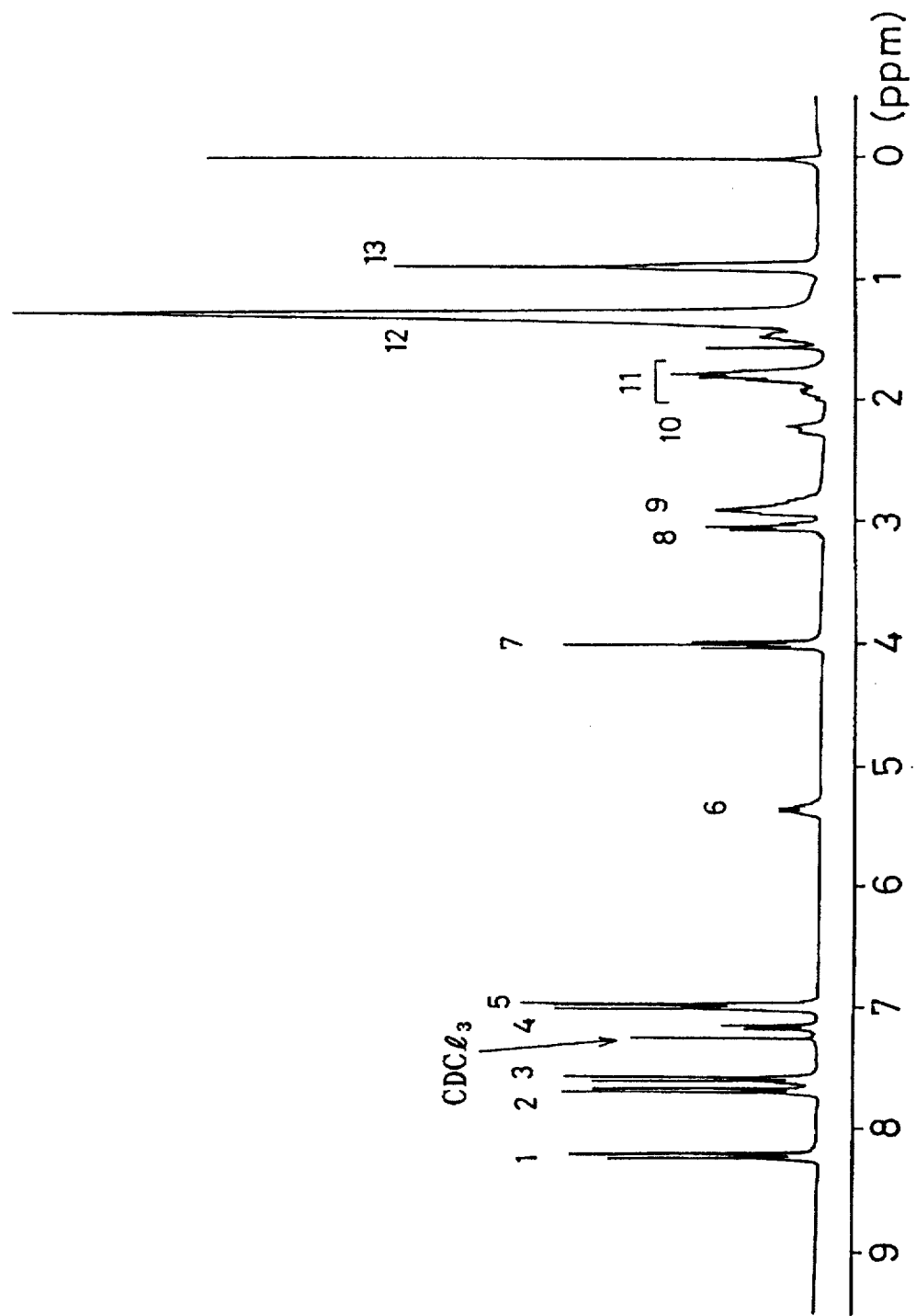
FIG. 8 shows $^1$H-NMR spectrum of 6-(4'-decyloxy-4-biphenylcarboxy)-1,2,3,4-tetrahydro-2-naphthalenecarboxylic acid (R)-1-trifluoromethylheptyl ester [Exemplified compound (251)].

Still further, ¹H-NMR of 6-(4'-decyloxy-4-biphenylcarboxy)-1,2,3,4-tetrahydro-2-naphthalenecarboxylic acid (R)-1-trifluoromethylheptyl ester [Exemplified compound (251)] represented by the following formula is shown in FIG. 8.

Figure 9:
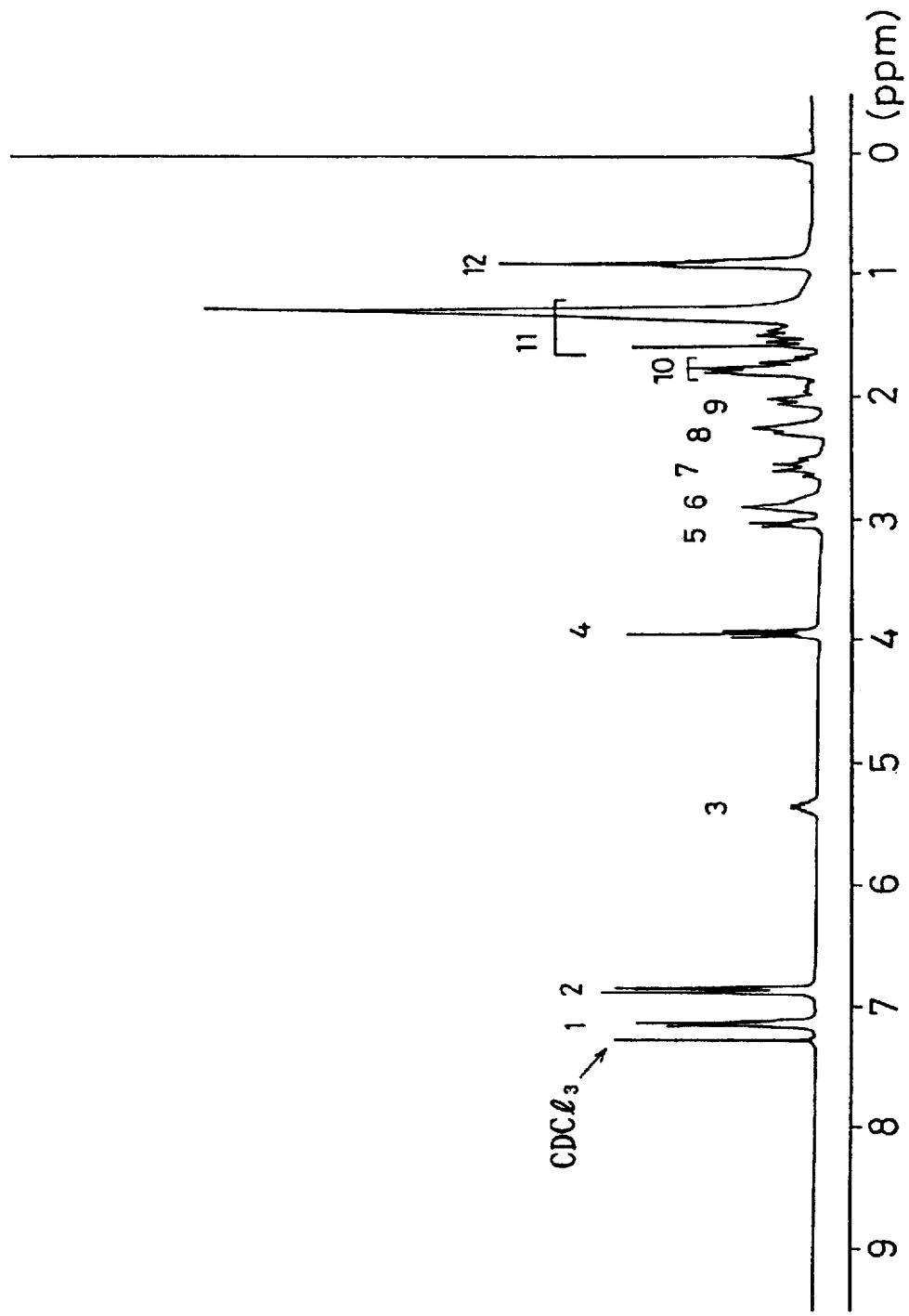
FIG. 9 shows $^1$H-NMR spectrum of 6-[4-(4-decyloxyphenyl)cyclohexylcarbonyloxy]-1,2,3,4-tetrahydro-2-naphthalenecarboxylic acid (R)-1-trifluoromethylheptyl ester [Exemplified compound (267)].

In this formula, the numbers 1 to 12 showing hydrogen atoms correspond to the peaks in FIG. 9.

Figure 10:
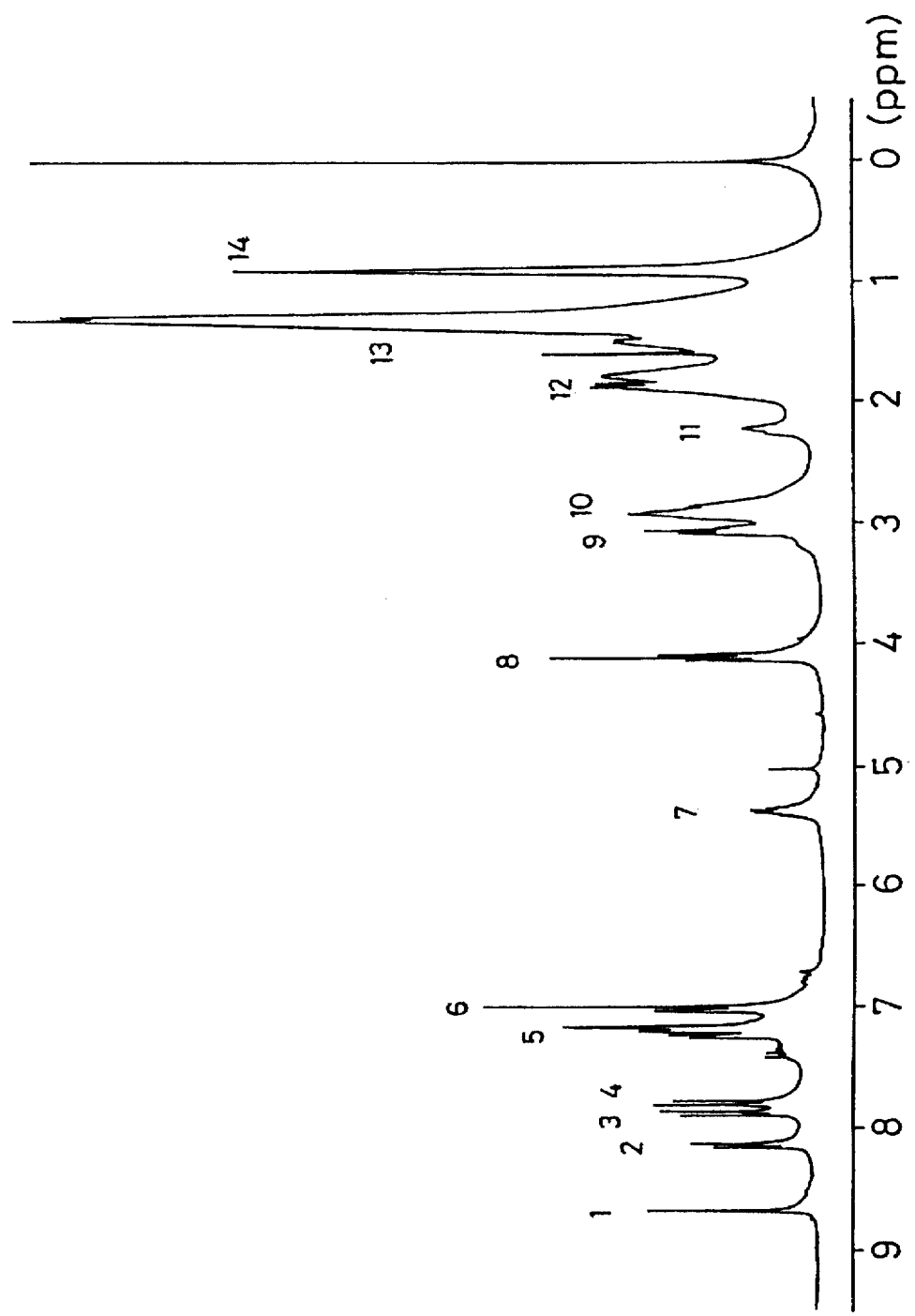
FIG. 10 shows $^1$H-NMR spectrum of 6-(6-heptyloxy-2-naphthoyloxy)-1,2,3,4-tetrahydro-2-naphthalenecarboxylic acid (R)-1-trifluoromethylheptyl ester [Exemplified compound (296)].

Still more, ¹H-NMR of 6-(6-heptyloxy-2-naphthoyloxy)-1,2,3,4-tetrahydro-2-naphthalenecarboxylic acid (R)-1-trifluoromethylheptyl ester [Exemplified compound (296)] represented by the formula is shown in FIG. 10.

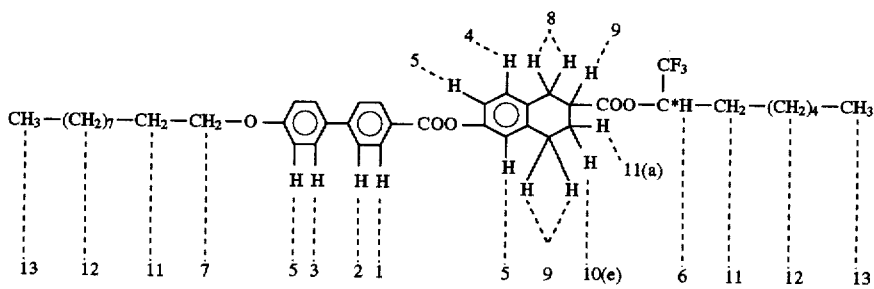

In this formula, the numbers 1 to 13 showing hydrogen atoms correspond to the peaks in FIG. 8.

Moreover, ¹H-NMR of 6-[4-(4-decyloxyphenyl)cyclohexylcarbonyloxy]-1,2,3,4-tetrahydro-2-naphthalenecarboxylic acid (R)-1-trifluoromethylheptyl ester [Exemplified compound (267)] represented by the formula is shown in FIG. 9.

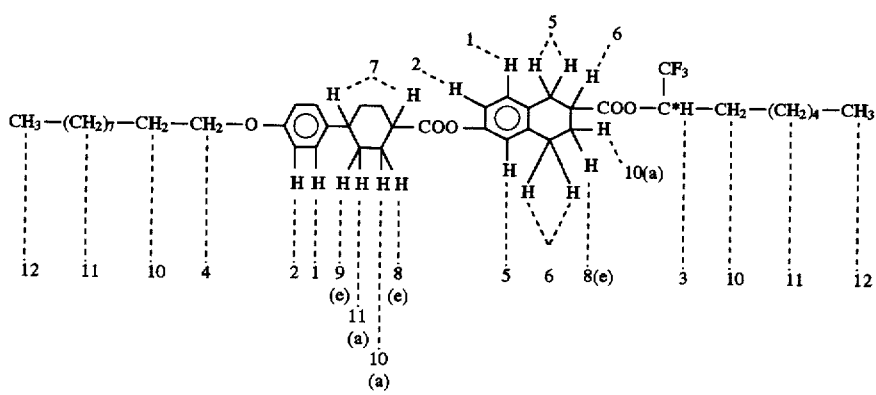

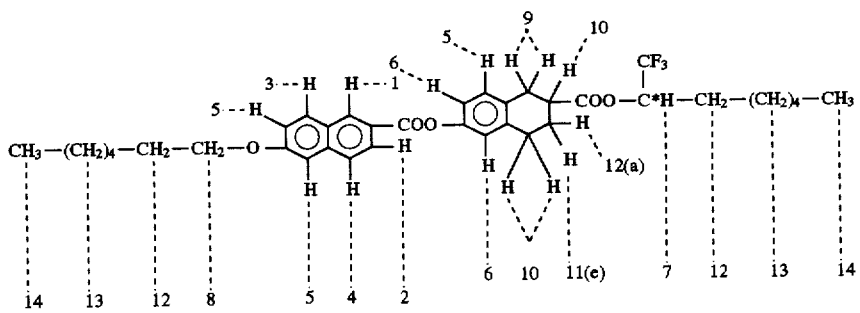

In this formula, the numbers 1 to 14 showing hydrogen atoms correspond to the peaks in FIG. 10.

Figure 11:
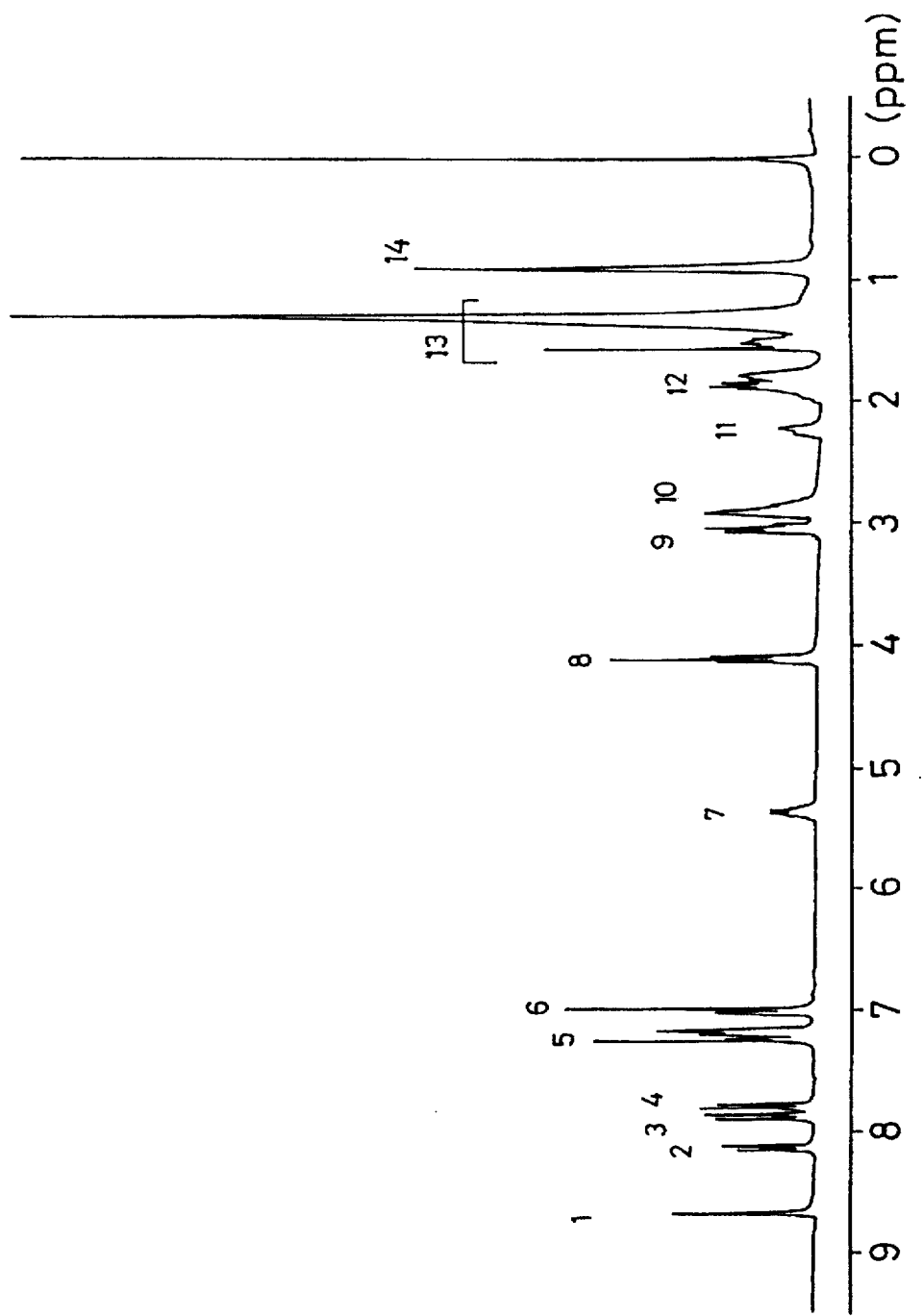
FIG. 11 shows $^1$H-NMR spectrum of 6-(6-decyloxy-2-naphthoyloxy)-1,2,3,4-tetrahydro-2-naphthalenecarboxylic acid (R)-1-trifluoromethylheptyl ester [Exemplified compound (299)].

Besides, $^1$H-NMR of 6-(6-decyloxy-2-naphthoyloxy)-1,2,3,4-tetrahydro-2-naphthalenecarboxylic acid (R)-1-trifluoromethylheptyl ester [Exemplified compound (299)] represented by the following formula is shown in FIG. 11.

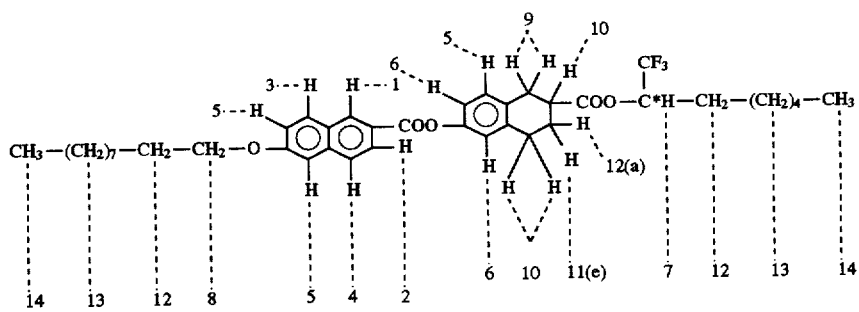

In this formula, the numbers 1 to 14 showing hydrogen atoms correspond to the peaks in FIG. 11.

Figure 12:
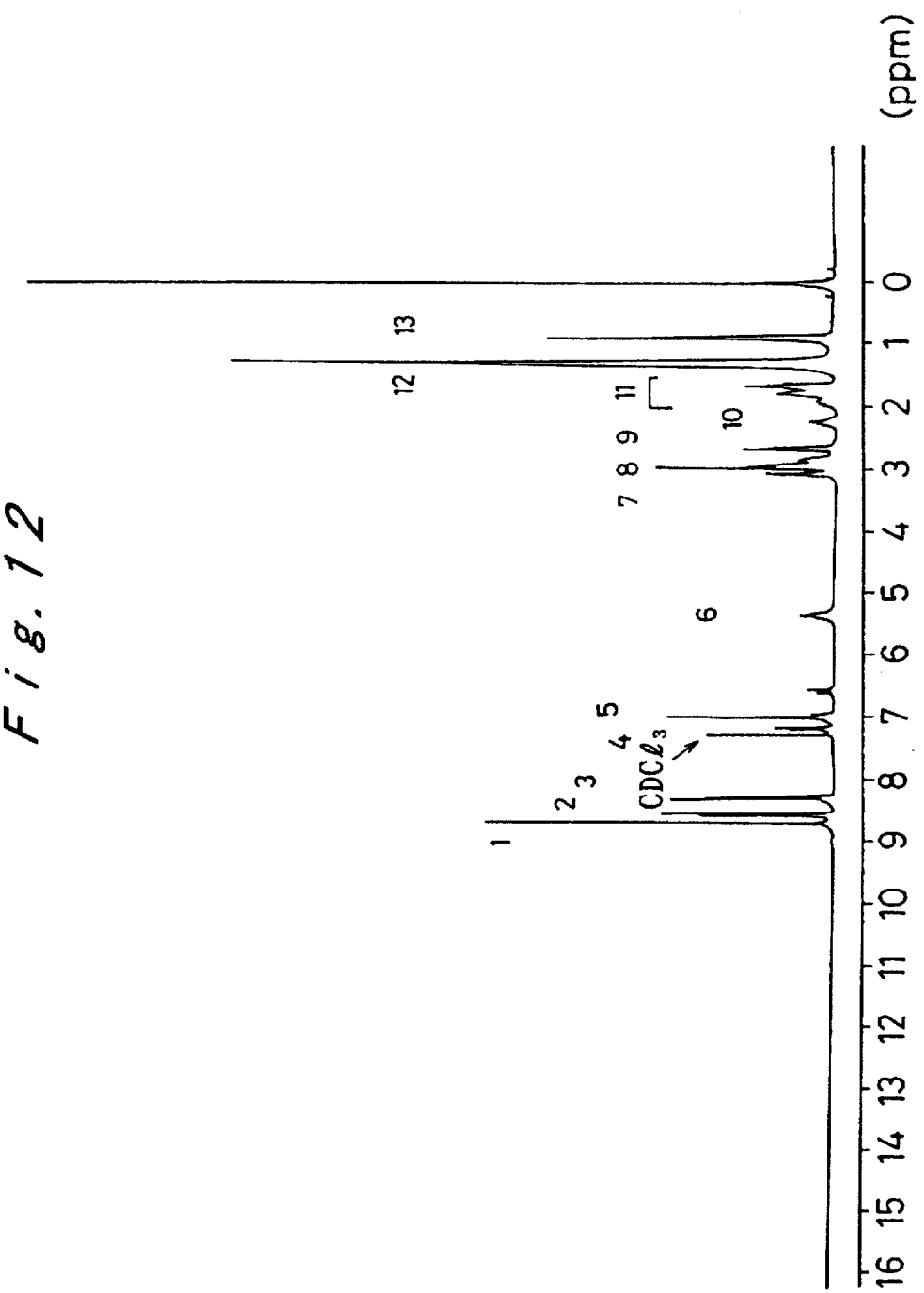
FIG. 12 shows $^1$H-NMR spectrum of 6-[4-(5-decyl-2-pyrimidinyl)benzoyloxy]-1,2,3,4-tetrahydro-2-naphthalenecarboxylic acid (R)-1-trifluoromethylheptyl ester [Exemplified compound (331)].

Furthermore, $^1$H-NMR of 6-[4-(5-decyl-2-pyrimidinyl)benzoyloxy]-1,2,3,4-tetrahydro-2-naphthalenecarboxylic acid (R)-1-trifluoromethylheptyl ester [Exemplified compound (331)] represented by the following formula is shown in FIG. 12.

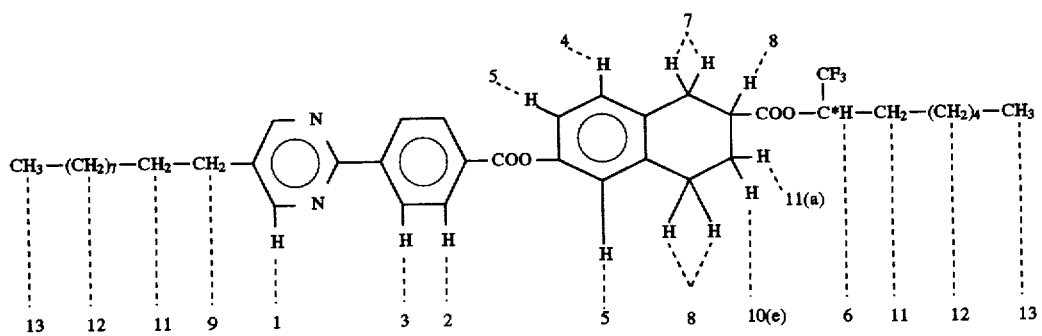

In this formula, the numbers 1 to 13 showing hydrogen atoms correspond to the peaks in FIG. 12.

Figure 37:
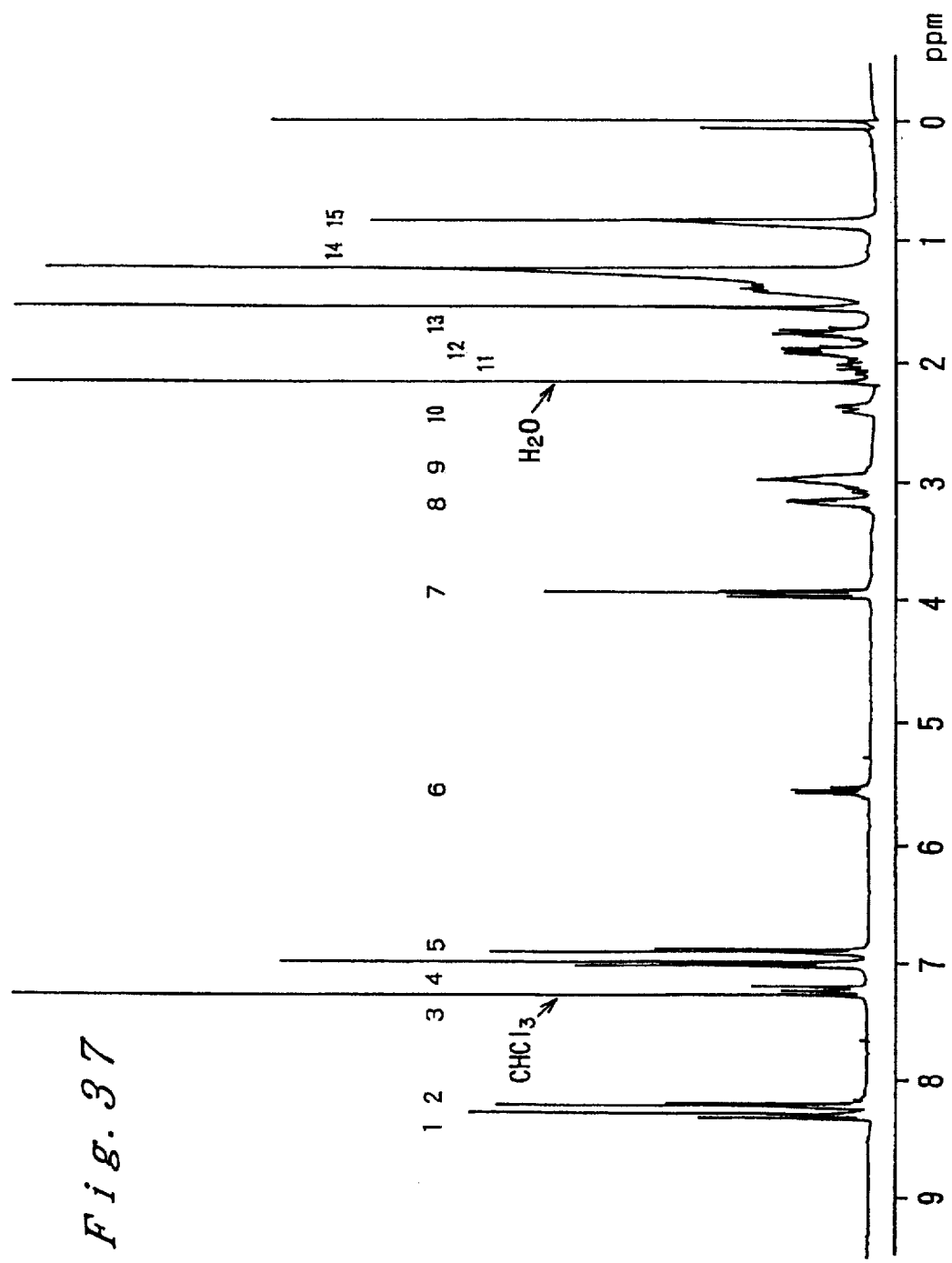
FIG. 37 shows ¹H-NMR spectrum of 6-[4-((R)-1-trifluoromethylheptyloxycarbonyl)benzoyloxy]-1,2,3,4-tetrahydro- 2-naphthalenecarboxylic acid 4-decyloxyphenyl ester. [Exemplified compound (154)].

$^1$H-NMR of 6-[4-((R)-1-trifluoromethylheptyloxycarbonyl)benzoyloxy]-1,2,3,4-tetrahydro-2-naphthalenecarboxylic acid 4-decyloxyphenyl ester [Examplified compound (154)] is shown in FIG. 37.

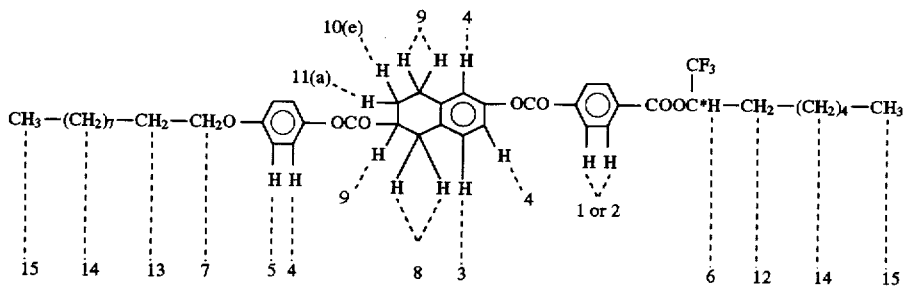

In this formula, (e) represents an equatorial sterio conformation, (a) represents an axial steric conformation, and the numbers 1 to 15 showing hydrogen atoms corresponding to the peaks in FIG. 37.

Figure 38:
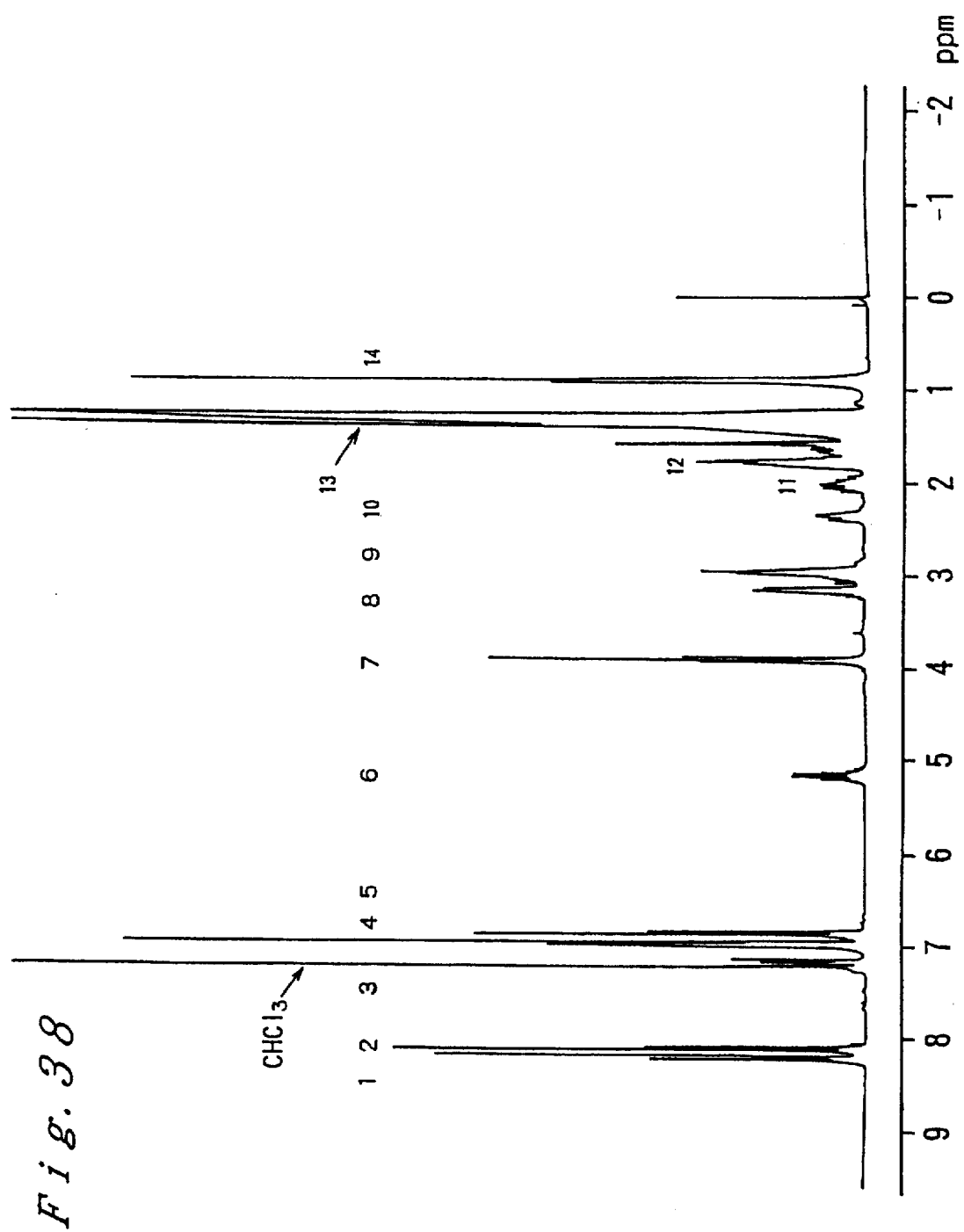
FIG. 38 shows ¹H-NMR spectrum of 6-[4-((R)-1-methylheptyloxycarbonyl)benzoyloxy]-1,2,3,4-tetrahydro-2-naphthalenecarboxylic acid 4-decyloxyphenyl ester. [Exemplified compound (162)]

¹H-NMR of 6-[4-(R)-1-methylheptyloxycarbonyl)-benzoyloxy]-1,2,3,4-tetrahydro-2-naphthalenecarboxylic acid 4-decyloxyphenyl ester [Examplified compound (162)] is shown in FIG. 38.

Figure 39:
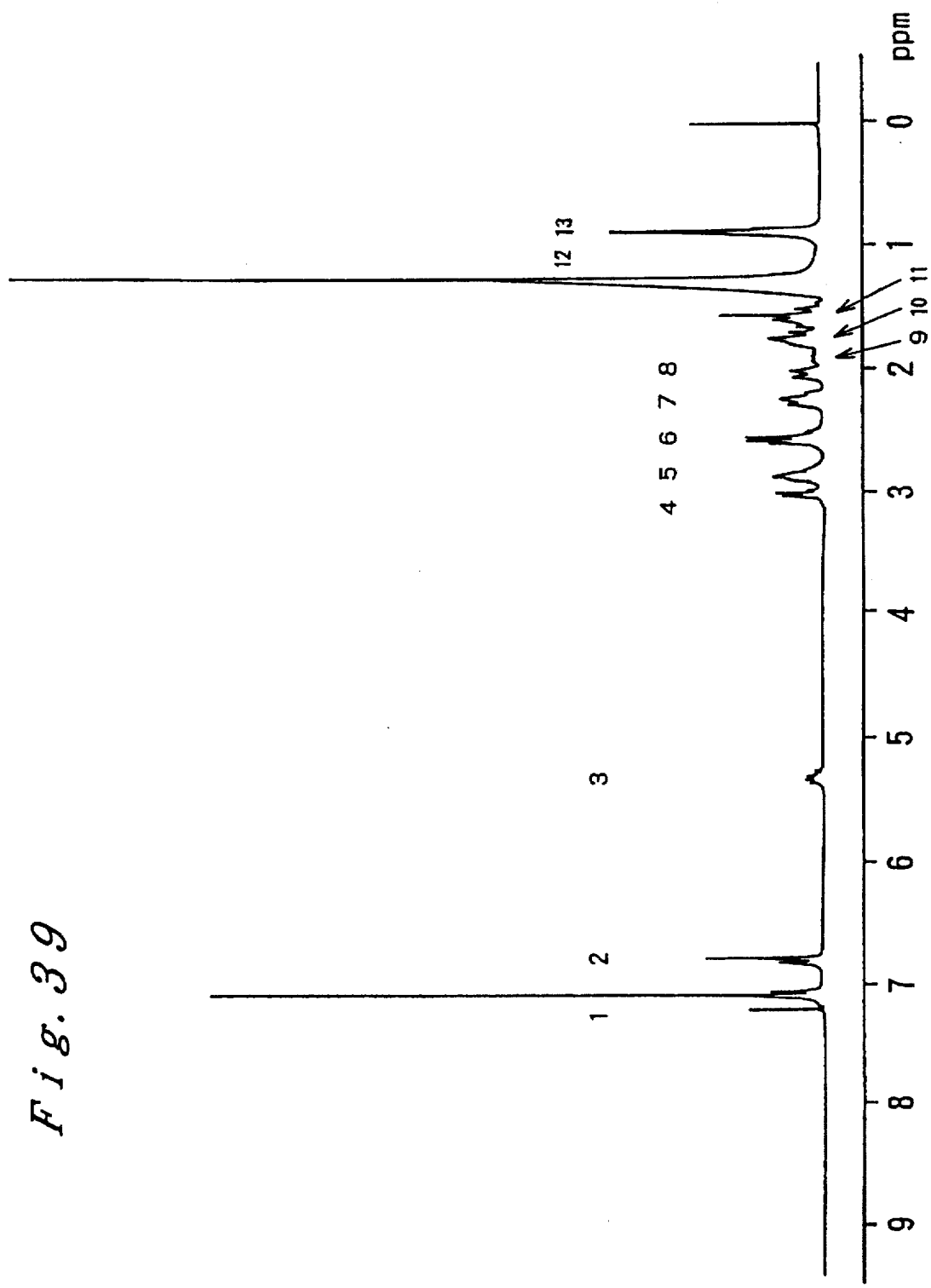
FIG. 39 shows ¹H-NMR spectrum of 6-[4-(4-dodecylphenyl)cyclohexylcarbonyloxy]-1,2,3,4-tetrahydro-2-naphthalenecarboxylic acid (R)-1-trifluoromethylheptyl ester. [Exemplified compound (365)]

In this formula, (e) represents an equatorial sterio conformation, (a) represents an axial steric conformation, and the numbers 1 to 13 showing hydrogen atoms corresponding to the peaks in FIG. 39.

Figure 40:
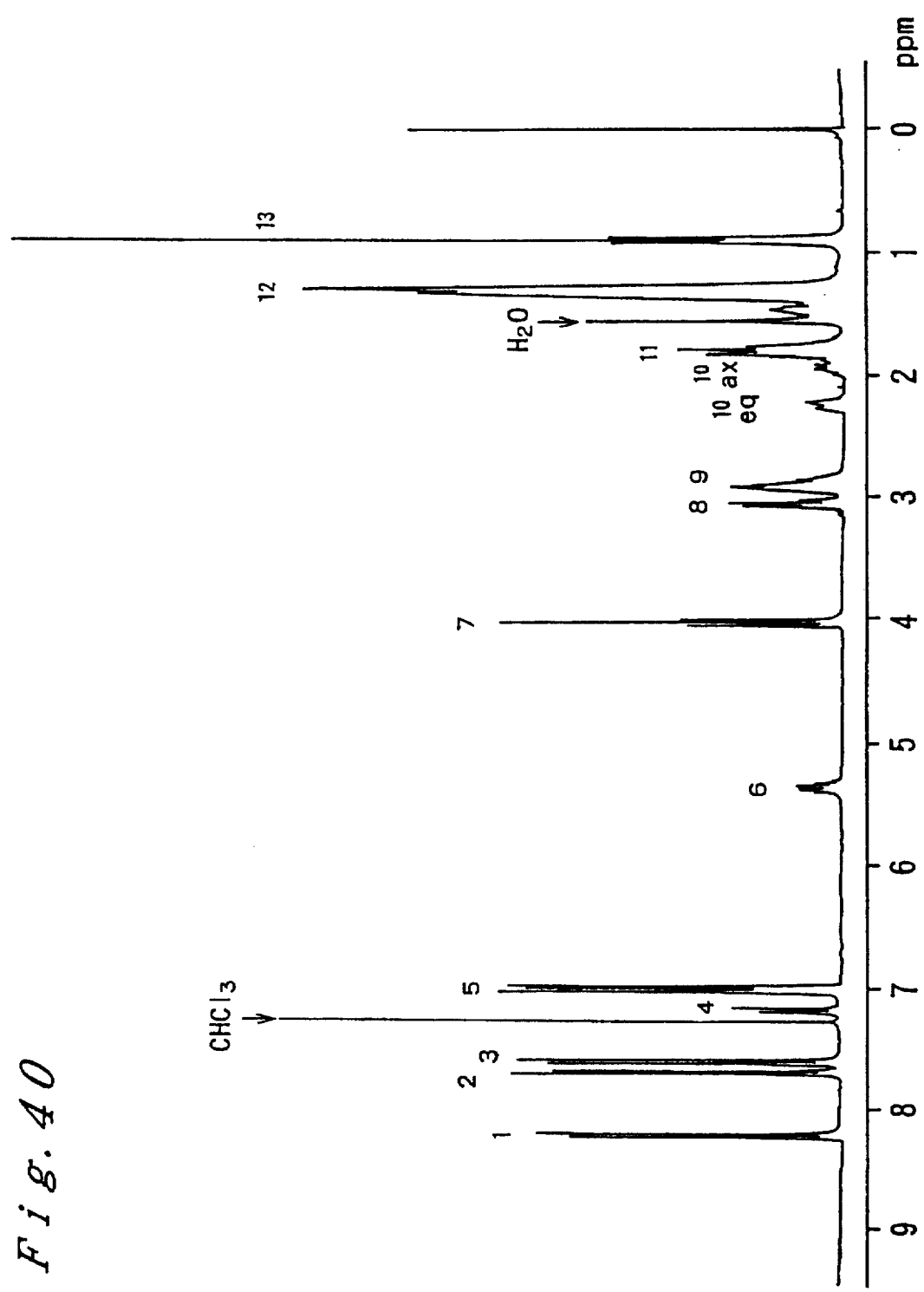
FIG. 40 shows ¹H-NMR spectrum of 6-[(4'-octyloxy-4-biphenyl) carbonyloxy]-1,2,3,4-tetrahydro-2-naphthalenecarboxylic acid (R)-1-trifluoromethylheptyl ester. [Exemplified compound (249)]

¹H-NMR of 6-[(4'-octyloxy-4-biphenyl)carbonyloxy]-1, 2,3,4-tetrahydro-2-naphthalenecarboxylic acid (R)-1-trifluoromethylheptyl ester [Examplified compound (249)] is shown in FIG. 40.

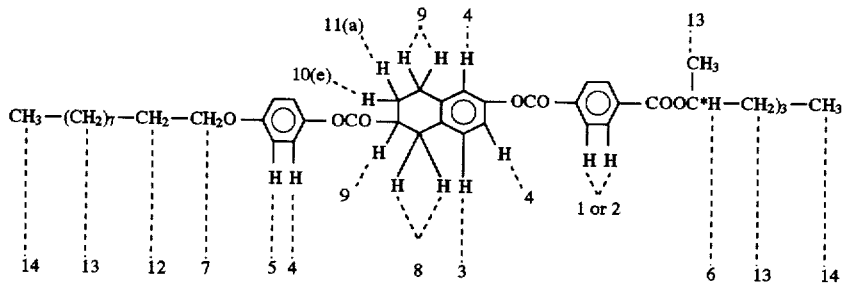

In this formula, (e) represents an equatorial sterio conformation, (a) represents an axial steric conformation, and the numbers 1 to 14 showing hydrogen atoms corresponding to the peaks in FIG. 38.

¹H-NMR of 6-[4-(4-dodecylpheny)cyclohexylcarbonyloxy]-1,2,3,4-tetrahydro-2-naphthalenecarboxylic acid (R)-1-trifluoromethylheptyl ester [Examplified compound (365)] is shown in FIG. 39.

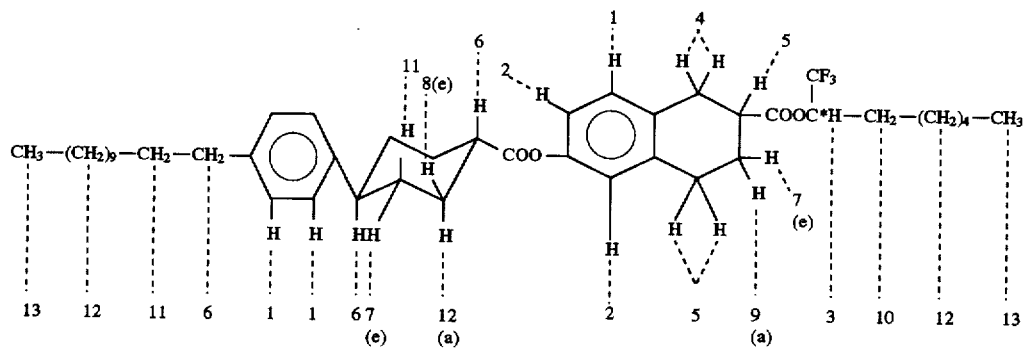

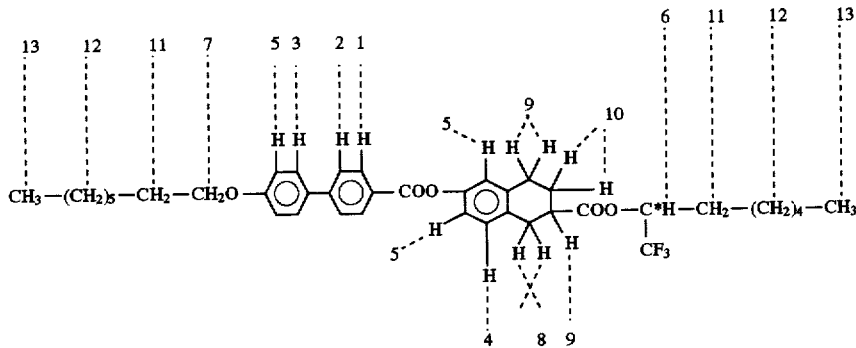

In this formula, numbers 1 to 13 showing hydrogen atoms corresponding to the peaks in FIG. 40.

Figure 41:
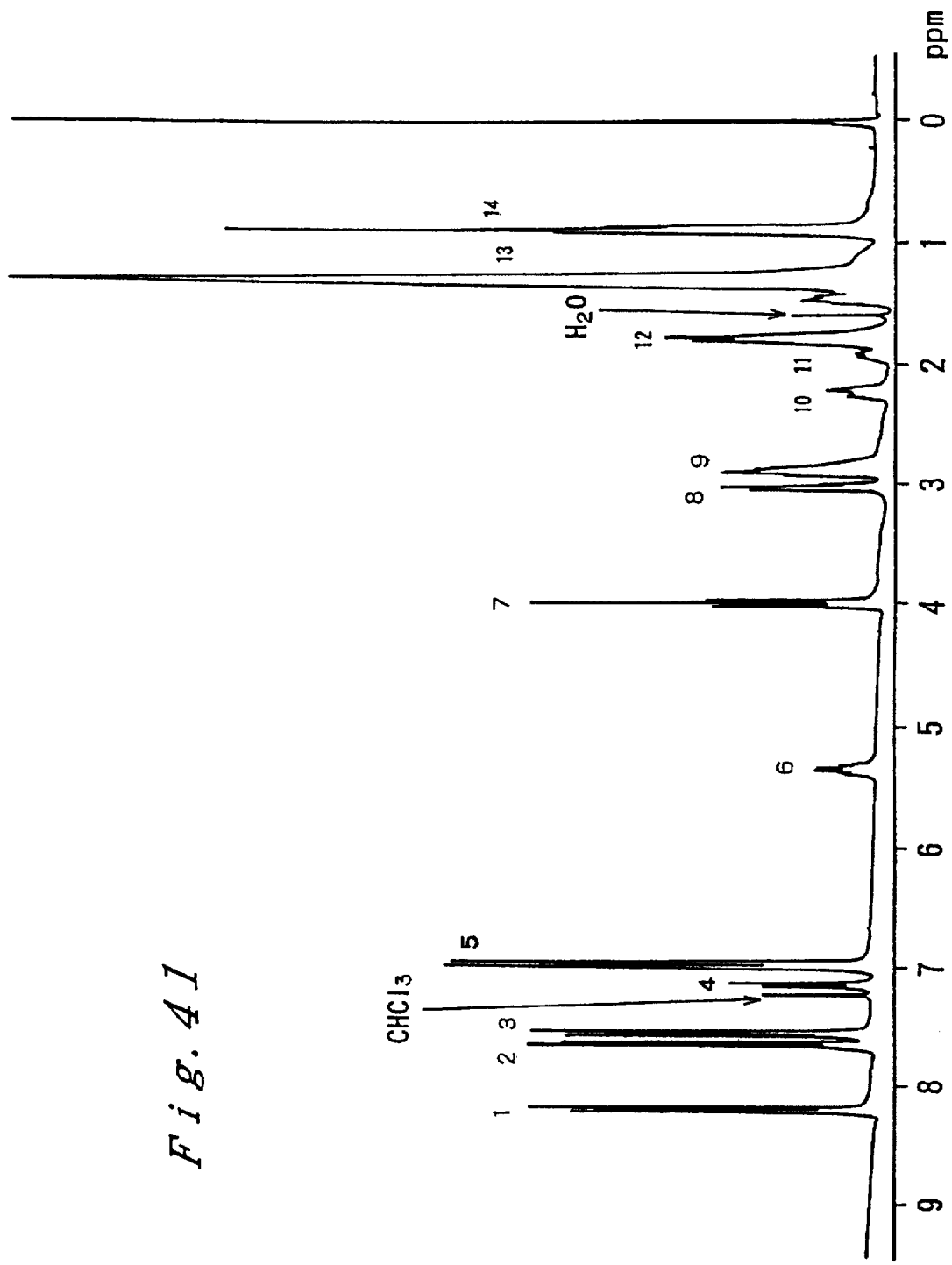
FIG. 41 shows ¹H-NMR spectrum of 6-[(4'-nonyloxy-4-biphenyl)carbonyloxy]-1,2,3,4-tetrahydro-2-naphthalenecarboxylic acid (R)-1-trifluoromethylheptyl ester. [Exemplified compound (250)]

$^1$H-NMR of 6-[(4'-nonyloxy-4-biphenyl)carbonyloxy]-1,2,3,4-tetrahydro-2-naphthalenecarboxylic acid (R)-1-trifluoromethylheptyl ester [Examplified compound (250)] is shown in FIG. 41.

Figure 42:
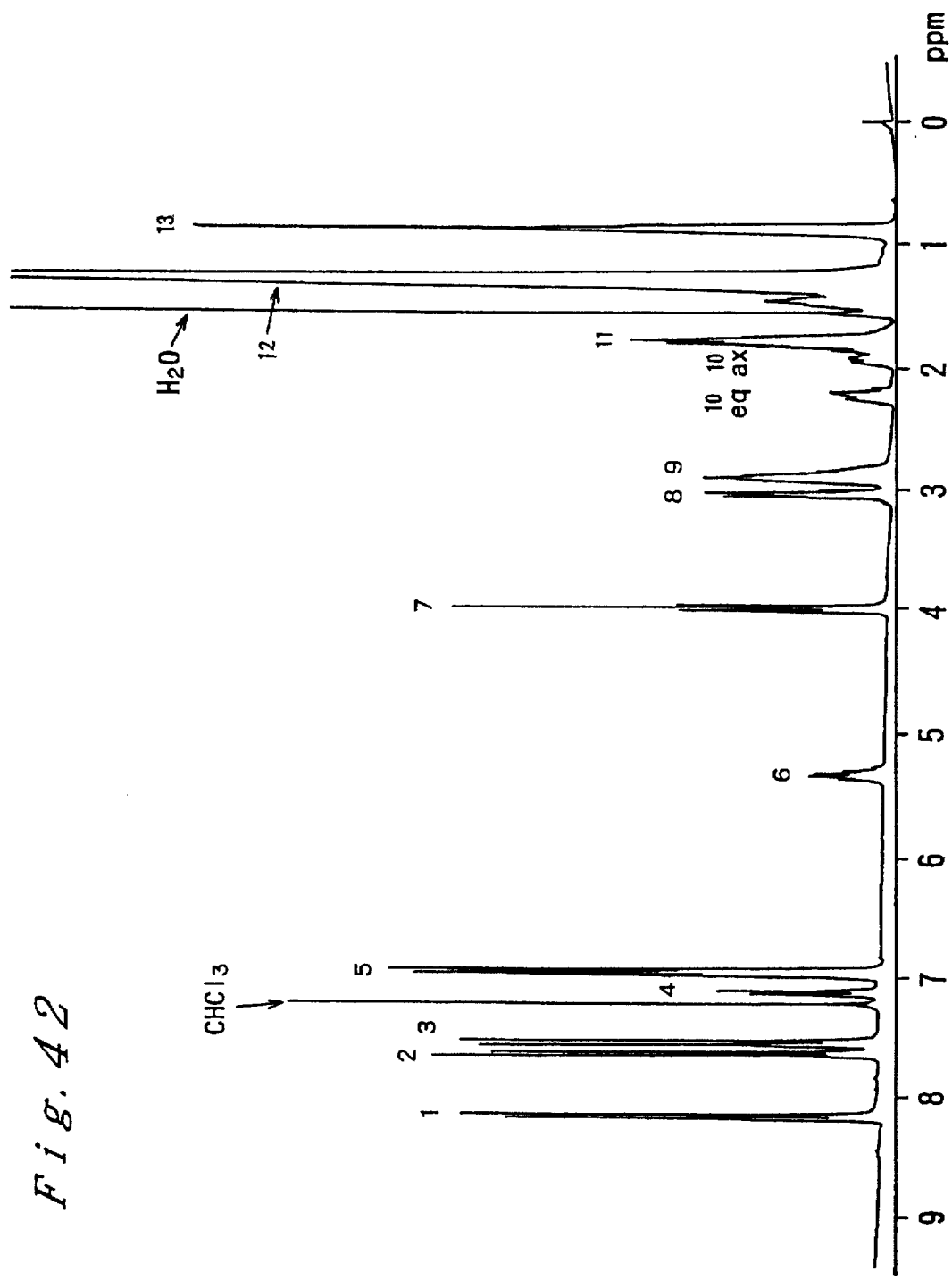
FIG. 42 shows ¹H-NMR spectrum of 6-[(4'-tetradecyloxy-4-biphenyl)carbonyloxy]-1,2,3,4-tetrahydro-2-naphthalenecarboxylic acid (R)-1-trifluoromethylheptyl ester. [Exemplified compound (254)]

In this formula, the numbers 1 to 13 showing hydrogen atoms corresponding to the peaks in FIG. 42.

Figure 43:
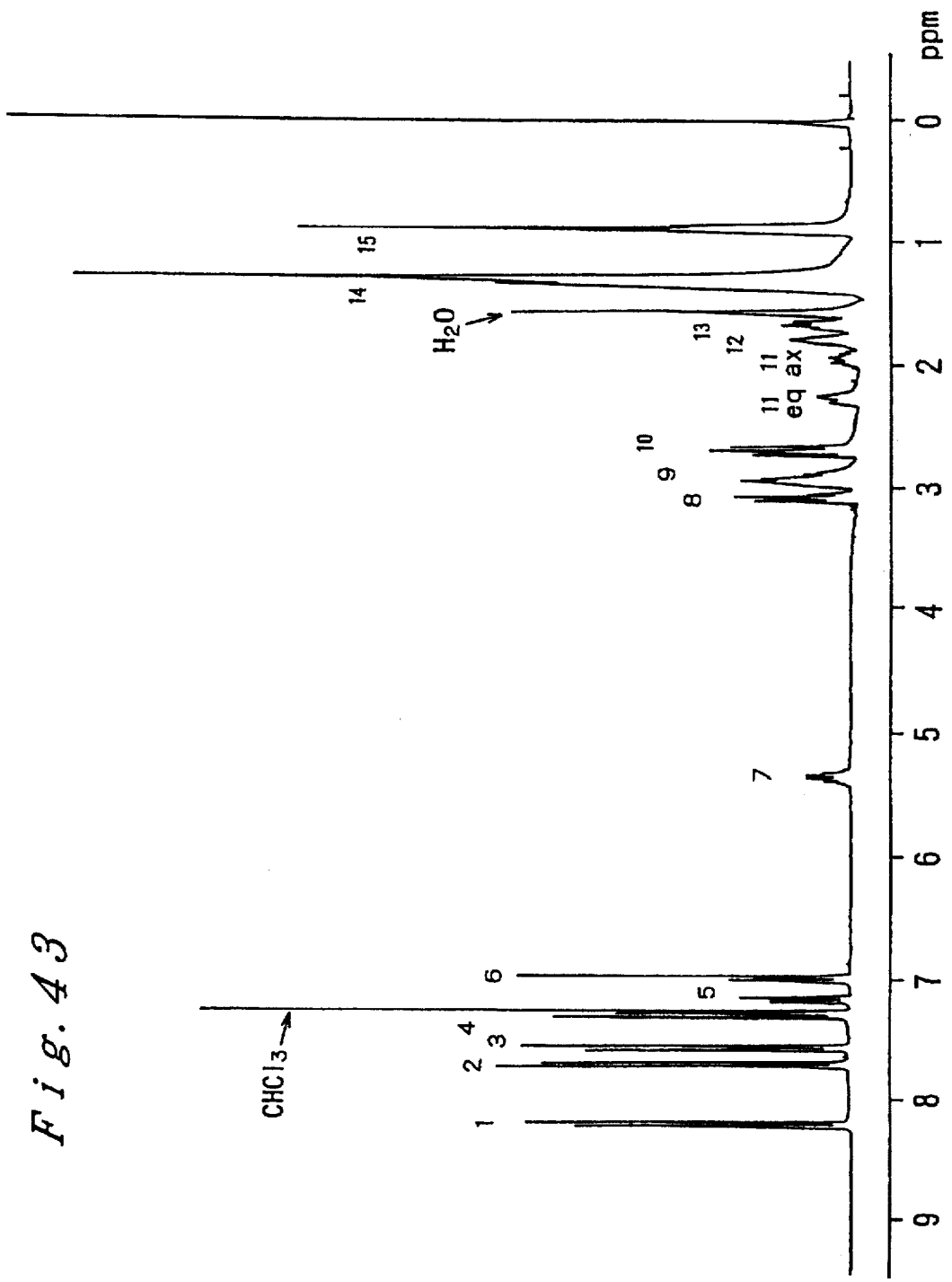
FIG. 43 shows ¹H-NMR spectrum of 6-[(4'-nonyl-4-biphenyl) carbonyloxy]-1,2,3,4-tetrahydro-2-naphthalenecarboxylic acid (R)-1-trifluoromethylheptyl ester. [Exemplified compound (354)]

$^1$H-NMR of 6-[(4'nonyl-4-biphenyl)carbonyloxy]-1,2,3,4-tetrahydro-2-naphthalenecarboxylic acid (R)-1-trifluoromethylheptyl ester [Examplified compound (354)] is shown in FIG. 43.

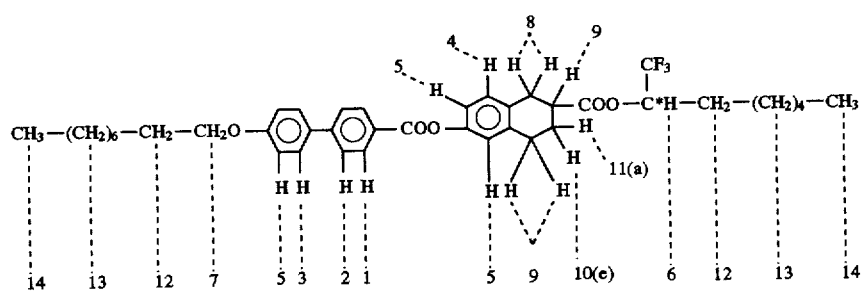

In this formula, (e) represents an equatorial sterio conformation, (a) represents an axial steric conformation, and the numbers 1 to 14 showing hydrogen atoms corresponding to the peaks in FIG. 41.

$^1$H-NMR of 6-[(4'-tetradecyloxy-4-biphenyl)-carbonyloxy]-1,2,3,4-tetrahydro-2-naphthalenecarboxylic acid (R)-1-trifluoromethylheptyl ester [Examplified compound (254)] is shown in FIG. 42.

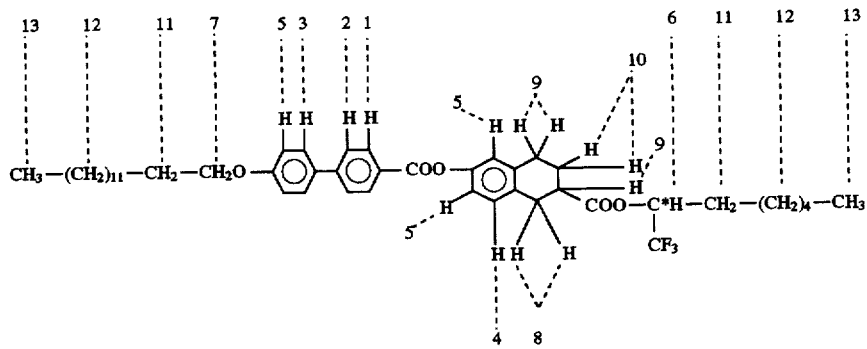

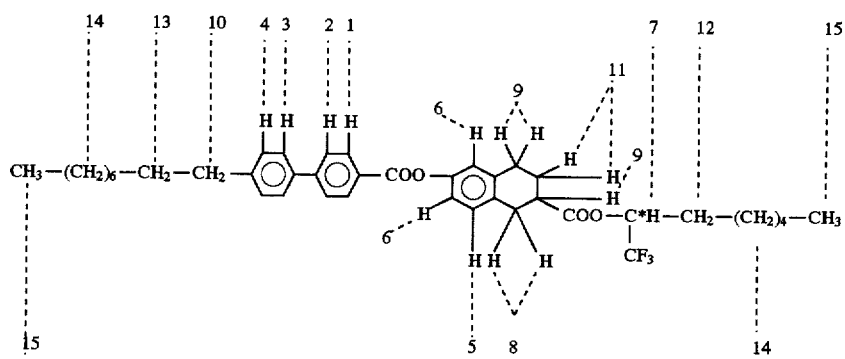

In this formula, the numbers 1 to 15 showing hydrogen atoms corresponding to the peaks in FIG. 43.

Figure 44:
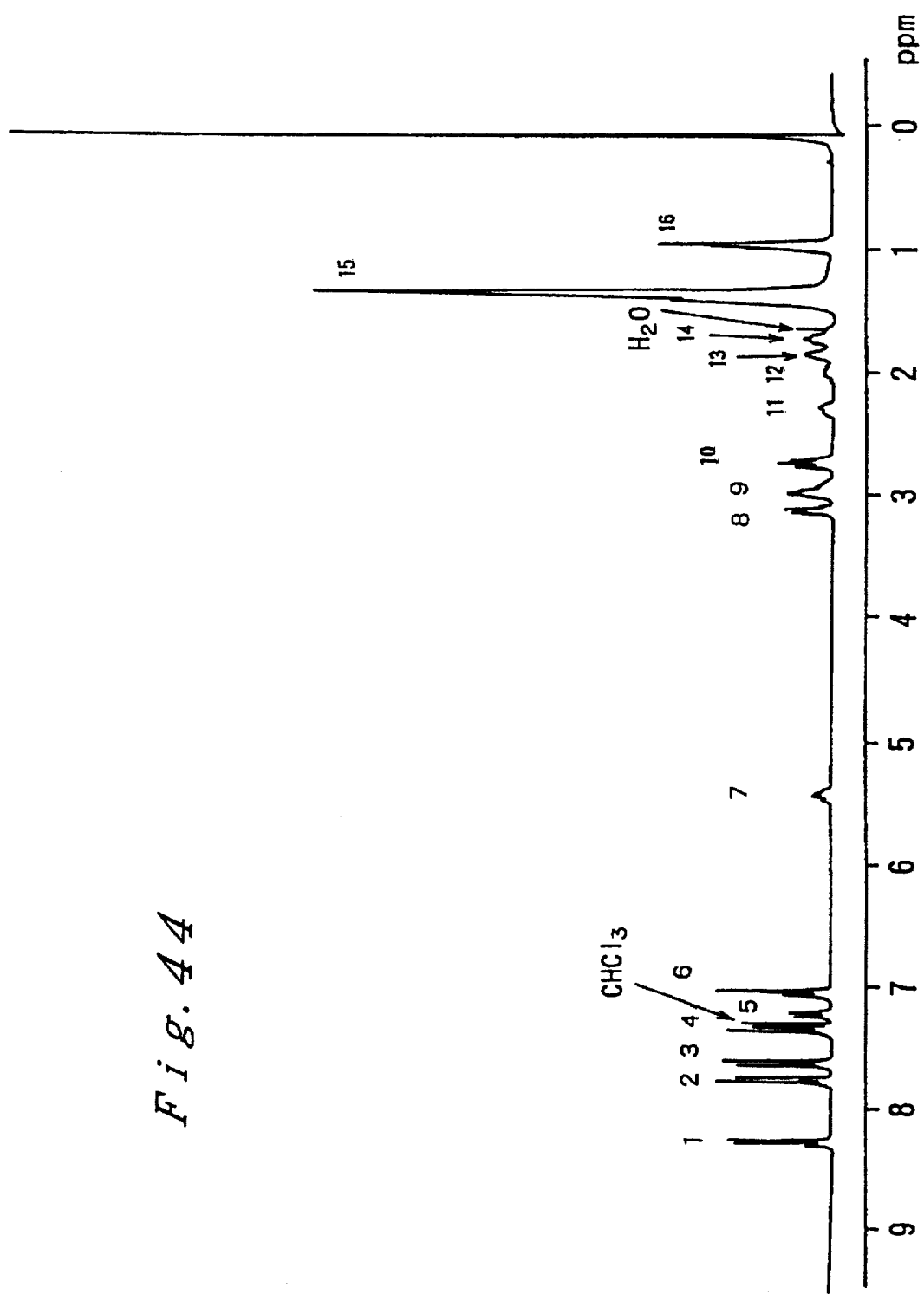
FIG. 44 shows ¹H-NMR spectrum of 6-[(4'-undecyl-4-biphenyl)carbonyloxy]-1,2,3,4-tetrahydro-2-naphthalenecarboxylic acid (R)-1-trifluoroheptyl ester. [Exemplified compound (356)]

¹H-NMR of 6-[(4'-undecyl-4-biphenyl)carbonyloxy]-1,2,3,4-tetrahydro-2-naphthalenecarboxylic acid (R)-1-triluoroheptyl ester [Examplified compound (356)] is shown in FIG. 44.

Figure 46:
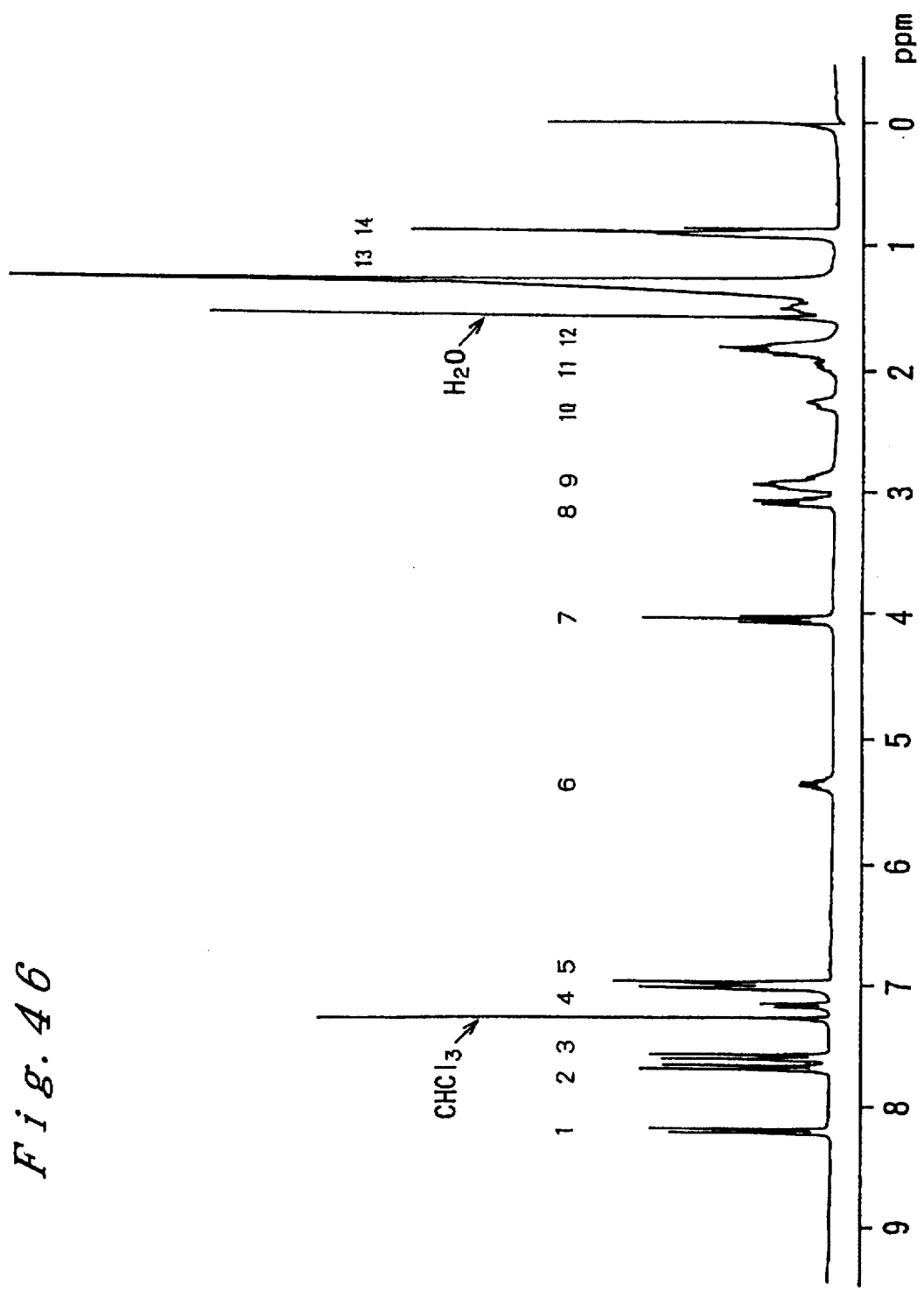
FIG. 46 shows ¹H-NMR spectrum of 6-[(4'-decyloxy-4-biphenyl)carbonyloxy]-1,2,3,4-tetrahydro-2-naphthalenecarboxylic acid (R)-1-trifluoromethylnonyl ester. [Exemplified compound (371)]

¹H-NMR of 6-[(4'-decyloxy-4-biphenyl)carbonyloxy]-1,2,3,4-tetrahydro-2-naphthalenecarboxylic acid (R)-1-trifluoromethylnonyl ester [Examplified compound (371)] is shown in FIG. 46.

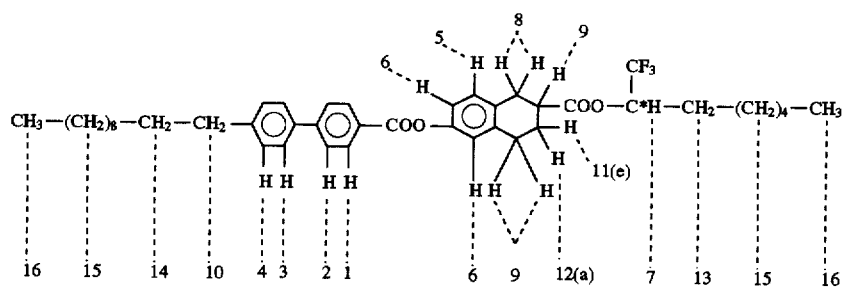

In this formula, (e) represents an equatorial sterio conformation, (a) represents an axial steric conformation, and the numbers 1 to 16 showing hydrogen atoms corresponding to the peaks in FIG. 44.

Figure 45:
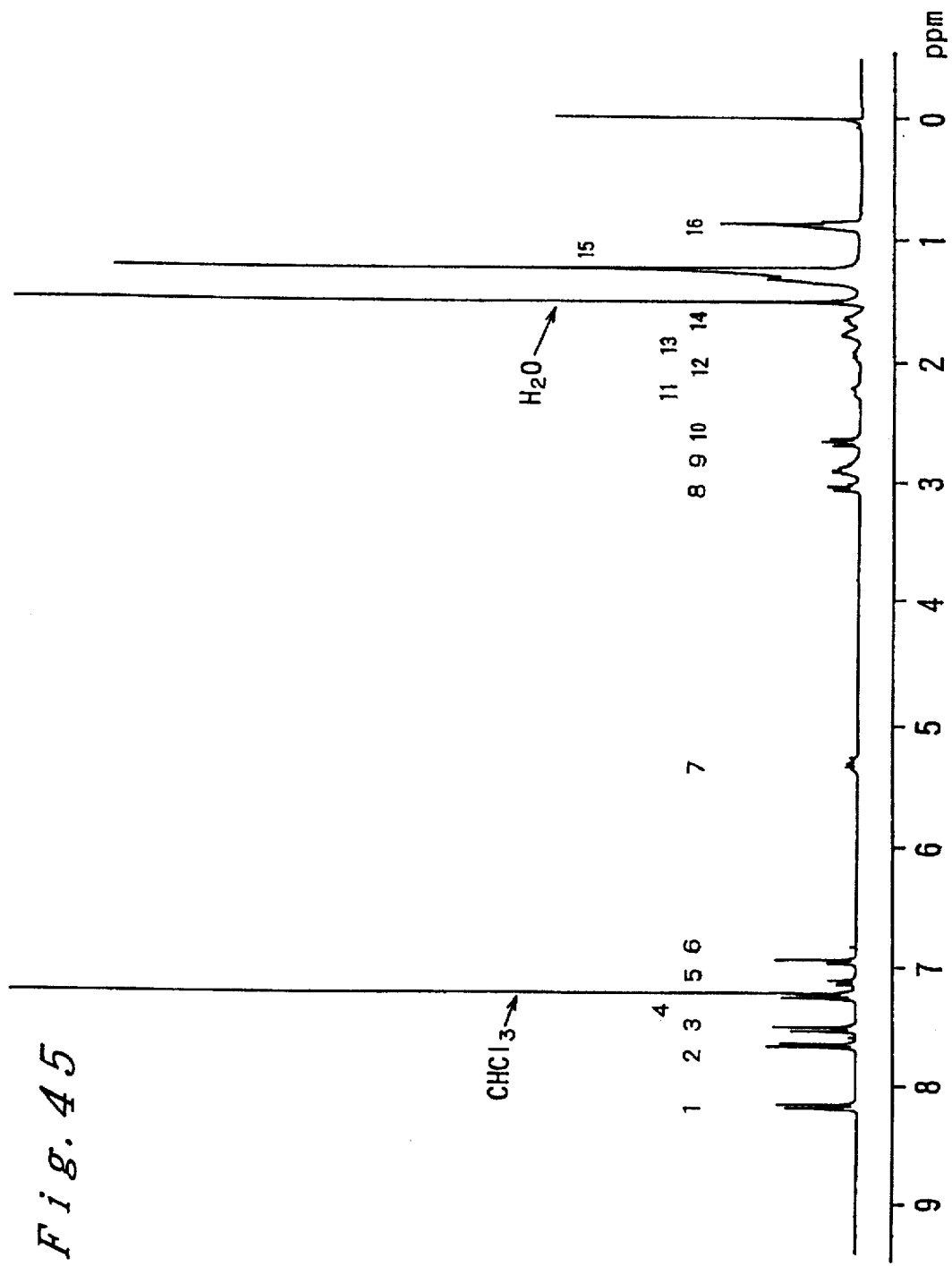
FIG. 45 shows ¹H-NMR spectrum of 6-[(4'-tetradecyl-4-biphenyl)carbonyloxy]-1,2,3,4-tetrahydro-2-naphthalenecarboxylic acid (R)-1-trifluoromethylheptyl ester. [Exemplified compound (358)]

¹H-NMR of 6-[(4'-tetradecyl-4-biphenyl)carbonyloxy]-1,2,3,4-tetrahydro-2-naphthalenecarboxylic acid (R)-1-trifluoromethylheptyl ester [Examplified compound (358)] is shown in FIG. 45.

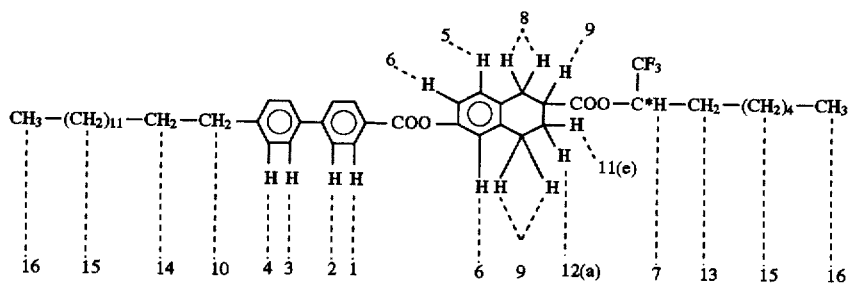

In this formula, (e) represents an equatorial sterio conformation, (a) represents an axial steric conformation, and the numbers 1 to 16 showing hydrogen atoms corresponding to the peaks in FIG. 45.

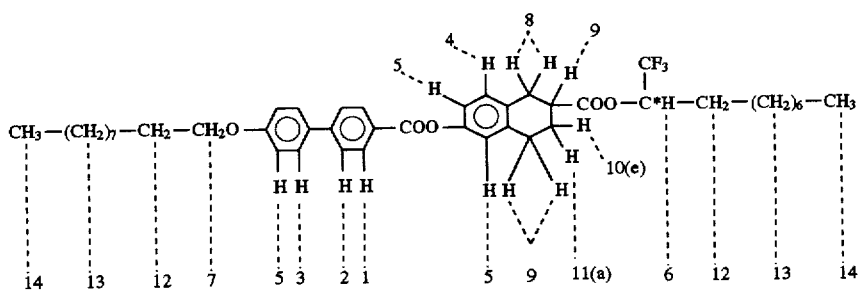

In this formula, (e) represents an equatorial sterio conformation, (a) represents an axial steric conformation, and the numbers 1 to 14 showing hydrogen atoms corresponding to the peaks in FIG. 46.

Figure 47:
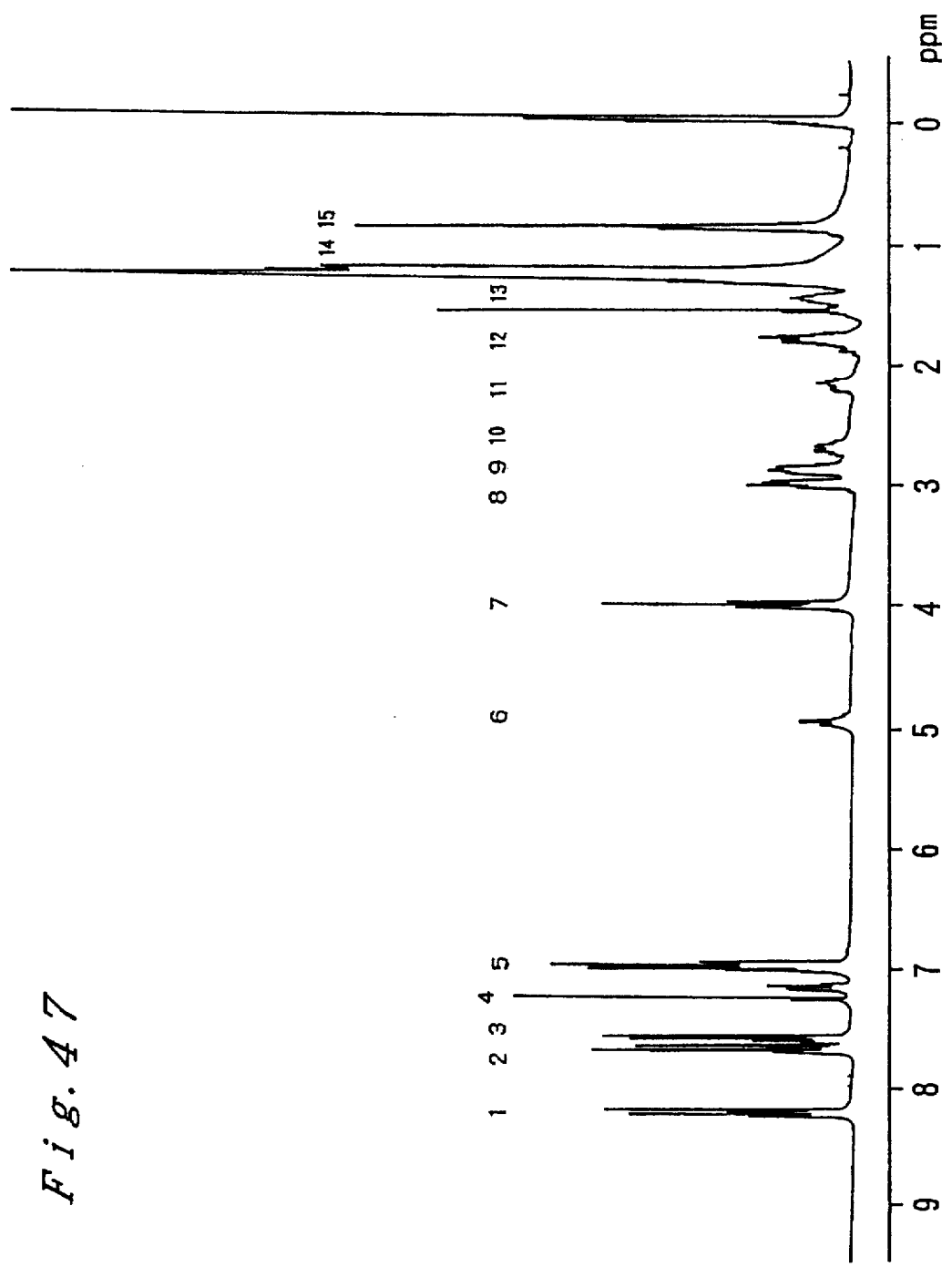
FIG. 47 shows ¹H-NMR spectrum of 6-[4'-decyloxy-4-biphenyl)carboyloxy]-1,2,3,4-tetrahydro-2-naphthalenecarboxylic acid (R)-1-methylheptyl ester. [Exemplified compound (467)]

¹H-NMR of 6-[(4'-decyloxy-4-biphenyl)carbonyloxy]-1,2,3,4-tetrahydro-2-naphthalenecarboxylic acid (R)-1-trifluoromethylnonyl ester [Examplified compound (371)] is shown in FIG. 47.

Figure 49:
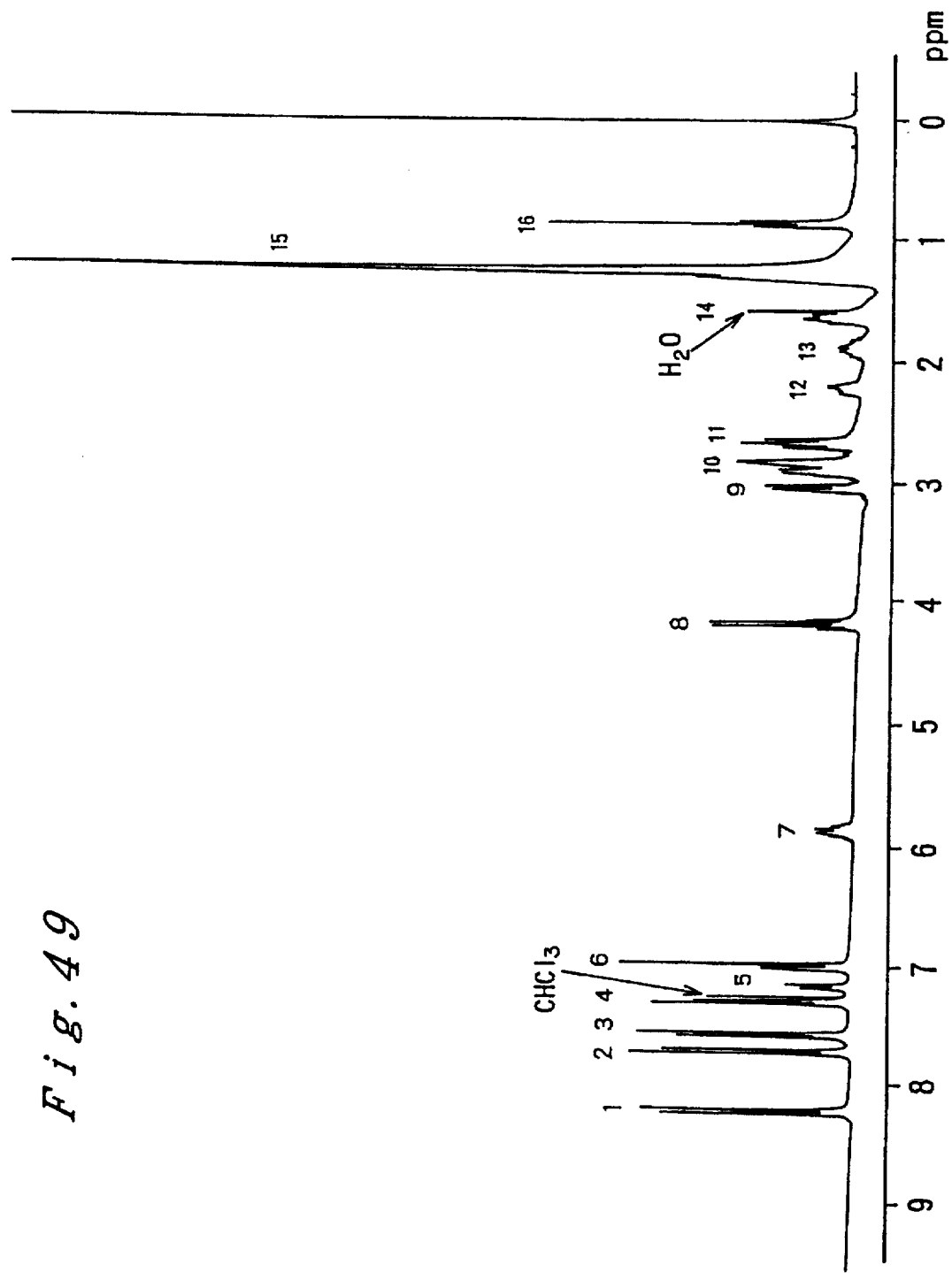
FIG. 49 shows ¹H-NMR spectrum of 6-[(4'-decyl-4-biphenyl)carbonyloxy]-1,2,3,4-tetrahydro-2-naphthalenecarboxylic acid (R)-1-trifluoromethyl)-2-(ethoxycarbonyl)ethyl ester. [Exemplified compound (491)]

¹H-NMR of 6-[(4'-decyl-4-biphenyl)carbonyloxy]-1,2,3,4-tetrahydro-2-naphthalenecarboxylic acid (R)-1-trifluoromethyl)-2-(ethoxycarbonyl)ethyl ester [Examplified compound (491)] is shown in FIG. 49.

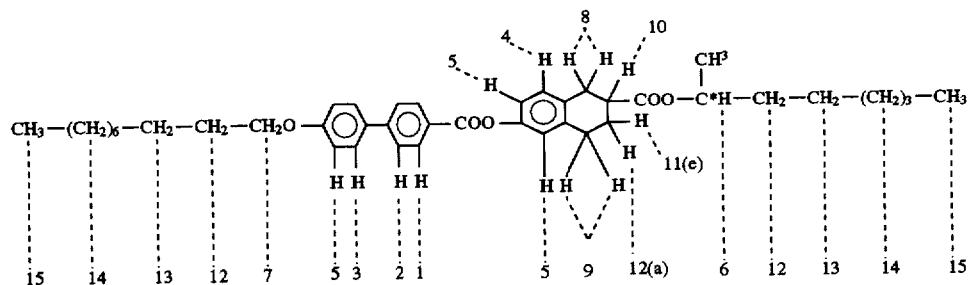

In this formula, (e) represents an equatorial sterio conformation, (a) represents an axial steric conformation, and the numbers 1 to 14 showing hydrogen atoms corresponding to the peaks in FIG. 47.

Figure 48:
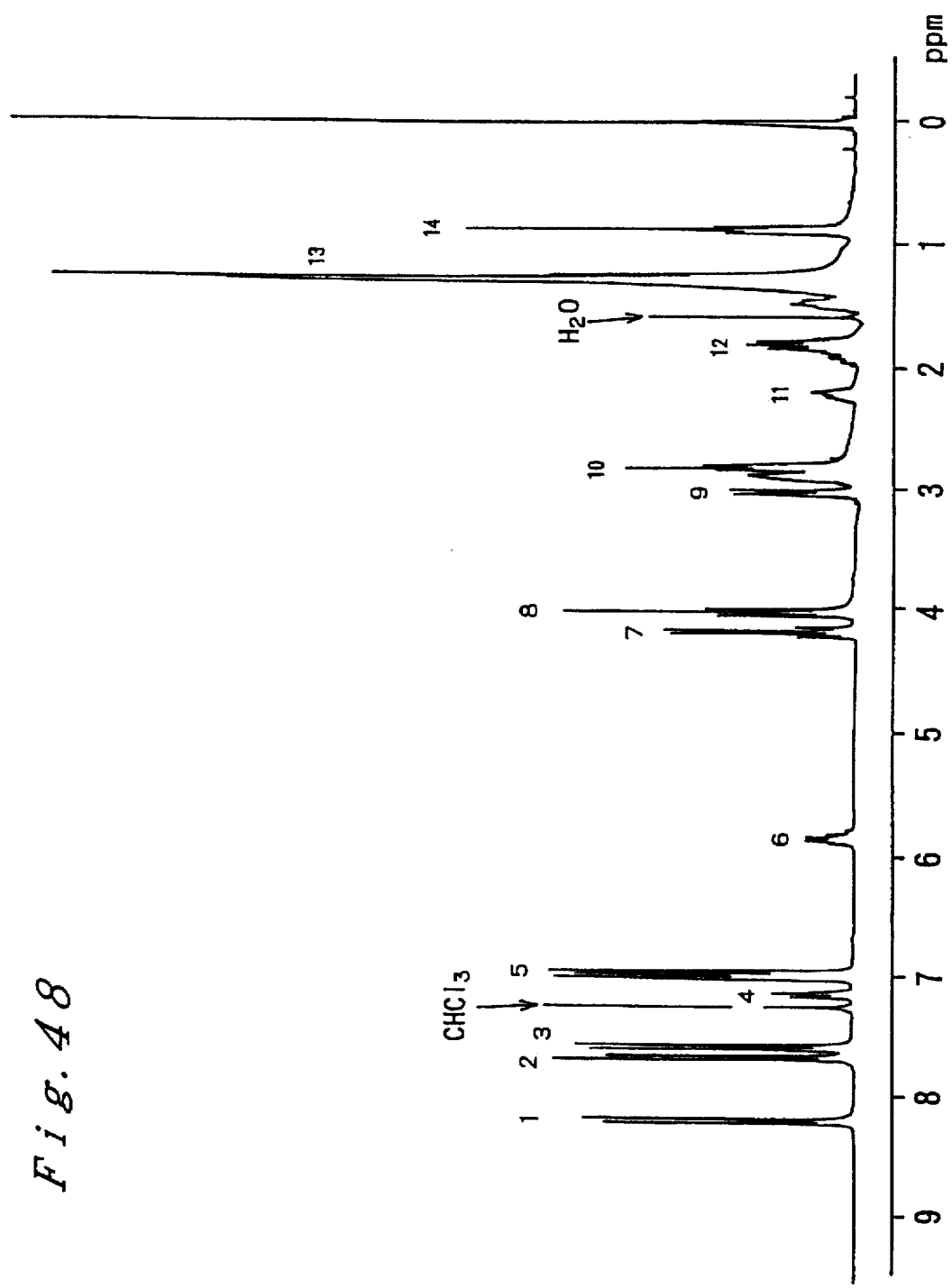
FIG. 48 shows ¹H-NMR spectrum of 6-[4'-decyloxy-4-biphenyl)carbonyloxy]-1,2,3,4-tetrahydro-2-naphthalenecarboxylic acid (R)-1-(tryfluoromethyl)-2-(ethoxycarbonyl)ethyl ester. [Exemplified compound (483)]

¹H-NMR of 6-[4'-decyloxy-4-biphenyl)carbonyloxy)-1,2,3,4-tetrahydro-2-naphthalenecarboxylic acid (R)-1-(tryfluoromethyl)-2-(ethoxycarbonyl)ethyl ester [Examplified compound (483)] is shown in FIG. 48.

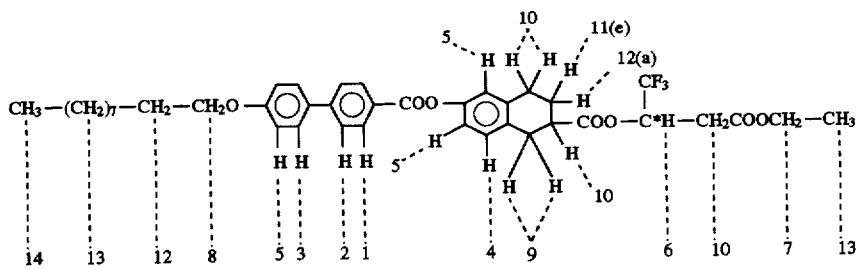

In this formula, (e) represents an equatorial sterio conformation, (a) represents an axial steric conformation, and the numbers 1 to 14 showing hydrogen atoms corresponding to the peaks in FIG. 48.

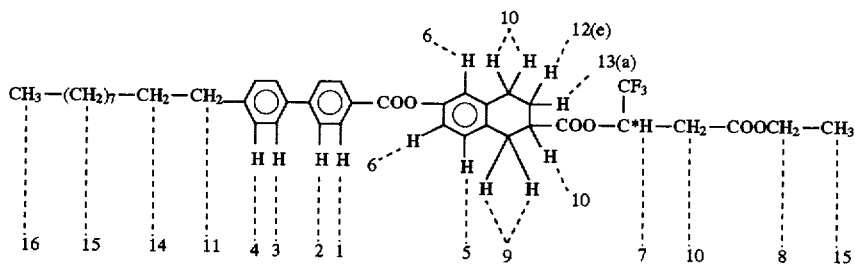

In this formula, (e) represents an equatorial sterio conformation, (a) represents an axial steric conformation, and the numbers 1 to 16 showing hydrogen atoms corresponding to the peaks in FIG. 49.

Figure 50:
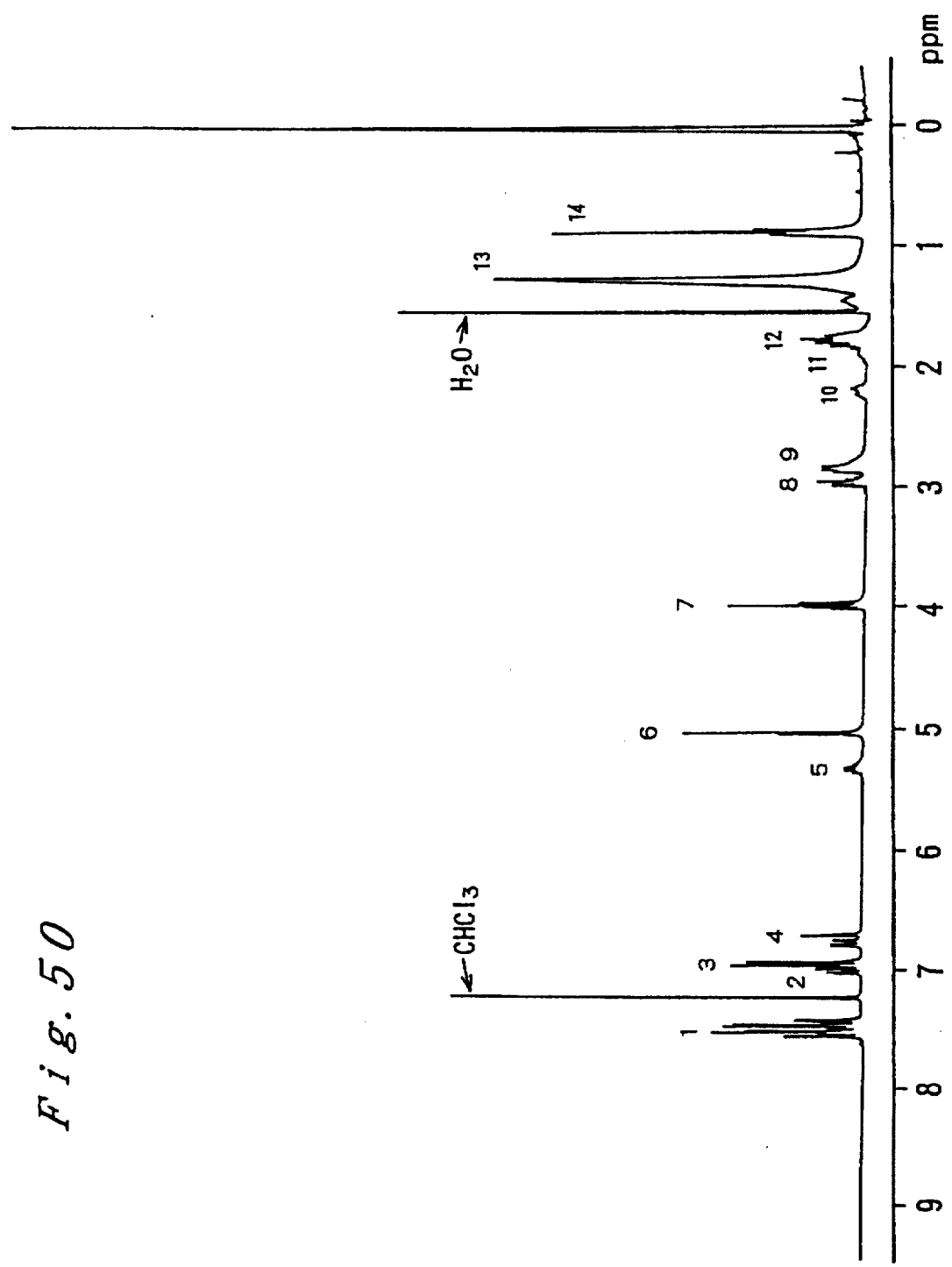
FIG. 50 shows ¹H-NMR spectrum of 6-[(4'-decyloxy-4-biphenyl)methoxy]-1,2,3,4-tetrahydro-2-naphthalenecarboxylic acid (R)-1-trifluoromethylheptyl ester. [Exemplified compound(419)]

$^1$H-NMR of 6-[(4'-decyloxy-4-biphenyl)methoxy]-1,2,3,4-tetrahydro-2-naphthalenecarboxylic acid (R)-1-trifluoromethylheptyl ester [Examplified compound(419)] is shown in FIG. 50.

Figure 52:
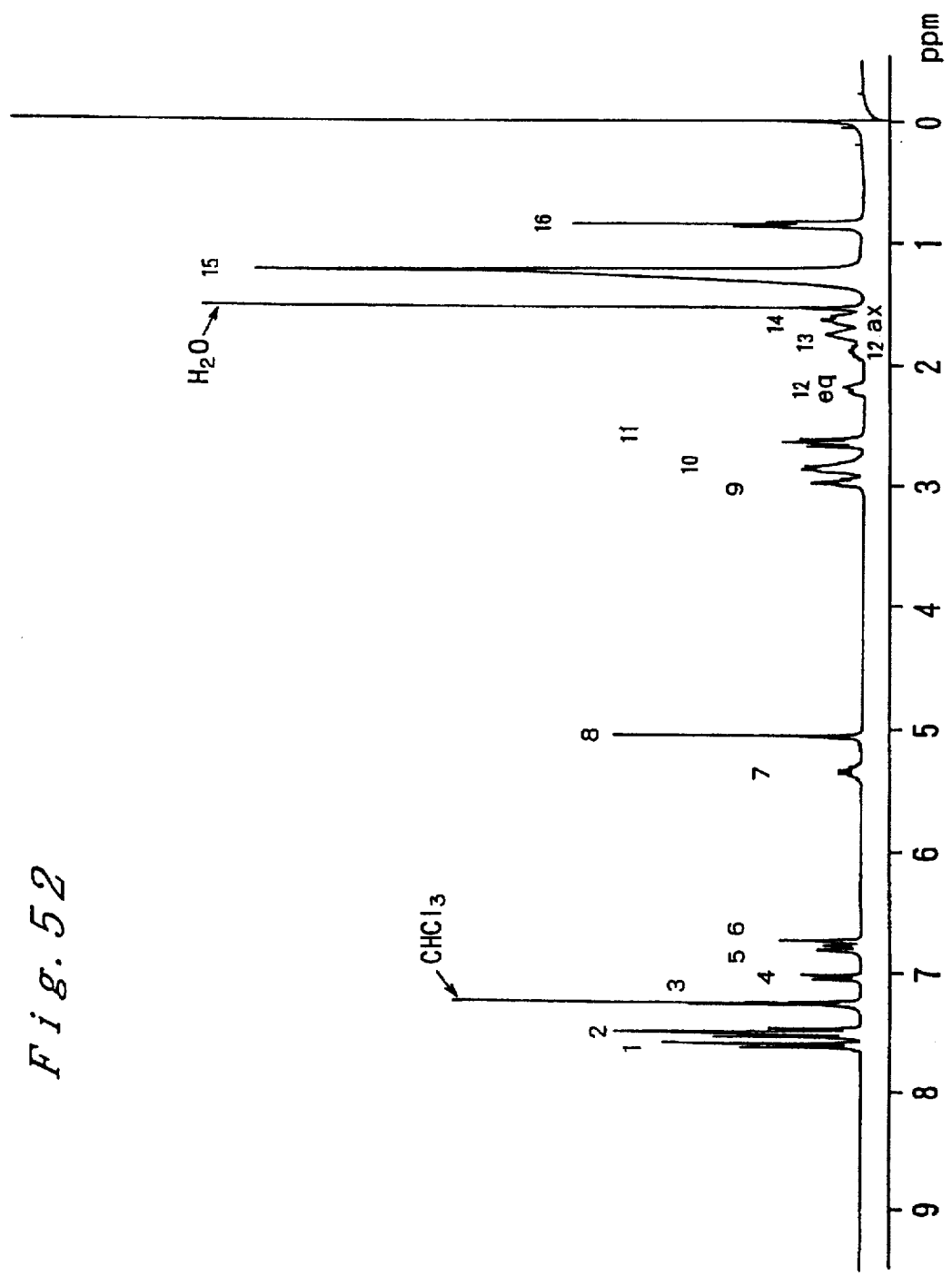
FIG. 52 shows ¹H-NMR spectrum of 6-[(4'-decyl-4-biphenyl)methoxy]-1,2,3,4-tetrahydro-2-naphthalenecarboxylic acid (R)-1-trifluoromethylheptyl ester. [Exemplified compound (427)]

$^1$H-NMR of 6-[(4'-decyl-4-biphenyl)methoxy]-1,2,3,4-tetrahydro-2-naphthalenecarboxylic acid (R)-1-trifluoromethylheptyl ester [Examplified compound (427)] is shown in FIG. 52.

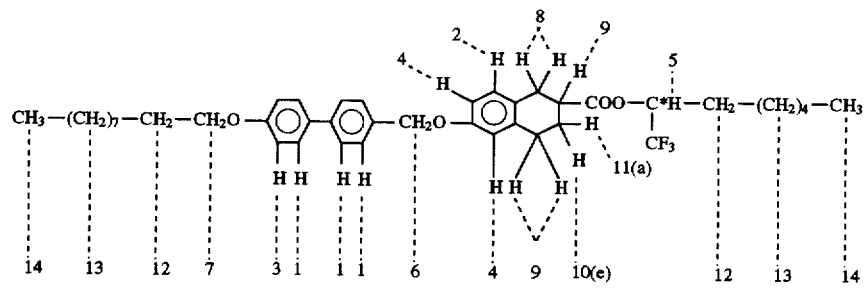

In this formula, (e) represents an equatorial sterio conformation, (a) represents an axial steric conformation, and the numbers 1 to 14 showing hydrogen atoms corresponding to the peaks in FIG. 50.

Figure 51:
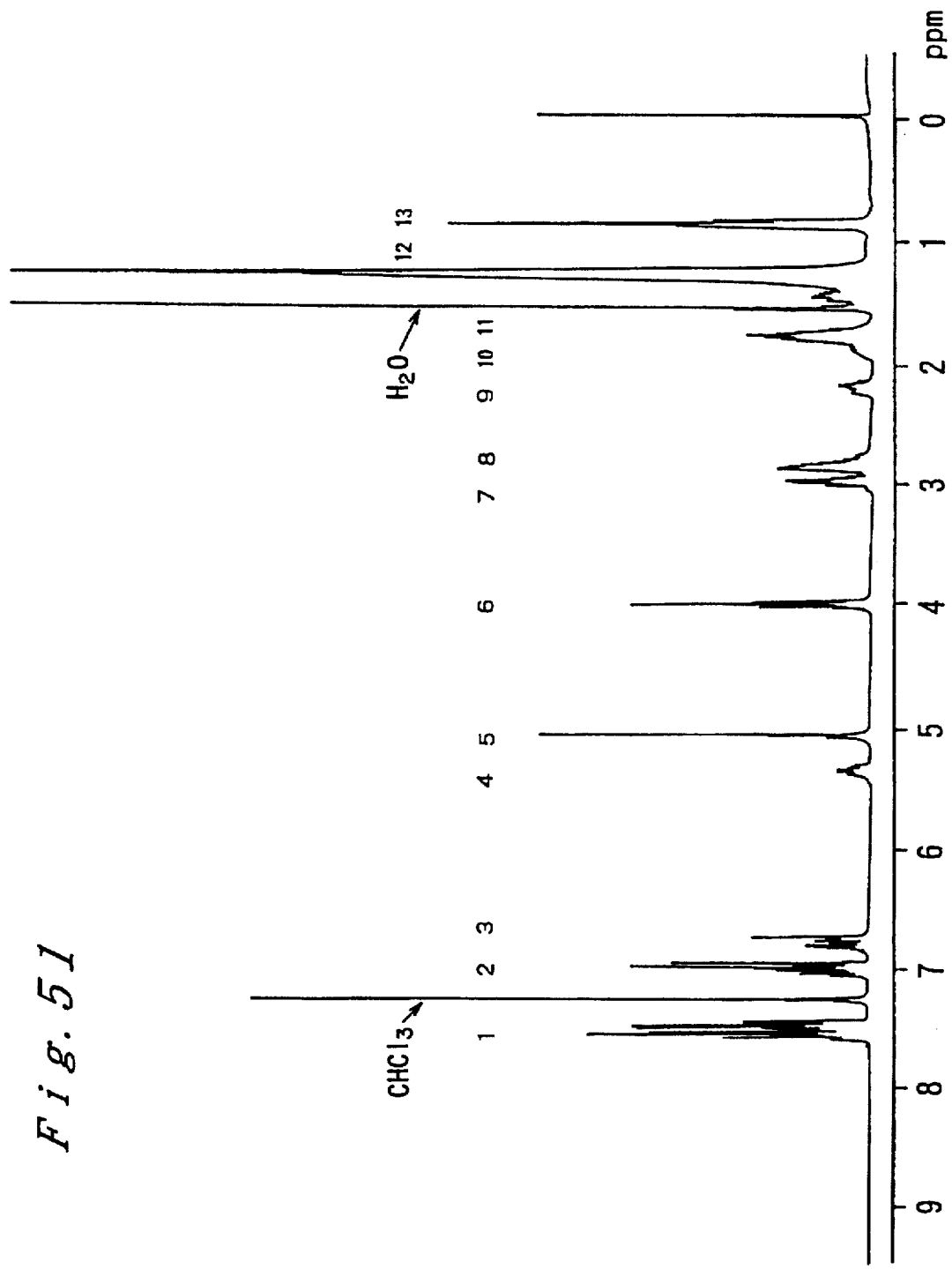
FIG. 51 shows ¹H-NMR spectrum of 6-[(4'-dodecyloxy-4-biphenyl)methoxy]-1,2,3,4-tetrahydro-2-naphthalenecarboxylic acid (R)-1-trifluoromethylheptyl ester. [Exemplified compound (421)]

$^1$H-NMR of 6-[(4'-dodecyloxy-4-biphenyl)methoxy]-1,2,3,4-tetrahydro-2-naphthalenecarboxylic acid (R)-1-trifluoromethylheptyl ester [Examplified compound (421)] is shown in FIG. 51.

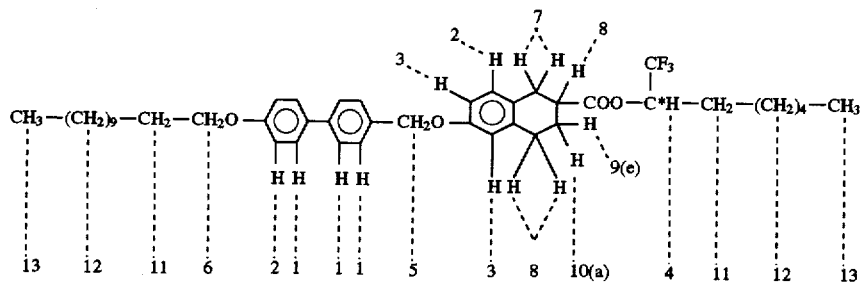

In this formula, (e) represents an equatorial sterio conformation, (a) represents an axial steric conformation, and the numbers 1 to 13 showing hydrogen atoms corresponding to the peaks in FIG. 51.

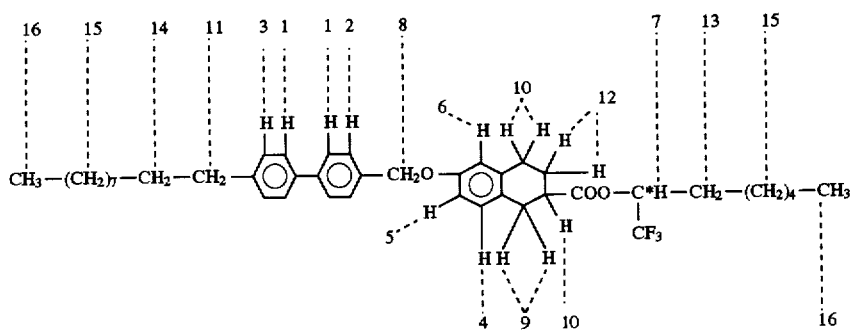

In this formula, the numbers 1 to 16 showing hydrogen atoms corresponding to the peaks in FIG. 52.

Figure 53:
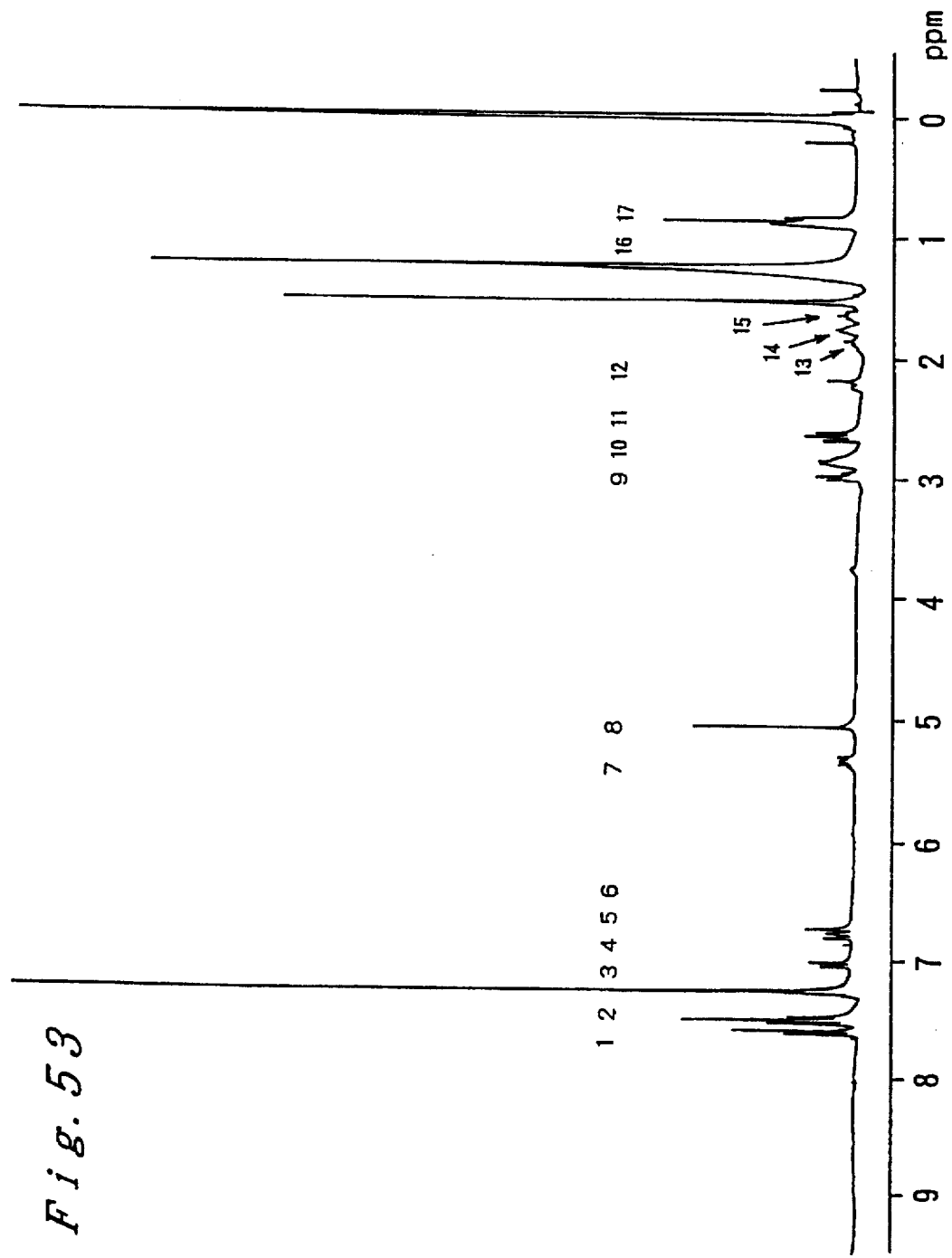
FIG. 53 shows ¹H-NMR spectrum of 6-[(4'-dodecyl-4-biphenyl)methoxy]-1,2,3,4-tetrahydro-2-naphthalenecarboxylic acid (R)-1-trifluoromethylheptyl ester. [Exemplified compound (429)]

$^1$H-NMR of 6-[(4'-dodecyl-4-biphenyl)methoxy]-1,2,3,4-tetrahydro-2-naphthalenecarboxylic acid (R)-1-trifluoromethylheptyl ester [Examplified compound (429)] is shown in FIG. 53.

Figure 55:
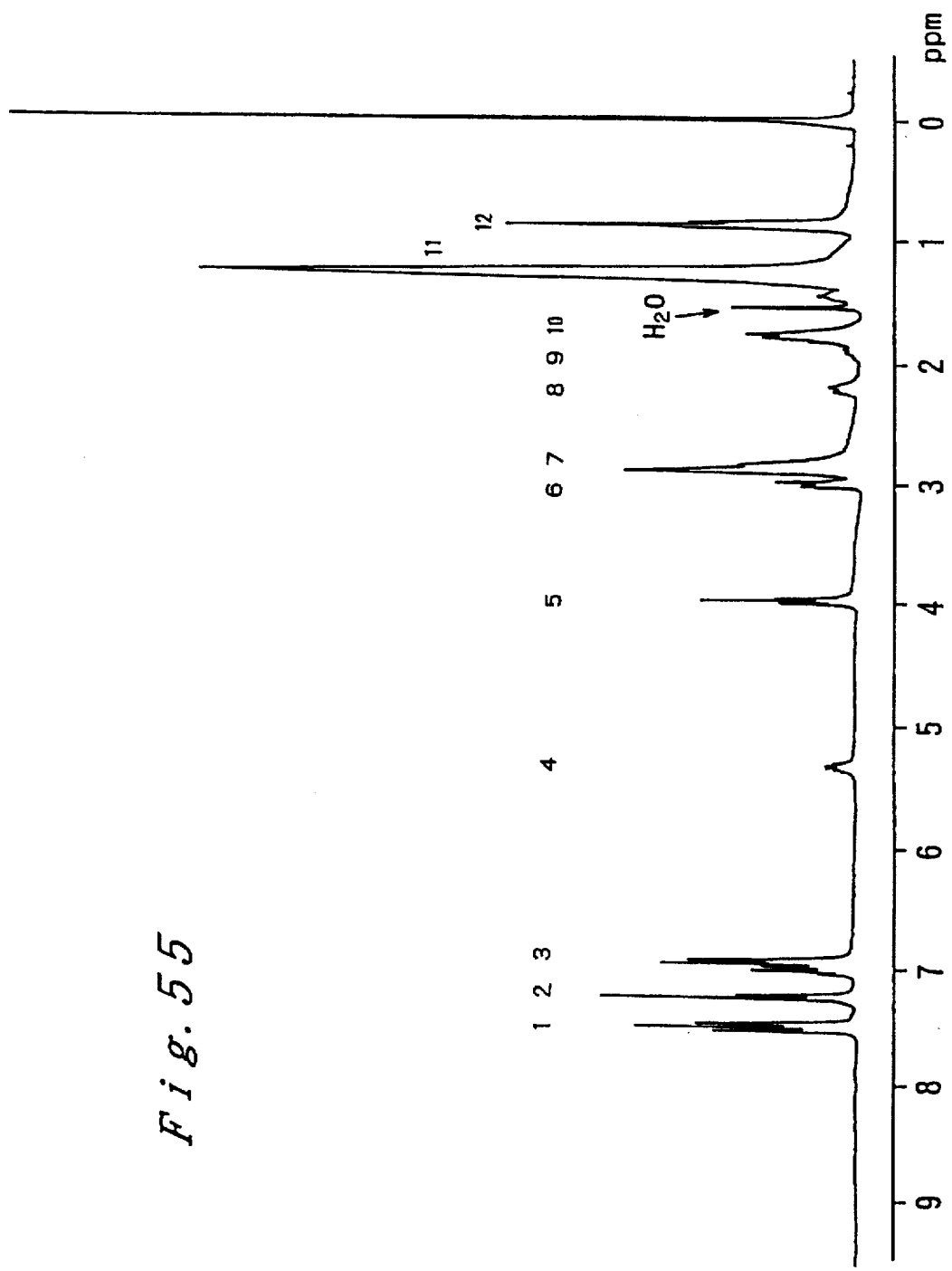
FIG. 55 shows ¹H-NMR spectrum of 6-[2-(4'-decyloxy-4-biphenyl)ethyl]-1,2,3,4-tetrahydro-2-naphthalenecarboxylic acid (R)-1-trifluoromethylheptyl ester. [Exemplified compound (451)]

$^1$H-NMR of 6-(2-(4'-decyloxy-4-biphenyl)ethyl]-1,2,3,4-tetrahydro-2-naphthalenecarboxylic acid (R)-1-trifluoromethyl ester [Examplified compound (451)] is shown in FIG. 55.

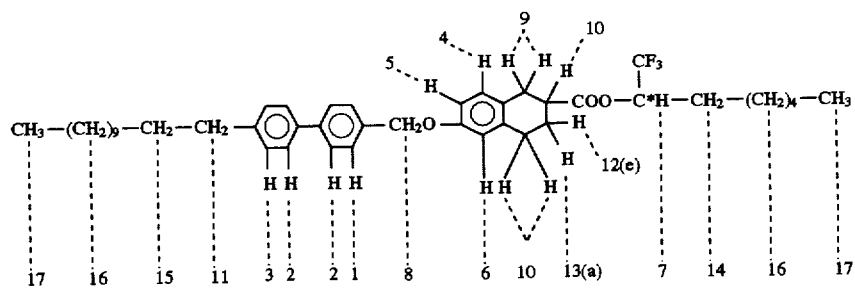

In this formula, (e) represents an equatorial sterio conformation, (a) represents an axial steric conformation, and the numbers 1 to 17 showing hydrogen atoms corresponding to the peaks in FIG. 53.

Figure 54:
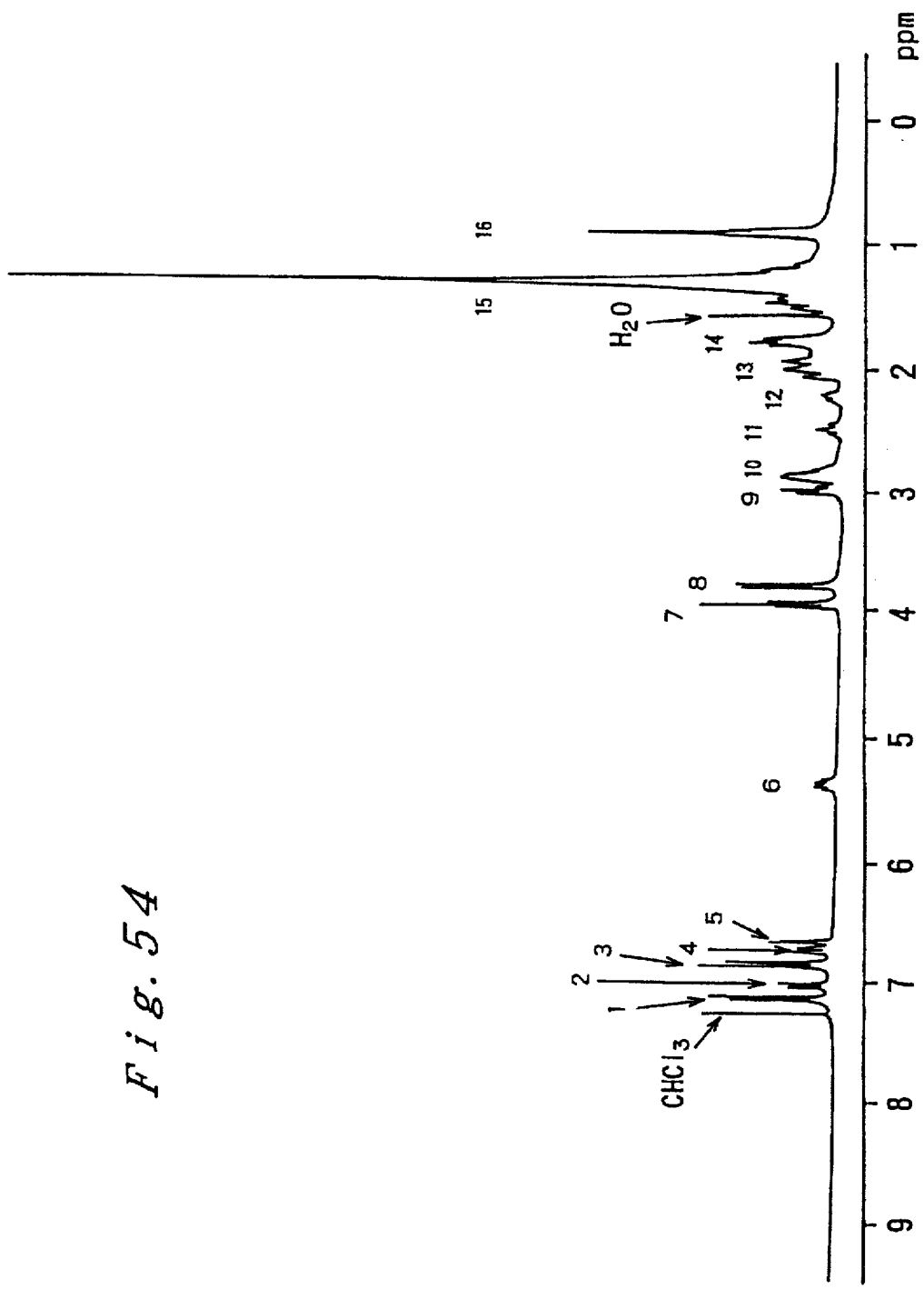
FIG. 54 shows ¹H-NMR spectrum of 6-[(4'-dodecyloxy-4-biphenyl)methoxy]-1,2,3,4-tetrahydro-2-naphthalenecarboxylic acid (R)-1-trifluoromethylheptyl ester. [Exemplified compound (437)]

$^1$H-NMR of 6-[(4'-dodecyloxy-4-biphenyl)methoxy]-1,2,3,4-tetrahydro-2-naphthalenecarboxylic acid (R)-1-trifluoromethylheptyl ester [Examplified compound (437)] is shown in FIG. 54.

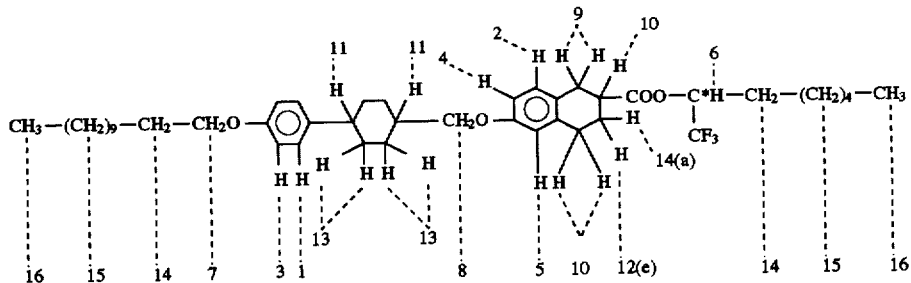

In this formula, (e) represents an equatorial sterio conformation, (a) represents an axial steric conformation, and the numbers 1 to 16 showing hydrogen atoms corresponding to the peaks in FIG. 54.

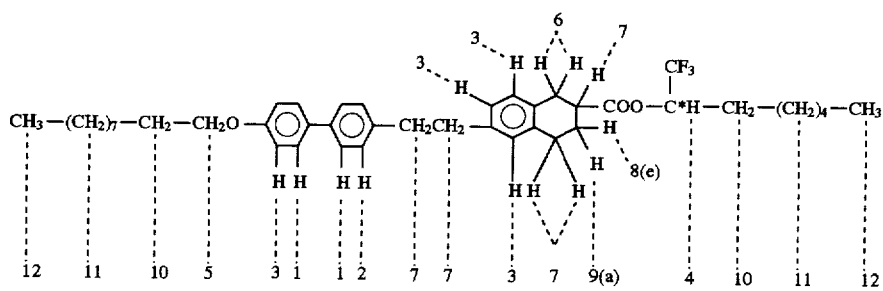

In this formula, (e) represents an equatorial sterio conformation, (a) represents an axial steric conformation, and the numbers 1 to 12 showing hydrogen atoms corresponding to the peaks in FIG. 55.

Figure 56:
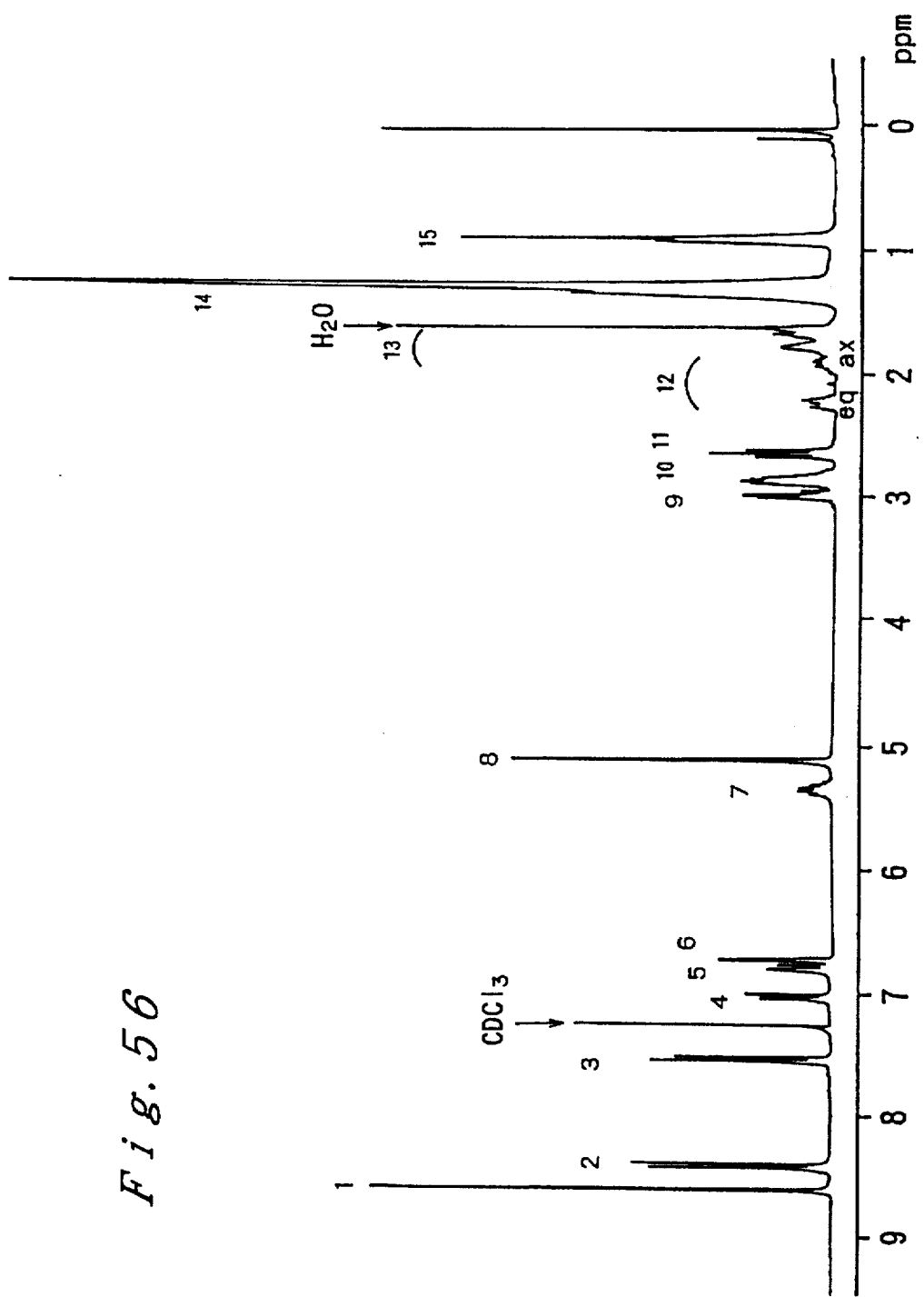
FIG. 56 shows ¹H-NMR spectrum of 6-[(4-(5-decyl-2-pyrimidyl)phenylmethoxy)]-1,2,3,4-tetrahydro-2-naphthalenecarboxylic acid (R)-1-trifluoromethylheptyl ester. [Exemplified compound (507)]

¹H-NMR of 6-[(4-(5-decyl-2-pyrimidyl)phenylmethoxy)]-1,2,3,4-tetrahydro-2-naphthalenecarboxylic acid (R)-1-trifluoromethylheptyl ester [Examplified compound (507)] is shown in FIG. 56.

Figure 58:
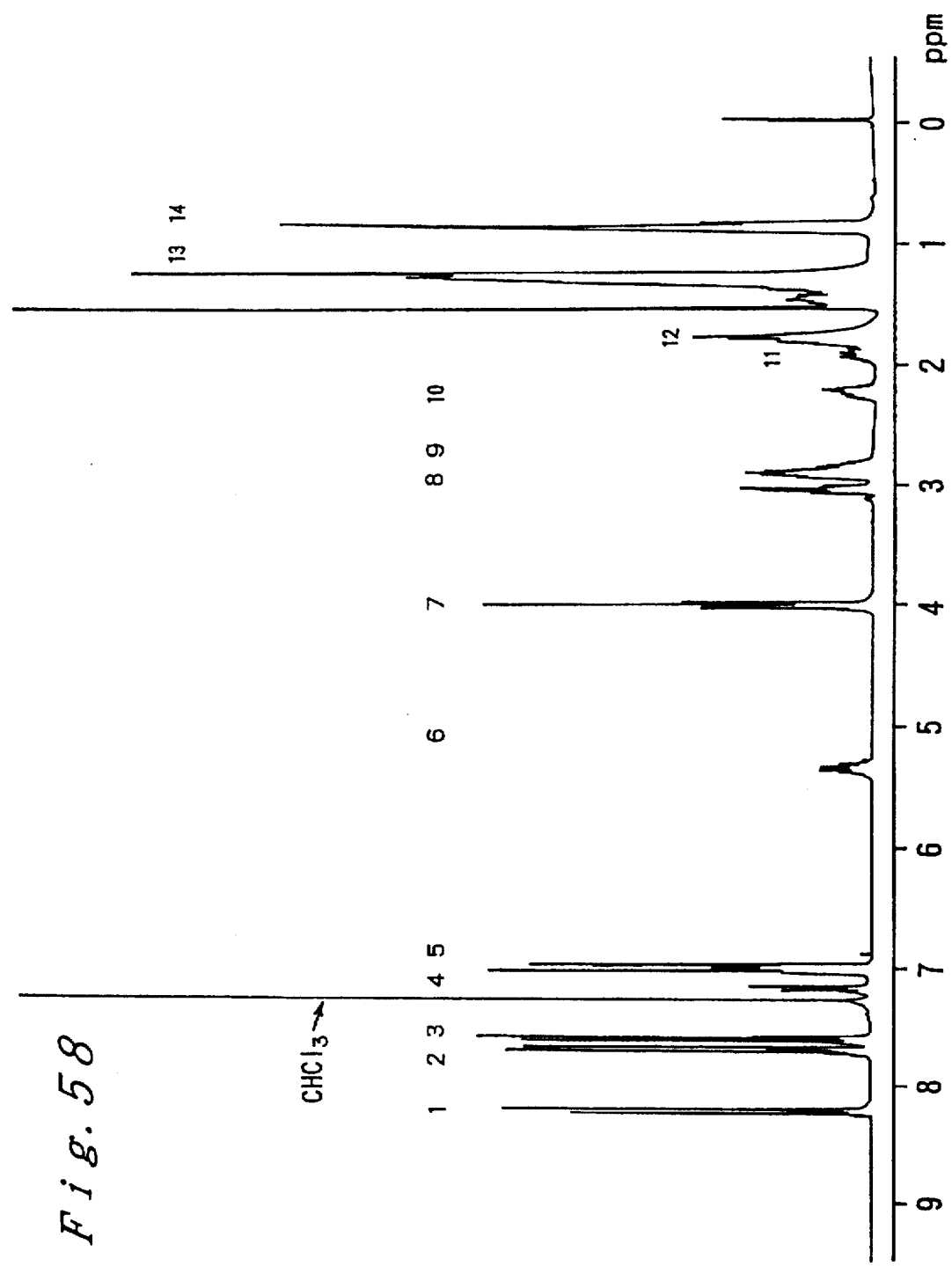
FIG. 58 shows ¹H-NMR spectrum of 6-[(4'-decyloxy-4-biphenyl)carbonyloxy]-1,2,3,4-tetrahydro-2-naphthalenecarboxylic acid (R)-1-trifluoromethylhexyl ester. [Exemplified compound (387)]

2,3,4-tetrahydro-2-naphthalenecarboxylic acid (R)-1-trifluoromethylhexyl ester [Examplified compound (387)] is shown in FIG. 58.

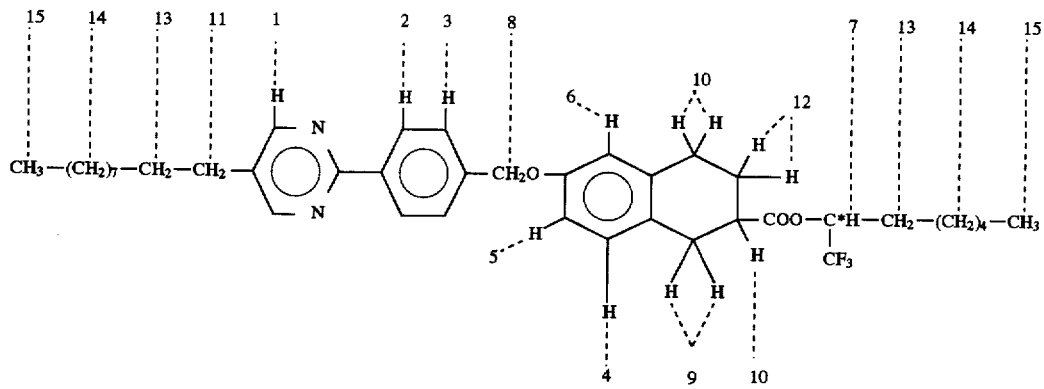

In this formula, the numbers 1 to 15 showing hydrogen atoms corresponding to the peaks in FIG. 56.

Figure 57:
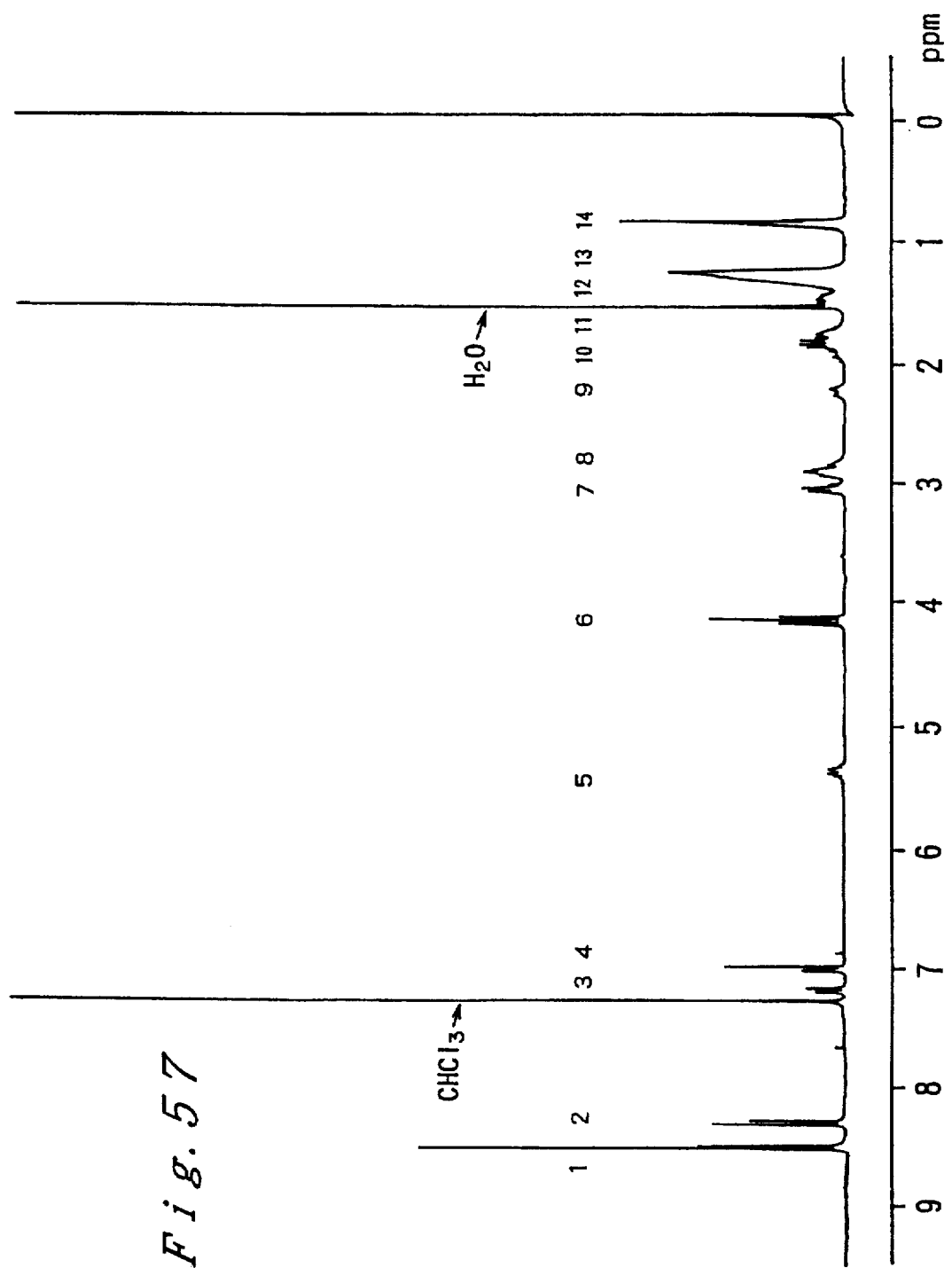
FIG. 57 shows ¹H-NMR spectrum of 6-[4-(5-octyloxy-2-pyrimidyl)benzoyloxy]-1,2,3,4-tetrahydro-2-naphthalenecarboxylic acid (R)-1-trifluoromethylheptyl ester. [Exemplified compound (313)]

¹H-NMR of 6-[4-(5-octyloxy-2-pyrimidyl)benzoyloxy]-1,2,3,4-tetrahydro-2-naphthalenecarboxylic acid (R)-1-trifluoromethylheptyl ester [Examplified compound (313)] is shown in FIG. 57.

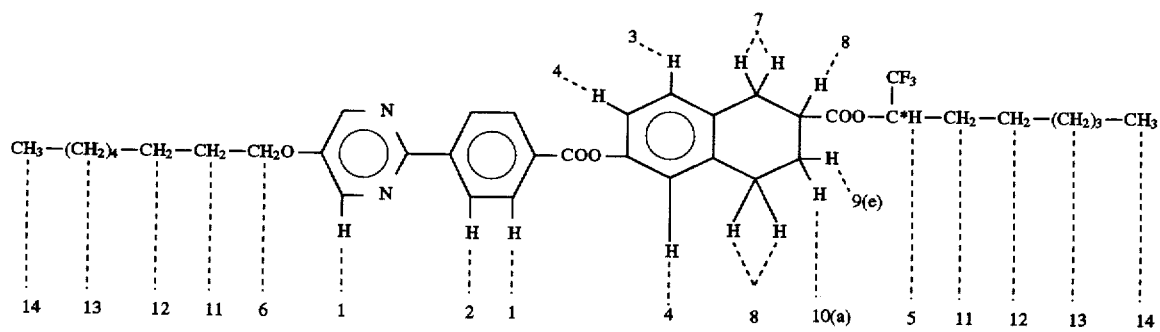

In this formula, (e) represents an equatorial sterio conformation, (a) represents an axial steric conformation, and the numbers 1 to 14 showing hydrogen atoms corresponding to the peaks in FIG. 57.

¹H-NMR of 6-[(4'-decyloxy-4-biphenyl)carbonyloxy]-1,

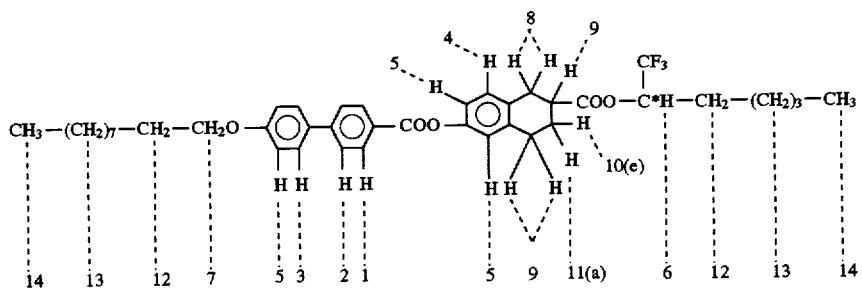

In this formula, (e) represents an equatorial sterio conformation, (a) represents an axial steric conformation, and the numbers 1 to 14 showing hydrogen atoms corresponding to the peaks in FIG. 58.

Figure 59:
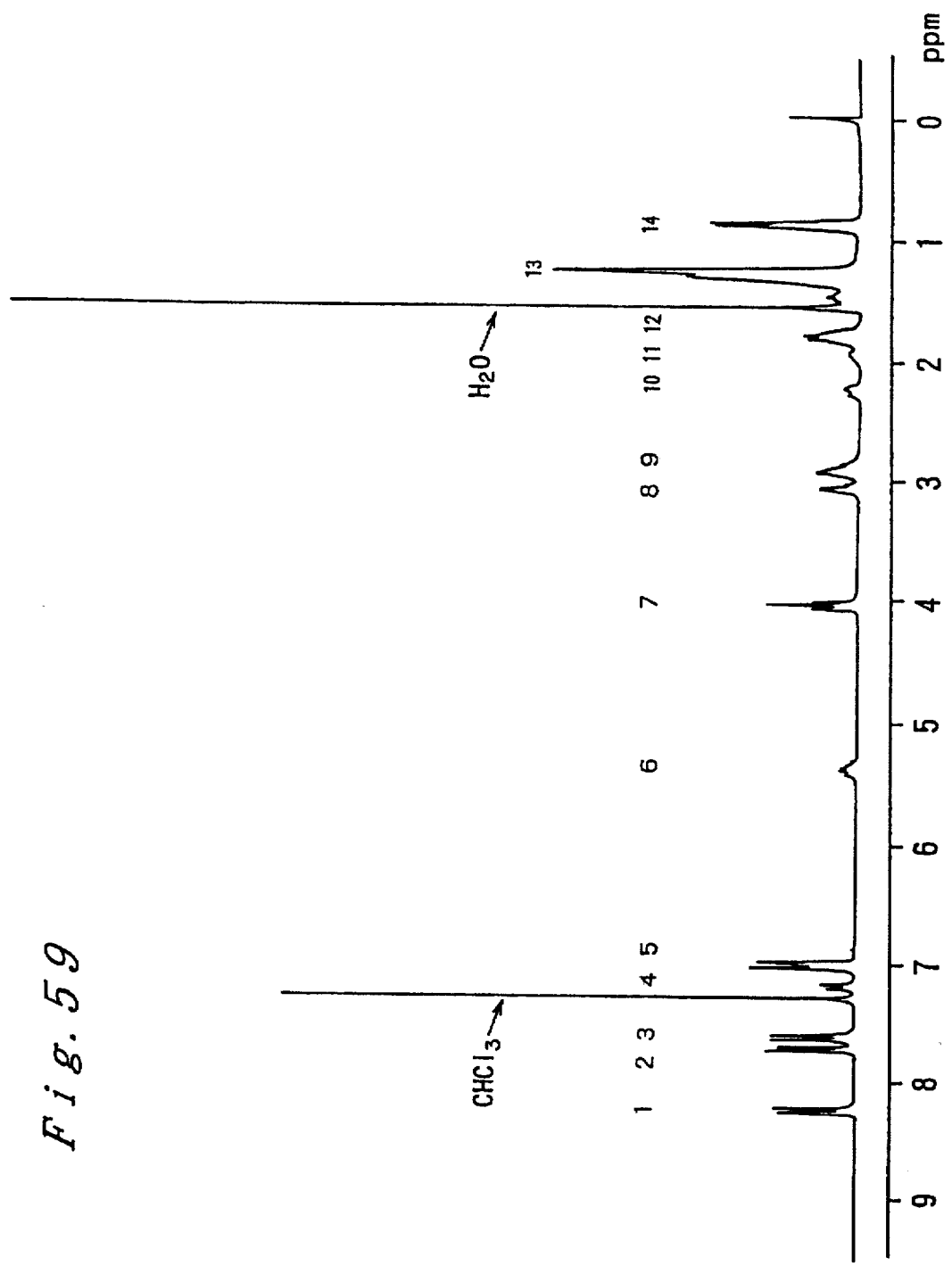
FIG. 59 shows ¹H-NMR spectrum of 6-[(4'-undecyloxy-4-biphenyl)carbonyloxy]-1,2,3,4-tetrahydro-2-naphthalenecarboxylic acid (R)-1-trifluoromethylhexyl ester. [Exemplified compound (388)]

¹H-NMR of 6-[(4'-undecyloxy-4-biphenyl)carbonyloxy]-1,2,3,4-tetrahydro-2-naphthalenecarboxylic acid (R)-1-trifluoromethylhexyl ester [Examplified compound (388)] is shown in FIG. 59.

Figure 61:
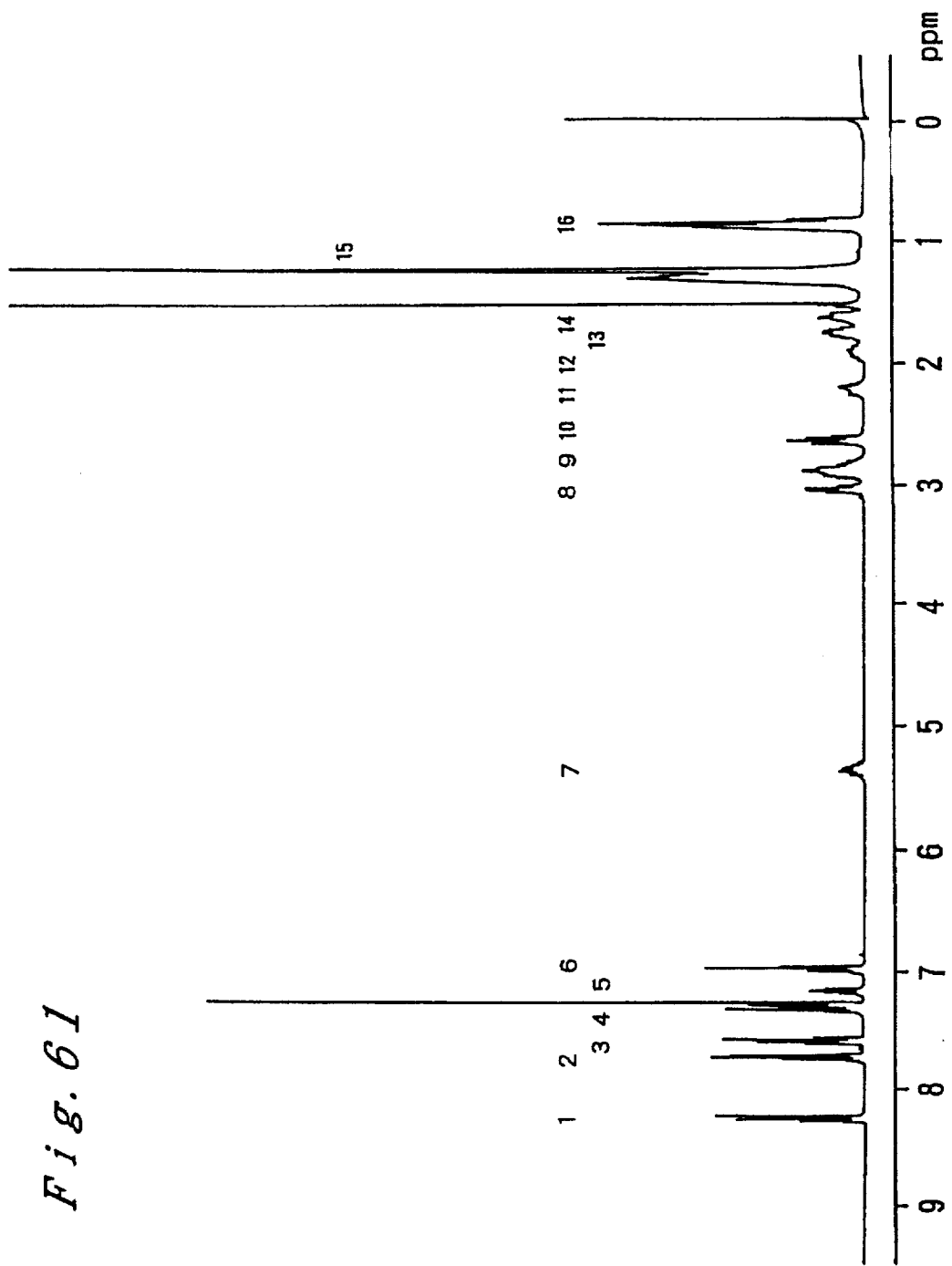
FIG. 61 shows ¹H-NMR spectrum of 6-[(4'-dodecyl-4-biphenyl)carbonyloxy]-1,2,3,4-tetrahydro-2-naphthalenecarboxylic acid (R)-1-trifluoromethylhexyl ester. [Exemplified compound (397)]

¹H-NMR of 6-[(4'-dodecyl-4-biphenyl)carbonyloxy]-1,2,3,4-tetrahydro-2-naphthalenecarboxylic acid (R)-1-trifluoromethylhexyl ester [Examplified compound (397)] is shown in FIG. 61.

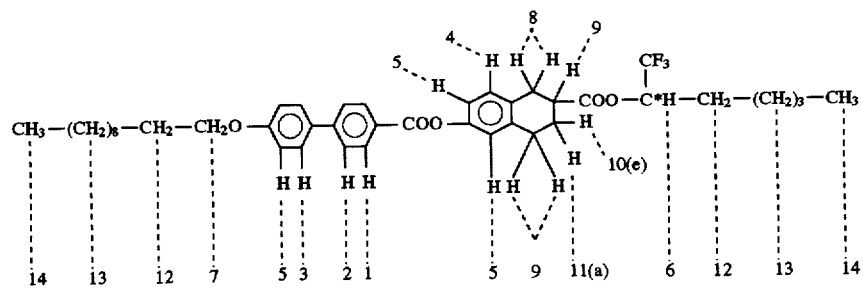

In this formula, (e) represents an equatorial sterio conformation, (a) represents an axial steric conformation, and the numbers 1 to 14 showing hydrogen atoms corresponding to the peaks in FIG. 59.

Figure 60:
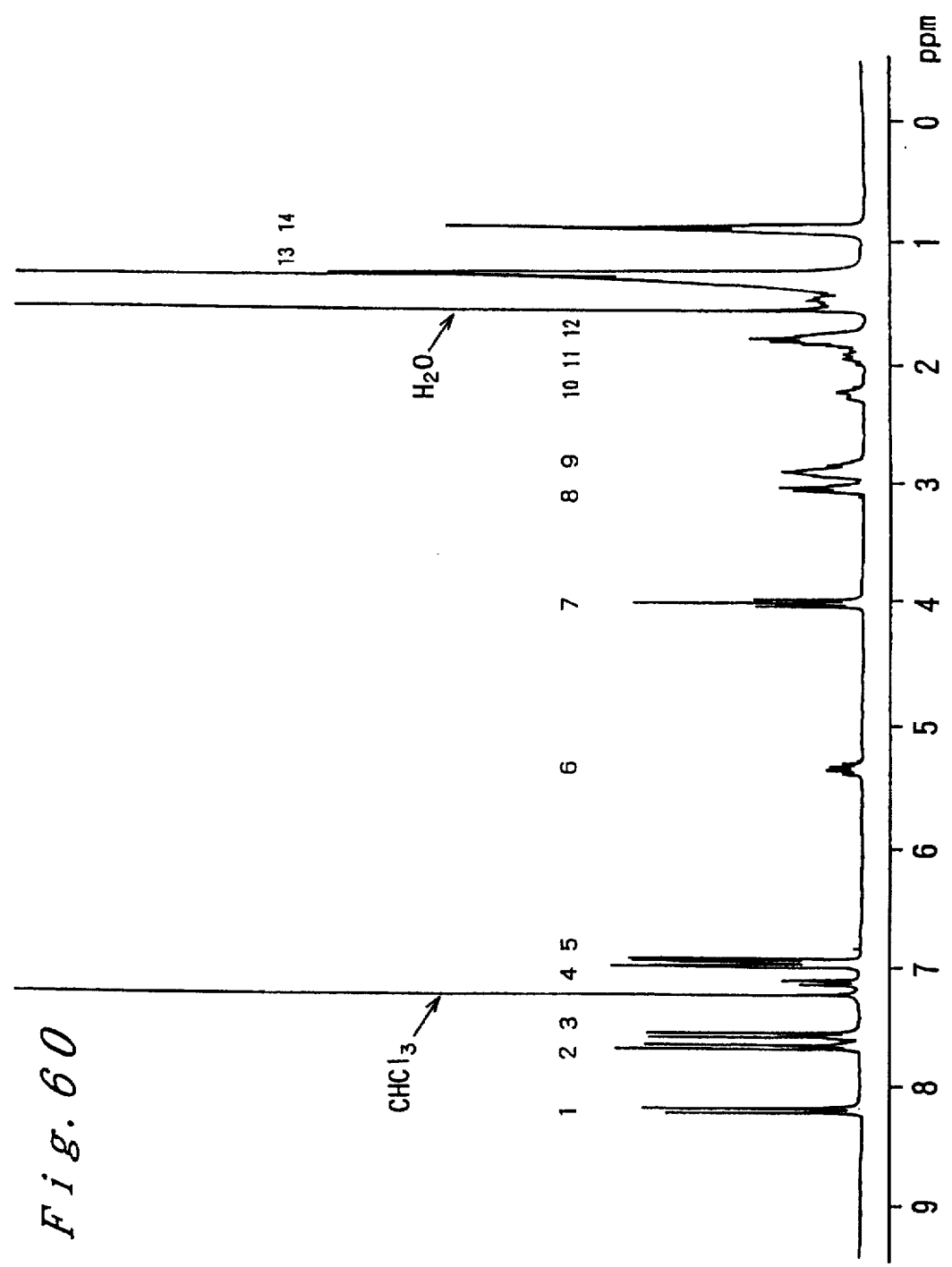
FIG. 60 shows ¹H-NMR spectrum of 6-[(4'-dodecyloxy-4-biphenyl)carbonyloxy]-1,2,3,4-tetrahydro-2-naphthalenecarboxylic acid (R)-1-trifluoromethylhexyl ester. [Exemplified compound (389)]

¹H-NMR of 6-[(4'-dodecyloxy-4-biphenyl)carbonyloxy]-1,2,3,4-tetrahydro-2-naphthalenecarboxylic acid (R)-1-trifluoromethylhexyl ester [Examplified compound (389)] is shown in FIG. 60.

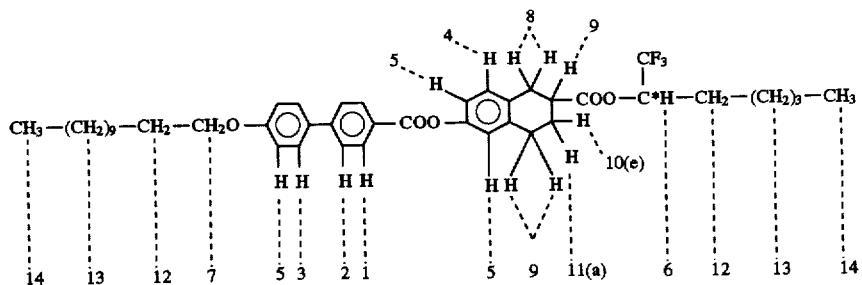

In this formula, (e) represents an equatorial sterio conformation, (a) represents an axial steric conformation, and the numbers 1 to 14 showing hydrogen atoms corresponding to the peaks in FIG. 60.

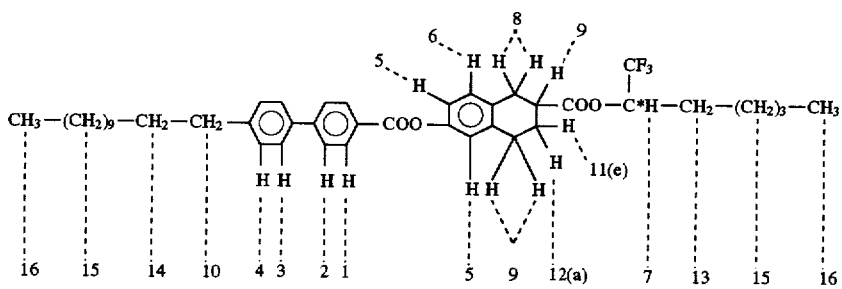

In this formula, (e) represents an equatorial sterio conformation, (a) represents an axial steric conformation, and the numbers 1 to 16 showing hydrogen atoms corresponding to the peaks in FIG. 61.

Figure 62:
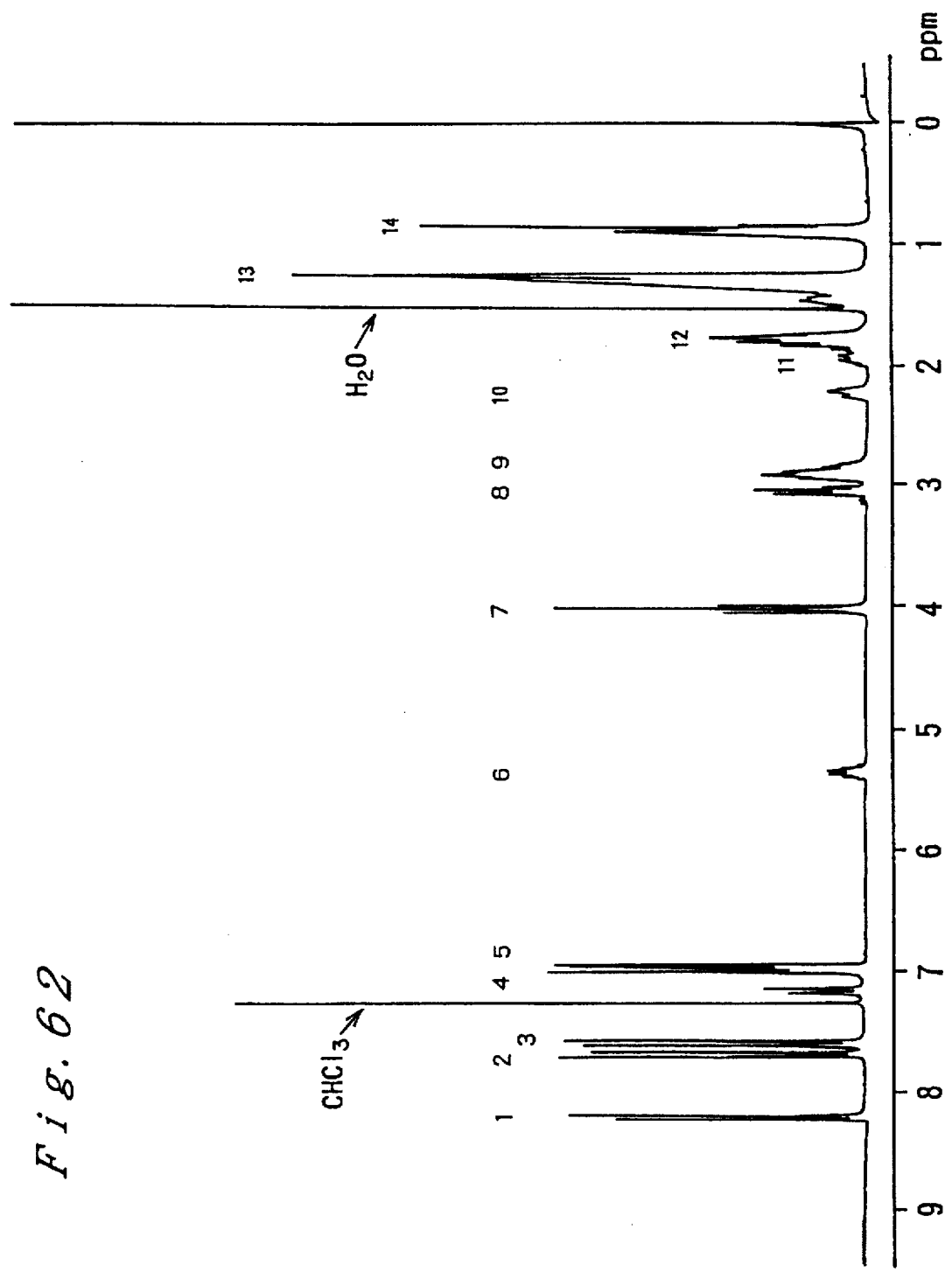
FIG. 62 shows ¹H-NMR spectrum of 6-[(4'-decyloxy-4-biphenyl)carbonyloxy]-1,2,3,4-tetrahydro-2-naphthalenecarboxylic acid (R)-1-trifluoromethylpentyl ester. [Exemplified compound (403)]

$^1$H-NMR of 6-[(4'-decyloxy-4-biphenyl)carbonyloxy]-1,2,3,4-tetrahydro-2-naphthalenecarboxylic acid (R)-1-trifluoromethylpentyl ester [Examplified compound (403)] is shown in FIG. 62.

Figure 64:
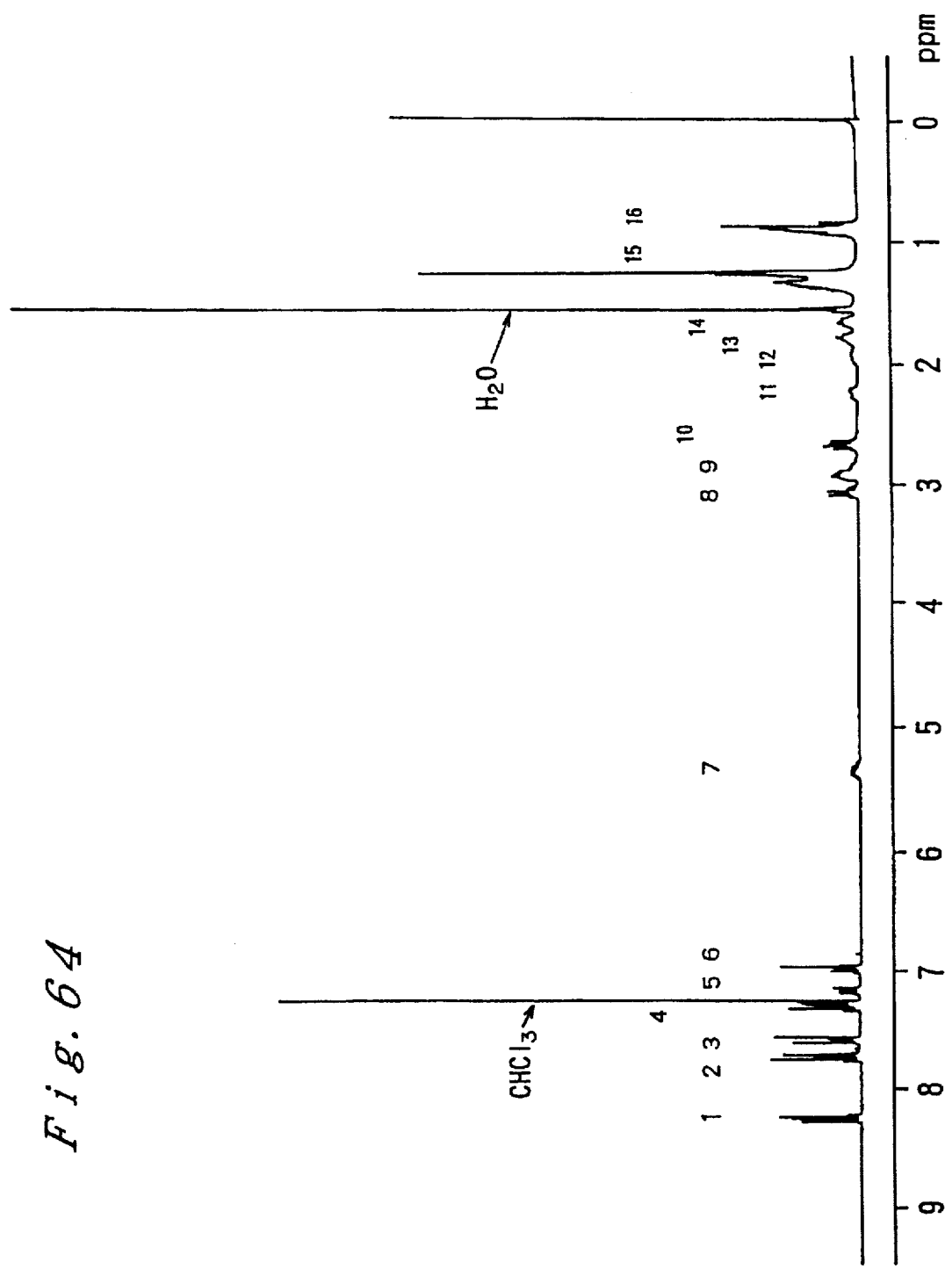
FIG. 64 shows ¹H-NMR spectrum of 6-[(4'-dodecyl-4-biphenyl)carbonyloxy]-1,2,3,4-tetrahydro-2-naphthalenecarboxylic acid (R)-1-trifluoromethylpentyl ester. [Exemplified compound (413)]

$^1$H-NMR of 6-[(4'-dodecyl-4-biphenyl)carbonyloxy]-1,2,3,4-tetrahydro-2-naphthalenecarboxylic acid (R)-1-trifluoromethylpentyl ester [Examplified compound (413)] is shown in FIG. 64.

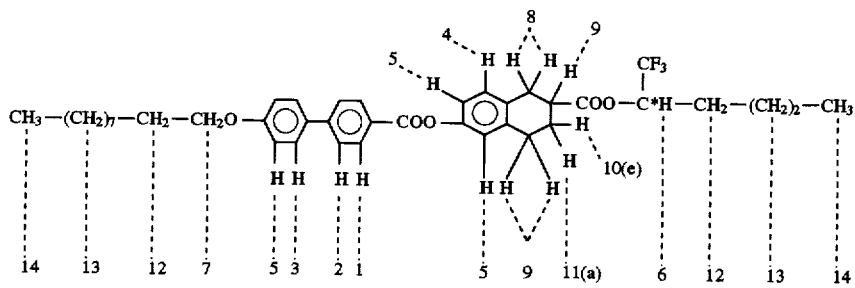

In this formula, (e) represents an equatorial sterio conformation, (a) represents an axial steric conformation, and the numbers 1 to 14 showing hydrogen atoms corresponding to the peaks in FIG. 62.

Figure 63:
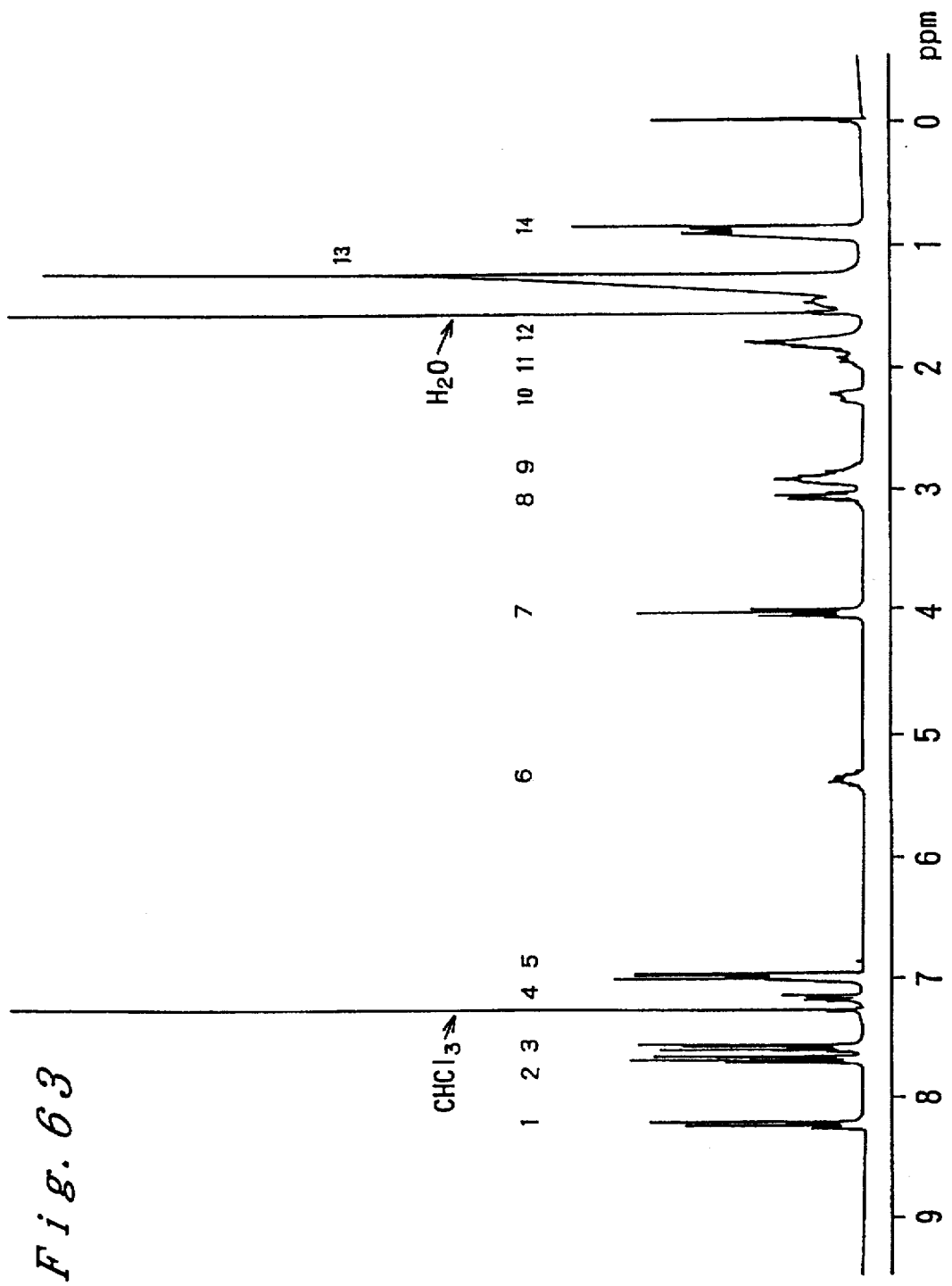
FIG. 63 shows ¹H-NMR spectrum of 6-[(4'-dodecyloxy-4-biphenyl)carbonyloxy-1,2,3,4-tetrahydro-2-naphthalenecarboxylic acid (R)-1-trifluoromethylpentyl ester. [Exemplified compound(405)]

$^1$H-NMR of 6-[(4'-dodecyloxy-4-biphenyl)carbonyloxy-1,2,3,4-tetrahydro-2-naphthalenecarboxylic acid (R)-1-trifluoromethylpentyl ester [Examplified compound(405)] is shown in FIG. 63.

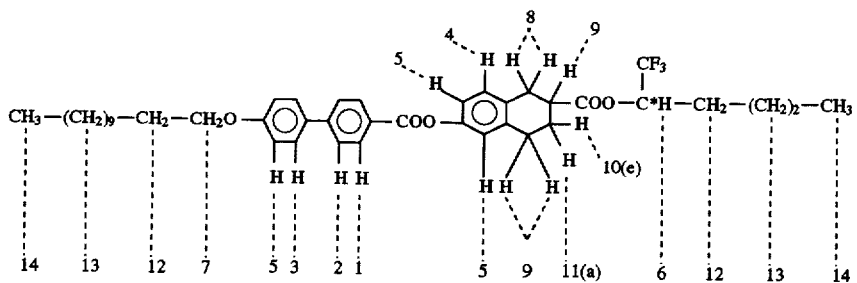

In this formula, (e) represents an equatorial sterio conformation, (a) represents an axial steric conformation, and the numbers 1 to 14 showing hydrogen atoms corresponding to the peaks in FIG. 63.

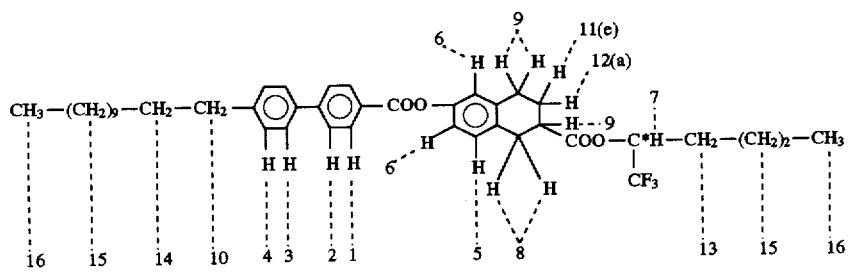

In this formula, (e) represents an equatorial sterio conformation, (a) represents an axial steric conformation, and the numbers 1 to 16 showing hydrogen atoms corresponding to the peaks in FIG. 64.

Figure 65:
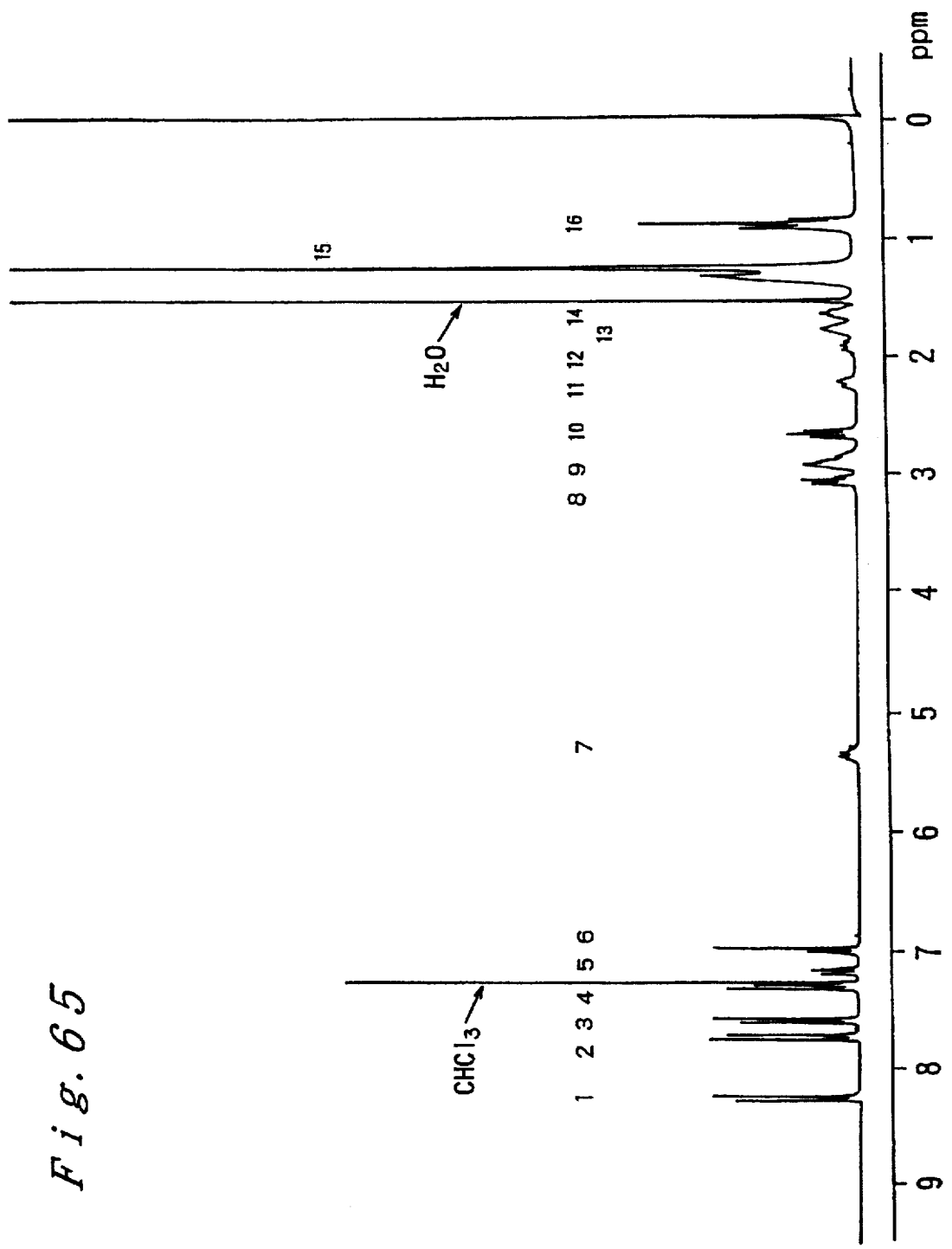
FIG. 65 shows ¹H-NMR spectrum of 6-[(4'-tetradecyl-4-biphenyl)carbonyloxy]-1,2,3,4-tetrahydro-2-naphthalenecarboxylic acid (R)-1-trifluoromethylpentyl ester. [Exemplified compound (414)]

$^1$H-NMR of 6-[(4'-tetradecyl-4-biphenyl)carbonyloxy]-1, 2,3,4-tetrahydro-2-naphthalenecarboxylic acid (R)-1-trifluoromethylpentyl ester [Examplified compound (414)] is shown in FIG. 65.

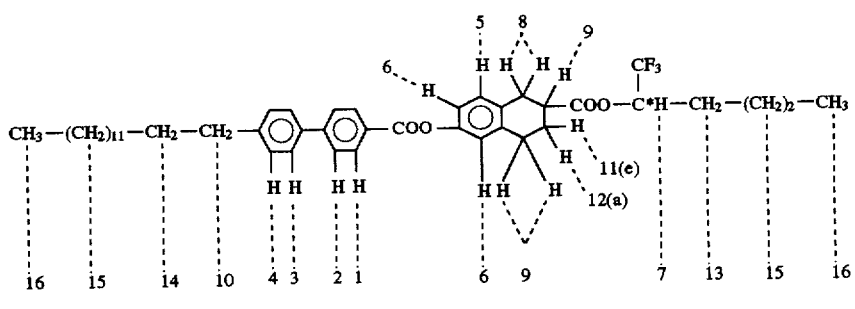

In this formula, (e) represents an equatorial sterio conformation, (a) represents an axial steric conformation, and the numbers 1 to 16 showing hydrogen atoms corresponding to the peaks in FIG. 65.

Next, the second carboxylate compounds of the invention are illustrated hereinafter.

The second carboxylate compounds of the invention may be represented by the following formula [III] or [IV].

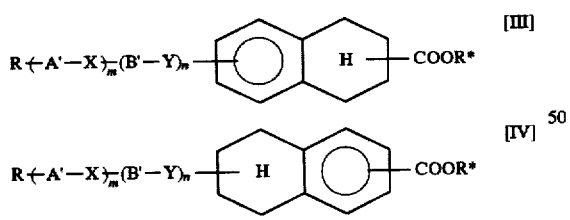

The 1,2,3,4-tetrahydro-naphthyl group constituting the main skeleton of the formula [III] includes 1,2,3,4-tetrahydro-1,5-naphthyl, 1,2,3,4-tetrahydro-1,6-naphthyl, 1,2,3,4-tetrahydro-2,6-naphthyl and 1,2,3,4-tetrahydro-1,7-naphthyl.

Particularly, for the use of the carboxylate compounds of the invention as liquid crystal materials, it is preferable that the molecule of the compound is linear as a whole. On that account, 1,2,3,4-tetrahydro-2,6-naphthyl is particularly preferred.

In the above formula [III] or [IV], R, R*, X and Y are as defined in the formula [I] or [II], provided that R may further be a hydrocarbon group having —OCO— wherein at least a part of hydrogen atoms constituting said hydrocarbon group may be substituted with halogen atoms. Such hydrocarbon group includes $C_2H_5$—OCO—$CH_2$—$C^*H(CF_3)$— and $C_2H_5$—OCO—$CH_2$—$CH(CF_3)$—.

In the above formula [III] or [IV], A' and B' represent independently a group selected from the group consisting of

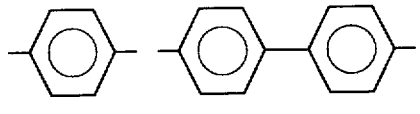

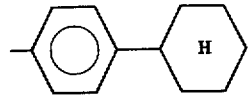

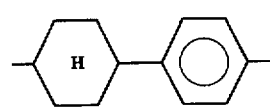

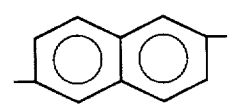

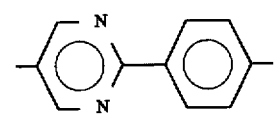

and

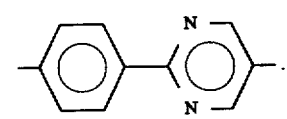

Further, in the formula [III] or [IV], m is 1 or 2, n is 0 to 2, and m+n≧2. Particularly, for the use of the carboxylate compounds of the formula [III] or [IV] as liquid crystal materials, n is preferably 0 or 1.

Examples of the compounds represented by the formula [III] are shown in the following Tables 3-1 to 3-8.

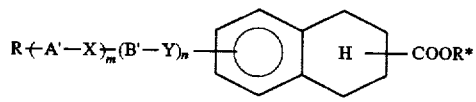

[III]
R+A'—X)ₘ(B'—Y)ₙ—⬡H—COOR*

TABLE 3-1

| Compound Number | R | A' | X | m | B' | Y | n | R* | Exam. No. |
|---|---|---|---|---|---|---|---|---|---|
| 601 | $C_7H_{15}O-$ | -⬡- | -COO- | 2 | — | — | 0 | $-C^*H(CF_3)-C_6H_{13}$ | |
| 602 | $C_8H_{17}O-$ | " | " | 2 | — | — | 0 | " | |
| 603 | $C_9H_{19}O-$ | " | " | 2 | — | — | 0 | " | |
| 604 | $C_{10}H_{21}O-$ | " | " | 2 | — | — | 0 | " | |
| 605 | $C_{11}H_{23}O-$ | " | " | 2 | — | — | 0 | " | 23 |
| 606 | $C_{12}H_{25}O-$ | " | " | 2 | — | — | 0 | " | |
| 607 | $C_{14}H_{29}O-$ | " | " | 2 | — | — | 0 | " | |
| 608 | $C_{16}H_{33}O-$ | " | " | 2 | — | — | 0 | " | |
| 609 | $C_7H_{15}-$ | -⬡- | -COO- | 2 | — | — | 0 | $-C^*H(CF_3)-C_6H_{13}$ | |
| 610 | $C_8H_{17}-$ | " | " | 2 | — | — | 0 | " | |
| 611 | $C_9H_{19}-$ | " | " | 2 | — | — | 0 | " | |
| 612 | $C_{10}H_{21}-$ | " | " | 2 | — | — | 0 | " | |
| 613 | $C_{11}H_{23}-$ | " | " | 2 | — | — | 0 | " | |
| 614 | $C_{12}H_{25}-$ | " | " | 2 | — | — | 0 | " | |
| 615 | $C_{14}H_{29}-$ | " | " | 2 | — | — | 0 | " | |
| 616 | $C_{16}H_{33}-$ | " | " | 2 | — | — | 0 | " | |
| 617 | $C_{10}H_{21}O-$ | -⬡- | -COO- | 2 | — | — | 0 | $-C^*H(CF_3)-C_6H_{13}$ | |
| 618 | $C_{10}H_{21}O-$ | " | " | 2 | — | — | 0 | $-C^*H(CH_3)-C_6H_{13}$ | |
| 619 | $C_{10}H_{21}O-$ | " | " | 2 | — | — | 0 | $-C^*H(C_2H_5)-C_5H_{11}$ | |
| 620 | $C_{10}H_{21}O-$ | " | " | 2 | — | — | 0 | $-C^*H(C_2H_5)-C_6H_{11}$ | |
| 621 | $C_{10}H_{21}O-$ | " | " | 2 | — | — | 0 | $-CH_2-C^*H(CH_3)-C_2H_5$ | |
| 622 | $C_{10}H_{21}O-$ | " | " | 2 | — | — | 0 | $-(CH_2)_3-C^*H(CH_3)-C_2H_5$ | |
| 623 | $C_{10}H_{21}O-$ | " | " | 2 | — | — | 0 | $-C^*H(CF_3)-CH_2-COO-C_2H_5$ | |

TABLE 3-2

| Compound Number | R | A' | X | m | B' | Y | n | R* | Exam. No. |
|---|---|---|---|---|---|---|---|---|---|
| 624 | $C_7H_{15}O-$ | -⬡- | -OCO- | 1 | -⬡- | -COO- | 1 | $-C^*H(CF_3)-C_6H_{13}$ | |
| 625 | $C_8H_{17}O-$ | " | " | 1 | " | " | 1 | " | |
| 626 | $C_9H_{19}O-$ | " | " | 1 | " | " | 1 | " | |
| 627 | $C_{10}H_{21}O-$ | " | " | 1 | " | " | 1 | " | |
| 628 | $C_{11}H_{23}O-$ | " | " | 1 | " | " | 1 | " | |
| 629 | $C_{12}H_{25}O-$ | " | " | 1 | " | " | 1 | " | |
| 630 | $C_{14}H_{29}O-$ | " | " | 1 | " | " | 1 | " | |
| 631 | $C_{16}H_{33}O-$ | " | " | 1 | " | " | 1 | " | |

TABLE 3-2-continued

| Compound Number | R | A' | X | m | B' | Y | n | R* | Exam. No. |
|---|---|---|---|---|---|---|---|---|---|
| 632 | $C_7H_{15}O-$ |  | $-CH_2O-$ | 1 |  | $-COO-$ | 1 | $-C*H(CF_3)-C_6H_{13}$ | |
| 633 | $C_8H_{17}O-$ | " | " | 1 | " | " | 1 | " | |
| 634 | $C_9H_{19}O-$ | " | " | 1 | " | " | 1 | " | |
| 635 | $C_{10}H_{21}O-$ | " | " | 1 | " | " | 1 | " | |
| 636 | $C_{11}H_{23}O-$ | " | " | 1 | " | " | 1 | " | |
| 637 | $C_{12}H_{25}O-$ | " | " | 1 | " | " | 1 | " | |
| 638 | $C_{14}H_{29}O-$ | " | " | 1 | " | " | 1 | " | |
| 639 | $C_{16}H_{33}O-$ | " | " | 1 | " | " | 1 | " | |
| 640 | $C_7H_{15}O-$ |  | $-OCH_2-$ | 1 |  | $-COO-$ | 1 | $-C*H(CF_3)-C_6H_{13}$ | |
| 641 | $C_8H_{17}O-$ | " | " | 1 | " | " | 1 | " | |
| 642 | $C_9H_{19}O-$ | " | " | 1 | " | " | 1 | " | |
| 643 | $C_{10}H_{21}O-$ | " | " | 1 | " | " | 1 | " | |
| 644 | $C_{11}H_{23}O-$ | " | " | 1 | " | " | 1 | " | |
| 645 | $C_{12}H_{25}O-$ | " | " | 1 | " | " | 1 | " | |
| 646 | $C_{14}H_{29}O-$ | " | " | 1 | " | " | 1 | " | |
| 647 | $C_{16}H_{33}O-$ | " | " | 1 | " | " | 1 | " | |

TABLE 3-3

| Compound Number | R | A' | X | m | B' | Y | n | R* | Exam. No. |
|---|---|---|---|---|---|---|---|---|---|
| 648 | $C_7H_{15}O-$ | 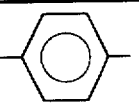 | $-CH_2-CH_2-$ | 1 |  | $-COO-$ | 1 | $-C*H(CF_3)-C_6H_{13}$ | |
| 649 | $C_8H_{17}O-$ | " | " | 1 | " | " | 1 | " | |
| 650 | $C_9H_{19}O-$ | " | " | 1 | " | " | 1 | " | 43 |
| 651 | $C_{10}H_{21}O-$ | " | " | 1 | " | " | 1 | " | |
| 652 | $C_{11}H_{23}O-$ | " | " | 1 | " | " | 1 | " | |
| 653 | $C_{12}H_{25}O-$ | " | " | 1 | " | " | 1 | " | |
| 654 | $C_{14}H_{29}O-$ | " | " | 1 | " | " | 1 | " | |
| 655 | $C_{16}H_{33}O-$ | " | " | 1 | " | " | 1 | " | |
| 656 | $C_7H_{15}O-$ | " | $-COO-$ | 1 | " | $-OCO-$ | 1 | " | |
| 657 | $C_8H_{17}O-$ | " | " | 1 | " | " | 1 | " | |
| 658 | $C_9H_{19}O-$ | " | " | 1 | " | " | 1 | " | |
| 659 | $C_{10}H_{21}O-$ | " | " | 1 | " | " | 1 | " | |
| 660 | $C_{11}H_{23}O-$ | " | " | 1 | " | " | 1 | " | |
| 661 | $C_{12}H_{25}O-$ | " | " | 1 | " | " | 1 | " | |
| 662 | $C_{14}H_{29}O-$ | " | " | 1 | " | " | 1 | " | |
| 663 | $C_{16}H_{33}O-$ | " | " | 1 | " | " | 1 | " | |
| 664 | $C_7H_{15}O-$ | " | " | 1 | " | $-CH_2O-$ | 1 | " | |
| 665 | $C_8H_{17}O-$ | " | " | 1 | " | " | 1 | " | |
| 666 | $C_9H_{19}O-$ | " | " | 1 | " | " | 1 | " | |
| 667 | $C_{10}H_{21}O-$ | " | " | 1 | " | " | 1 | " | |
| 668 | $C_{11}H_{23}O-$ | " | " | 1 | " | " | 1 | " | |
| 669 | $C_{12}H_{25}O-$ | " | " | 1 | " | " | 1 | " | |
| 670 | $C_{14}H_{29}O-$ | " | " | 1 | " | " | 1 | " | |
| 671 | $C_{16}H_{33}O-$ | " | " | 1 | " | " | 1 | " | |

TABLE 3-4

| Compound Number | R | A' | X | m | B' | Y | n | R* | Exam. No. |
|---|---|---|---|---|---|---|---|---|---|
| 672 | $C_7H_{15}O-$ | biphenyl | $-COO-$ | 1 | phenyl | $-COO-$ | 1 | $-C^*H(CF_3)-C_6H_{13}$ | |
| 673 | $C_8H_{17}O-$ | " | " | 1 | " | " | 1 | " | |
| 674 | $C_9H_{19}O-$ | " | " | 1 | " | " | 1 | " | |
| 675 | $C_{10}H_{21}O-$ | " | " | 1 | " | " | 1 | " | |
| 676 | $C_{11}H_{23}O-$ | " | " | 1 | " | " | 1 | " | |
| 677 | $C_{12}H_{25}O-$ | " | " | 1 | " | " | 1 | " | |
| 678 | $C_{14}H_{29}O-$ | " | " | 1 | " | " | 1 | " | |
| 679 | $C_{16}H_{33}O-$ | " | " | 1 | " | " | 1 | " | |
| 680 | $C_7H_{15}O-$ | phenyl-cyclohexyl (H) | $-COO-$ | 1 | phenyl | $-COO-$ | 1 | $-C^*H(CF_3)-C_6H_{13}$ | |
| 681 | $C_8H_{17}O-$ | " | " | 1 | " | " | 1 | " | |
| 682 | $C_9H_{19}O-$ | " | " | 1 | " | " | 1 | " | |
| 683 | $C_{10}H_{21}O-$ | " | " | 1 | " | " | 1 | " | |
| 684 | $C_{11}H_{23}O-$ | " | " | 1 | " | " | 1 | " | |
| 685 | $C_{12}H_{25}O-$ | " | " | 1 | " | " | 1 | " | |
| 686 | $C_{14}H_{29}O-$ | " | " | 1 | " | " | 1 | " | |
| 687 | $C_{16}H_{33}O-$ | " | " | 1 | " | " | 1 | " | |
| 688 | $C_7H_{15}O-$ | naphthyl | $-COO-$ | 1 | phenyl | $-COO-$ | 1 | $-C^*H(CF_3)-C_6H_{13}$ | |
| 689 | $C_8H_{17}O-$ | " | " | 1 | " | " | 1 | " | |
| 690 | $C_9H_{19}O-$ | " | " | 1 | " | " | 1 | " | |
| 691 | $C_{10}H_{21}O-$ | " | " | 1 | " | " | 1 | " | |
| 692 | $C_{11}H_{23}O-$ | " | " | 1 | " | " | 1 | " | 44 |
| 693 | $C_{12}H_{25}O-$ | " | " | 1 | " | " | 1 | " | |
| 694 | $C_{14}H_{29}O-$ | " | " | 1 | " | " | 1 | " | |
| 695 | $C_{16}H_{33}O-$ | " | " | 1 | " | " | 1 | " | |

TABLE 3-5

| Compound Number | R | A' | X | m | B' | Y | n | R* | Exam. No. |
|---|---|---|---|---|---|---|---|---|---|
| 696 | $C_7H_{15}O-$ | pyrimidinyl-phenyl | $-COO-$ | 1 | phenyl | $-COO-$ | 1 | $-C^*H(CF_3)-C_6H_{13}$ | |
| 697 | $C_8H_{17}O-$ | " | " | 1 | " | " | 1 | " | |
| 698 | $C_9H_{19}O-$ | " | " | 1 | " | " | 1 | " | |
| 699 | $C_{10}H_{21}O-$ | " | " | 1 | " | " | 1 | " | |
| 700 | $C_{11}H_{23}O-$ | " | " | 1 | " | " | 1 | " | |
| 701 | $C_{12}H_{25}O-$ | " | " | 1 | " | " | 1 | " | |
| 702 | $C_{14}H_{29}O-$ | " | " | 1 | " | " | 1 | " | |
| 703 | $C_{16}H_{33}O-$ | " | " | 1 | " | " | 1 | " | |
| 704 | $C_7H_{15}-$ | pyrimidinyl-phenyl | $-COO-$ | 1 | phenyl | $-COO-$ | 1 | $-C^*H(CF_3)-C_6H_{13}$ | |
| 705 | $C_8H_{17}-$ | " | " | 1 | " | " | 1 | " | |
| 706 | $C_9H_{19}-$ | " | " | 1 | " | " | 1 | " | |
| 707 | $C_{10}H_{21}-$ | " | " | 1 | " | " | 1 | " | |
| 708 | $C_{11}H_{23}-$ | " | " | 1 | " | " | 1 | " | |
| 709 | $C_{12}H_{25}-$ | " | " | 1 | " | " | 1 | " | |
| 710 | $C_{14}H_{29}-$ | " | " | 1 | " | " | 1 | " | |
| 711 | $C_{16}H_{33}-$ | " | " | 1 | " | " | 1 | " | |

TABLE 3-5-continued

| Compound Number | R | A' | X | m | B' | Y | n | R* | Exam. No. |
|---|---|---|---|---|---|---|---|---|---|
| 712 | C$_7$H$_{15}$O— | 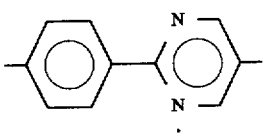 | —COO— | 1 | 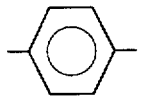 | —COO— | 1 | —C*H(CF$_3$)—C$_6$H$_{13}$ | |
| 713 | C$_8$H$_{17}$O— | " | " | 1 | " | " | 1 | " | |
| 714 | C$_9$H$_{19}$O— | " | " | 1 | " | " | 1 | " | |
| 715 | C$_{10}$H$_{21}$O— | " | " | 1 | " | " | 1 | " | |
| 716 | C$_{11}$H$_{23}$O— | " | " | 1 | " | " | 1 | " | |
| 717 | C$_{12}$H$_{25}$O— | " | " | 1 | " | " | 1 | " | |
| 718 | C$_{14}$H$_{29}$O— | " | " | 1 | " | " | 1 | " | |
| 719 | C$_{16}$H$_{33}$O— | " | " | 1 | " | " | 1 | " | |

TABLE 3-6

| Compound Number | R | A' | X | m | B' | Y | n | R* | Exam. No. |
|---|---|---|---|---|---|---|---|---|---|
| 720 | C$_7$H$_{15}$O— | 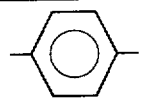 | —COO— | 1 | 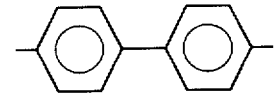 | —COO— | 1 | —C*H(CF$_3$)—C$_6$H$_{13}$ | |
| 721 | C$_8$H$_{17}$O— | " | " | 1 | " | " | 1 | " | |
| 722 | C$_9$H$_{19}$O— | " | " | 1 | " | " | 1 | " | |
| 723 | C$_{10}$H$_{21}$O— | " | " | 1 | " | " | 1 | " | |
| 724 | C$_{11}$H$_{23}$O— | " | " | 1 | " | " | 1 | " | |
| 725 | C$_{12}$H$_{25}$O— | " | " | 1 | " | " | 1 | " | |
| 726 | C$_{14}$H$_{29}$O— | " | " | 1 | " | " | 1 | " | |
| 727 | C$_{16}$H$_{33}$O— | " | " | 1 | " | " | 1 | " | |
| 728 | C$_7$H$_{15}$O— | 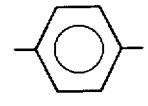 | —COO— | 1 | 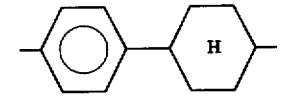 | —COO— | 1 | —C*H(CF$_3$)—C$_6$H$_{13}$ | |
| 729 | C$_8$H$_{17}$O— | " | " | 1 | " | " | 1 | " | |
| 730 | C$_9$H$_{19}$O— | " | " | 1 | " | " | 1 | " | |
| 731 | C$_{10}$H$_{21}$O— | " | " | 1 | " | " | 1 | " | |
| 732 | C$_{11}$H$_{23}$O— | " | " | 1 | " | " | 1 | " | |
| 733 | C$_{12}$H$_{25}$O— | " | " | 1 | " | " | 1 | " | |
| 734 | C$_{14}$H$_{29}$O— | " | " | 1 | " | " | 1 | " | |
| 735 | C$_{16}$H$_{33}$O— | " | " | 1 | " | " | 1 | " | |
| 736 | C$_7$H$_{15}$O— | 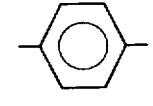 | —COO— | 1 | 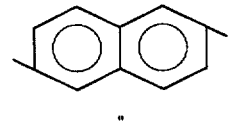 | —COO— | 1 | —C*H(CF$_3$)—C$_6$H$_{13}$ | |
| 737 | C$_8$H$_{17}$O— | " | " | 1 | " | " | 1 | " | |
| 738 | C$_9$H$_{19}$O— | " | " | 1 | " | " | 1 | " | |
| 739 | C$_{10}$H$_{21}$O— | " | " | 1 | " | " | 1 | " | |
| 740 | C$_{11}$H$_{23}$O— | " | " | 1 | " | " | 1 | " | |
| 741 | C$_{12}$H$_{25}$O— | " | " | 1 | " | " | 1 | " | |
| 742 | C$_{14}$H$_{29}$O— | " | " | 1 | " | " | 1 | " | |
| 743 | C$_{16}$H$_{33}$O— | " | " | 1 | " | " | 1 | " | |

TABLE 3-7

| Com. No. | R | A' | X | m | B' | Y | n | R* | Exam. No. |
|---|---|---|---|---|---|---|---|---|---|
| 744 | C$_6$H$_{13}$—C*H(CF$_3$)O— | 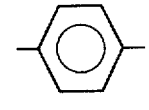 | —COO— | 2 | — | — | 0 | —C*H(CF$_3$)—C$_6$H$_{13}$ | |

TABLE 3-7-continued

| Com. No. | R | A' | X | m | B' | Y | n | R* | Exam. No. |
|---|---|---|---|---|---|---|---|---|---|
| 745 | $C_6H_{13}-C^*H(CH_3)O-$ | " | " | 2 | — | — | 0 | " | 24 |
| 746 | $C_5H_{11}-C^*H(C_2H_5)O-$ | " | " | 2 | — | — | 0 | " | |
| 747 | $C_6H_{13}-C^*H(C_2H_5)O-$ | " | " | 2 | — | — | 0 | " | |
| 748 | $C_2H_5-C^*H(CH_3)-CH_2O-$ | " | " | 2 | — | — | 0 | " | |
| 749 | $C_2H_5-C^*H(CH_3)-(CH_2)_3O-$ | " | " | 2 | — | — | 0 | " | |
| 750 | $C_2H_5-OCO-CH_2-C^*H(CF_3)O-$ | " | " | 2 | — | — | 0 | " | |
| 751 | $C_6H_{13}-CH(CF_3)O-$ |  | $-COO-$ | 2 | — | — | 0 | $-C^*H(CF_3)-C_6H_{13}$ | |
| 752 | $C_6H_{13}-CH(CH_3)O-$ | " | " | 2 | — | — | 0 | " | |
| 753 | $C_5H_{11}-CH(C_2H_5)O-$ | " | " | 2 | — | — | 0 | " | |
| 754 | $C_6H_{13}-CH(C_2H_5)O-$ | " | " | 2 | — | — | 0 | " | |
| 755 | $C_2H_5-CH(CH_3)-CH_2O-$ | " | " | 2 | — | — | 0 | " | |
| 756 | $C_2H_5-CH(CH_3)-(CH_2)_3O-$ | " | " | 2 | — | — | 0 | " | |
| 757 | $C_2H_5-OCO-CH_2-CH(CF_3)O-$ | " | " | 2 | — | — | 0 | " | |
| 758 | $C_6H_{13}-C^*H(CF_3)O-$ |  | $-COO-$ | 2 | — | — | 0 | $-C^*H(CH_3)-C_6H_{13}$ | |
| 759 | $C_6H_{13}-C^*H(CH_3)O-$ | " | " | 2 | — | — | 0 | " | |
| 760 | $C_5H_{11}-C^*H(C_2H_5)O-$ | " | " | 2 | — | — | 0 | " | |
| 761 | $C_6H_{13}-C^*H(C_2H_5)O-$ | " | " | 2 | — | — | 0 | " | |
| 762 | $C_2H_5-C^*H(CH_3)-CH_2O-$ | " | " | 2 | — | — | 0 | " | |
| 763 | $C_2H_5-C^*H(CH_3)-(CH_2)_3O-$ | " | " | 2 | — | — | 0 | " | |
| 764 | $C_2H_5-OCO-CH_2-C^*H(CF_3)O-$ | " | " | 2 | — | — | 0 | " | |

TABLE 3-8

| Com. No. | R | A' | X | m | B' | Y | n | R* | Exam. No. |
|---|---|---|---|---|---|---|---|---|---|
| 765 | $C_6H_{13}-CH(CF_3)O-$ |  | $-COO-$ | 2 | — | — | 0 | $-C^*H(CH_3)-C_6H_{13}$ | |
| 766 | $C_6H_{13}-CH(CH_3)O-$ | " | " | 2 | — | — | 0 | " | |
| 767 | $C_5H_{11}-CH(C_2H_5)O-$ | " | " | 2 | — | — | 0 | " | |
| 768 | $C_6H_{13}-CH(C_2H_5)O-$ | " | " | 2 | — | — | 0 | " | |
| 769 | $C_2H_5-CH(CH_3)-CH_2O-$ | " | " | 2 | — | — | 0 | " | |
| 770 | $C_2H_5-CH(CH_3)-(CH_2)_3O-$ | " | " | 2 | — | — | 0 | " | |
| 771 | $C_2H_5-OCO-CH_2-CH(CF_3)O-$ | " | " | 2 | — | — | 0 | " | |
| 772 | $C_2H_5C^*H-(CH_2)_5O-$<br>$\|$<br>$CH_3$ (S) |  | — | 1 |  | $-COO-$ | 1 | $-C^*H(CF_3)-C_6H_{13}$ | 76, 77 |
| 773 | $C_2H_5C^*H-(CH_2)_4O-$<br>$\|$<br>$CH_3$ | " | " | 1 | " | " | 1 | " | 75 |
| 774 | $C_2H_5C^*H-CH_2O-$<br>$\|$<br>$CH_3$ | " | " | 1 | " | " | 1 | " | 74 |
| 775 | $C_6H_{13}C^*H-CH_2O-$<br>$\|$<br>$CH_3$ | " | " | 1 | " | " | 1 | " | 79 |
| 776 | $C_6H_{13}C^*H-O-$<br>$\|$<br>$CH_3$ | " | " | 1 | " | " | 1 | " | 78 |

TABLE 3-9

| Com. No. | R | A' | X | m | B' | Y | n | R* | Exam. No. |
|---|---|---|---|---|---|---|---|---|---|
| 777 | C₂H₅CH—(CH₂)₅O—<br>      \|<br>      CH₃ | ⌬ | — | 1 | ⌬ | —COO— | 1 | —C*H(CF₃)—C₆H₁₃ | |
| 778 | C₂H₅CH—(CH₂)₄O—<br>      \|<br>      CH₃ | " | " | 1 | " | " | 1 | " | |
| 779 | C₂H₅CH—CH₂O—<br>      \|<br>      CH₃ | " | " | 1 | " | " | 1 | " | |
| 780 | C₆H₁₃CH—CH₂O—<br>      \|<br>      CH₃ | " | " | 1 | " | " | 1 | " | |
| 781 | C₆H₁₃CH—O—<br>      \|<br>      CH₃ | " | " | 1 | " | " | 1 | " | |
| 782 | C₂H₅C*H—(CH₂)₅O—<br>      \|<br>      CH₃ | ⌬ | — | 1 | ⌬ | —COO— | 1 | —C*H(CH₃)—C₆H₁₃ | |
| 783 | C₂H₅C*H—(CH₂)₄O—<br>      \|<br>      CH₃ | " | " | 1 | " | " | 1 | " | |
| 784 | C₂H₅C*H—CH₂O—<br>      \|<br>      CH₃ | " | " | 1 | " | " | 1 | " | |
| 785 | C₆H₁₃C*H—CH₂O—<br>      \|<br>      CH₃ | " | " | 1 | " | " | 1 | " | |
| 786 | C₆H₁₃C*H—O—<br>      \|<br>      CH₃ | " | " | 1 | " | " | 1 | " | |

TABLE 3-10

| Com. No. | R | A' | X | m | B' | Y | n | R* | Exam. No. |
|---|---|---|---|---|---|---|---|---|---|
| 787 | C₂H₅CH—(CH₂)₅O—<br>      \|<br>      CH₃ | ⌬ | — | 1 | ⌬ | —COO— | 1 | —C*H(CH₃)—C₆H₁₃ | |
| 788 | C₂H₅CH—(CH₂)₄O—<br>      \|<br>      CH₃ | " | " | 1 | " | " | 1 | " | |
| 789 | C₂H₅CH—CH₂O—<br>      \|<br>      CH₃ | " | " | 1 | " | " | 1 | " | |
| 790 | C₆H₁₃CH—CH₂O—<br>      \|<br>      CH₃ | " | " | 1 | " | " | 1 | " | |
| 791 | C₆H₁₃CH—O—<br>      \|<br>      CH₃ | " | " | 1 | " | " | 1 | " | |

Further, examples of the compounds represented by the formula [IV] are shown in the following Tables 4-1 to 4-8.

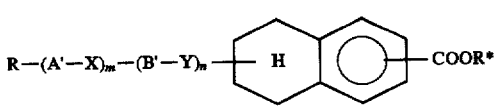

$$R-(A'-X)_m-(B'-Y)_n-\text{[naphthalene]}-COOR^* \quad [IV]$$

TABLE 4-1

| Com. No. | R | A' | X | m | B' | Y | n | R* | Exam. No. |
|---|---|---|---|---|---|---|---|---|---|
| 792 | $C_7H_{15}O-$ |  | $-COO-$ | 2 | — | — | 0 | $-C^*H(CF_3)-C_6H_{13}$ | |
| 793 | $C_8H_{17}O-$ | " | " | 2 | — | — | 0 | " | |
| 794 | $C_9H_{19}O-$ | " | " | 2 | — | — | 0 | " | |
| 795 | $C_{10}H_{21}O-$ | " | " | 2 | — | — | 0 | " | 25 |
| 796 | $C_{11}H_{23}O-$ | " | " | 2 | — | — | 0 | " | |
| 797 | $C_{12}H_{25}O-$ | " | " | 2 | — | — | 0 | " | |
| 798 | $C_{14}H_{29}O-$ | " | " | 2 | — | — | 0 | " | |
| 799 | $C_{16}H_{33}O-$ | " | " | 2 | — | — | 0 | " | |
| 800 | $C_7H_{15}-$ |  | $-COO-$ | 2 | — | — | 0 | $-C^*H(CF_3)-C_6H_{13}$ | |
| 801 | $C_8H_{17}-$ | " | " | 2 | — | — | 0 | " | |
| 802 | $C_9H_{19}-$ | " | " | 2 | — | — | 0 | " | |
| 803 | $C_{10}H_{21}-$ | " | " | 2 | — | — | 0 | " | |
| 804 | $C_{11}H_{23}-$ | " | " | 2 | — | — | 0 | " | |
| 805 | $C_{12}H_{25}-$ | " | " | 2 | — | — | 0 | " | |
| 806 | $C_{14}H_{29}-$ | " | " | 2 | — | — | 0 | " | |
| 807 | $C_{16}H_{33}-$ | " | " | 2 | — | — | 0 | " | |
| 808 | $C_{10}H_{21}O-$ |  | $-COO-$ | 2 | — | — | 0 | $-C^*H(CF_3)-C_6H_{13}$ | |
| 809 | $C_{10}H_{21}O-$ | " | " | 2 | — | — | 0 | $-C^*H(CH_3)-C_6H_{13}$ | |
| 810 | $C_{10}H_{21}O-$ | " | " | 2 | — | — | 0 | $-C^*H(C_2H_5)-C_5H_{11}$ | |
| 811 | $C_{10}H_{21}O-$ | " | " | 2 | — | — | 0 | $-C^*H(C_2H_5)-C_6H_{13}$ | |
| 812 | $C_{10}H_{21}O-$ | " | " | 2 | — | — | 0 | $-CH_2C^*H(CH_3)-C_2H_5$ | |
| 813 | $C_{10}H_{21}O-$ | " | " | 2 | — | — | 0 | $-(CH_2)_3-C^*H(CH_3)-C_2H_5$ | |
| 814 | $C_{10}H_{21}O-$ | " | " | 2 | — | — | 0 | $-C^*H(CF_3)-CH_2-COO-C_2H_5$ | |

TABLE 4-2

| Compound Number | R | A' | X | m | B' | Y | n | R* | Exam. No. |
|---|---|---|---|---|---|---|---|---|---|
| 815 | $C_7H_{15}O-$ |  | $-OCO-$ | 1 | 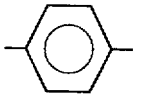 | $-COO-$ | 1 | $-C^*H(CF_3)-C_6H_{13}$ | |
| 816 | $C_8H_{17}O-$ | " | " | 1 | " | " | 1 | " | |
| 817 | $C_9H_{19}O-$ | " | " | 1 | " | " | 1 | " | |
| 818 | $C_{10}H_{21}O-$ | " | " | 1 | " | " | 1 | " | |
| 819 | $C_{11}H_{23}O-$ | " | " | 1 | " | " | 1 | " | |
| 820 | $C_{12}H_{25}O-$ | " | " | 1 | " | " | 1 | " | |
| 821 | $C_{14}H_{29}O-$ | " | " | 1 | " | " | 1 | " | |
| 822 | $C_{16}H_{33}O-$ | " | " | 1 | " | " | 1 | " | |
| 823 | $C_7H_{15}O-$ | 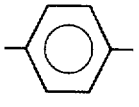 | $-CH_2O-$ | 1 | 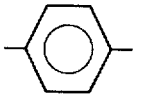 | $-COO-$ | 1 | $-C^*H(CF_3)-C_6H_{13}$ | |
| 824 | $C_8H_{17}O-$ | " | " | 1 | " | " | 1 | " | |
| 825 | $C_9H_{19}O-$ | " | " | 1 | " | " | 1 | " | |
| 826 | $C_{10}H_{21}O-$ | " | " | 1 | " | " | 1 | " | |
| 827 | $C_{11}H_{23}O-$ | " | " | 1 | " | " | 1 | " | |
| 828 | $C_{12}H_{25}O-$ | " | " | 1 | " | " | 1 | " | |
| 829 | $C_{14}H_{29}O-$ | " | " | 1 | " | " | 1 | " | |
| 830 | $C_{16}H_{33}O-$ | " | " | 1 | " | " | 1 | " | |

TABLE 4-2-continued

| Compound Number | R | A' | X | m | B' | Y | n | R* | Exam. No. |
|---|---|---|---|---|---|---|---|---|---|
| 831 | $C_7H_{15}O-$ | 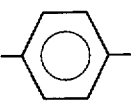 | $-OCH_2-$ | 1 | 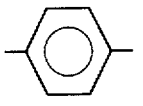 | $-COO-$ | 1 | $-C^*H(CF_3)-C_6H_{13}$ | |
| 832 | $C_8H_{17}O-$ | " | " | 1 | " | " | 1 | " | |
| 833 | $C_9H_{19}O-$ | " | " | 1 | " | " | 1 | " | |
| 834 | $C_{10}H_{21}O-$ | " | " | 1 | " | " | 1 | " | |
| 835 | $C_{11}H_{23}O-$ | " | " | 1 | " | " | 1 | " | |
| 836 | $C_{12}H_{25}O-$ | " | " | 1 | " | " | 1 | " | |
| 837 | $C_{14}H_{29}O-$ | " | " | 1 | " | " | 1 | " | |
| 838 | $C_{16}H_{33}O-$ | " | " | 1 | " | " | 1 | " | |

TABLE 4-3

| Compound Number | R | A' | X | m | B' | Y | n | R* | Exam. No. |
|---|---|---|---|---|---|---|---|---|---|
| 839 | $C_7H_{15}O-$ |  | $-CH_2-CH_2-$ | 1 |  | $-COO-$ | 1 | $-C^*H(CF_3)C_6H_{13}$ | |
| 840 | $C_8H_{17}O-$ | " | " | 1 | " | " | 1 | " | |
| 841 | $C_9H_{19}O-$ | " | " | 1 | " | " | 1 | " | |
| 842 | $C_{10}H_{21}O-$ | " | " | 1 | " | " | 1 | " | |
| 843 | $C_{11}H_{23}O-$ | " | " | 1 | " | " | 1 | " | |
| 844 | $C_{12}H_{25}O-$ | " | " | 1 | " | " | 1 | " | |
| 845 | $C_{14}H_{29}O-$ | " | " | 1 | " | " | 1 | " | |
| 846 | $C_{16}H_{33}O-$ | " | " | 1 | " | " | 1 | " | |
| 847 | $C_7H_{15}O-$ | 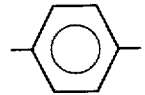 | $-COO-$ | 1 | 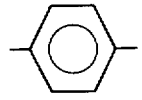 | $-OCO-$ | 1 | $-C^*H(CF_3)-C_6H_{13}$ | |
| 848 | $C_8H_{17}O-$ | " | " | 1 | " | " | 1 | " | |
| 849 | $C_9H_{19}O-$ | " | " | 1 | " | " | 1 | " | |
| 850 | $C_{10}H_{21}O-$ | " | " | 1 | " | " | 1 | " | |
| 851 | $C_{11}H_{23}O-$ | " | " | 1 | " | " | 1 | " | |
| 852 | $C_{12}H_{25}O-$ | " | " | 1 | " | " | 1 | " | |
| 853 | $C_{14}H_{29}O-$ | " | " | 1 | " | " | 1 | " | |
| 854 | $C_{16}H_{33}O-$ | " | " | 1 | " | " | 1 | " | |
| 855 | $C_7H_{15}O-$ | 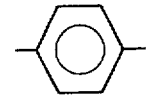 | $-COO-$ | 1 | 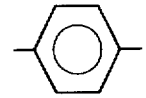 | $-CH_2O-$ | 1 | $-C^*H(CF_3)-C_6H_{13}$ | |
| 856 | $C_8H_{17}O-$ | " | " | 1 | " | " | 1 | " | |
| 857 | $C_9H_{19}O-$ | " | " | 1 | " | " | 1 | " | |
| 858 | $C_{10}H_{21}O-$ | " | " | 1 | " | " | 1 | " | |
| 859 | $C_{11}H_{23}O-$ | " | " | 1 | " | " | 1 | " | |
| 860 | $C_{12}H_{25}O-$ | " | " | 1 | " | " | 1 | " | |
| 861 | $C_{14}H_{29}O-$ | " | " | 1 | " | " | 1 | " | |
| 862 | $C_{16}H_{33}O-$ | " | " | 1 | " | " | 1 | " | |

TABLE 4-4

| Compound Number | R | A' | X | m | B' | Y | n | R* | Exam. No. |
|---|---|---|---|---|---|---|---|---|---|
| 863 | $C_7H_{15}O-$ | 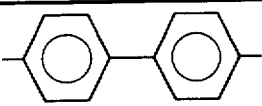 | $-COO-$ | 1 | 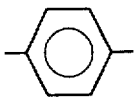 | $-COO-$ | 1 | $-C^*H(CF_3)-C_6H_{13}$ | |
| 864 | $C_8H_{17}O-$ | " | " | 1 | " | " | 1 | " | |

TABLE 4-4-continued

| Compound Number | R | A' | X | m | B' | Y | n | R* | Exam. No. |
|---|---|---|---|---|---|---|---|---|---|
| 865 | $C_9H_{19}O-$ | " | " | 1 | " | " | 1 | " | |
| 866 | $C_{10}H_{21}O-$ | " | " | 1 | " | " | 1 | " | |
| 867 | $C_{11}H_{23}O-$ | " | " | 1 | " | " | 1 | " | |
| 868 | $C_{12}H_{25}O-$ | " | " | 1 | " | " | 1 | " | |
| 869 | $C_{14}H_{29}O-$ | " | " | 1 | " | " | 1 | " | |
| 870 | $C_{16}H_{33}O-$ | " | " | 1 | " | " | 1 | " | |
| 871 | $C_7H_{15}O-$ | —⟨phenyl⟩—⟨cyclohexyl-H⟩— | —COO— | 1 | —⟨phenyl⟩— | —COO— | 1 | $-C*H(CF_3)-C_6H_{13}$ | |
| 872 | $C_8H_{17}O-$ | " | " | 1 | " | " | 1 | " | |
| 873 | $C_9H_{19}O-$ | " | " | 1 | " | " | 1 | " | |
| 874 | $C_{10}H_{21}O-$ | " | " | 1 | " | " | 1 | " | |
| 875 | $C_{11}H_{23}O-$ | " | " | 1 | " | " | 1 | " | |
| 876 | $C_{12}H_{25}O-$ | " | " | 1 | " | " | 1 | " | |
| 877 | $C_{14}H_{29}O-$ | " | " | 1 | " | " | 1 | " | |
| 878 | $C_{16}H_{33}O-$ | " | " | 1 | " | " | 1 | " | |
| 879 | $C_7H_{15}O-$ | —⟨naphthyl⟩— | —COO— | 1 | —⟨phenyl⟩— | —COO— | 1 | $-C*H(CF_3)-C_6H_{13}$ | |
| 880 | $C_8H_{17}O-$ | " | " | 1 | " | " | 1 | " | |
| 881 | $C_9H_{19}O-$ | " | " | 1 | " | " | 1 | " | |
| 882 | $C_{10}H_{21}O-$ | " | " | 1 | " | " | 1 | " | |
| 883 | $C_{11}H_{23}O-$ | " | " | 1 | " | " | 1 | " | |
| 884 | $C_{12}H_{25}O-$ | " | " | 1 | " | " | 1 | " | |
| 885 | $C_{14}H_{29}O-$ | " | " | 1 | " | " | 1 | " | |
| 886 | $C_{16}H_{33}O-$ | " | " | 1 | " | " | 1 | " | |

TABLE 4-5

| Com. No. | R | A' | X | m | B' | Y | n | R* | Exam. No. |
|---|---|---|---|---|---|---|---|---|---|
| 887 | $C_7H_{15}O-$ | —⟨pyrimidine⟩—⟨phenyl⟩— | —COO— | 1 | —⟨phenyl⟩— | —COO— | 1 | $-C*H(CF_3)-C_6H_{13}$ | |
| 888 | $C_8H_{17}O-$ | " | " | 1 | " | " | 1 | " | |
| 889 | $C_9H_{19}O-$ | " | " | 1 | " | " | 1 | " | |
| 890 | $C_{10}H_{21}O-$ | " | " | 1 | " | " | 1 | " | |
| 891 | $C_{11}H_{23}O-$ | " | " | 1 | " | " | 1 | " | |
| 892 | $C_{12}H_{25}O-$ | " | " | 1 | " | " | 1 | " | |
| 893 | $C_{14}H_{29}O-$ | " | " | 1 | " | " | 1 | " | |
| 894 | $C_{16}H_{33}O-$ | " | " | 1 | " | " | 1 | " | |
| 895 | $C_7H_{15}-$ | —⟨pyrimidine⟩—⟨phenyl⟩— | —COO— | 1 | —⟨phenyl⟩— | —COO— | 1 | $-C*H(CF_3)-C_6H_{13}$ | |
| 896 | $C_8H_{17}-$ | " | " | 1 | " | " | 1 | " | |
| 897 | $C_9H_{19}-$ | " | " | 1 | " | " | 1 | " | |
| 898 | $C_{10}H_{21}-$ | " | " | 1 | " | " | 1 | " | |
| 899 | $C_{11}H_{23}-$ | " | " | 1 | " | " | 1 | " | |
| 900 | $C_{12}H_{25}-$ | " | " | 1 | " | " | 1 | " | |
| 901 | $C_{14}H_{29}-$ | " | " | 1 | " | " | 1 | " | |
| 902 | $C_{16}H_{33}-$ | " | " | 1 | " | " | 1 | " | |
| 903 | $C_7H_{15}O-$ | —⟨phenyl⟩—⟨pyridine⟩— | —COO— | 1 | —⟨phenyl⟩— | —COO— | 1 | $-C*H(CF_3)-C_6H_{13}$ | |

TABLE 4-5-continued

| Com. No. | R | A' | X | m | B' | Y | n | R* | Exam. No. |
|---|---|---|---|---|---|---|---|---|---|
| 904 | $C_8H_{17}O-$ | " | " | 1 | " | " | 1 | " | |
| 905 | $C_9H_{19}O-$ | " | " | 1 | " | " | 1 | " | |
| 906 | $C_{10}H_{21}O-$ | " | " | 1 | " | " | 1 | " | |
| 907 | $C_{11}H_{23}O-$ | " | " | 1 | " | " | 1 | " | |
| 908 | $C_{12}H_{25}O-$ | " | " | 1 | " | " | 1 | " | |
| 909 | $C_{14}H_{29}O-$ | " | " | 1 | " | " | 1 | " | |
| 910 | $C_{16}H_{33}O-$ | " | " | 1 | " | " | 1 | " | |

TABLE 4-6

| Com. No. | R | A' | X | m | B' | Y | n | R* | Exam. No. |
|---|---|---|---|---|---|---|---|---|---|
| 911 | $C_7H_{15}O-$ | phenyl | $-COO-$ | 1 | biphenyl | $-COO-$ | 1 | $-C^*H(CF_3)-C_6H_{13}$ | |
| 912 | $C_8H_{17}O-$ | " | " | 1 | " | " | 1 | " | |
| 913 | $C_9H_{19}O-$ | " | " | 1 | " | " | 1 | " | |
| 914 | $C_{10}H_{21}O-$ | " | " | 1 | " | " | 1 | " | |
| 915 | $C_{11}H_{23}O-$ | " | " | 1 | " | " | 1 | " | |
| 916 | $C_{12}H_{25}O-$ | " | " | 1 | " | " | 1 | " | |
| 917 | $C_{14}H_{29}O-$ | " | " | 1 | " | " | 1 | " | |
| 918 | $C_{16}H_{33}O-$ | " | " | 1 | " | " | 1 | " | |
| 919 | $C_7H_{15}O-$ | phenyl | $-COO-$ | 1 | phenyl-cyclohexyl(H) | $-COO-$ | 1 | $-C^*H(CF_3)-C_6H_{13}$ | |
| 920 | $C_8H_{17}O-$ | " | " | 1 | " | " | 1 | " | |
| 921 | $C_9H_{19}O-$ | " | " | 1 | " | " | 1 | " | |
| 922 | $C_{10}H_{21}O-$ | " | " | 1 | " | " | 1 | " | |
| 923 | $C_{11}H_{23}O-$ | " | " | 1 | " | " | 1 | " | |
| 924 | $C_{12}H_{25}O-$ | " | " | 1 | " | " | 1 | " | |
| 925 | $C_{14}H_{29}O-$ | " | " | 1 | " | " | 1 | " | |
| 926 | $C_{16}H_{33}O-$ | " | " | 1 | " | " | 1 | " | |
| 927 | $C_7H_{15}O-$ | phenyl | $-COO-$ | 1 | naphthyl | $-COO-$ | 1 | $C^*H(CF_3)-C_6H_{13}$ | |
| 928 | $C_8H_{17}O-$ | " | " | 1 | " | " | 1 | " | |
| 929 | $C_9H_{19}O-$ | " | " | 1 | " | " | 1 | " | |
| 930 | $C_{10}H_{21}O-$ | " | " | 1 | " | " | 1 | " | |
| 931 | $C_{11}H_{23}O-$ | " | " | 1 | " | " | 1 | " | |
| 932 | $C_{12}H_{25}O-$ | " | " | 1 | " | " | 1 | " | |
| 933 | $C_{14}H_{29}O-$ | " | " | 1 | " | " | 1 | " | |
| 934 | $C_{16}H_{33}O-$ | " | " | 1 | " | " | 1 | " | |

TABLE 4-7

| Com. No. | R | A' | X | m | B' | Y | n | R* | Exam. No. |
|---|---|---|---|---|---|---|---|---|---|
| 935 | $C_6H_{13}-C^*H(CF_3)O-$ | phenyl | $-COO-$ | 2 | — | — | 0 | $-C^*H(CF_3)-C_6H_{13}$ | 26 |
| 936 | $C_6H_{13}-C^*H(CH_3)O-$ | " | " | 2 | — | — | 0 | " | |
| 937 | $C_5H_{11}-C^*H(C_2H_5)O-$ | " | " | 2 | — | — | 0 | " | |
| 938 | $C_6H_{13}-C^*H(C_2H_5)O-$ | " | " | 2 | — | — | 0 | " | |
| 939 | $C_2H_5-C^*H(CH_3)-CH_2O-$ | " | " | 2 | — | — | 0 | " | |
| 940 | $C_2H_5-C^*H(CH_3)-(CH_2)_3O-$ | " | " | 2 | — | — | 0 | " | |
| 941 | $C_2H_5-OCO-CH_2-C^*H(CF_3)O$ | " | " | 2 | — | — | 0 | " | |

TABLE 4-7-continued

| Com. No. | R | A' | X | m | B' | Y | n | R* | Exam. No. |
|---|---|---|---|---|---|---|---|---|---|
| 942 | $C_6H_{13}-CH(CF_3)O-$ |  | $-COO-$ | 2 | — | — | 0 | $C^*H(CF_3)-C_6H_{13}$ | |
| 943 | $C_6H_{13}-CH(CF_3)O-$ | " | " | 2 | — | — | 0 | " | |
| 944 | $C_5H_{11}-CH(C_2H_5)O-$ | " | " | 2 | — | — | 0 | " | |
| 945 | $C_6H_{13}-CH(C_2H_5)O-$ | " | " | 2 | — | — | 0 | " | |
| 946 | $C_2H_5-CH(CH_3)-CH_2O-$ | " | " | 2 | — | — | 0 | " | |
| 947 | $C_2H_5-CH(CH_3)-(CH_2)_3O-$ | " | " | 2 | — | — | 0 | " | |
| 948 | $C_2H_5-OCO-CH_2-CH(CF_3)O-$ | " | " | 2 | — | — | 0 | " | |
| 949 | $C_6H_{13}-C^*H(CF_3)O-$ |  | $-COO-$ | 2 | — | — | 0 | $-C^*H(CH_3)-C_6H_{13}$ | |
| 950 | $C_6H_{13}-C^*H(CH_3)O-$ | " | " | 2 | — | — | 0 | " | |
| 951 | $C_5H_{11}-C^*H(C_2H_5)-O$ | " | " | 2 | — | — | 0 | " | |
| 952 | $C_6H_{13}-C^*H(C_2H_5)O-$ | " | " | 2 | — | — | 0 | " | |
| 953 | $C_2H_5-C^*H(CH_3)-CH_2O-$ | " | " | 2 | — | — | 0 | " | |
| 954 | $C_2H_5-C^*H(CH_3)-(CH_2)_3O-$ | " | " | 2 | — | — | 0 | " | |
| 955 | $C_2H_5-OCO-CH_2-C^*H(CF_3)O-$ | " | " | 2 | — | — | 0 | " | |

TABLE 4-8

| Com. No. | R | A' | X | m | B' | Y | n | R* | Exam. No. |
|---|---|---|---|---|---|---|---|---|---|
| 956 | $C_6H_{13}-CH(CF_3)O-$ |  | $-COO-$ | 2 | — | — | 0 | $C^*H(CH_3)-C_6H_{13}$ | |
| 957 | $C_6H_{13}-CH(CF_3)O-$ | " | " | 2 | — | — | 0 | " | |
| 958 | $C_5H_{11}-CH(C_2H_5)O-$ | " | " | 2 | — | — | 0 | " | |
| 959 | $C_6H_{13}-CH(C_2H_5)O-$ | " | " | 2 | — | — | 0 | " | |
| 960 | $C_2H_5-CH(CH_3)-CH_2O-$ | " | " | 2 | — | — | 0 | " | |
| 961 | $C_2H_5-CH(CH_3)-(CH_2)_3O-$ | " | " | 2 | — | — | 0 | " | |
| 962 | $C_2H_5-OCO-CH_2-C^*H(CF_3)O-$ | " | " | 2 | — | — | 0 | " | |

These carboxylate compounds as mentioned above may be prepared by means of a combination of known synthesis techniques.

For example, the carboxylate compounds of the above formula [III] may be prepared according to the following synthesis route.

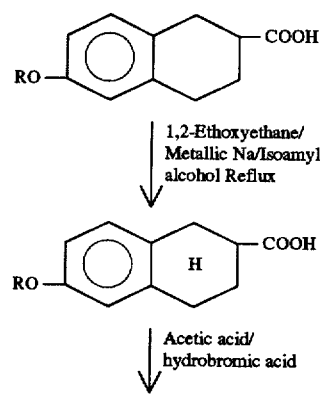

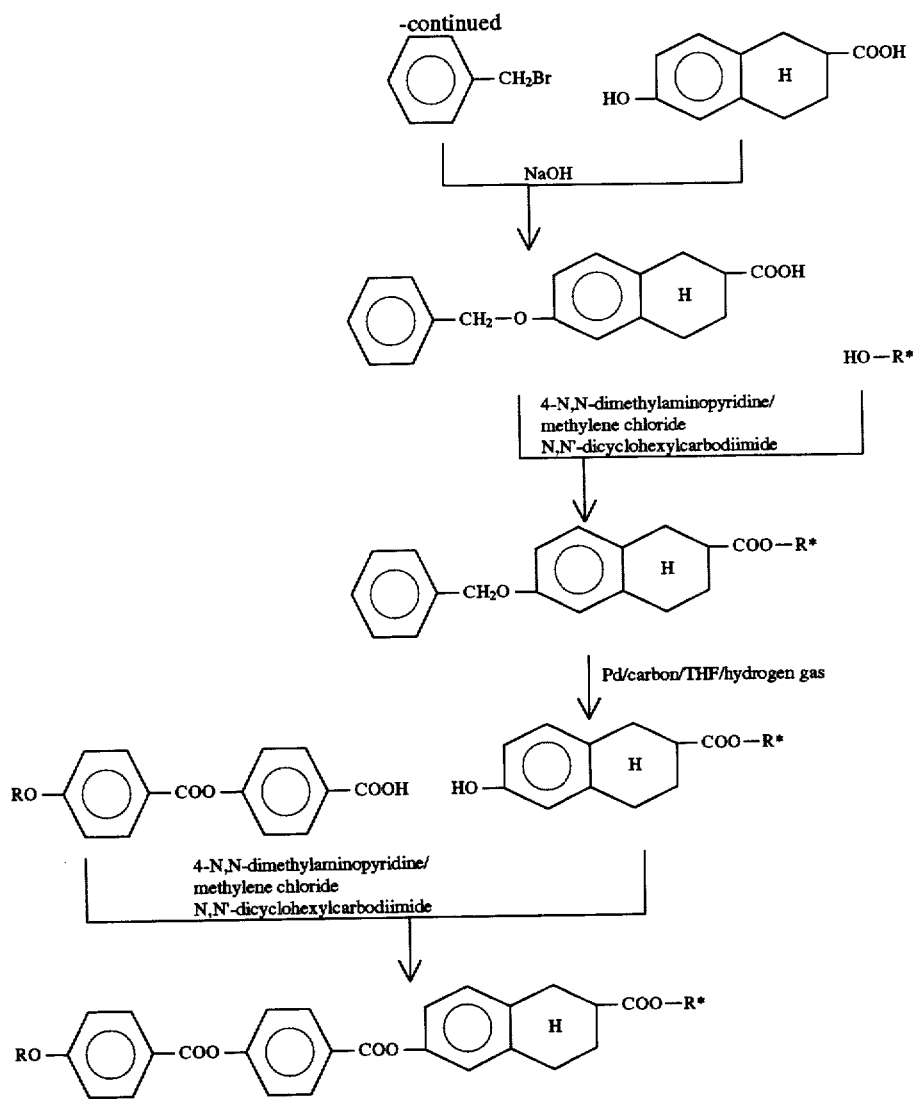

For example, a mixture of 6-n-alkoxy-2-naphthalenecarboxylic acid and 1,2-ethoxyethane is refluxed in the presence of metallic sodium while adding dropwise isoamyl alcohol to obtain 1,2,3,4-tetrahydro-6-n-alkoxy-2-naphthalenecarboxylic acid.

The thus obtained 1,2,3,4-tetrahydro-6-n-alkoxy-2-naphthalenecarboxylic acid is reacted with acetic acid and hydrobromic acid to obtain 1,2,3,4-tetrahydro-6-hydroxy-2-naphthalenecarboxylic acid.

The 1,2,3,4-tetrahydro-6-hydro-2-naphthalenecarboxylic acid is reacted with benzyl bromide in the presence of potassium hydroxide to produce 1,2,3,4-tetrahydro-6-benzyloxy-2-naphthalenecarboxylic acid.

Subsequently, in the presence of 4-N,N-dimethylaminopyridine and a solvent such as methylene chloride, an alcohol having an asymmetric carbon is reacted with the 1,2,3,4-tetrahydro-6-benzyloxy-2-naphthalenecarboxylic acid while adding dropwise N,N-dicyclohexylcarbodiimide to the reaction mixture, thereby obtaining 1,2,3,4-tetrahydro-6-benzyloxy-2-naphthalenecarboxylate.

The thus obtained 1,2,3,4-tetrahydro-6-benzyloxy-2-naphthalenecarboxylate in a solvent such as tetrahydrofuran is reduced with hydrogen gas in the presence of a reducing catalyst such as a palladium/carbon to obtain 1,2,3,4-tetrahydro-6-hydroxy-2-naphthalenecarboxylate.

Then, 4-(4-alkoxybenzoyloxy)benzoic acid prepared separately is reacted with the 1,2,3,4-tetrahydro-6-hydroxy-2-naphthalenecarboxylate obtained in the above step in the presence of 4-N,N-dimethylaminopyridien and a solvent such as methylene chloride while adding dropwise N,N'-dicyclohexylcarbodiimide, whereby the above-mentioned carboxylate compound may be obtained.

These processes for the preparation of the carboxylate compounds of the invention are provided only by way of non-limiting illustration.

Figure 13:
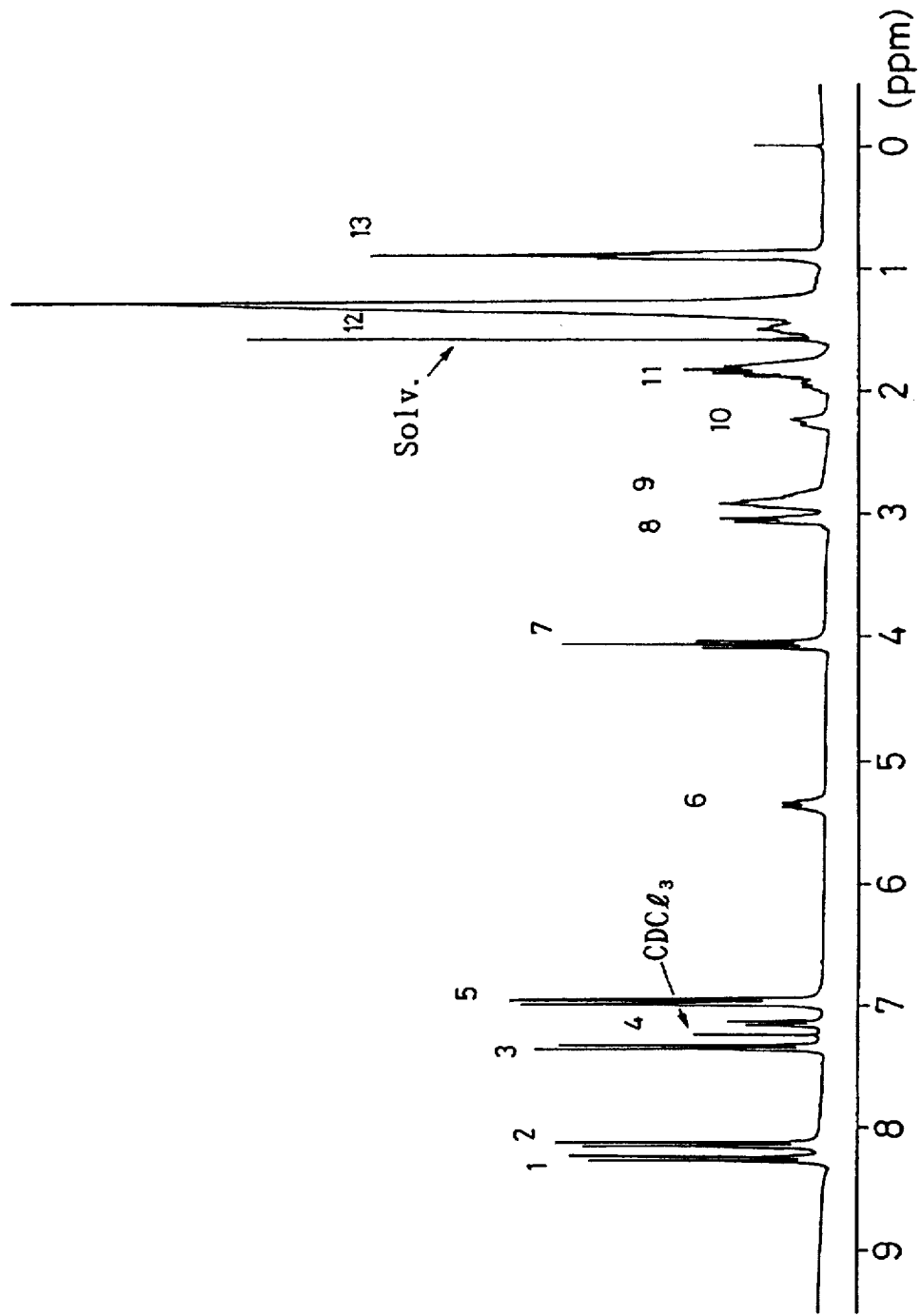
FIG. 13 shows $^1$H-NMR spectrum of 6-[4-(4-decyloxybenzoyloxy)benzoyloxy]-1,2,3,4-tetrahydro-2-naphthalenecarboxylic acid (R)-1-trifluoromethylheptyl ester [Exemplified compound (404)].

Among the carboxylate compounds of the invention prepared by the above-mentioned processes, $^1$H-NMR of 6-[4-(4-decyloxybenzoyloxy)benzoyloxy]-1,2,3,4-tetrahydro-2-naphthalenecarboxylic acid (R)-1-trifluoromethylheptyl ester [Exemplified compound (604)] represented by the following formula is shown in FIG. 13.

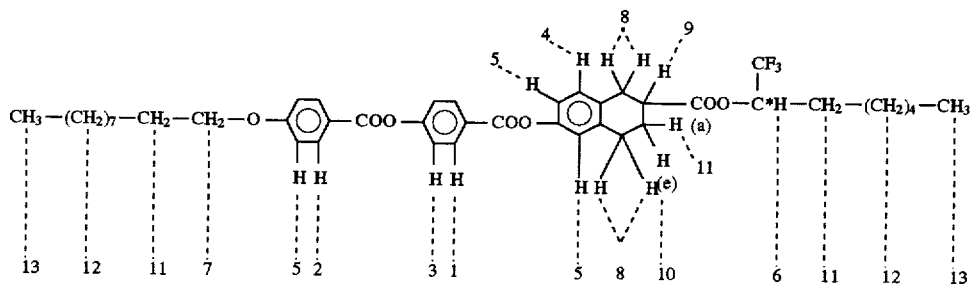

In this formula, (e) represents an equatorical steric conformation, (a) represents an exial steric conformation, and the numbers 1 to 13 showing hydrogen atoms correspond to the peaks in FIG. 13.

Figure 14:
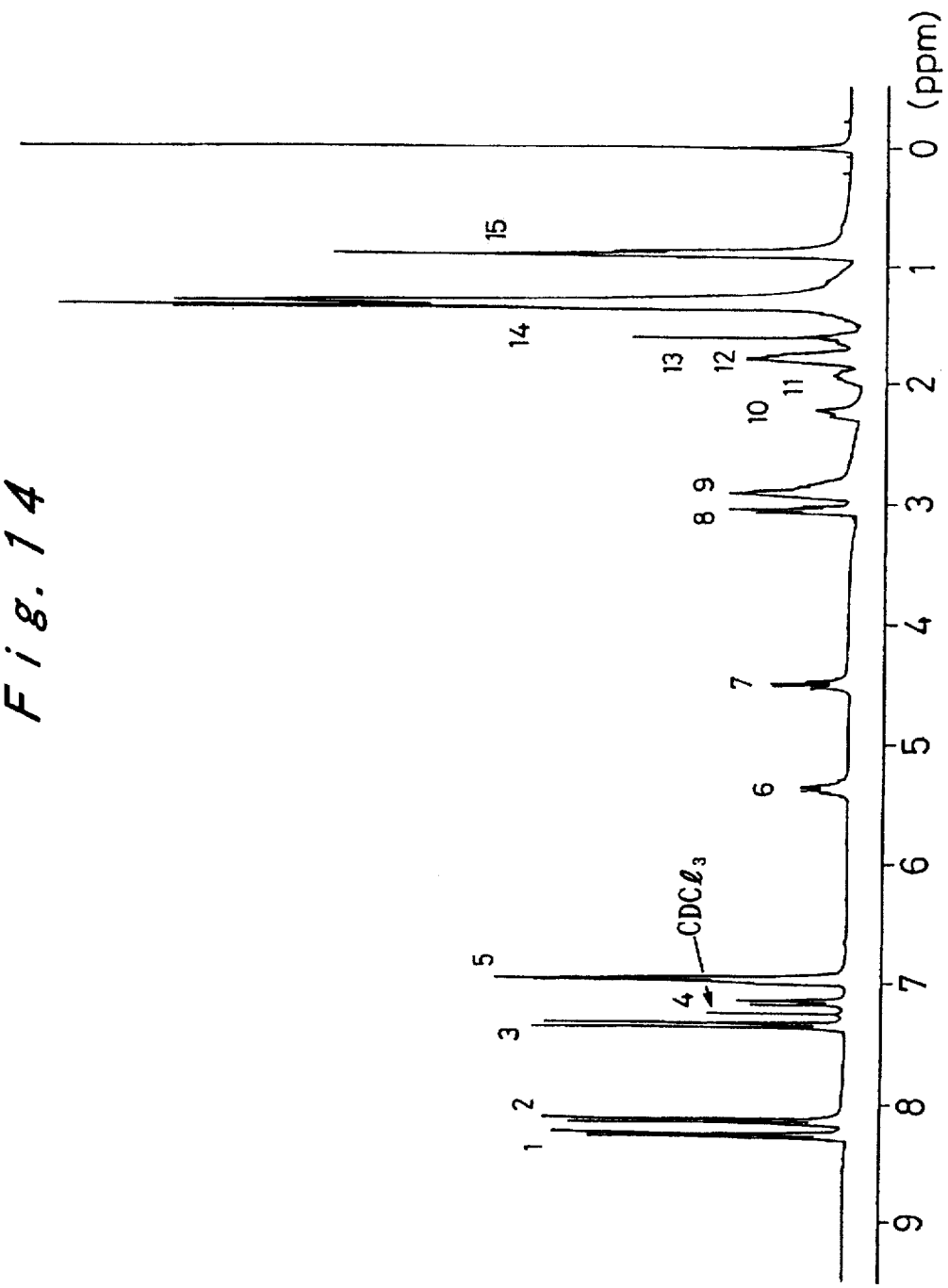
FIG. 14 shows $^1$H-NMR spectrum of 6-{4-[4-((R)-1-methylheptyloxy)benzoyloxy}benzoyloxy]-1,2,3,4-tetrahydro-2-naphthalenecarboxylic acid (R)-1-trifluoromethylheptyl ester [Exemplified compound (545)].

Further, $^1$H-NMR of 6-{4-[4-((R)-1-methylheptyloxy)benzoyloxy]benzoyloxy}-1,2,3,4-tetrahydro-2-naphthalenecarboxylic acid (R)-1-trifluoromethylheptyl ester [Exemplified compound (745)] represented by the following formula is shown in FIG. 14.

Figure 16:
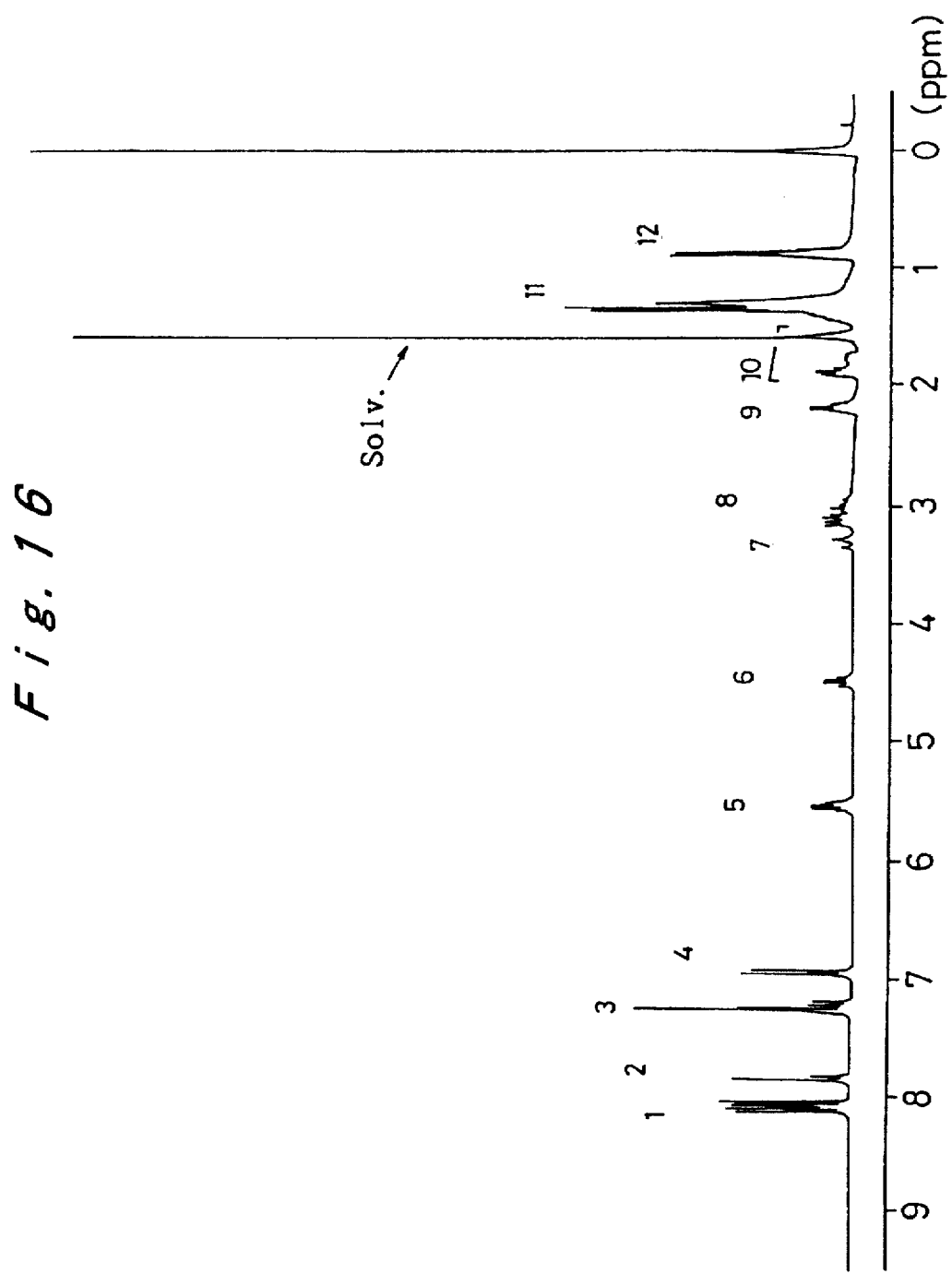
FIG. 16 shows $^1$H-NMR spectrum of 6-{4-[4-((R)-1-methylheptyloxy)benzoyloxy)benzoyloxy]-5,6,7,8-tetrahydro-2-naphthalenecarboxylic acid (R)-1-trifluoromethylheptyl ester [Exemplified compound (716)].

Further, $^1$H-NMR of 6-{4-[4-((R)-1-methylheptyloxy)benzoyloxy)benzoyloxy]-5,6,7,8-tetrahydro-2-naphthalenecarboxylic acid (R)-1-trifluoromethylheptyl ester [Exemplified compound (936)] represented by the following formula is shown in FIG. 16.

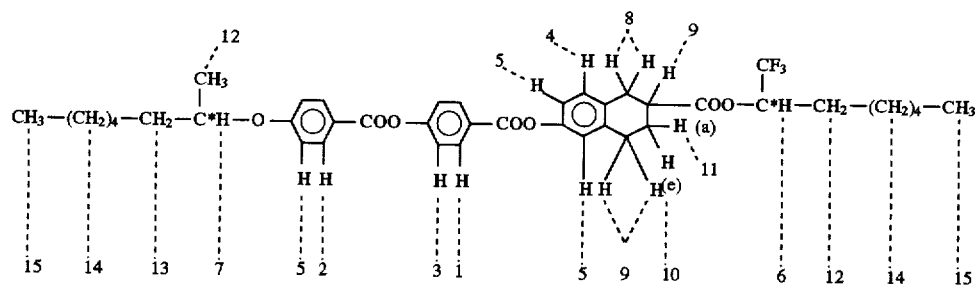

In this formula, the numbers 1 to 15 showing hydrogen atoms correspond to the peaks in FIG. 14.

Figure 15:
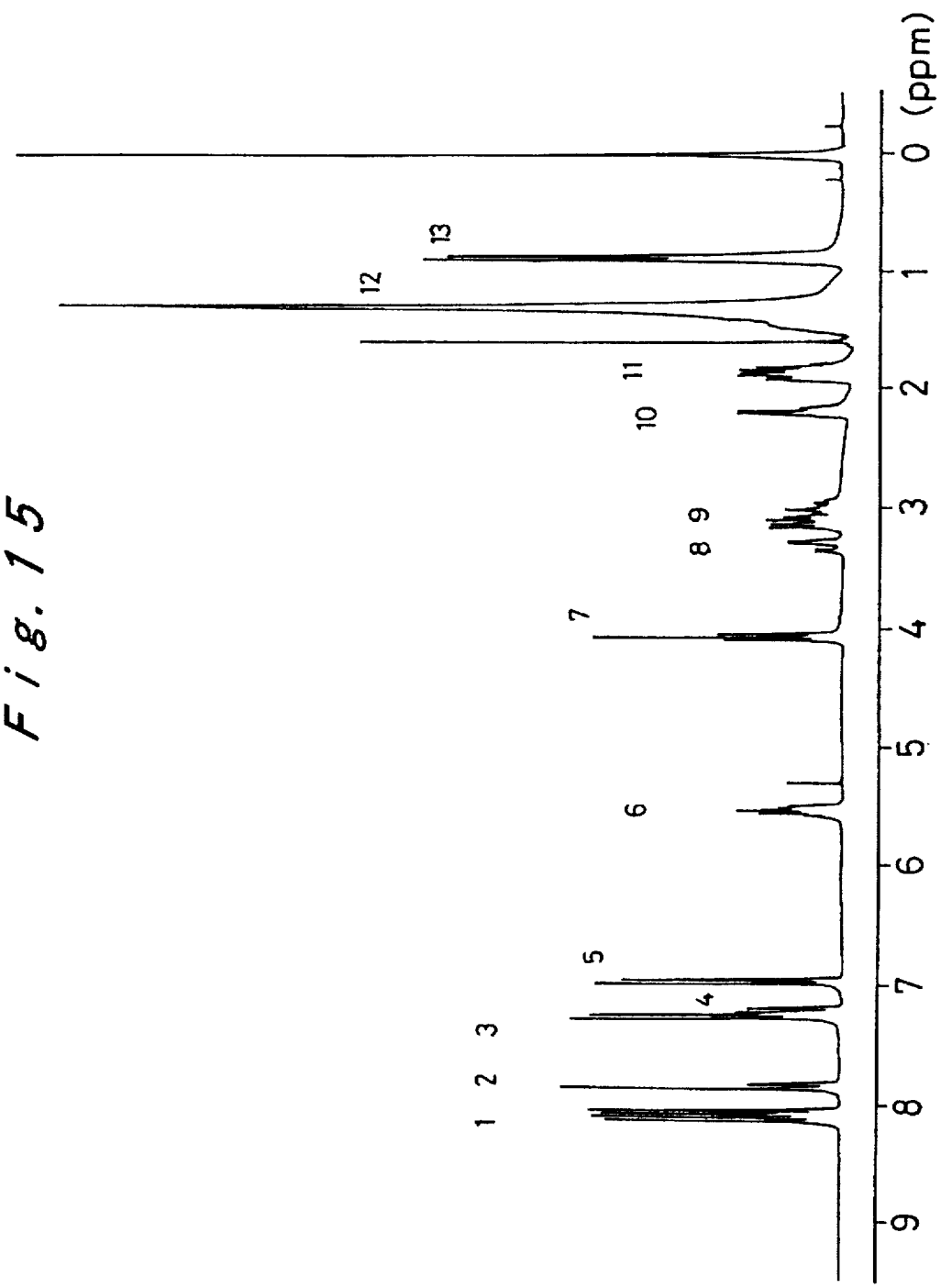
FIG. 15 shows $^1$H-NMR spectrum of 6-[4-(4-decyloxybenzoyloxy)benzoyloxy]-5,6,7,8-tetrahydro-2-naphthalenecarboxylic acid (R)-1-trifluoromethylheptyl ester [Exemplified compound (575)).

Among the carboxylate compounds of the formula [IV] of the invention, $^1$H-NMR of 6-[4-(4-decyloxybenzoyloxy)benzoyloxy]-5,6,7,8-tetrahydro-2-naphthalenecarboxylic acid (R)-1-trifluoromethylheptyl ester [Exemplified compound (795)] represented by the following formula is shown in FIG. 15.

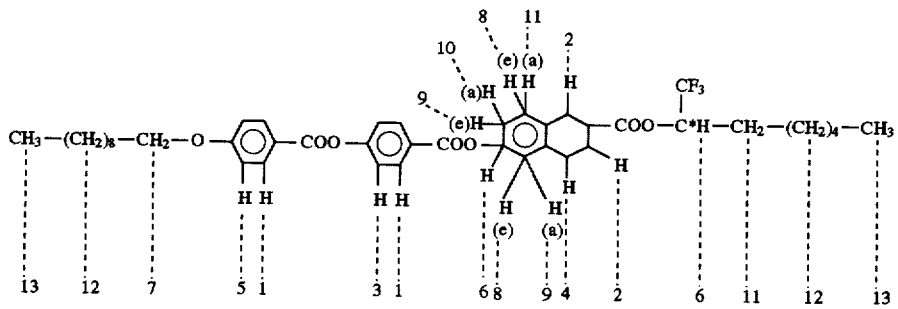

In this formula, the numbers 1 to 15 showing hydrogen atoms correspond to the peaks in FIG. 15.

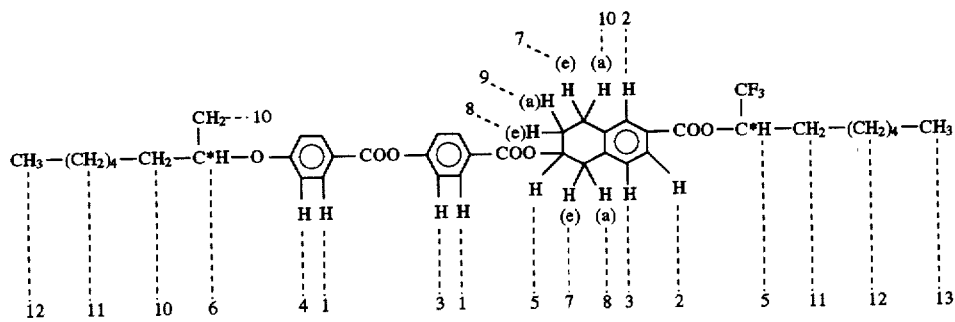

In this formula, the numbers 1 to 13 showing hydrogen atoms correspond to the peaks in FIG. 16.

FIGS. 23-34 show 1H-NMR spectra of other compounds according to the present invention.

FIG. 23:

6-(4-decyloxybenzoyloxy)-1,2,3,4-tetrahydro-2-naphthalenecarboxylic acid (R)-1-trifluoromethylheptyl ester [Compound (235)] represented by the following formula

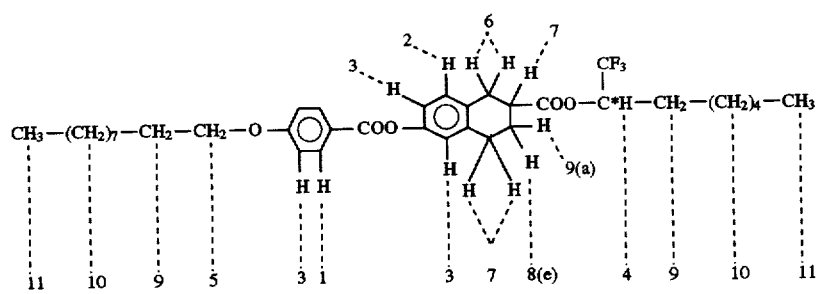

FIG. 24:

6-(4'-undecyloxy-4-biphenylcarbonyloxy)-1,2,3,4-tetrahydro-2-naphthalenecarboxylic acid (R)-1-trifluoromethylheptyl ester [Compound (252)] represented by the following formula

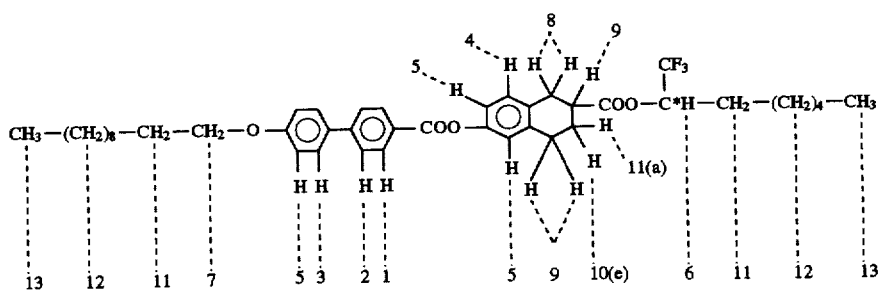

FIG. 25:

6-(4'-dodecyloxy-4-biphenylcarbonyloxy)-1,2,3,4-tetrahydro-2-naphthalenecarboxylic acid (R)-1-trifluoromethylheptyl ester [Compound (253)] represented by the following formula

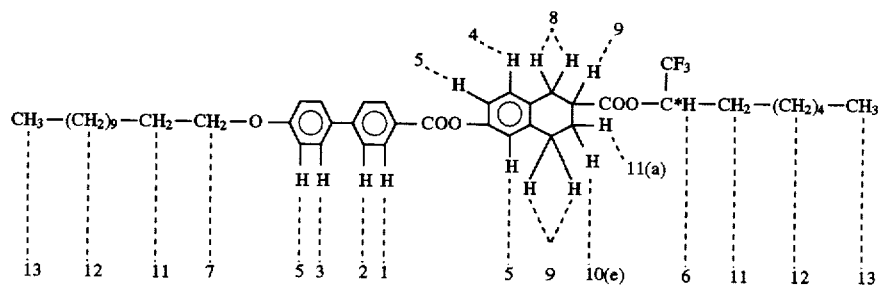

FIG. 26:

6-(4'-octyl-4-biphenylcarbonyloxy]-1,2,3,4-tetrahydro-2-naphthalenecarboxylic acid (R)-1-trifluoromethylheptyl ester [Compound (353)] represented by the following formula

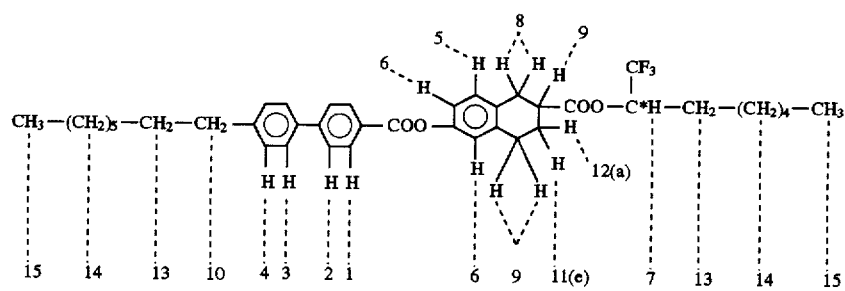

FIG. 27:

6-(4'-decyl-4-biphenylcarbonyloxy]-1,2,3,4-tetrahydro-2-naphthalenecarboxylic acid (R)-1-trifluoromethylheptyl ester [Compound (355)] represented by the following formula

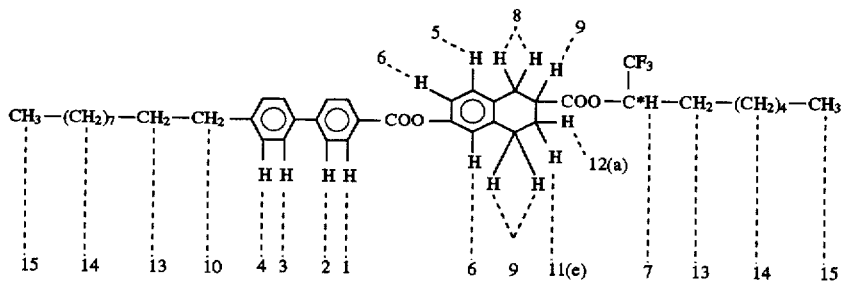

FIG. 28:

6-(4'-dodecyl-4-biphenylcarbonyloxy)-1,2,3,4-tetrahydro-2-naphthalenecarboxylic acid (R)-1-trifluoromethylheptyl ester [Compound (357)] represented by the following formula

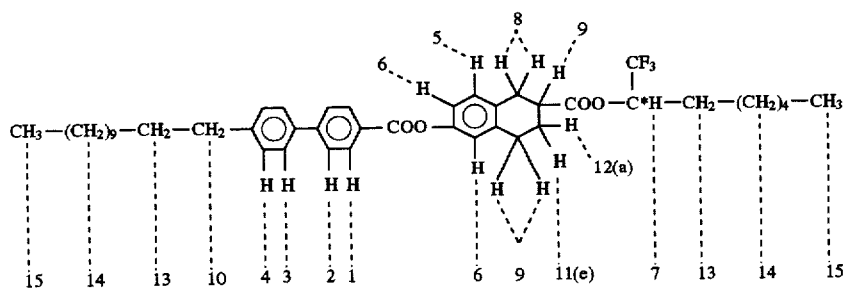

Figure 29:
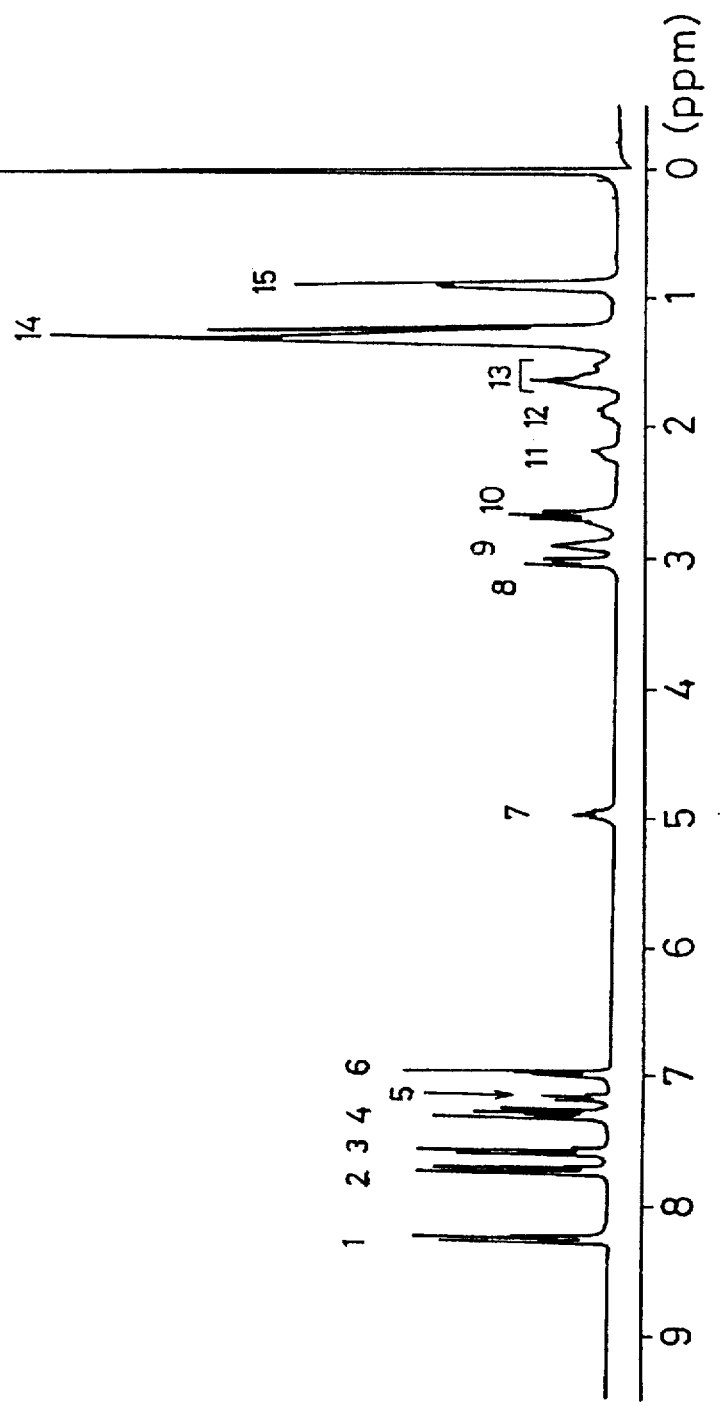
FIG. 29 shows $^1$H-NMR spectrum of 6-(4'-octyl-4-biphenylcarbonyloxy)-1,2,3,4-tetrahydro-2-naphthalenecarboxylic acid (R)-1-methylheptyl ester [Compound (473)].

FIG. 29:
6-(4'-octyl-4-biphenylcarbonyloxy)-1,2,3,4-tetrahydro-2-naphthalenecarboxylic acid (R)-1-methylheptyl ester [Compound (473)] represented by the following formula

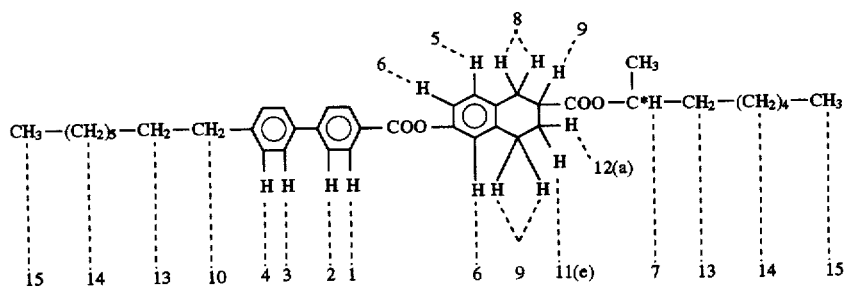

Figure 30:
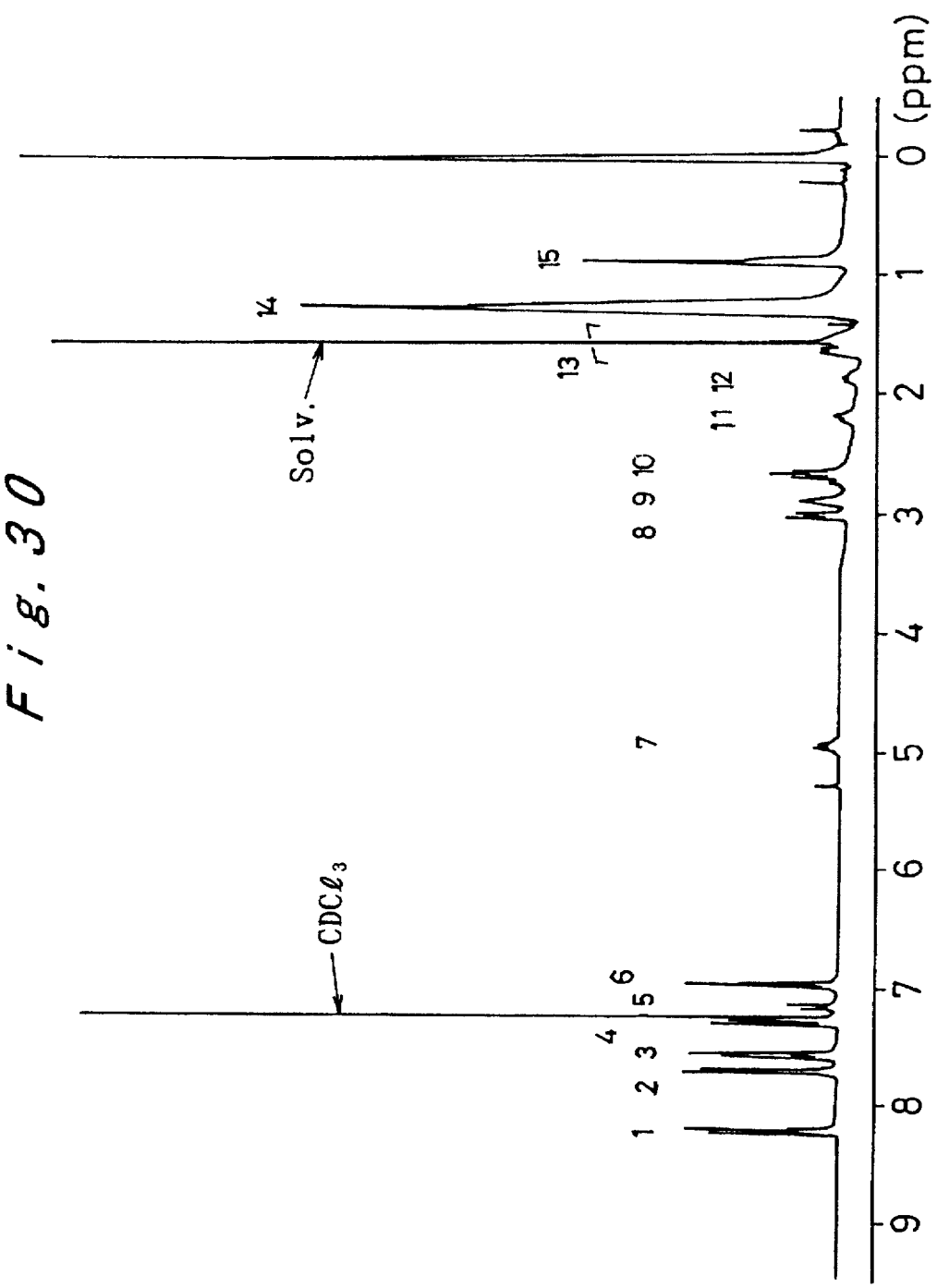
FIG. 30 shows $^1$H-NMR spectrum of 6-(4'-decyl-4-biphenylcarbonyloxy]-1,2,3,4-tetrahydro-2-naphthalenecarboxylic acid (R)-1-methylheptyl ester [Compound (475)].

FIG. 30:
6-(4'-decyl-4-biphenylcarbonyloxy)-1,2,3,4-tetrahydro-2-naphthalenecarboxylic acid (R)-1-methylheptyl ester [Compound (475)] represented by the following formula

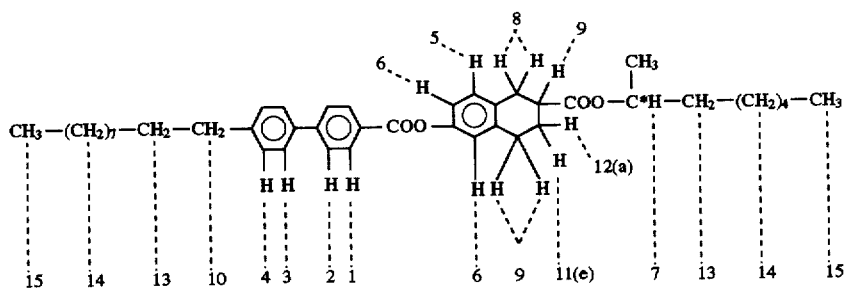

Figure 31:
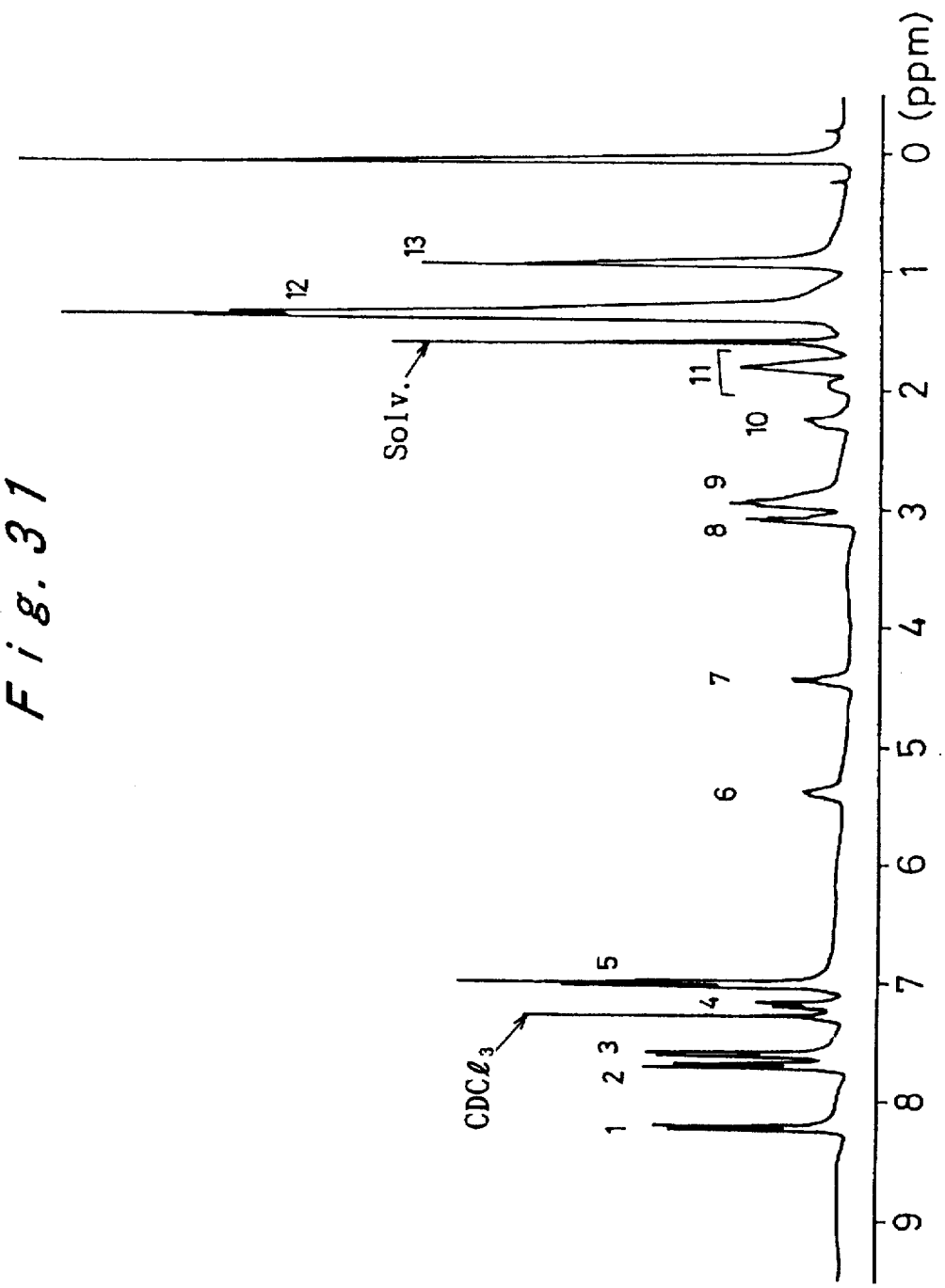
FIG. 31 shows $^1$H-NMR spectrum of 6-[4'-((S)-1-methylheptyloxy)biphenylcarbonyloxy]-1,2,3,4-tetrahydro-2-naphthalenecarboxylic acid (R)-1-trifluoromethylheptyl ester [Compound (776)).

FIG. 31:
6-[4'-(S)-1-methylheptyloxy)biphenylcarbonyloxy]-1,2,3,4-tetrahydro-2-naphthalenecarboxylic acid (R)-1-trifluoromethylheptyl ester [Compound (776)] represented by the following formula

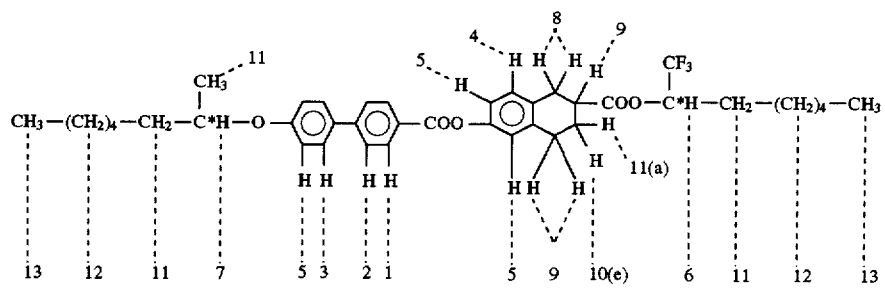

FIG. 32:

6-[4-(4-octyloxyphenyl)cyclohexylcarbonyloxy]-1,2,3,4-tetrahydro-2-naphthalenecarboxylic acid (R)-1-trifluoromethylheptyl ester [Compound (265)] represented by the following formula

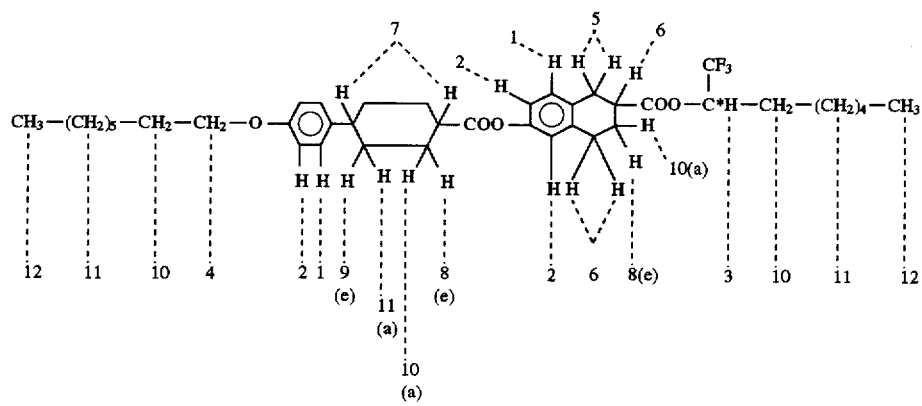

FIG. 33:

6-[4-(4-dodecyloxyphenyl)cyclohexylcarbonyloxy]-1,2,3,4-tetrahydro-2-naphthalenecarboxylic acid (R)-1-trifluoromethylheptyl ester [Compound (269)] represented by the following formula

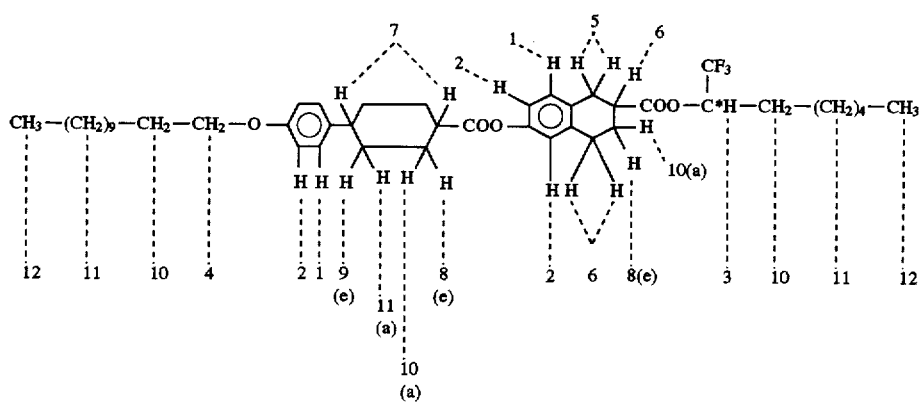

FIG. 34:

6-[4-(4-decylphenyl)cyclohexylcarbonyloxy]-1,2,3,4-tetrahydro-2-naphthalenecarboxylic acid (R)-1-trifluoromethylheptyl ester [Compound (363)] represented by the following formula

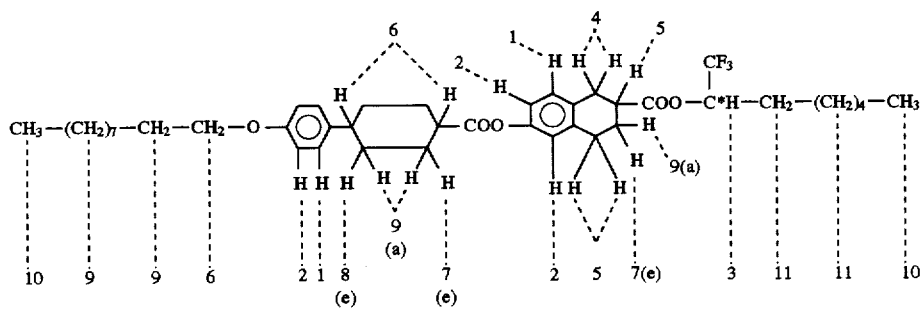

Figure 35:
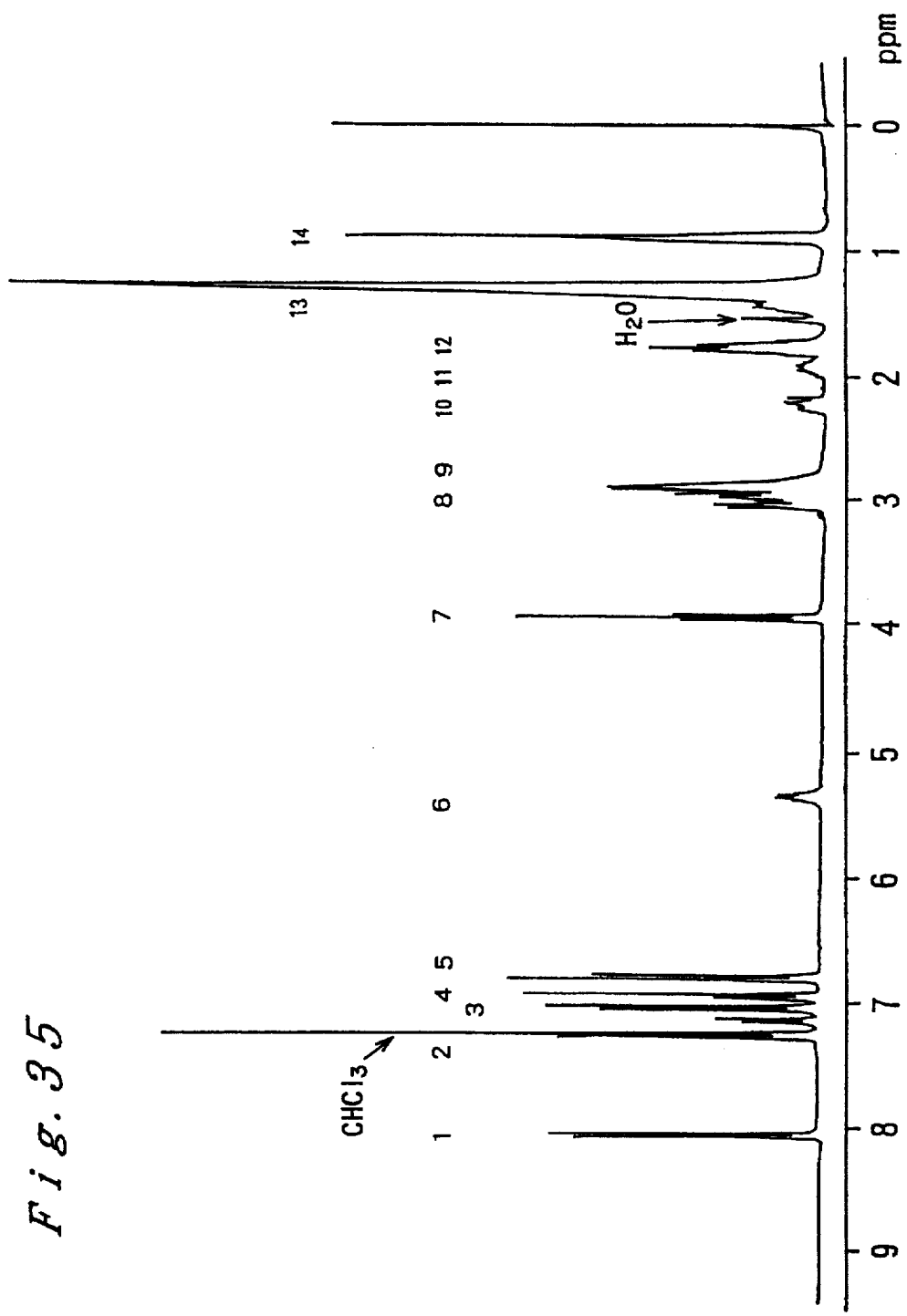
FIG. 35 shows ¹H-NMR spectrum of 6-[4-(2-(4-decyloxy-phenyl)ethyl)benzoyloxy]-1,2,3,4-tetrahydro-2-naphthalenecarboxylic acid (R)-1-trifluoromethylheptyl ester. [Exemplified compound (651)].

FIG. 35:
6-[4-(2-(4-decyloxy-phenyl)ethyl)benzoyloxy]-1,2,3,4-tetrahydro-2-naphthalenecarboxylic acid (R)-1-trifluoromethylheptyl ester [Compound (651)] represented by the following formula

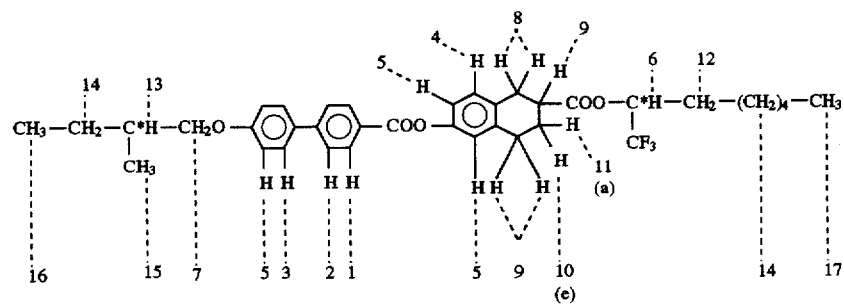

Figure 67:
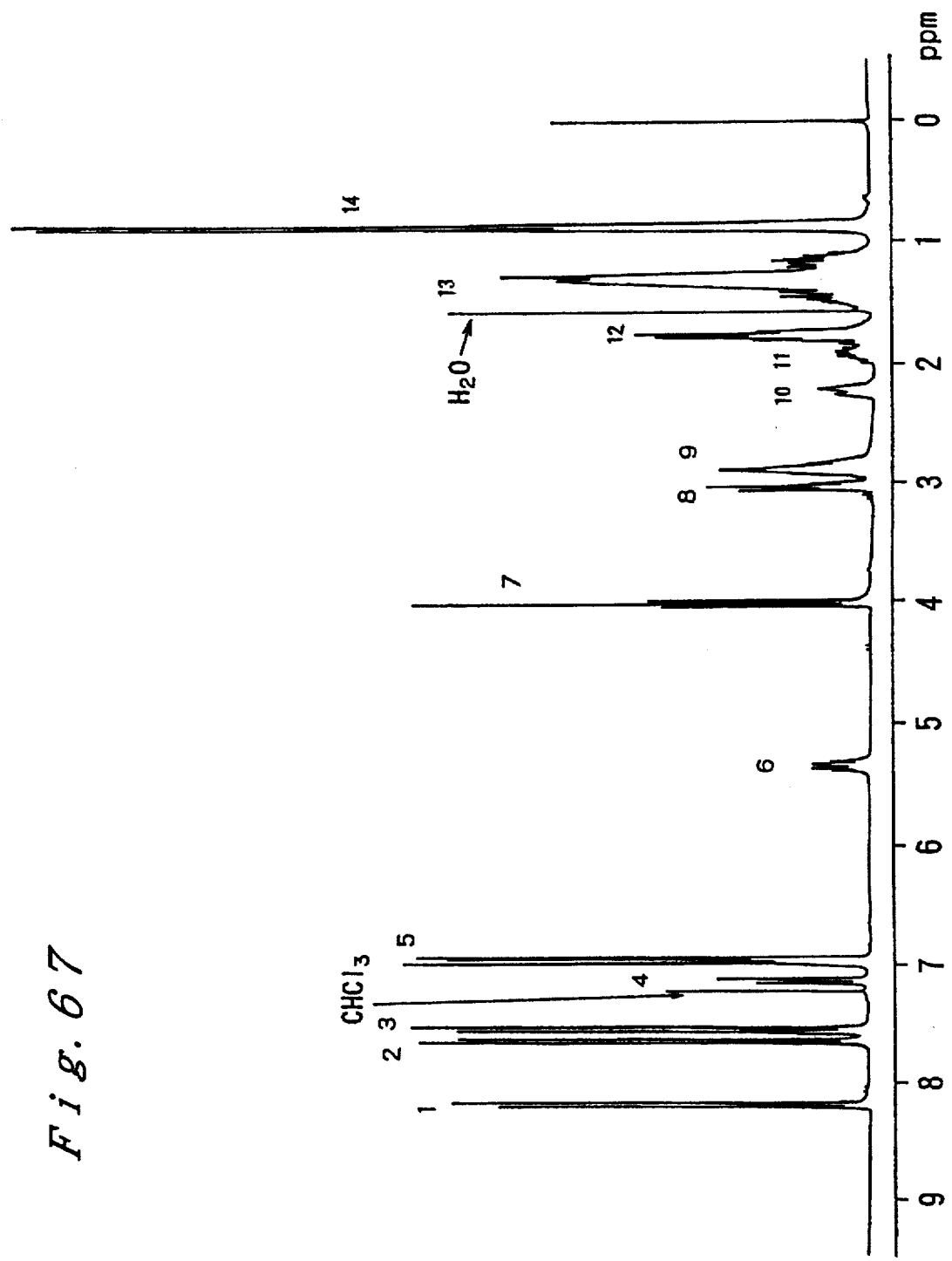
FIG. 67 shows $^1$H-NMR spectrum of 6-[4'-((S)-5-methylheptyloxy)-4-biphenylcarbonyloxy]-1,2,3,4-tetrahydro-2-naphthalenecarboxylic acid (R)-1-trifluoromethylheptyl ester. [Examplified compound (773)]

FIG. 67:
6-[4'-((S)-5-methylheptyloxy)-4-biphenylcarbonyloxy-1,2,3,4-tetrahydro-2-naphthalenecarboxylic acid (R)-1-trifluoromethylheptyl ester [Compound (773)] represented by the following formula

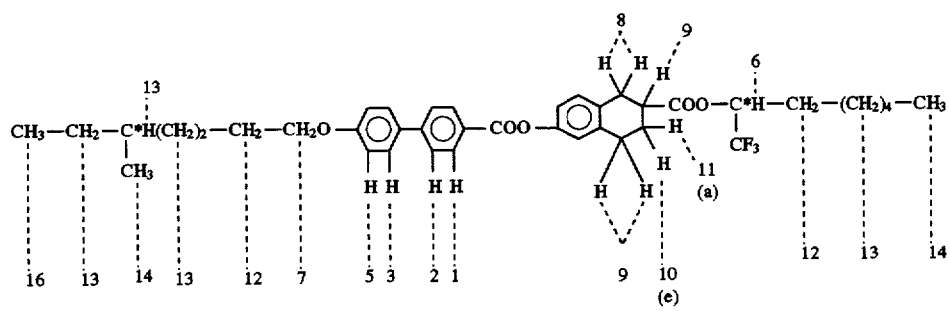

Figure 68:
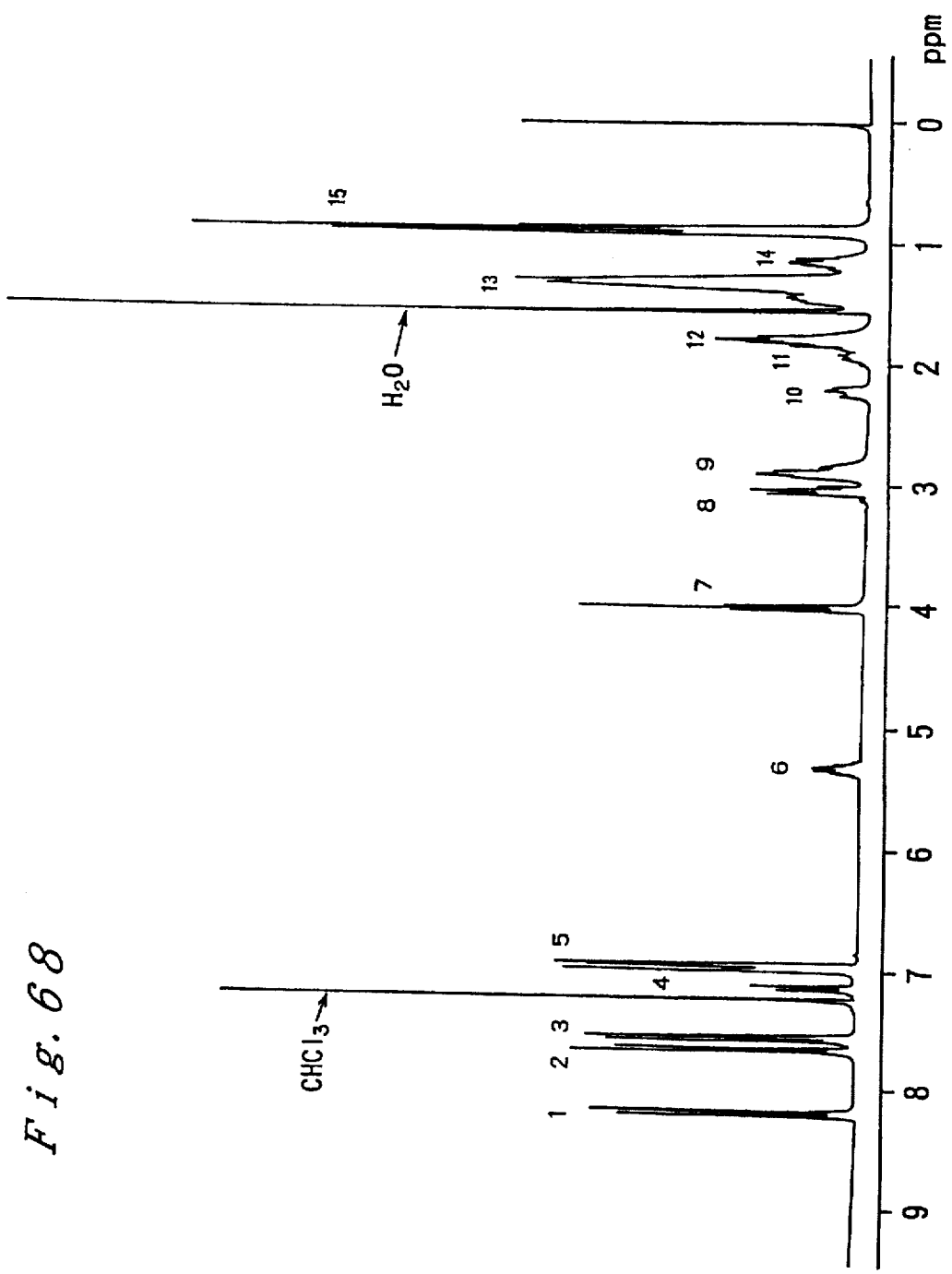
FIG. 68 shows $^1$H-NMR spectrum of 6-[4'-((S)-6-methyloctyloxy)-4-biphenylcarbonyloxy]-1,2,3,4-tetrahydro-2-naphthalenecarboxylic acid (R)-1-trifluoromethylheptyl ester. [Examplified compound (772)]

FIG. 68:
6-[4'-((S)-6-methyloctyloxy)-4-biphenylcarbonyloxy]-1,2,3,4-tetrahydro-2-naphthalenecarboxylic acid (R)-1-trifluoromethylheptyl ester [Compound (772)] represented by the following formula

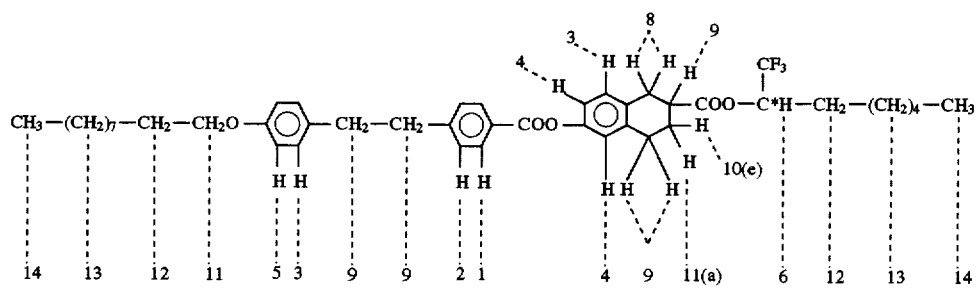

Figure 36:
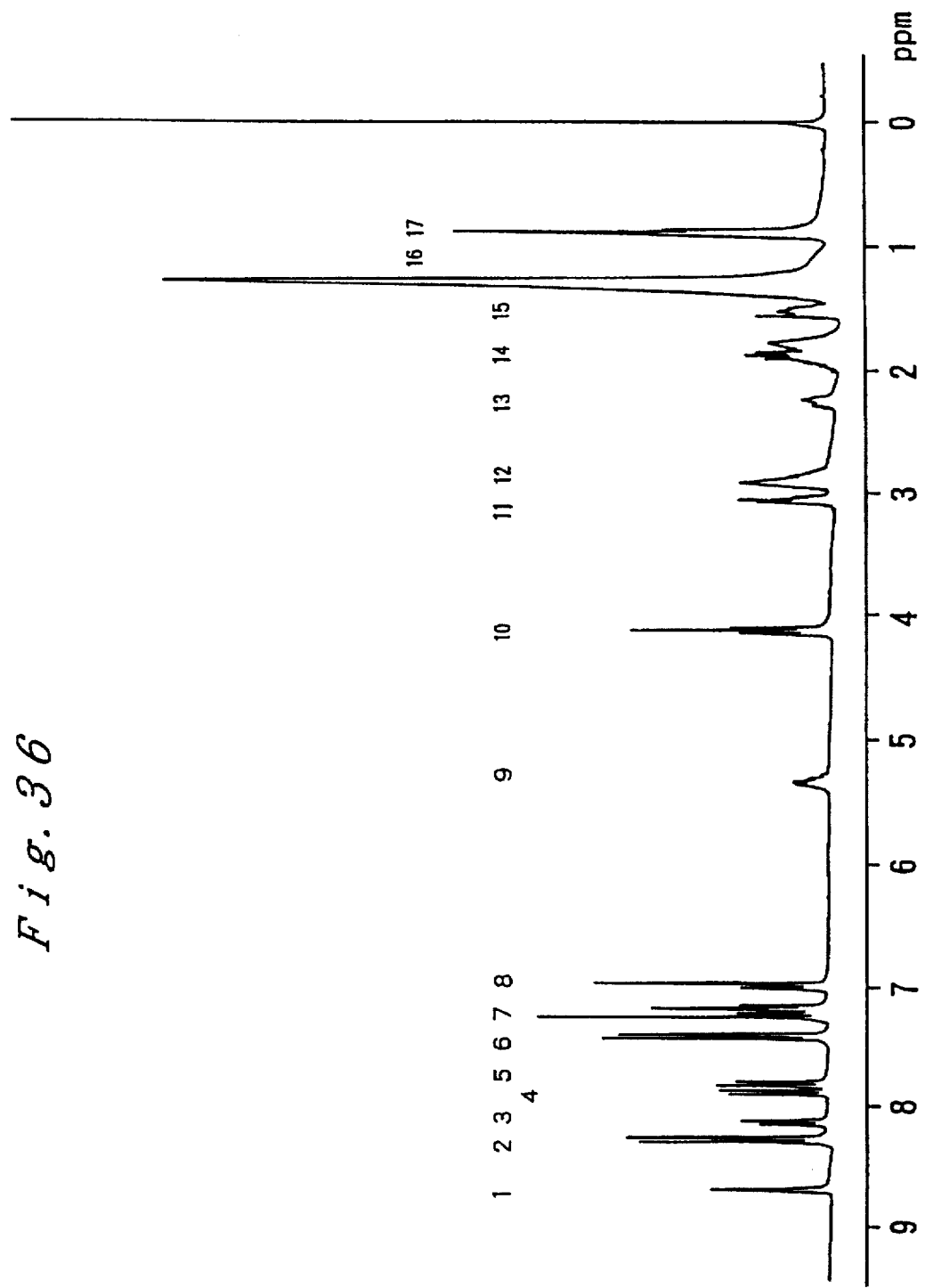
FIG. 36 shows ¹H-NMR spectrum of 6-[(4-(6-decyloxy-2-naphthoxyloxy)-benzoyloxy)]-1,2,3,4-tetrahydro-2-naphthalenecarboxylic acid (R)-1-trifluoromethylheptyl ester. [Exemplified compound (691)].

FIG. 36:
6-[(4-(6-decyloxy-2-naphthoxyloxy)-benzoyloxy)]-1,2,3,
4-tetrahydro-2-naphthalenecarboxylic acid (R)-1-trifluoromethylheptyl ester [Compound (691)] represented by the following formula

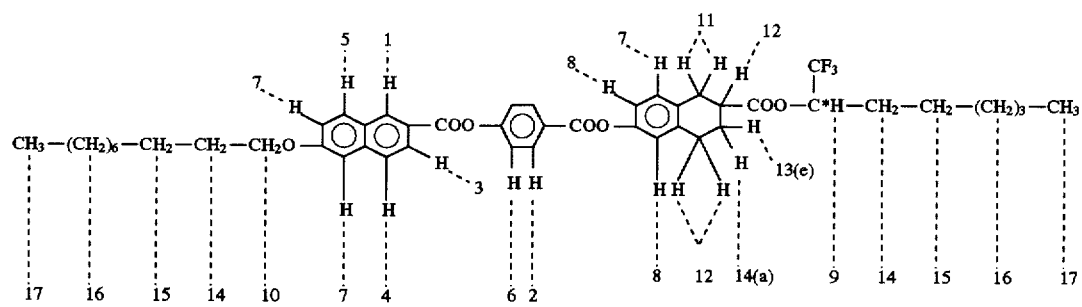

Figure 66:
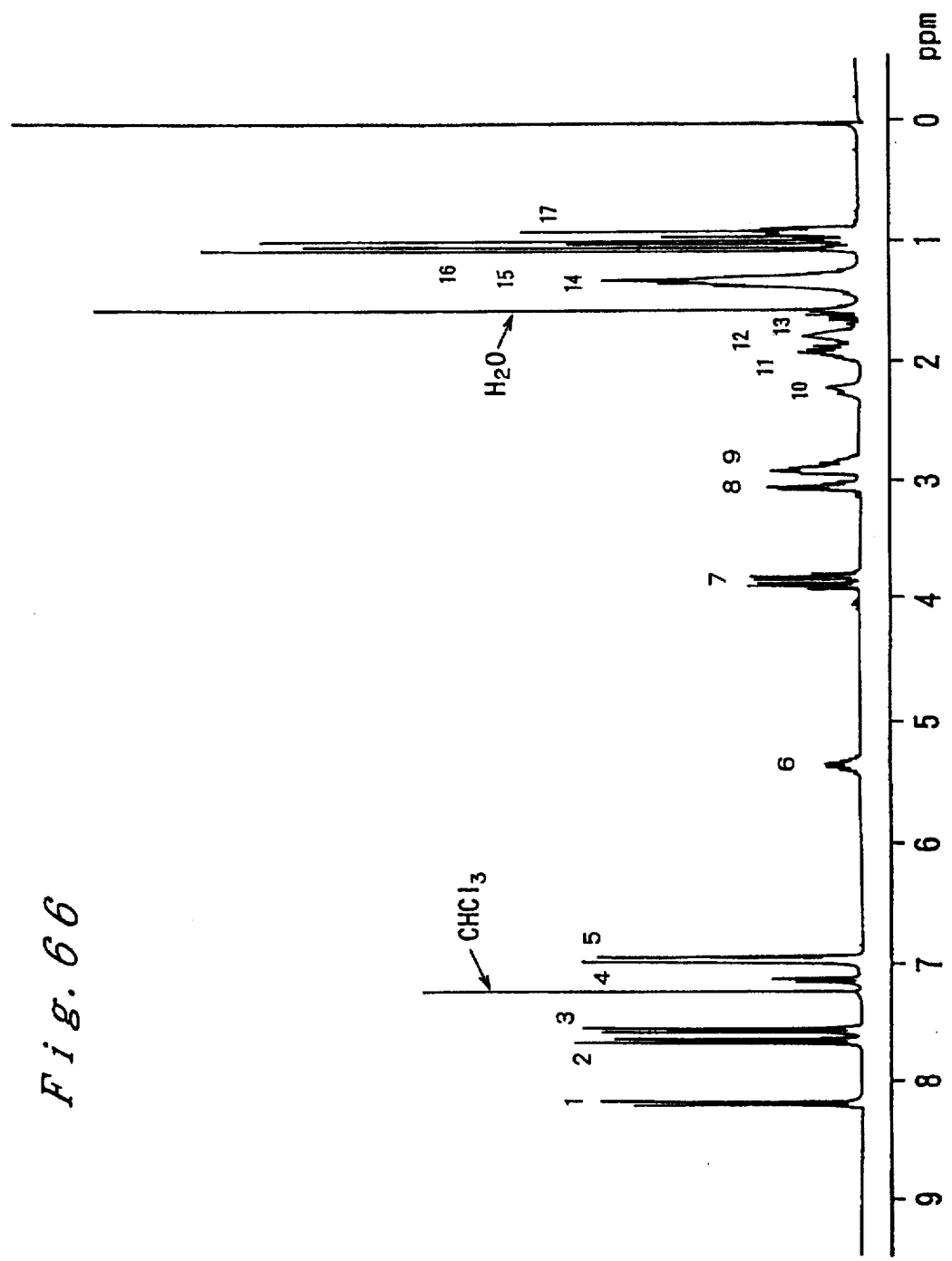
FIG. 66 shows $^1$H-NMR spectrum of 6-[4'-((S)-2-methylbutyloxy)-4-biphenylcarbonyloxy]-1,2,3,4-tetrahydro-2-naphthalenecarboxylic acid (R)-1-trifluoromethylheptyl ester. [Examplified compound (774)]

FIG. 66:
6-[4'-((S)-2-methylbutyloxy)-4-biphenylcarbonyloxy]-1,
2,3,4-tetrahydro-2-naphthalenecarboxylic acid(R)-1-trifluoromethylheptyl ester [Compound (774)] represented by the following formula

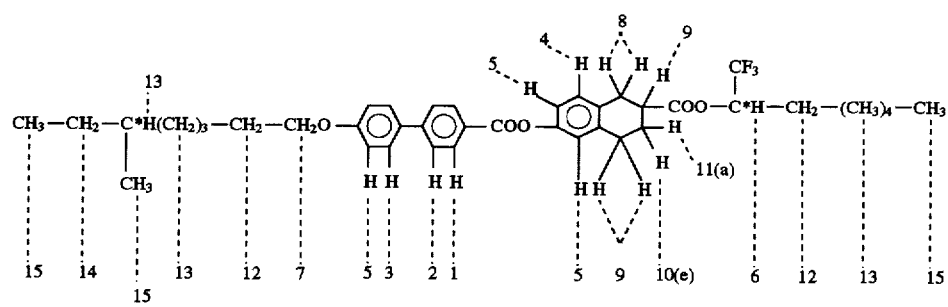

Figure 69:
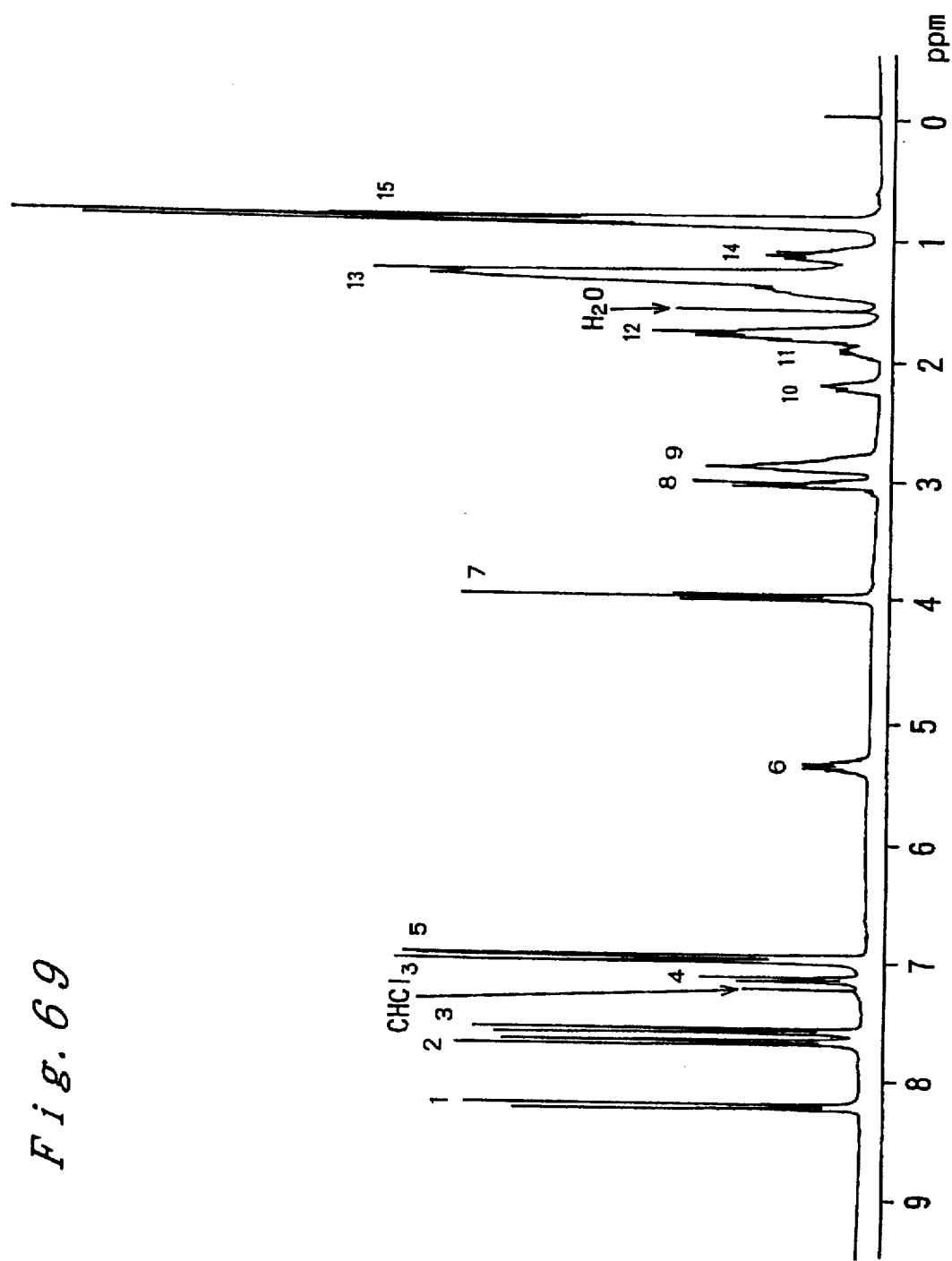
FIG. 69 shows $^1$H-NMR spectrum of 6-[4'-((S)-6-methyloctyloxy)-4-biphenylcarbonyloxy]-1,2,3,4-tetrahydro-2-naphthalenecarboxylic acid (S)-1-trifluoromethylheptyl ester. [Examplified compound (772)]

FIG. 69:
6-[4'-(R)-6-methyloctyloxy)-4-biphenylcarbonyloxy]-1,
2,3,4-tetrahydro-2-naphthalenecarboxylic acid (S)-1-trifluoromethylheptyl ester [Compound (772)] represented by the following formula

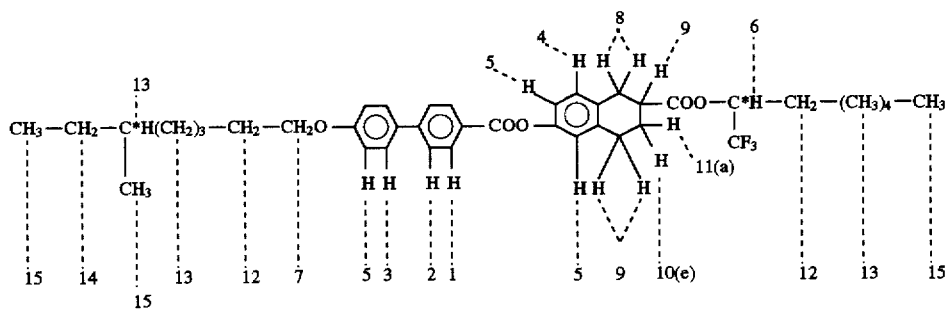

FIG. 70:

6-[4'-((S)-1-methylheptyloxy)-4-biphenylcarbonyloxy]-1,2,3,4-tetrahydro-2-naphthalenecarboxylic acid (R)-1-trifluoromethylhepthyl ester [Compound (776)] represented by the following formula

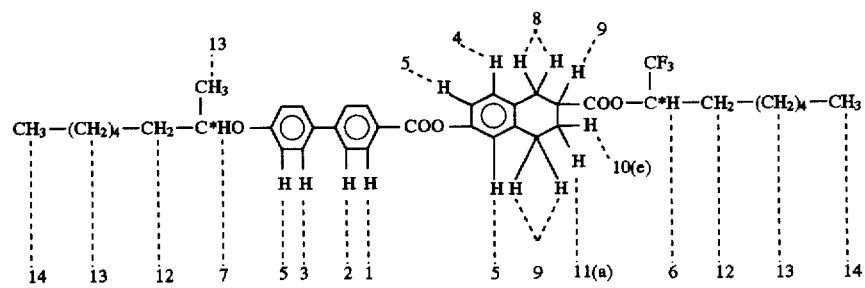

FIG. 71:

6-[4-((S)-2-methyloctyloxy)-4-biphenylcarbonyloxy]-1,2,3,4-tetrahydro-2-naphthalenecarboxylic acid (R)-1-trifluoromethylheptyl ester [Compound (775)] represented by the following formula

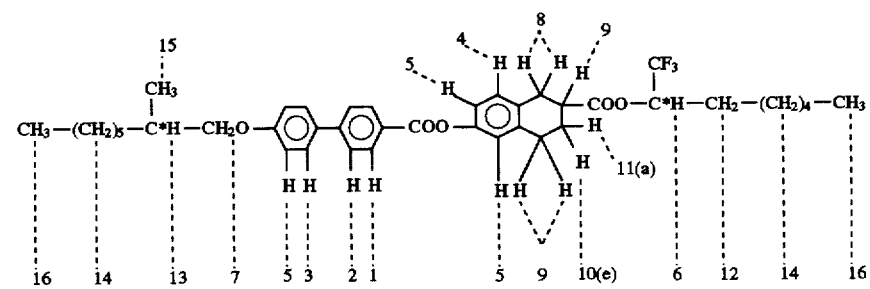

The carboxylate compounds represented by the above-mentioned formula [I], [II], [III] or [IV] may be used, for example, as liquid crystal materials.

Particularly, the carboxylate compounds of the invention can be used as ferroelectric liquid crystal compounds or antiferroelectric liquid crystal compounds.

Of the carboxylate compounds of the above formula [I], the following compounds [b 4], [21], [22], [130], [154] and [162] exhibit particularly excellent liquid crystal properties.

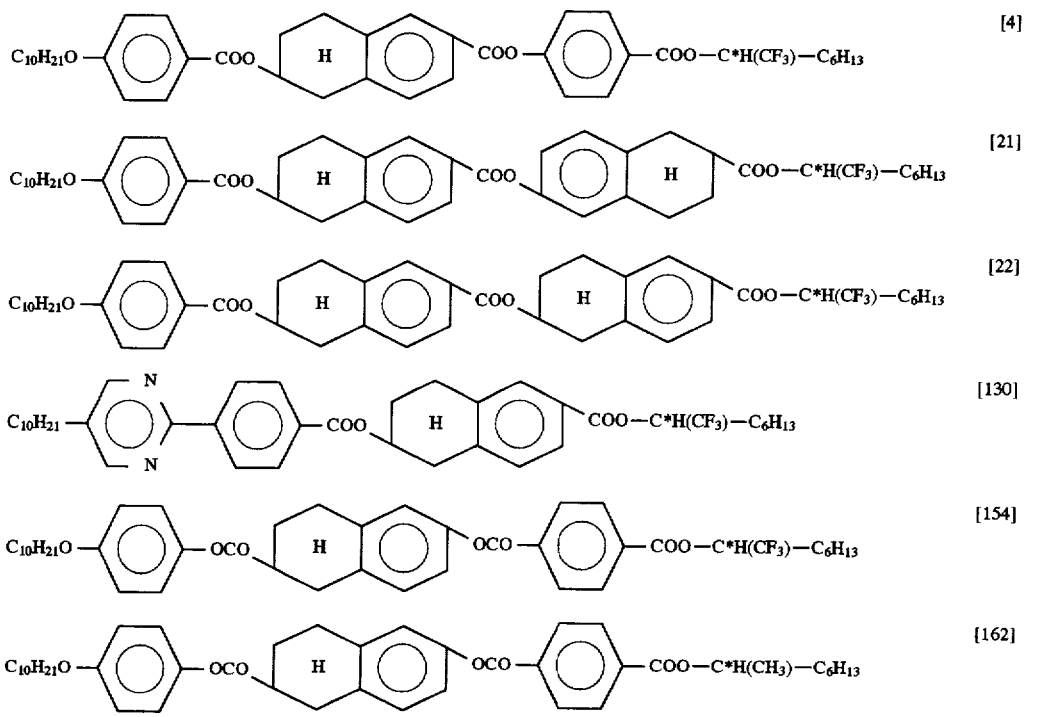

Phase transition temperatures of these compounds are shown in Table 5. Provided that, in Tables of the specification, Cry represents a crystal phase, SmX represents an unidentified smectic phase, SmC$_A$* represents an antiferroelectric phase, SmA represents a smectic A phase, Iso represents an isotropic liquid and SmC* represents a ferroelectric phase and SmCγ* represents a ferrielectric phase.

TABLE 5

| Compound No. | Cry-Smx or SmC$_A$* or Iso | Cry-SmA | SmC$_A$*-SmX | SmC$_A$*-SmA | SmC$_A$* or SmA-Iso | Example No. |
|---|---|---|---|---|---|---|
| (4) | 21° C. | — | 49° C. | — | 61° C. | 1 |
| (21) | 43° C. | — | — | 47° C. | 72° C. | 2 |
| (22) | 43° C. | — | — | — | — | 3 |
| (130) | 54° C. | — | — | — | — | 4 |
| (154) | — | 35° C. | — | — | 110° C. | 45 |
| (162) | — | 55° C. | — | — | 105° C. | 46 |

Furthermore, of the carboxylate compounds of the above formula [II], the following compounds exhibit particularly excellent liquid crystal characteristics.

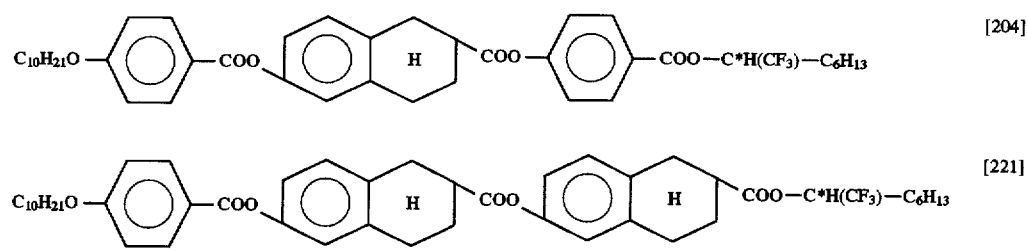

-continued
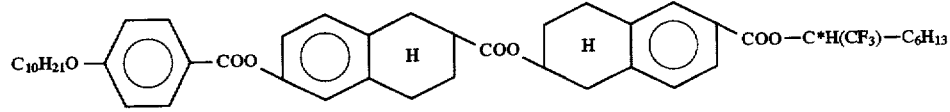  [222]
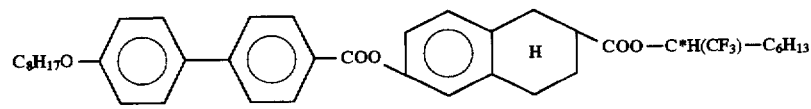  [249]
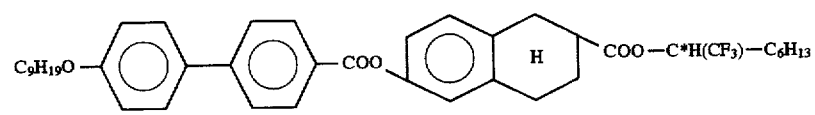  [250]
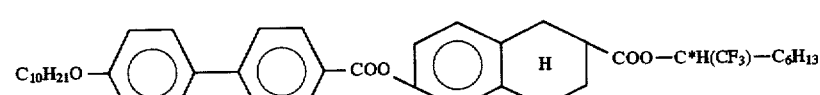  [251]
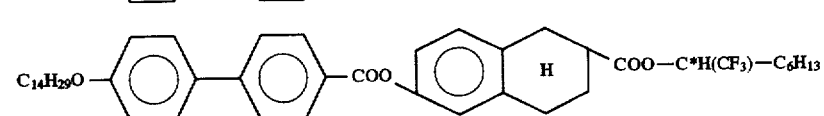  [254]
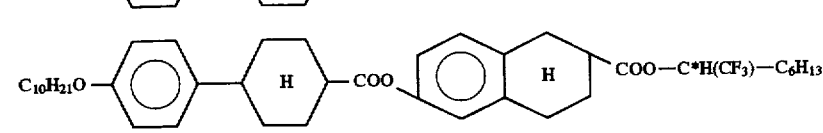  [267]
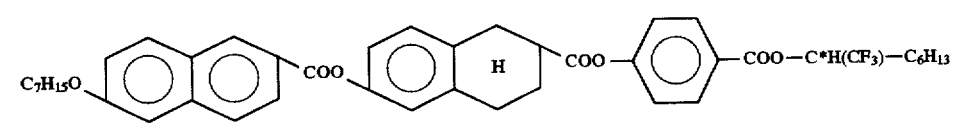  [288]
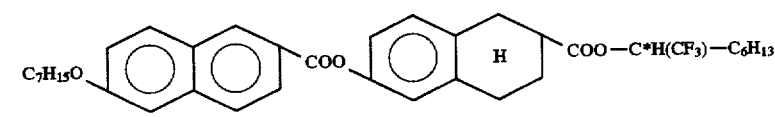  [296]
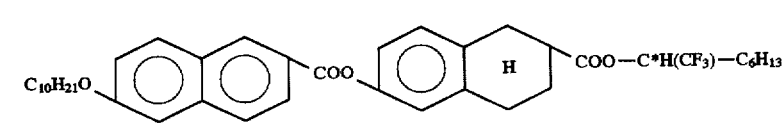  [299]
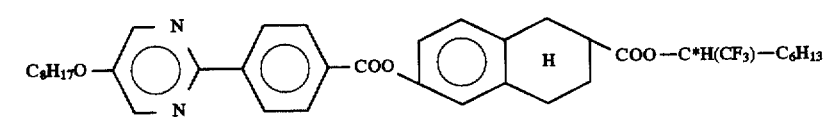  [313]
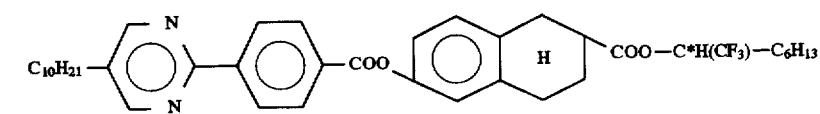  [331]
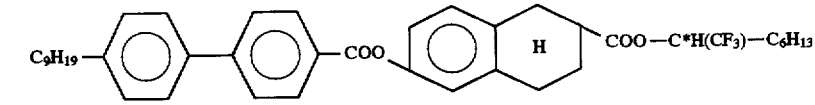  [354]
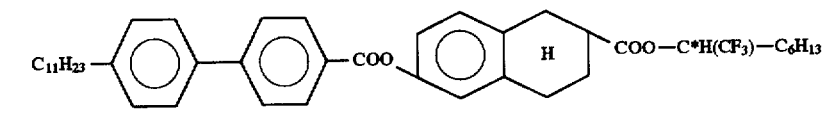  [356]
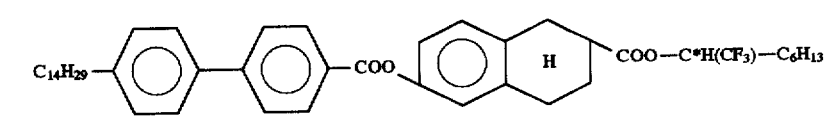  [358]

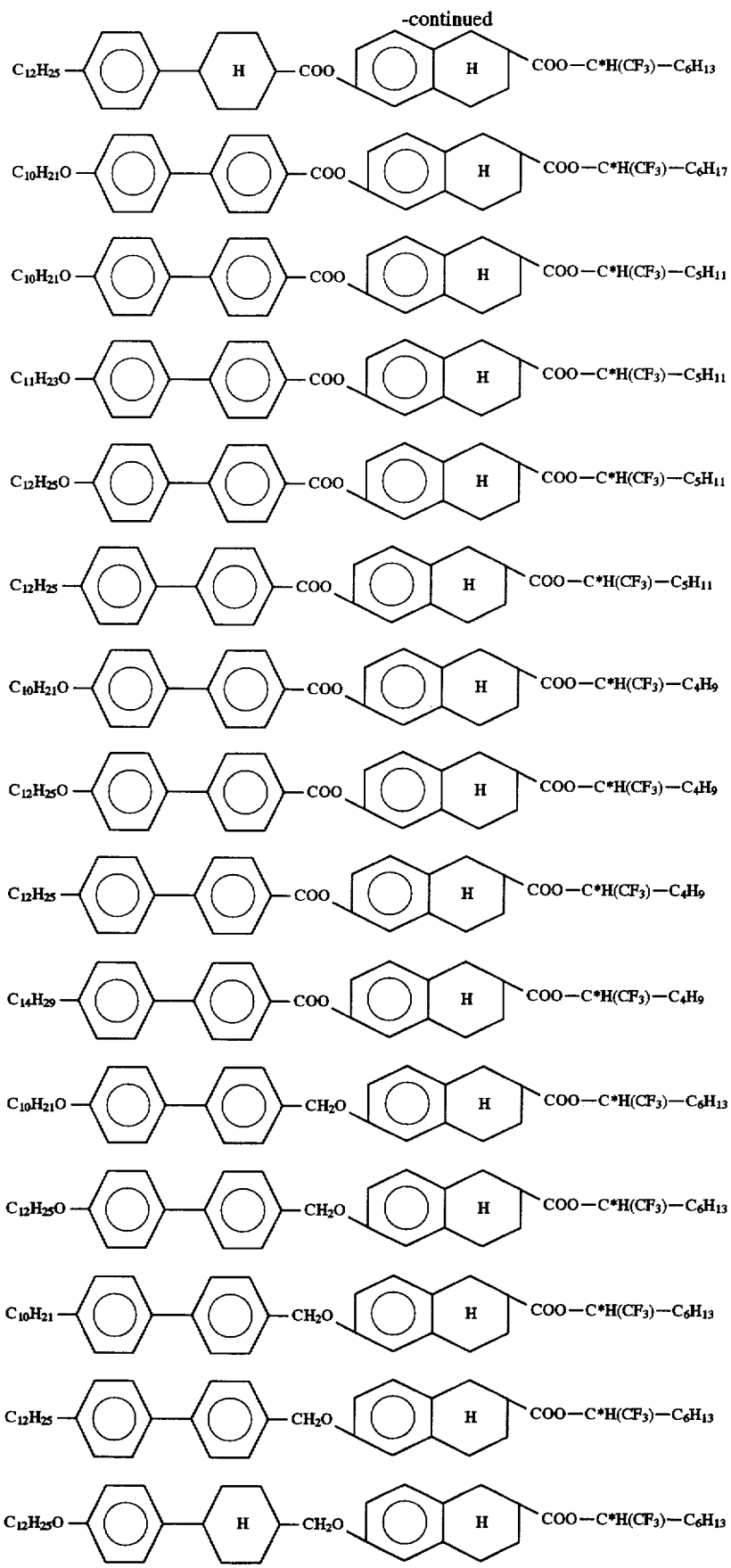

-continued

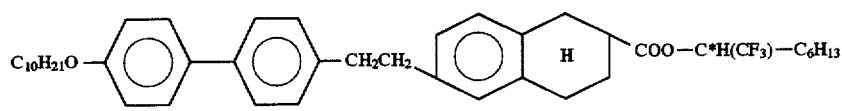
[451]

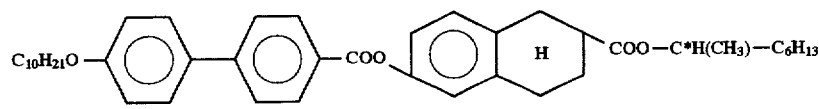
[467]

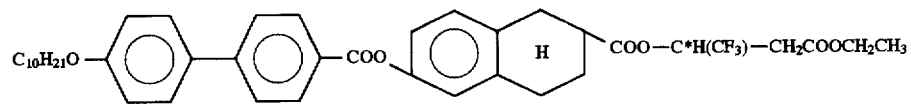
[483]

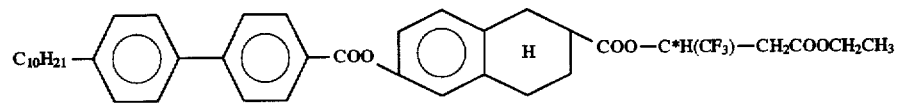
[491]

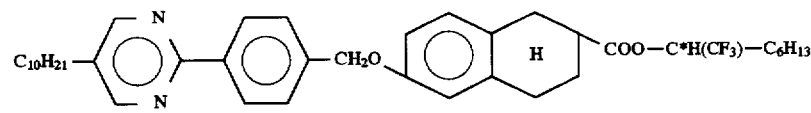
[507]

Phase transition temperatures of these compounds are shown in Table 6-1 and 6-2.

TABLE 6-1

| Compound No. | Cry-SmC$_A$* or SmC* or SmA | SmC$_A$*-SmA SmC*-SmA (222) | SmA-Iso |
|---|---|---|---|
| [204] | −23° C. | 81° C. | 113° C. |
| [221] | 46° C. | 71° C. | 109° C. |
| [222] | 30° C. | 36° C. | 52° C. |
| [251] | 21° C. | 99° C. | 130° C. |
| [267] | −5° C. | 44° C. | 87° C. |
| [288] | <−30° C. | 42° C. | 165° C. |
| [296] | 80° C. | — | — |
| [299] | 44° C. | — | 50° C. |
| [331] | 48° C. | — | 82° C. |

TABLE 6-2

| Compound No. | Cry | SmC$_A$* | SmC* | SmX | SmA | Iso | Example No. |
|---|---|---|---|---|---|---|---|
| [249] | · 65 | · 101 | — | — | · 142 | · | 48 |
| [250] | · 61 | · 96 | · 100 | · 101 | · 135 | · | 49 |
| [254] | · 47 | · 89 | — | — | · 108 | · | 50 |
| [313] | · 82 | (· 81) | · 99 | — | · 140 | · | 65 |
| [354] | · 40 | · 66 | — | — | · 106 | · | 51 |
| [356] | · 38 | · 71 | — | — | · 97 | · | 52 |
| [358] | · 28 | · 59 | — | · 71 | · 89 | · | 53 |
| [365] | · 23 | — | — | — | · 53 | · | 47 |
| [371] | · 50 | · 91 | — | — | · 122 | · | 54 |
| [387] | · 57 | — | · 108 | — | · 132 | · | 66 |
| [388] | · 37 | — | · 106 | — | · 130 | · | 67 |
| [389] | · 41 | — | · 107 | — | · 123 | · | 68 |
| [397] | · 41 | — | · 77 | — | · 98 | · | 69 |
| [403] | · 57 | · 89 | · 116 | — | · 142 | · | 70 |
| [405] | · 53 | · 103 | · 114 | — | · 134 | · | 71 |
| [413] | · 47 | — | · 84 | — | · 134 | · | 72 |
| [414] | · 54 | · 57 | · 84 | — | · 100 | · | 73 |
| [419] | · 45 | · 87 | · 92 | — | · 102 | · | 58 |
| [421] | · 50 | · 85 | · 91 | — | · 98 | · | 51 |
| [427] | · 38 | · 61 | — | · 66 | · 76 | · | 60 |
| [429] | · 40 | (· 27) | · 43 | — | · 62 | · | 61 |
| [437] | · 68 | — | — | — | (· 55) | · | 62 |
| [451] | · 65 | · 85 | — | — | · 95 | · | 63 |
| [467] | · 35 | · 85 | · 106 | · 108 | · 131 | · | 55 |

TABLE 6-2-continued

| Compound No. | Cry | SmC$_A$* | SmC* | SmX | SmA | Iso | Example No. |
|---|---|---|---|---|---|---|---|
| [483] | · 50 | — | · 104 | — | · 129 | · | 56 |
| [491] | · 45 | — | · 76 | — | · 103 | · | 57 |
| [507] | · 85 | — | — | — | (· 72) | · | 64 |

In Table 6-2, a dot indicates that the compound takes the phase when the temperature thereof is elevated and the number shows the elevated temperature (° C.) in order to change the left-hand phase to the right-hand phase-Provided that, in parenthesis, a dot indicate that the compound takes the phase when the temperature thereof is lowered and the number shows the lowered temperature in order to change the right-hand phase to the left-hand phase.

Of the carboxylate compounds represented by the above formula [III] or [IV], the following compounds exhibit particularly excellent liquid crystal characteristics.

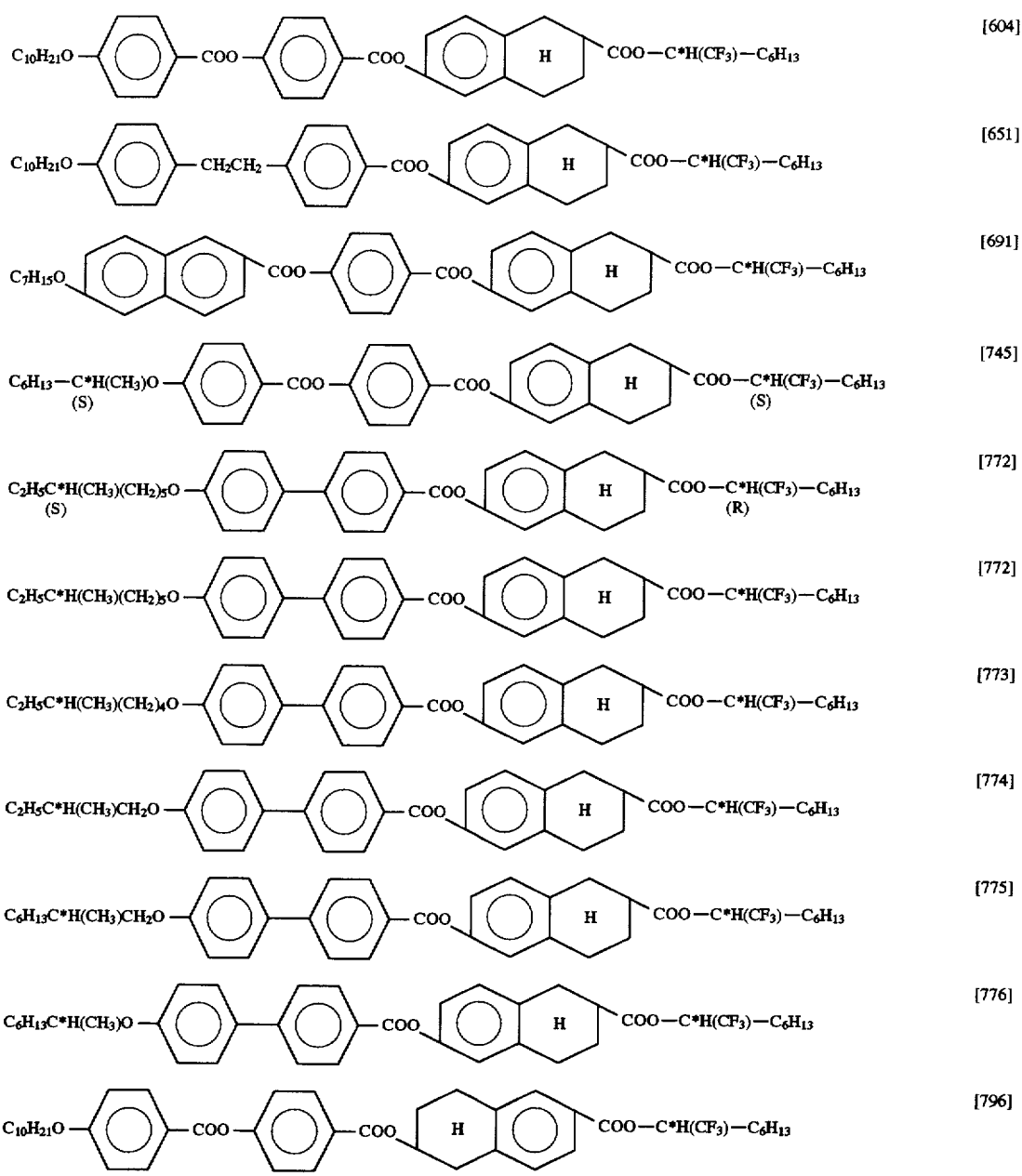

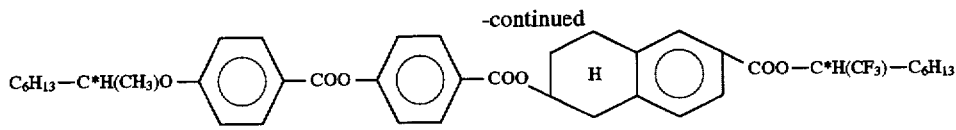

[937]

Phase transition temperatures of these compounds are shown in Table 7-1 and 7-2.

TABLE 7-1

| Compound No. | Cry-SmC$_A$* or SmA or Iso | SmC$_A$*-SmC* | SmC* or SmC* or Iso | SmA-Iso |
|---|---|---|---|---|
| (604) | 50° C. | 77° C. | 85° C. | 122° C. |
| (745) | 45° C. | — | — | — |
| (795) | 23° C. | — | 57° C. | — |
| (936) | −15° C. | — | — | — |

TABLE 7-2

| Compound No. | Cry | SmC$_A$* | SmC* | SmX | SmA | Iso | Example No. |
|---|---|---|---|---|---|---|---|
| (651) | · 46 | · 68 | — | — | · 78 | · | 43 |
| (691) | · 59 | · 81 | · 105 | — | · 170 | · | 44 |
| (772) | · 33 | · 81 | — | — | · 111 | · | 76 |
| (772) | · 64 | · 81 | — | — | · 113 | · | 77 |
| (773) | · 48 | · 51 | · 64 | — | · 109 | · | 75 |
| (774) | · 75 | — | — | — | · 109 | · | 74 |
| (775) | · 58 | — | — | — | — | · | 79 |
| (776) | · 29 | — | — | — | (· 26) | · | 78 |

In the Table 7-2, a dot indicates that the compound takes the phase when the temperature thereof is elevated and the number shows the elevated temperature (° C.) in order to change the left-hand phase to the right-hand phase-Provided that, in parenthesis, a dot indicate that the compound takes the phase when the temperature thereof is lowered and number shows the lowered temperature in order to change the right-hand phase to the left-hand phase.

In the liquid crystal materials of the invention, there are many compounds exhibiting a smectic phase over a broad temperature range, as shown in Tables 5 to 7.

There have been known few liquid crystal compounds which, if used alone as a liquid crystal material, exhibit a smectic phase over such a broad temperature range as in the above-mentioned compounds.

In addition to the fact that the liquid crystal materials of the invention exhibit a smectic phase in a broad temperature range, optical switching elements prepared by using said materials are excellent in high speed response.

The liquid crystal materials of the invention may be used either singly or in a mixture with other liquid crystal materials in the form of liquid crystal compositions. For example, the liquid crystal materials of the invention may be used as a principal component of antiferrodielectric liquid crystal compositions or as an assistant of liquid crystal compositions which contain other compounds exhibiting a smectic phase as a principal component. That is, the carboxylate compounds of the invention exhibiting a smectic phase may be used as a principal component of liquid crystal compositions or as an assistant of liquid crystal compositions which contain other liquid crystal materials as a principal component, while the carboxylate compounds which do not exhibit a smectic phase may be used as-an assistant of the latter liquid crystal compositions.

Examples of known liquid crystal compounds which may be used along with the compounds of the invention represented by the formulas [I] to [IV] include those listed below.

(+)-4'-(2"-methylbutyloxy)phenyl-6-octyloxynaphthalene-2-carboxylate,

4'-decyloxyphenyl-6-((+)-2"-methylbutyloxy)naphthalene-2-carboxylate,

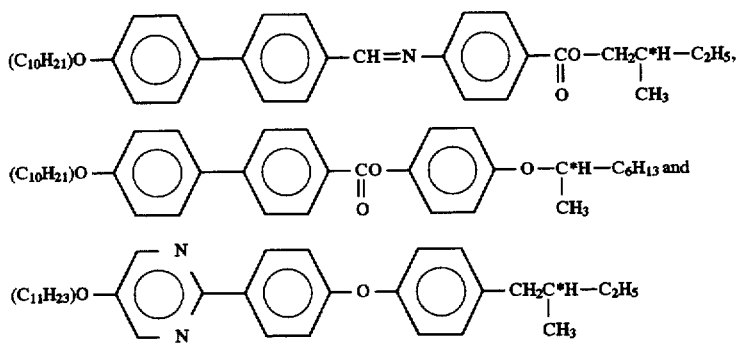

In addition to the above, there may be mentioned compounds having a cyclic system and an optical activity,

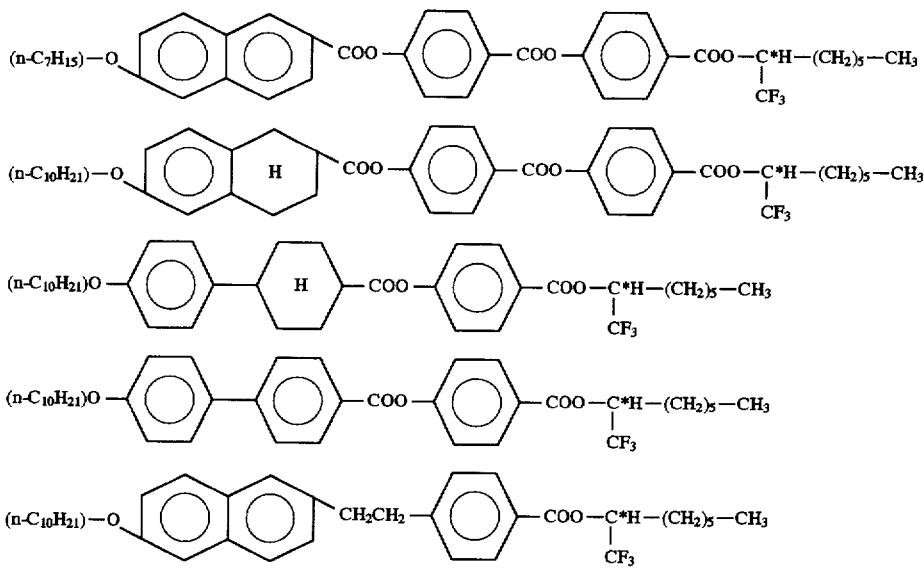

Further, there also may be mentioned Schiff base type liquid crystal compounds such as

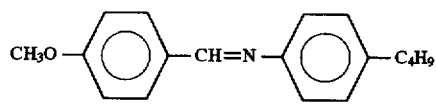

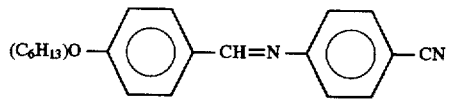

azoxy type liquid crystal compounds such as

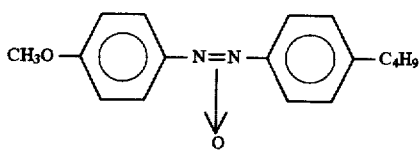

benzoate type liquid crystal compounds such as

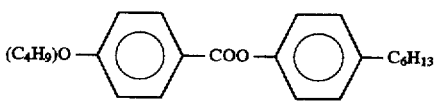

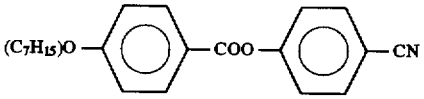

cyclohexylcarboxylate type liquid crystal compounds such as

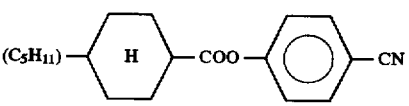

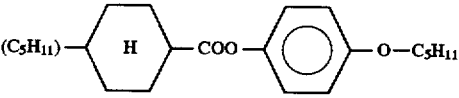

phenyl type liquid crystal compounds such as

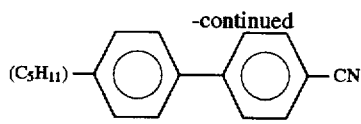

-continued terphenol type liquid crystal compounds such as

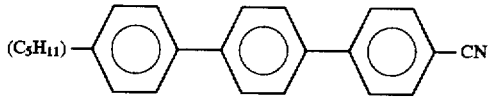

cyclohexyl type liquid crystal compounds such as

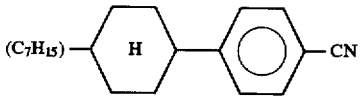

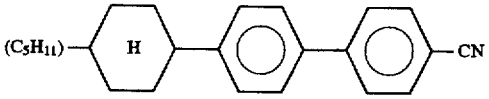

and pyrimidine type liquid crystal compound such as

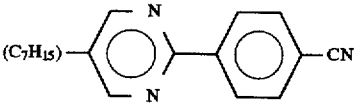

The liquid crystal compositions of the invention contain the carboxylate compounds of the formulas [I] to [IV] and other compounds including the compounds exemplified above.

The amount of the carboxylate compounds of the formulas [I] to [IV] in the liquid crystal composition may be selected depending on characteristics of the resulting composition. The composition of the invention contains the carboxylate compound of the formulas [I] to [IV] in an amount of usually 1–99 parts by weight, preferably 5–75 parts by weight based on 100 parts by weight of total amount of the liquid crystal present in the composition.

In addition to the liquid crystal material mentioned above, the liquid crystal composition may contain further additives conventionally used in liquid crystal compositions, for example, electrical conductivity-imparting agents and life-improving agents.

The liquid crystal composition of the invention may be prepared by mixing the above-mentioned carboxylate compound and, if desired, other liquid crystal compounds and additives.

When a voltage is applied to the liquid crystal composition (liquid crystal substance) containing the above-mentioned liquid crystal material, an optical switching phenomenon causes, and hence a display device exhibiting a good response due to this phenomenon can be produced. In the invention, with regard to the elements utilizing such phenomenon or the method of driving such elements, reference may be made, for example to Japanese Patent L-O-P Publns. Nos. 107216/1981 and 118744/1984.

The liquid crystal substance that may be used in the display device referred to above may include such compounds as exhibiting any of a smectic C phase, smectic F phase, smectic G phase, smectic H phase, smectic I phase, smectic J phase and smectic K phase. Because the display devices using the liquid crystal substances other than exhibiting the smectic C phase, have in general a low response speed, it has heretofore been considered that it is effective to drive the display device by means of the liquid crystal substance exhibiting the smectic C phase having a high speed response.

However, it have been found that it is possible in the invention to use advantageously the liquid crystal substances exhibiting not only a smectic C phase but also a smectic A phase by a method where the display device is driven by means of the liquid crystal substance exhibiting a smectic A phase as proposed by the present inventors in Japanese Patent L-O-P Publn. No. 3632/1989. That is, by virtue of the utilization of this driving method, the liquid crystal elements of the invention may be driven in a wide phase range and, at the same time, it is possible to speed up an electro-optical response.

Figure 17:
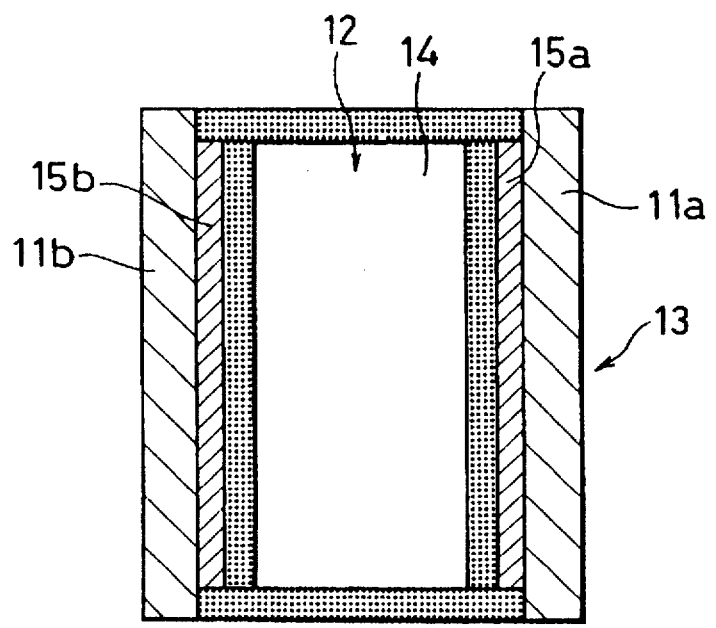
FIG. 17 is a schematical sectional view of the liquid crystal element of the present invention.

The liquid crystal element of the present invention is composed of a cell filled with a liquid crystal substance, and polarizing plates. For example, the liquid crystal element of the invention, as shown in FIG. 17, may be formed from a cell 13 comprising two transparent substrates 11a and 11b arranged so as to form a gap 14 to be filled with a liquid crystal substance 12, and transparent electrodes 15a and 15b formed on the surfaces of the transparent substrates 11a and 11b, said surfaces individually facing the liquid crystal substance 12, the liquid crystal substance 12 charged in the gap 14 of the cell 13, and polarizing plates (not shown) arranged outside at both sides of the cell 13.

In the invention, usable as the substrate are, for example, glass and transparent polymer plates. When glass substrates are used, in order to prevent deterioration of the liquid crystal substance owing to elution of alkali components of the glass, the glass surfaces may be provided, for example, with an undercoat layer (layer for shielding or prevention for unnecessary components) comprising silicon oxide as an essential ingredient. The transparent substrates, for example, glass substrates, have a thickness of usually 0.01–1.0 mm.

In the invention, there may also be used flexible transparent substrates as the transparent substrates. In this case, at least one of the substrates may be the flexible transparent substrates, and both substrates may be the flexible transparent substrates. Useful as such flexible transparent substrates are polymer films. When the flexible transparent substrates are used as the transparent substrates of the invention, it is preferable that a thickness t (mm) of said flexible transparent substrates, a modulus of elasticity E (kgf/m$^2$) and a width a (mm) of the gap formed in the cell which have the relationship represented by the following formula:

$$\frac{a^4}{Et^3} < 0.32$$

The transparent substrates as-mentioned above are provided on the surface of the transparent electrodes. The transparent electrodes may be formed, for example, by coating the transparent substrate surfaces with iridium oxide, tin oxide, etc. The transparent electrodes may be prepared by the method known. The thickness of the transparent electrodes is usually 100–2,000 Å.

The transparent substrates having such transparent electrodes may further be provided on the surfaces of the transparent electrodes with an orientation layer or a ferrodielectric material layer. The orientation layer may include, for example, an organic film and inorganic film formed by chemical adsorption thereon of an organic silane coupling agent or a carboxylic acid polynuclear complex. Examples of the organic film include films of polymers such as polyethylene, polypropylene, polyester, polyamide, polyvinyl alcohol and polyimide. The organic films may be formed by such techniques as coating, adhesion, vacuum deposition or polymerization (e.g. plasma polymerization) on the substrate.

Examples of the inorganic film may include films of oxides such as silicon oxide, germanium oxide and alumina, films of nitrides such as silicon nitride, and films of other semi-conductors. The inorganic films may be formed by such techniques as vacuum deposition (e.g. rhombic vacuum deposition) and sputtering.

The films as mentioned above may be imparted with orientation by imparting anisotropism or form specificity to the film itself in the film formation, or imparting externally orientation to the film after the film formation. Specifically, there may be mentioned a method in which the film is formed by coating polymer substance such as polyimide resin on the transparent electrode, followed by rubbing the film in a definite direction, a method in which a polymer film is subjected to stretching to thereby imparting orientation to the stretched film; and a method in which an oxide is subjected to rhombic vacuum depositing to thereby forming the oriented oxide film.

Such film (for example, orientation layer) may be so formed that it may serve simultaneously as a spacer, as mentioned below.

Two transparent substrates as mentioned above are arranged so that the transparent electrodes formed on the substrates face each other and a gap to be filled with a liquid crystal is formed by these two transparent substrates. The gap thus formed has a width of usually 1–10 μm, preferably 1–5 μm. Such gap may be formed, for example, by arranging two substrates so as to hold a spacer between them. Usable as such a spacer mentioned above, for example, is a polymer having a structure of polyimide obtained, for example, by patterning a photosensitive polyimide precursor. By the use of the spacer, a monodomain is formed by the interfacial effect between the spacer and the liquid crystal.

Figure 18:
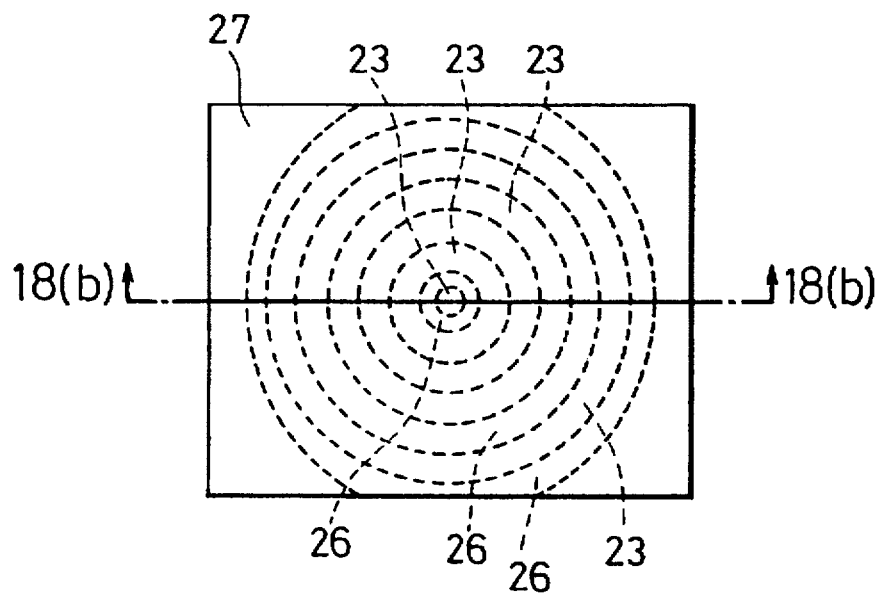
FIG. 18 (a) is a sectional view of the liquid crystal element having a concentric spacer, and FIG. 18 (b) is an A—A corss sectional view of the FIG. 18 (a).
Figure 18:
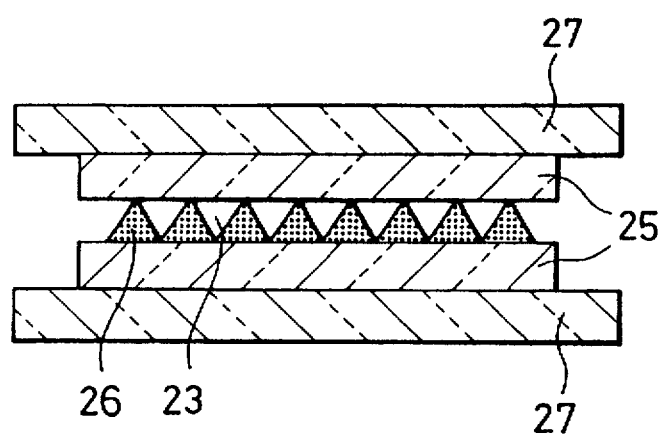

As shown in FIG. 18(a), and FIG. 18(b) showing an A—A cross section of (a), integration of the orientation film with the spacer may be made, for example, by using a concentric spacer 26 which acts as an orientation film. In FIGS. 18(a) and (b), 27 is transparent substrates, 25 is transparent electrodes, and 23 is a liquid crystal substance.

Figure 19:
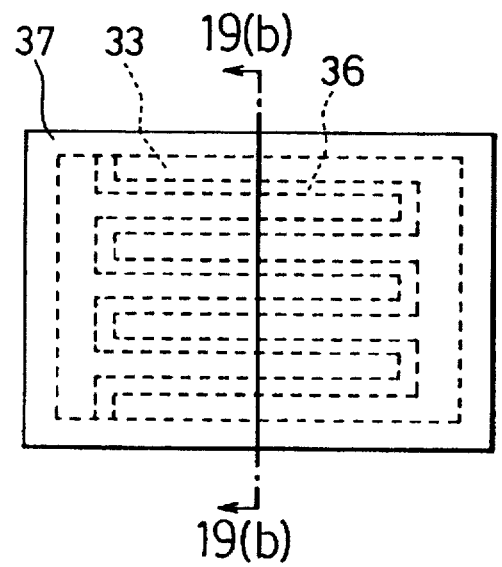
FIG. 19 (a) is a sectional view of the liquid crystal element having a comb-shaped spacer, and FIG. 19 (b) is an A—A cross sectional view of the FIG. 19 (a).
Figure 19:
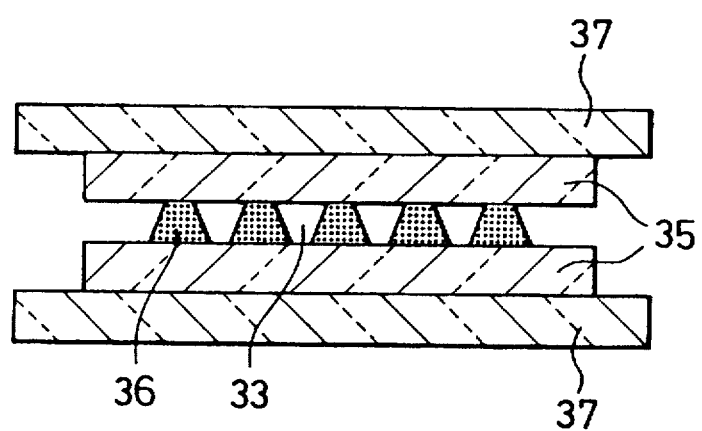

As shown in FIG. 19(a), and FIG. 19(b) showing an A—A cross section of(a), integration of the orientation film with spacer may be made, for example, by using a comb-like spacer 36 which acts as an orientation film. In FIGS. 19(a) and (b), 37 is transparent substrates, 35 is transparent electrodes, and 33 is a liquid crystal substance.

Figure 20:
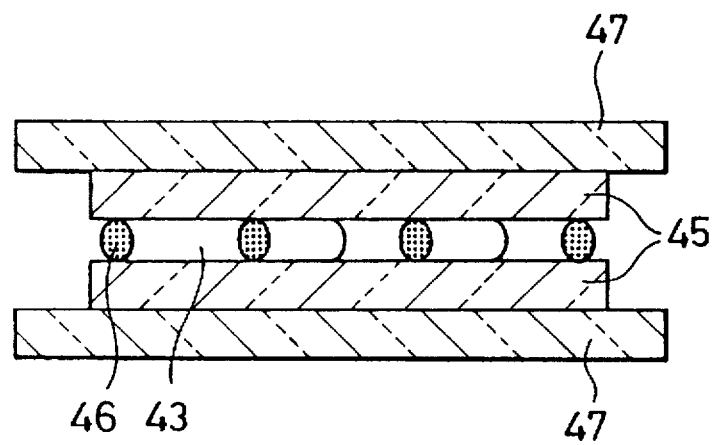
FIG. 20 is a sectional view showing the structure of the liquid crystal element having a fiber spacer of the present invention.

In stead of the above-mentioned spacers, fibers 46 may also be incorporated into a liquid crystal substance 43 in the manner as shown in FIG. 20, where the fibers 46 hold transparent substrates 47 bearing transparent electrodes 45 so as to form a definite gap between them.

Preferably, the fibers used herein are those having an average diameter and average length represented by the following formula:

$$3 \leq \frac{q}{d} \leq 100$$

wherein d is an average diameter of the fiber, and q is an average length of the fiber. The fibers used herein include preferably those obtained by spinning particularly alkali glass among various kinds of fibers useful therefor.

Further, it is also possible to incorporate particulate materials into the liquid crystal substance in place of or in combination with said fibers.

The particulate materials include those of melamine resin, urea resin or benzoguanamine resin having a particle diameter of 1–10 μm.

The two transparent substrates arranged so as to form the gap in the manner mentioned above are combined together by sealing their periphery with a sealer. Useful as the sealer are, for example, epoxy resin and silicone resin. The epoxy resin and the like used as the sealer may be modified with acrylic materials or silicone rubbers.

The gap of the liquid crystal cell having such a structure as mentioned above is filled with the liquid crystal substance containing the carboxylate compound represented by the above formula [I], [II], [III] or [IV].

The liquid crystal substance thus filled in the gap of the liquid crystal cell may be oriented, for example, by utilizing a monoaxial orientation control method such as a temperature gadient method utilizing a spacer edge or a surface treatment method using an orientation film. In the invention, moreover, it is possible to carry out the initial orientation of the liquid crystal substance, for example, by applying a direct bias voltage to the liquid crystal substance while heating said substance.

Figure 21:
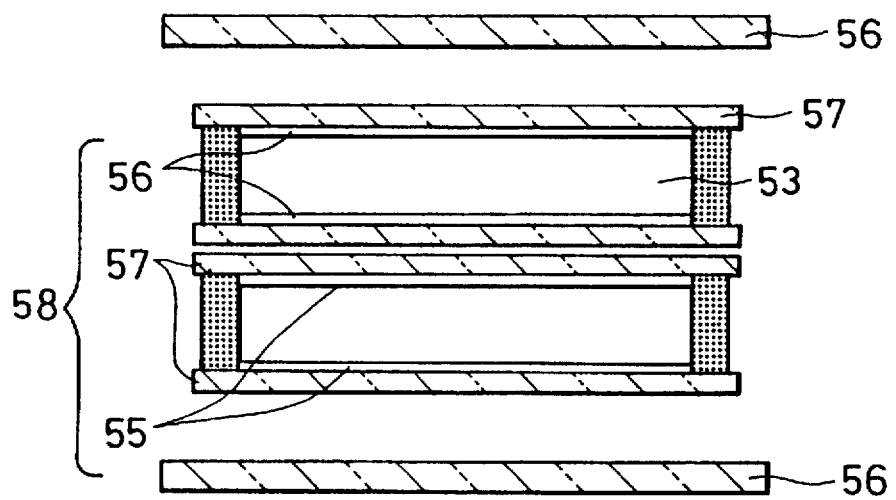
FIG. 21 is a sectional view showing the structure of the liquid crystal element of the invention, in which a cell composed of two polarizing plates is arranged.

The liquid crystal cell filled with the liquid crystal substance and subjected to initial orientation in the manner mentioned above is arranged between two polarizing plates. As shown in FIG. 21, two or more cells 58 comprising two transparent substrates 57, two transparent electrodes 55 and the liquid crystal substance 53 may also disposed between two polarizing plates 56.

In the liquid crystal element of the invention, two polarising plates may be disposed so that the directions of polarized light passed through the plates cross at an angle of 70°–110°, preferably at right angles, i.e., 90°.

Usable as such polarizing plates mentioned above are polarizing films which may be obtained by stretching a resin film such as polyvinyl alcohol resin film, polyvinyl butyral resin film or the like in the presence of iodine or the like and thereby absorbing the iodine thereinto, imparting polarizability. The polarizing films may have a mult-layer construction by coating their surface with other resin or the like.

In the present invention, the above-mentioned liquid crystal cell may be disposed between two polarizing plates disposed in the manner mentioned above so that a cross angle of two polarized directions of light passed through the polarizing plates is within the range of ±10° based on the cross angle corresponding to the darkest state where the amount of light passed through the plates is the least, preferably the darkest state is attained. The liquid crystal cell may also disposed between the polarized plates so that a cross angle of two polarized directions of light passed through the polarized plates is within the range of ±10° based on the brightest state where the amount of light passed through the plates is the most, preferably the brightest state is attained.

The liquid crystal element of the invention may be prepared, as shown in FIG. 21, by filling the gap 14 of the cell 13 with the liquid crystal substance 15 mentioned above, and subjecting said crystal substance 15 to initial orientation.

The liquid crystal substance 15 is heated usually until it reaches a molten state, and the molten substance is injected into the vacuumized gap 14 of the cell 13 through an inlet provided in the cell. After the injection operation, the inlet is sealed.

After sealing the inlet, the cell 13 is heated to a temperature higher than the temperature at which the liquid crystal substance 15 filled in the cell 13 exhibits an isotropic phase, and then the cell is cooled to a temperature at which the liquid crystal substance 15 is as a liquid crystal state.

The cooling may be carried out at a rate of, preferably lower than 2° C./min, more preferably 0.1°–2.0° C./min and particularly 0.1°–0.5° C./min. By cooling the cell 13 at such cooling rate, the state of initial orientation of the liquid crystal substance 15 is improved, and thus it is possible to form a liquid crystal element having a liquid crystal phase consisting of a monodomain of less orientation defect. The initial orientation referred to herein implies the state of arrangement of the liquid crystal substance prior to changing the orientation vector of liquid crystal substance by applying to said substance a voltage or the like.

In comparison with the prior art liquid crystal elements, the liquid crystal elements of the invention prepared in the manner as mentioned above are markedly excellent in characteristics such as contrast and the like, and are suitable for use, for example, as surface stabilized ferrodielectric liquid crystal elements, helical modulation elements, excess scattering type elements, guest-host type elements, vertical orientation liquid crystal elements and the like.

For instance, the liquid crystal element of the invention may be driven by application of an electric field wherein the frequency is controlled to usually 1 Hz–100 KHz, preferably 10 Hz–10 KHz, and the voltage to usually 0.01–60 Vp-p/μm', (voltage per thickness of 1 μm), preferably 0.05–30 Vp-p/μm'.

When the liquid crystal element of the invention using an optically active liquid crystal substance containing the carboxylate compound represented by the above formulas [I] to [IV] is driven by application of an electric field, two kinds of hysteresis curves are drawn, depending on the light volume passing through the liquid crystal element, by changing a width of the wave (driving wave) of the electric field to be applied. One of the procedures for describing two kinds of the hysteresis curves is a driving method in which a so-called bi-stability type is utilized, and the other is a driving method in which a so-called tri-stability type is utilized.

The liquid crystal element of the invention in which a liquid cell filled with an optically active liquid crystal substance is disposed between two polarizing plates so that the polarizing planes cross at right angles and the darkest state is attained when no electric field is applied, may be driven, for example, by application of an electric field of any wave form having a frequency of 50 Hz–100 KHz, preferably 70 Hz–10 KHz, such as a rectangular wave (or pulse wave), triangular wave, sine wave and a combination thereof. For example, when an electric field of a rectangular wave or a pulse wave or a combination thereof is applied, the driving speed of the liquid crystal element can be increased by employing a width of the electric field of not more than 10 millisec., preferably 0.01–10 millisec. In this range, the liquid crystal element of the invention may be used as a bi-stability type liquid crystal element. On the other hand, by employing the width of the electric field of larger than 10 millisec., preferably 33–1,000 millisec., the liquid crystal element of the invention may be used a tri-stability type liquid crystal element in the region where not so high driving speed is required.

"Width of the electric field" used herein means that, in the electric field of rectangular wave, for example, the time span for which a designated voltage is maintained.

By using the liquid crystal elements of the invention, there may be manufactured various liquid crystal display devices and electro-optical display devices. Of the liquid crystal elements of the invention, those filled with liquid crystal materials exhibiting a smectic phase may be used for manufacturing memory-type liquid crystal display devices or electro-optical display devices using, for example, a thermal-write or laser-write type liquid display element. Further, in addition to the above-mentioned uses, by the use of liquid crystal materials containing carboxylate compounds having a ferrodielectricity, there can be manufactured liquid crystal display devices or elector-optical display devices using, for example, light switching elements of light shutter or liquid crystal printer, piezoelectric element and pyroelectric element.

That is, the liquid crystal materials of the invention exhibit tri-stability of bi-stability, and hence it makes the liquid crystal elements of the invention have light switching or display function by inverting the electric field so as to accomplish the bi-stable state.

The liquid crystal substance exhibiting bi-stability used in the invention have a spontaneous polarization, and hence when a voltage is applied once, the thus applied liquid crystal substance has a memory effect even after elimination of the electric field. It is not necessary to apply continuously the electric field to the liquid crystal element in order to keep this memory effect, thus in the display device using the liquid crystal element of the invention, the consumption of electric power can be reduced. Moreover, the display device is very clear because of its stable contrast.

Further, in the switching element in the invention using the liquid crystal material, it is possible to perform switching operation only by changing the direction of orientation of the molecule. In this case, the first order of the field strength acts on the driving of the switching element, and hence the switching element of the invention can be driven at low voltage.

By using this switching element, it is possible to attain a high speed response of not more than several 10 seconds, and hence the operating time of the element can be shortened sharply. Accordingly, a display (liquid crystal display device) having large numbers of scanning lines and a large screen can be easily manufactured by using the liquid crystal element of the invention. Further, in the case of the liquid crystal substance exhibiting tri-stability, its memorizing properties can also be maintained. Moreover, this display can be driven without using an auxiliary means for controlling a driving temperature, because it can be driven at room temperature or lower.

Further, in the liquid crystal substance used in the invention, the molecule inclines inducibly when an electric field is applied thereto even in a smectic A phase which has been generally considered not to exhibit a bi-stability, and hence the light switching can be performed in this phase by utilizing such properties of the liquid crystal substance. That is, it has been considered that when ferrodielectric liquid crystal compounds are used, a practical response speed cannot be attained, and the smectic A phase thereof is not used generally. However it is possible to drive the display device of the invention by utilizing the driving method and apparatus proposed by the present inventors in EP-A2-332, 456 (1989). Further, the liquid crystal substance used in the invention exhibits two or more stable states even in the smectic F phase which is higher in order than the smectic C phase, and hence the light switching can be performed in the same manner as above utilizing a plurality of stable states in these phases.

The display device using the liquid crystal element of the invention may be driven by various methods, only a few of which are illustrated as follows.

The first method comprises interposing the liquid crystal element of the invention between two polarizing plates, applying an external voltage to the liquid crystal element to change an orientation vector of the liquid crystal substance filled in the element, and thereby performing the display by double refraction between the polarizing plates and the liquid crystal substance.

The second method is to utilize dichroism of a dichromic dye (or pigment) incorporated in a liquid crystal substance. This method is to perform the display by changing the orientation direction of the liquid crystal compound to cause a change of wavelength of light absorbed by the dye or pigment. The dye or pigment which may be used in this case has a dichromatic property including, for example, azo dyes, naphthoquinone dyes, cyanine dyes and anthraquinone dyes.

The display device prepared by using the liquid crystal element of the invention may be driven by the electric address display system, light address display system, heat address display system and light beam display system where any driving means may be employed, such as static drive, simple matrix drive and composite matrix drive.

Figure 22:
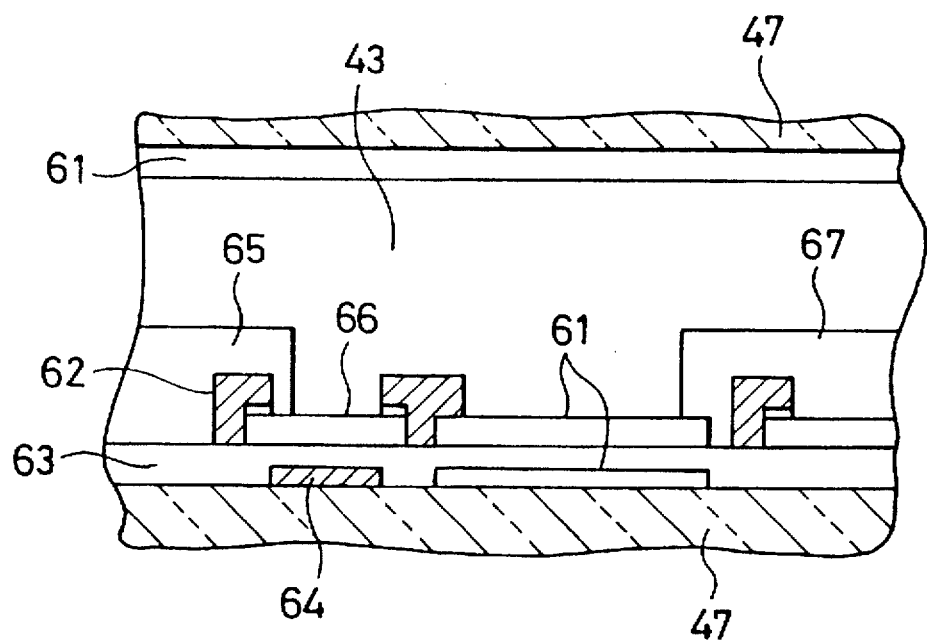
FIGS. 22 (a) and 22 (b) are a drawing showing examples of a nonlinear element and a three-terminal element, respectively.
Figure 22:
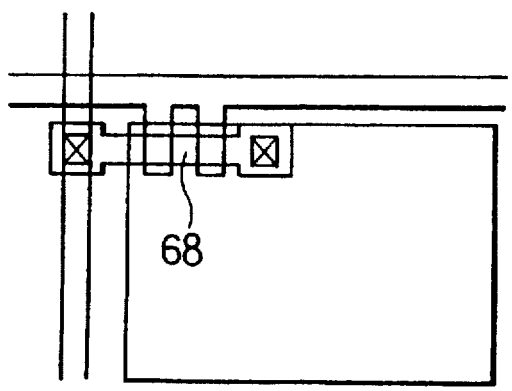

Further, when the display device in the invention is driven by application of an electric field, a nonlinear element or an active element as an element for driving each picture element. More particularly, as a nonlinear element of 2-terminal element, there may be mentioned, for example an element utilizing nonlinearities of a varistor, MIM (Metal Insulator Metal) and diode arranged on one transparent substrates, as shown in FIG. 22(a). In FIG. 22(a), 43 is a liquid crystal substance, 47 is a transparent substrate, 61 is an ITO (Indium Tin Oxide) layer, 62 is an Al/Mo layer, 63 is a SiO layer, 64 is a Mo layer, 65 is a n+α-Si, 66 is a iα-Si and 67 is a protecting layer. Further, as an active element of 3-terminal element, there may be mentioned, for example an element in which TFT (Thin Film Transistor), Si-MOS (Si-Metal Oxide Semi Conductor field-effect Transistor) or SOS (Silicon on Sapphire) is arranged on the picture element, as shown in FIG. 22(b). In FIG. 22(b), 68 is a TFT.

EFFECT OF THE INVENTION

As described above, according to the present invention, there are provided novel carboxylate compounds.

The novel carboxylate compounds are useful as liquid crystal materials, the liquid crystal element manufactured by using the compound as a liquid crystal material or a liquid crystal composition comprising the same are excellent in liquid crystal characteristics.

By combining two or more compounds of the invention or different kinds of liquid crystal substances, it is possible to broaden the temperature range within which the liquid crystal exhibits effective properties without marring ferroelectric properties and anti-ferroelectric properties of the compounds of the invention.

Accordingly, by the use of such compounds, it is possible to obtain liquid crystal elements or the like having a high speed response in a broad temperature range, high contrast and stable contrast.

Further, in the liquid crystal display prepared by using such an element, the operating time can be shortened sharply. In such display, the consumption of electric power can be reduced and, at the same time, a high contrast and a stable contrast are obtained. Further, a low voltage drive of the liquid crystal display is also possible.

Further, when the carboxylate compound of the invention is used as an anti-ferroelectric liquid crystal compound, the memory characteristics may be obtained without difficulty, and the orientation characteristics may also be improved.

By using the carboxylate compounds of the invention as liquid crystal materials, there can be obtained various devices having excellent characteristics such as a broad operating temperature range, high (fast) switching speed, very small consumption of electric power, and stable contrast.

The present invention is illustrated below with reference to examples, but it should construed that the invention is in no way limited to those examples. In the examples, R and S means R and S bodies of optically active compounds respectively.

EXAMPLE 1

Synthesis of 4-[6-(4-decyloxybenzoyloxy)-5,6,7,8-tetrahydro-2-naphthoyloxy]benzoic acid (R)-1-trifluoromethylheptyl ester [Compound (4)]

First Stage

In a 1-liter autoclave, 30 g (160 mmol) of 6-hydroxynaphthalene-2-carboxylic acid, 5 g of 5% palladium/carbon and 500 ml of tetrahydrofuran were mixed together, and the mixture was heated in a nitrogen atmosphere up to 105° C.

The mixture was allowed to undergo reaction in the autoclave maintained at a hydrogen pressure of 20 kg/cm² G, and a temperature of 105° C. with stirring for 3 hours.

After a three-hour reaction, the reaction system was allowed to cool to room temperature, the hydrogen gas was released, the reaction mixture obtained was filtered using Celite as a filter aid, and the filtrate obtained was concentrated.

The mixture thus obtained was recrystallized from toluene to obtain 16.1 g of a compound as a white crystal.

This compound had a M/e value in FD-mass spectrum of 192.

From this analytical result, this compound was identified as 5,6,7,8-tetrahydro-6-hydroxynaphthalene-2-carboxylic acid.

Second Stage

To a mixture of 0.96 g (a mmol) of 5,6,7,8-tetrahydro-6-hydroxynaphthalene-2-carboxylic acid, 1.52 g (5 mmol) 4-hydroxybenzoic acid R-1'-trifluoromethylheptyl ester synthesized separately by conventional means, 0.061 g (0.5 mmol) of 4-N,N-dimethylaminopyridine and 30 ml of methylene chloride was added dropwise 10 ml of a methylene chloride solution containing 1.13 g (5.5 mmol) of N,N'-dicyclohexylcarbodiimide with stirring at room temperature over a period of 5 hours.

Further, the reaction was carried out at room temperature for 14 hours.

The reaction mixture was filtered, and the filtrate was concentrated. The concentrate obtained was separated by column chromatography to obtain 2.18 g (4.56 mmol) of 4-(5',6',7',8'-tetrahydro-6'-hydroxy-2'-naphthoyloxy)benzoic acid (R)-1-trifluoromethylheptyl ester as a colorless transparent viscous liquid.

Third Stage

To a mixture of 0.48 g (1 mmol) of the 4-(5',6',7',8'-tetrahydro-6'-hydroxy-2'-naphthoyloxy)benzoic acid (R)-1-trifluoromethylheptyl ester obtained in the second stage, 0.278 g (1 mmol) of 4-decyloxybenzoic acid synthesized separately by conventional means, 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 3 hours.

Further, the reaction was carried out at room temperature for 3 hours.

The reaction mixture was filtered, and the filtrate was concentrated. The concentrate obtained was separated by column chromatography to obtain 0.45 g of a compound as a white solid.

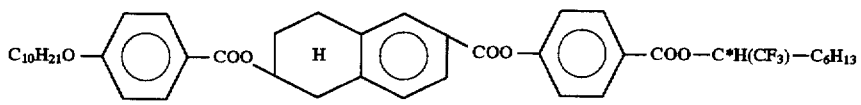

[4]

This compound had a M/e value in FD-mass spectrum of 738.

FIG. 1 shows ¹H-NMR spectrum of this compound.

From these analytical results, this compound was identified as the title compound as desired.

EXAMPLE 2

Synthesis of 6-[6-(4-decyloxybenzoyloxy)-5,6,7,8-tetrahydro-2-naphthoyloxy]-1,2,3,4-tetrahydro-2-naphthalenecarboxylic acid (R)-1trifluoromethylheptyl ester [Compound (21)]

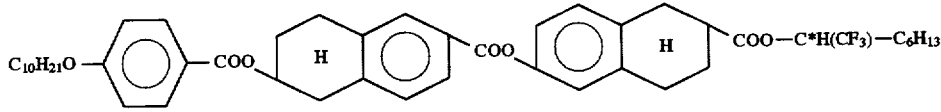

[21]

First Stage

To a mixture of 3.86 g (11.8 mmol) of 6-n-decyloxynaphthalene-2- acid and 130 ml of 1,2-diethoxyethane was added 3.0 g (130 mg atom) of metallic sodium with stirring in a nitrogen atmosphere at 120° C., and the resulting mixture was heated further up to the reflux temperature.

To this mixture was added dropwise 10 g (114 mmol) of isoamyl alcohol over a period of 1 hour, and the resulting mixture was allowed to undergo reaction under reflux for 11 hours. After cooling the reaction system to room temperature, the remaining metallic sodium was solubilized in the form of sodium alcoholate by the addition of ethanol, and the reaction mixture was acidified with 20% hydrochloric acid.

After addition to this reaction mixture of 100 ml of water, the organic phase was separated, followed by water washing.

The organic phase was then concentrated under reduced pressure to obtain 4.25 g of a solid. This solid was recrystallized from toluene to obtain 2.95 g (8.89 mmol) of 1,2,3,4-tetrahydro-6-n-decyloxynaphthalene-2-carboxylic acid.

Second Stage

A mixture of 16.6 g (50 mmol) of the 6-decyloxynaphthalene-2-carboxylic acid obtained in the first stage, 250 cc of acetic acid and 86.5 g (0.5 mol) of 47% hydrobromic acid was heated under reflux at 130° C. for 7 hours. After addition to the reaction system of distilled water, the reaction mixture was concentrated under reduced pressure to obtain 10.60 g (50 mmol) of 1,2,3,4-tetrahydro-6-hydroxynaphthalene-2-carboxylic acid.

Third Stage

A mixture of 10.60 g (50 mmol) of 1,2,3,4-tetrahydro-6-hydroxynaphthalene-2-carboxylic acid, 12.85 g (75 mmol) of benzyl bromide, 6.6 g (100 mmol) of 85% potassium hydrooxide, 0.525 g (3.5 mmol) of sodium iodide, 200 ml of ethanol and 25 ml of distilled water was heated under reflux at 100° C. for 12 hours. To this reaction mixture was added 50 ml of 10% potassium hydroxide, followed by heating under reflux at that temperature for 2 hours. After allowing the reaction system to cool up to room temperature, the reaction mixture in cold water was acidified with 36% hydrochloric acid. The resulting deposited product was filtered, and recrystallized from toluene to obtain 13.08 g (46.4 mmol) of 1,2,3,4-tetrahydro-6-benzyloxynaphthalene-2-carboxylic acid.

Fourth Stage

To a mixture of 5.64 g (20 mmol) of the 1,2,3,4-tetrahydro-6-benzyloxynaphthalene-2-carboxylic acid obtained in the third stage, 3.68 g (20 mmol) of R-1-trifluoromethylheptanol, 0.244 g (0.2 mmol) of 4-N,N-dimethylaminopyridine and 70 ml of methylene chloride was added dropwise 25 ml of a methylene chloride solution containing 4.53 g (22 mmol) of N,N'-dicylohexylcarbodiimide with stirring at room temperature for a period of 2 hours.

Further, the reaction was carried out at room temperature for 2 hours.

The reaction mixture was then filtered, and the filtrate was concentrated. The concentrate obtained was separated by column chromatography to obtain 8.19 g (18.3 mmol) of 1,2,3,4-tetrahydro-6-benzyloxynaphthalene-2-carboxylic acid (R)-1-trifluoromethylheptyl ester.

Fifth Stage

Hydrogen gas was blown into a mixture of 8.19 g (18.3 mmol) of the 1,2,3,4-tetrahydro-6-benzyloxynaphthalene-2-carboxylic acid (R)-1-trifluoromethylheptyl ester obtained in the fourth stage, 3.6 g of 5% palladium/carbon and 50 ml of tetrahydrofuran with stirring at room temperature and ordinary pressure for 24 hours. The reaction mixture was filtered using Celite as a filter aid, and the resulting filtrate was then concentrated to obtain 6.78 g (18.3 mmol) of 1,2,3,4-tetrahydro-6-hydroxynaphthalene-2-carboxylic acid (R)-1-tri-fluoromethylheptyl ester as a brown liquid.

Sixth Stage

To a mixture of 1.07 g (3 mmol) of the 1,2,3,4-tetrahydro-6-hydroxynaphthalene-2-carboxylic acid (R)-1-trifluoromethylheptyl ester obtained in the fifth stage, 0.576 g (3 mmol) of the 5,6,7,8-tetrahydro-6-hyydroxynaphthalene-2-carboxylic acid obtained in the first stage of Example 1, 0.037 g (0.3 mmol) of 4-N,N-dimethylaminopyridine and 20 ml of methylene chloride was added dropwise 10 ml of a methylene chloride solution containing 0.68 g (3.3 mmol) of N,N'-dicyclohexylcarbodiimide with stirring at room temperature over a period of 2 hours.

Further, the reaction was carried out at room temperature for 18 hours.

The reaction mixture was filtered, and the filtrate was then concentrated. The concentrate obtained was separated by column chromatography to obtain 0.55 g (1.03 mmol) of 5',6',7',8'-tetrahydro-6'-hydroxy-2'-naphthoyloxy]-5,6,7,8-tetrahydronaphthalene-2-carboxylic acid (R)-1-trifluoromethylheptyl ester.

Seventh Stage

To a mixture of 0.55 g (1.03 mmol) of the 5',6',7',8'-tetrahydro-6'-hydroxy-2'-naphthoyloxy]-5.6.7.8-tetrahyddronaphthalene-2-carboxylic acid (R)-1-trifluoromethylheptyl ester obtained in the sixth stage, 0.286 g (1.03 mmol) of 4-decyloxy-benzoic acid synthesized separately by conventional means, 0.013 g (0.103 mmol) of 4-N,N-dimethylaminopyridine and 10 ml of methylene chloride was added dropwise 5 ml of a methylene chloride solution containing 0.255 g (1.2 mmol) of N,N'-dicyclohexylcarbodiimide with stirring at room temperature over a period of 4 hours.

Further, the reaction was carried out for 4 hours.

The reaction mixture was distilled, and the filtrate was then concentrated. The concentrate obtained was separated by column chromatography to obtain 0.46 g of a compound as a white solid.

This compound had a M/e value in FD-mass spectrum of 792.

FIG. 2 shows $^1$H-NMR spectrum of this compound.

From these analytical results, this compound was identified as the title compound as desired.

EXAMPLE 3

Synthesis of 6-[6-(4-decyloxybenzoyloxy)-5,6,7,8-tetrahydro-2-naphthoyloxy]-5,6,7,8-tetrahydro-2-naphthalenecarboxylic acid (R)-1-trifluoromethylheptyl ester [Compound (22)]

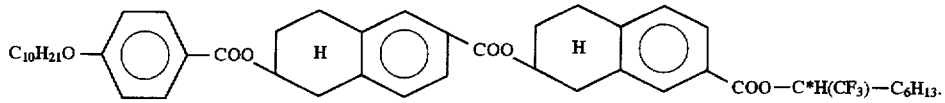

[22]

First Stage

To a mixture of 0.38 g (2 mmol) of 5,6,7,8-tetrahydro-6-hydroxynaphthalene-2-carboxylic acid, 0.22 g (2 mmol) of benzyl alcohol, 0.024 g (0.2 mmol) of 4-N,N-dimethylaminopyridine and 15 ml of methylene chloride was added dropwise 10 ml of a methylene chloride solution containing 0.45 g (2.2 mmol) of N,N'-dicyclohexylcarbodiimide with stirring at room temperature over a period of 1.5 hours.

Further, the reaction was carried out for 14 hours.

The reaction mixture was filtered, and the filtrate was concentrated. The concentrate obtained was separated by column chromatography to obtain 0.40 g (1.4 mmol) of 5,6,7,8-tetrahydro-6-hydroxynaphthalene-2-carboxylic acid benzyl ester.

Second Stage

To a mixture of 0.04 g (1.42 mmol) of the 5,6,7,8-tetrahydro-6-hydroxynaphthalene-2-carboxylic acid benzyl ester obtained in the first stage, 0.395 g (1.42 mmol) of 4-decyloxy-benzoic acid synthesized separately by conventional means, 0.017 g (0.14 mmol) of 4-N,N-dimethylaminopyridine and 10 ml of methylene chloride was added dropwise 5 ml of a methylene chloride solution containing 0.35 g (1.42 mmol) of N,N'-dicyclohexylcarbodiimide with stirring at room temperature over a period of 4 hours.

Further, the reaction was carried out for 16 hours.

The reaction mixture was filtered, and the filtrate was concentrated. The concentrate obtained was separated by column chromatography to obtain 0.53 g (1.42 mmol) of 6-(4'-decyloxybenzoyloxy)-5,6,7,8-tetrahydronaphthalene-2-carboxylic acid benzyl ester.

Third Stage

Hydrogen gas was blown into a mixture of 0.53 g (1.0 mmol) of 6-(4'-decyloxybenzoyloxy)-5,6,7,8-tetrahydronaphthalene-2-carboxylic acid benzyl ester, 0.11 g of 5% palladium/carbon and 10 ml of tetrahydrofuran with stirring at room temperature and ordinary pressure for 15 hours. The reaction mixture was filtered using Celite as a filter aid, and the filtrate was concentrated to obtain 0.42 g (0.93 mmol) of 6-(4'-decyloxybenzoyloxy)-5,6,7,8-tetrahydronaphthalene-2-carboxylic acid.

Fourth Stage

To a mixture of 2.88 g (15 mmol) of the 5,6,7,8-tetrahydro-6-hydronaphthalene-2-carboxylic acid obtained in the first stage of Example 1, 2.76 g (15 mmol) of 1-trifluoromethylheptyl alcohol, 0.183 g (1.5 mmol) of 4-N,N-dimethylaminopyridine and 50 ml of methylene chloride was added dropwise 20 ml of a methylene chloride solution containing 3.40 g (16.5 mmol) of N,N'-dicyclohexylcarbodiimide with stirring at room temperature for a period of 24 hours.

Further, 2 ml of a methylene chloride solution containing 0.41 g (2.0 mmol) of N,N'-dicyclohexylcarbodiimide was added to the mixture, and the resulting mixture was allowed to undergo reaction at room temperature for 72 hours.

The reaction mixture was filtered, and the filtrate was then concentrated. The concentrate obtained was separated by column chromatography to obtain 3.11 g (8.69 mmol) of 5,6,7,8-tetrahydro-6-hydroxynaphthalene-2-carboxylic acid (R)-1-trifluoromethylheptyl ester.

Fifth Stage

To a mixture of 0.42 g (0.93 mmol) of the 6-(4'-decyloxybenzoyloxy)-5,6,7,8-tetrahydronaphthalene-2-carboxylic acid obtained in the third stage, 0.44 g (0.93 mmol) of the 5,6,7,8-tetrahydro-6-hydroxynaphthalene-2-carboxylic acid (R)-1-trifluoromethylheptyl ester obtained in the fourth stage, 0.011 g (0.092 mmol) of 4-N,N-dimethylamino pyridine and 10 ml of methylene chloride was added dropwise 5 ml of a methylene chloride solution containing 0.23 g (1.1 mmol) of N,N'-dicyclohexylcarbodiimide with stirring at room temperature over a period of 3 hours.

Further, the reaction was carried out at room temperature for 120 hours.

The reaction mixture was filtered, and the filtrate was concentrated. The concentrate obtained was separated by column chromatography to obtain 0.43 g of a compound as a white solid.

This compound had a M/e value in FD-mass spectrum of 792.

FIG. 3 shows $^1$H-NMR spectrum of this compound.

From these analytical results, this compound was identified as the title compound as desired.

EXAMPLE 4

Synthesis of 6-[4-(5-decyl-2-pyrimidinyl)benzoyloxy]-5,6,7,8-tetrahydro-2-naphthalenecarboxylic acid (R)-1-trifluoromethylheptyl ester [Compound (130)]

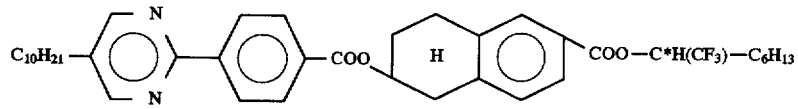

[130]

First Stage

To a mixture of 0.44 g (0.93 mmol) of the 5,6,7,8-tetrahydro-5,6-hydroxynaphthalene-2-carboxylic acid (R)-1-tri-fluoromethylheptyl ester obtained in the fourth stage of Example 3, 0.264 g (0.8 mmol) of 4-(5'-decyl-2'-pyrimidinyl)benzoic acid (produced and sold by Kojima Kagaku K.K.), 0.01 g (0.08 mmol) of 4-N,N-dimethylaminopyridine and 20 ml of methylene chloride was added dropwise 5 ml of a methylene chloride solution containing 0.18 g (0.88 mmol) of N,N'-dicyclohexylcarbodiimide with stirring at room temperature over a period of 1.5 hours.

Further, the reaction was carried out for 4 hours.

The reaction mixture was filtered and the filtrate was then concentrated. The concentrate obtained was separated by column chromatography to obtain 0.39 g of a white solid.

This compound had a M/e value in FD-mass spectrum of

FIG. 4 shows $^1$H-NMR spectrum of this compound is shown.

From these analytical results, this compound was identified as the title compound as desired.

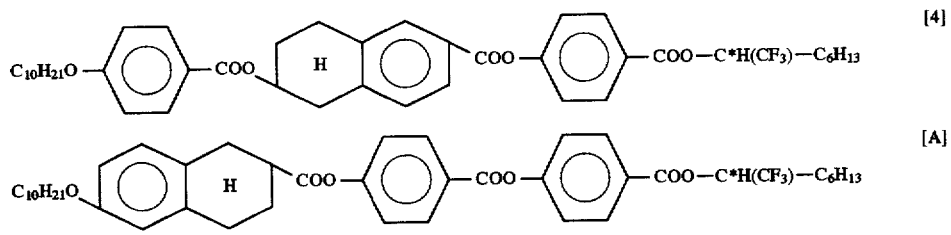

EXAMPLE 5

The compound (4) of the following formula [4] obtained in Example 1 was mixed with compound (A) represented by the following formula [A] in the weight ratio of 75:25 to obtain a liquid crystal composition of the invention.

Phase transition temperatures of this composition measured are shown in Table 8 together with those of the compound (4) and the compound (A).

TABLE 8

| Compound No. | Cry-SmC$_A$* or SmX | SmX-SmAC$_A$* or SmC$_A$*-SmA | SmA-Iso |
|---|---|---|---|
| (4) | 21° C. | 49° C. | 61° C. |
| (A) | 44° C. | 78° C. | 94° C. |
| (4) 75% + (A) 25% | 45° C. | 68° C. | 74° C. |

EXAMPLE 6

The compound (21) of the following formula [21] obtained in Example 2 was mixed with compound (A) represented by the following formula [A] in the weight ratio of 50:50 to obtain a liquid crystal composition of the invention.

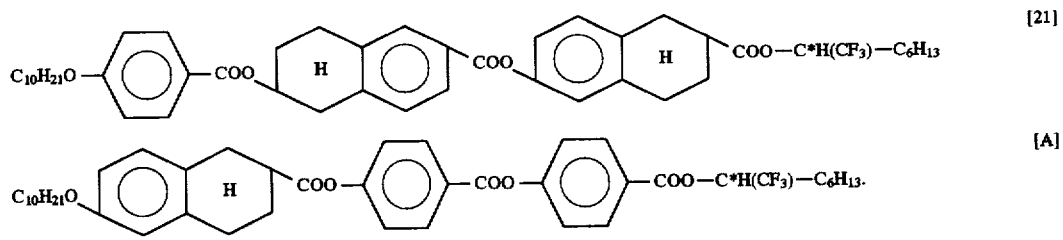

Phase transition temperatures of this composition measured are shown in Table 9 together with those of the compound (21) and the compound (A).

TABLE 9

| Compound Number | Cry-SmC$_A$* | SmC$_A$*-SmA | SmA-Iso |
|---|---|---|---|
| (21) | 43° C. | 47° C. | 72° C. |
| (A) | 44° C. | 78° C. | 94° C. |
| (21) 50% + (A) 50% | <−30° C. | 70° C. | 98° C. |

EXAMPLE 7

The compound (22) of the following formula [22] obtained in Example 3 was mixed with compound (A) represented by the following formula [A] in the weight ratio of 50:50 to obtain a liquid crystal composition of the invention.

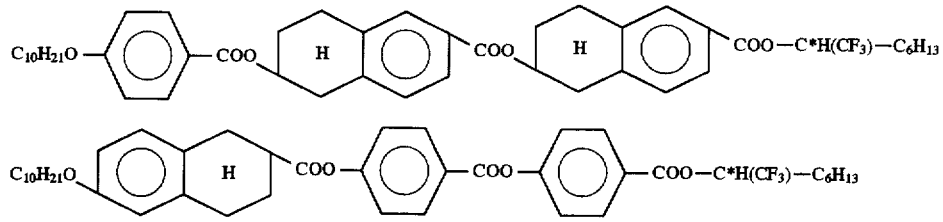

Phase transition temperatures of this composition measured are shown in Table 10 together with those of the compound (22) and the compound (A).

TABLE 10

| Compound Number | Cry-SmC$_A$* or Iso | SmC$_A$*-SmA or Iso | SmA-Iso |
| --- | --- | --- | --- |
| (22) | 43° C. | — | — |
| (A) | 44° C. | 78° C. | 94° C. |
| (22) 50% + (A) 50% | <–30° C. | 68° C. | — |

EXAMPLE 8

Synthesis of 6-(4'-decyloxy-4-biphenylcarboxy)-1,2,3,4-tetrahydro-2-naphthalenecarboxylic acid (R)-1-trifluoromethylheptyl ester [Compound (204)]

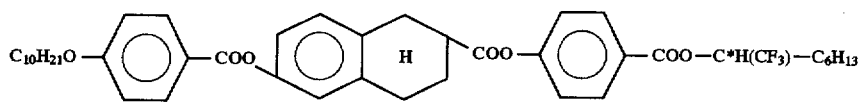

First Stage

To a mixture of 3.86 g (11.8 mmol) of 6-n-decyloxynaphthalene-2-carboxylic acid and 130 ml of 1,2-diethoxyethane was added 3.0 g (130 mg atom) of metallic sodium with stirring in a nitrogen atmosphere at 120° C., and the resulting mixture was further heated up to the reflux temperature.

To this mixture was added dropwise 10 g (114 mmol) of isoamyl alcohol over a period of 1 hour, and the resulting mixture was allowed to undergo reaction under reflux for 11 hours. After cooling the reaction system to room temperature, the remaining mettalic sodium was converted to alcoholate by the addition of ethanol, and the reaction mixture was acidified with 20% hydrochloric acid.

To the reaction mixture was added 100 ml of water, and then the organic phase was separated and washed with water.

The organic phase was concentrated under reduced pressure to obtain 4.25 g of a solid, which was recrystallized from toluene to obtain 2.95 g (8.89 mmol) of 1,2,3,4-tetrahydro-6-n-decyloxynaphthalene-2-carboxylic acid.

Second Stage 16.6 g (50 mmol) of the 6-decyloxynaphthalene-2-carboxylic acid obtained in the first stage was heated under reflux at 130° C. for 7 hours in the presence of 250 cc of acetic acid and 86.5 g (0.5 mol) of 47% hydrobromic acid. To the reaction mixture was added distilled water, and then the resulting mixture was concentrated under reduced pressure to obtain 10.60 g (50 mmol) of 1,2,3,4-tetrahydro-6-hydroxynaphthalene-2-carboxylic acid.

Third Stage

A mixture of 10.60 g (50 mmol) of the 1,2,3,4-tetrahydro-6-hydroxynaphthalene-2-carboxylic acid obtained in the second stage, 12.85 g (75 mmol) of benzyl bromide, 6.6 g (100 mmol) of 85% potassium hydroxide, 0.525 g (3.5 mmol) of sodium iodide , 200 ml of ethanol and 25 ml of distilled water was heated under reflux at 100° C. for 12 hours. After 50 ml of 10% potassium hydroxide was added, the mixture was further heated under reflux for 2 hours. After allowing the reaction system to cool up to room temperature, the reaction mixture in cold water was acidified with 36% hydrochloric acid. The deposited product was separated by filtration and recrystallized from toluene to obtain 13.08 g (46.4 mmol) of 1,2,3,4-tetrahydro-6-benzyloxynaphthalene-2-carboxylic acid.

Fourth Stage

To a mixture of 0.846 g (3 mmol) of the 1,2,3,4-tetrahydro-6-benzyloxynaphthalene-2-carboxylic acid obtained in the third stage, 0.912 g (3 mmol) of 4-hydroxybenzoic acid (R)-1-trifluoromethylheptyl ester synthesized separately by conventional means, 0.037 g (0.3 mmol) of 4-N,N-dimetylaminopyridine and 15 ml of methylene chloride was added dropwise 7 ml of a methylene chloride solution containing 0.68 g (3.3 mmol) of N,N'-dicyclohexylcarbodiimide with stirring at room temperature over a period of 1 hour.

Further, the reaction was carried out at room temperature for 3 hours.

The reaction mixture was filtered, and the filtrate was concentrated. The concentrate obtained was separated by column chromatography to obtain 1.56 g (2.75 mmol) of 4-(1',2',3',4'-tetrahydro-6'-benzyloxy-2'-naphhoyloxy)benzoic acid (R)-1-trifluoromethylheptyl ester as a white solid.

Fifth Stage

Hydrogen gas was blown into a mixture of 1.56 g (2.75 mmol) of the 4-(1',2',3',4'-tetrahydro-6'-benzyloxy-2'-naphthoyloxy)benzoic acid (R)-1-trifluoromethylheptyl ester obtained in the fourth stage, 0.16 g of 5% palladium/carbon and 20 ml of tetrahydrofuran with stirring at room temperature and ordinary pressure for 20 hours. The reaction mixture was filtered using Celite as a filter aid, and the filtrate was concentrated to obtain 1.36 g (2.75 mmol) of 4-(1',2',3',4'-tetrahydro-6'-hydroxy-2'-naphthoyloxy) benzoic acid (R)-1-trifluoromethylheptyl ester.

Sixth Stage

To a mixture of 0.478 g (1 mmol) of the 4-(1',2',3',4'-tetrahydro-6'-hydroxy-2'-naphthoyloxy)benzoic acid (R)-1-trifluoromethylheptyl ester obtained in the fifth stage, 0.278 g (1 mmol) of 4-decyloxybenzoic acid synthesized separately by conventional means, 0.012 g (0.1 mmol) of 4-N, N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 1 hour.

Further, the reaction was carried out at room temperature for 5 hours.

The reaction mixture was filtered, and the filtrate was concentrated. The concentrated obtained was separated by column chromatography to obtain 0.43 g of a compound as a colorless semisolid.

This compound had a M/e value in FD-mass spectrum of 738.

FIG. 5 shows 1H-NMR spectrum of this compound.

From these analytical results, this compound was identified as the title compound as desired.

EXAMPLE 9

Synthesis of 6-[4-(4-decyloxyphenyl) cyclohexylcarbonyloxy]-1,2,3,4-tetrahydro-2-naphthalenecarboxylic acid (R)-1-trifluoromethylheptyl ester [Compound (221)]

Third Stage

To a mixture of 0.43 g (1.2 mmol) of the 1,2,3,4-tetrahydro-6-hydroxynaphthalene-2-carboxylic acid (R)-1-trifluoromethylheptyl ester obtained in the second stage, 0.34 g (1.2 mmol) of the 1,2,3,4-tetrahydro-6-benzyloxynaphthalene-2-carboxylic acid obtained in the third stage of Example 8, 0.015 g (0.12 mmol) of 4-N,N-dimethylaminopyridine and 10 ml of methylene chloride was added dropwise 5 ml of a methylene chloride solution containing 0.30 g (1.4 mmol) of N,N'-dicyclohexylcarbodiimide with stirring at room temperature over a period of 2 hours.

Further, the reaction was carried out at room temperature for 6 hours.

The reaction mixture was filtered, and the filtrate was concentrated. The concentrate obtained was separated by column chromatography to obtain 0.70 g (0.125 mmol) of 6-(1',2',3',4'-tetrahydro-6'-benzyloxy-21-naphthoyloxy)-1,2,3,4-tetrahydroxynaphthalene-2-carboxylic acid (R)-1-trifluoromethylheptyl ester as a white solid.

Fourth Stage

Hydrogen gas was blown into a mixture of 0.70 g (1.125 mmol) of the 6-(1',2',3',4'-tetrahydro-6'-benzyloxy-2'-naphthoyloxy)-1,2,3,4-tetrahydroxynaphthalene-2-carboxylic acid (R)-1-trifluoromethylheptyl ester obtained in the third stage, 0.14 g of 5% palladium/carbon and 10 ml of tetrahydrofuran with stirring at room temperature and ordinary pressure for 16 hours. The reaction mixture was filtered using Celite as a filter aid, and the filtrate obtained was concentrated to obtain 0.64 g (1.125 mmol) of 6-(1',2', 3',4'-tetrahydro-6'-benzyloxy-2'-naphthoyloxy)-1,2,3,4-tetrahydroxynaphthalene-2-carboxylic acid (R)-1-trifluoromethylheptyl ester as a white solid.

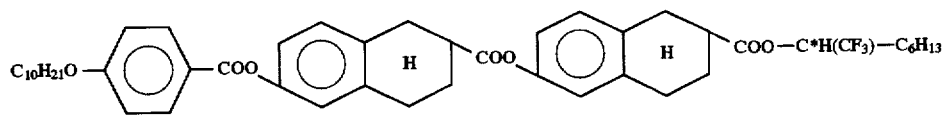

[221]

First Stage

To a mixture of 5.64 g (20 mmol) of the 1,2,3,4-tetrahydro-6-benzyloxynaphthalene-2-carboxylic acid obtained in the third stage of Example 8, 3.68 g (20 mmol) of (R)-1-trifluoromethylheptanol, 0.244 g (0.2 mmol) of 4-N,N-dimethylaminopyridine and 70 ml of methylene chloride was added dropwise 25 ml of a methylene chloride solution containing 4.53 g (22 mmol) of N,N'-dicyclohexylcarbodiimide with stirring at room temperature over a period of 2 hours.

Further, the reaction was carried out at room temperature for 2 hours.

The reaction mixture was filtered, and the filtrate was concentrated. The concentrated obtained was separated by column chromatography to obtain 8.19 g (18.3 mmol) of 1,2,3,4-tetrahydro-6-benzyloxynaphthalene-2-carboxylic acid (R)-1-trifluoromethylheptyl ester as a colorless liquid.

Second Stage

Hydrogen gas was blown into a mixture of 8.19 g (18.3 mmol) of the 1,2,3,4-tetrahydro-6-benzyloxynaphthalene-2-carboxylic acid (R)-1-trifluoromethylheptyl ester obtained in the first stage, 3.6 g of 5% palladium/carbon and 50 ml of tetrahydrofuran with stirring at room temperature and ordinary pressure for 24 hours. The reaction mixture was filtered using Celite as a filter aid, and the filtrate was concentrated to obtain 6.78 g (18.3 mmol) of 1,2,3,4-tetrahydro-6-hydroxynaphthalene-2-carboxylic acid (R)-1-trifluoromethylheptyl ester as a brown liquid.

Fifth Stage

To a mixture of 0.64 g (1.125 mmol) of 6-(1',2',3',4'-tetrahydro-6'-benzyloxy-2'-naphthoyloxy)-1,2,3,4-tetrahydroxynaphthalene-2-carboxylic acid (R)-1-trifluoromethylheptyl ester obtained in the fourth stage, 0.313 g (1.125 mmol) of 4-decyloxybenzoic acid synthesized separately by conventional means, 0.014 g (0.113 mmol) of 4-N,N-dimethylaminopyridine and 10 ml of methylene chloride was added dropwise 5 ml of a methylene chloride solution containing 0.28 g (1.5 mmol) of N,N'-dicyclohexylcarbodiimide with stirring over a period of 2 hours.

Further, the reaction was carried out at room temperature for 5.5 hours.

The reaction mixture was filtered, and the filtrate was concentrated. The concentrate obtained was separated by column chromatography to obtain 0.76 g of a compound as a colorless semisolid.

This compound had a M/e value in FD-mass spectrum of 792.

FIG. 6 shows 1H-NMR spectrum of this compound.

From these analytical results, this compound was identified as the title compound as desired.

EXAMPLE 10

Synthesis of 6-(6-heptyloxy-2-naphthoyloxy)-1,2,3,4-tetrahydro-2-naphthalenecarboxylic acid (R)-1-trifluoromethylheptyl ester [Compound (222)]

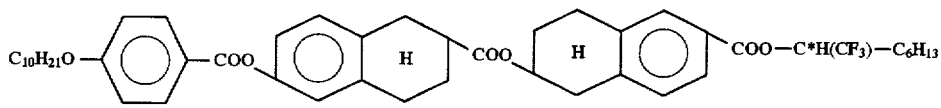

[222]

First Stage

In a 1-liter autoclave, 30 g (160 mmol) of 6-hydroxynaphthalene-2-carboxylic acid, 5 g of 5% palladium/carbon and 500 ml of tetrahydrofuran were mixed together, and the mixture was heated in a nitrogen atmosphere up to 105° C.

The mixture was allowed to undergo reaction in the autoclave maintained at a hydrogen pressure of 20 kg/cm² G and a temperature of 105° C. with stirring for 3 hours.

After a three-hour reaction, the reaction system was allowed to cool to room temperature, the hydrogen gas was released, the reaction mixture obtained was filtered using Celite as a filter aid, and the filtrate obtained was concentrated.

The mixture thus obtained was recrystallized from toluene to obtain 16.1 g of a compound of a white crystal.

This compound had a M/e value in FD-mass spectrum of 192.

From this analytical result, this compound was identified as 5,6,7,8-tetrahydro-6-hydroxynaphthalene-2-carboxylic acid.

Second Stage

To a mixture of 2.88 g (15 mmol) of the 5,6,7,8-tetrahydro-6-hydroxynaphthalene-2-carboxylic acid obtained in the first stage, 2.76 g (15 mmol) (R)-1-trifluoromethylheptanol, 0.183 g (1.5 mmol) of 4-N,N-dimethylaminopyridine and 50 ml of methylene chloride was added dropwise 20 ml of a methylene chloride solution containing 3.40 g (16.5 mmol) of N,N'-dicyclohexylcarbodiimide with stirring at room temperature over a period of 5 hours.

After the resulting mixture was further allowed to undergo reaction at room temperature for 24 hours, 2 ml of a methylene chloride solution containing 0.41 g (2 mmol) of N,N'-dicyclohexylcarbodiimide was added thereto, and allowed to undergo reaction for additional 3 days.

The reaction mixture was filtered, and the filtrate was concentrated. The concentrate obtained was separated by column chromatography to obtain 3.11 g (8.69 mmol) of 5,6,7,8-tetrahydro-6-hydroxynaphthalene-2-carboxylic acid (R)-1-trifluoromethylheptyl ester as a colorless viscous liquid.

Third Stage

To a mixture of 0.716 g (2 mmol) of the 5,6,7,8-tetrahydro-6-hydroxynaphthalene-2-carboxylic acid (R)-1-trifluoromethylheptyl ester obtained in the second stage, 0.564 g (2 mmol) of the 1,2,3,4-tetrahydro-6-benzyloxynaphthalene-2-carboxylic acid obtained in the third stage of Example 8, 0.0244 g (0.2 mmol) of 4-N,N-dimethylaminopyridine and 15 ml of methylene chloride was added dropwise 10 ml of a methylene chloride solution containing 0.45 g (2.2 mmol) of N,N'-dicyclohexylcarbodiimide with stirring at room temperature over a period of 4 hours.

Further, the reaction was carried out at room temperature for 23 hours.

The reaction mixture was filtered, and the filtrate was concentrated. The concentrate obtained was separated by column chromatography to obtain 1.15 g (1.85 mmol) of 6-(1',2',3',4'-tetrahydro-6'-benzyloxy-2'-naphthoyloxy)-5,6,7,8-tetrahydroxynaphthalene-2-carboxylic acid (R)-1-trifluoromethylheptyl ester as a white solid.

Fourth Stage

Hydrogen gas was blown into a mixture of 1.15 g (1.85 mmol) of the 6-(1',2',3',4'-tetrahydro-6'-benzyloxy-2'-naphthoyloxy)-5,6,7,8-tetrahydroxynaphthalene-2-carboxylic acid (R)-1-trifluoromethylheptyl ester obtained in the third stage, 0.23 g of 5% palladium/carbon and 10 ml of tetrahydrofuran with stirring at room temperature and ordinary pressure for 16 hours. The reaction mixture was filtered using Celite as a filter aid, and the resulting filtrate was then concentrated to obtain 0.98 g (1.84 mmol) of 6-(1',2',3',4'-tetrahydro-6'-hydroxy-2'-naphthoyloxy)-5,6,7,8-tetrahydroxynaphthalene-2-carboxylic acid (R)-1-trifluoromethylheptyl ester as a white solid.

Fifth Stage

To a mixture of 0.48 g (0.9 mmol) of the 6-(1',2',3',4'-tetrahydro-6'-hydroxy-2'-naphthoyloxy)-5,6,7,8-tetrahydroxynaphthalene-2-carboxylic acid (R)-1-trifluoromethylheptyl ester obtained in the fourth stage, 0.25 g (0.9 mmol) of 4-decyloxybenzoic acid synthesized separately by conventional means, 0.011 g (0.09 mmol) of 4-N,N-dimethylaminopyridine and 10 ml of methylene chloride was added dropwise 5 ml of a methylene chloride solution containing 0.22 g (1.1 mmol) of N,N'-dicyclohexylcarbodiimide with stirring at room temperature over a period of 1 hour.

Further, the reaction was carried out at room temperature for 65 hours.

The reaction mixture was filtered, and the filtrate was concentrated. The concentrate obtained was separated by column chromatography to obtain 0.51 g of a compound as a colorless semisolid.

This compound had a M/e value in FD-mass spectrum of 792.

FIG. 7 shows ¹H-NMR spectrum of this compound.

From these analytical results, this compound was identified as the title compound as desired.

EXAMPLE 11

Synthesis of 6-(4'-decyloxy-4-biphenylcarboxy)-1,2,3,4-tetrahydro-2-naphthalenecarboxylic acid (R)-1-trifluoromethylheptyl ester [Compound (251)]

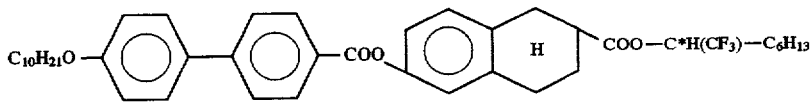

[251]

First Stage

A mixture of 21.4 g (0.1 mol) of 4'-hydroxybiphenyl-4-carboxylic acid, 33.15 g (0.15 mol) of n-decyl bromide, 13.20 g (0.2 mol) of 85% potassium hydroxide, 1.05 g (7 mmol) of sodium iodide, 500 ml of ethanol and 100 ml of distilled water was heated under reflux at 100° C. for 12 hours. After 40 ml of 25% potassium hydroxide was added, the mixture was further heated under reflux for 2 hours. After allowing the reaction system to cool up to room temperature, the reaction mixture in cold water was acidified with 36% hydrochloric acid. The deposited product was separated by filtration and dissolved in acetone with heating, followed by filtration. The resulting filtrate was concentrated to obtain 1.97 g (6 mmol) of 4'-decyloxybiphenyl-4-carboxylic acid.

Second Stage

To a mixture of 0.35 g (1 mmol) of the 4'-decyloxybiphenyl-4-carboxylic acid obtained in the first stage, 0.36 g (1 mmol) of the 1,2,3,4-tetrahydro-6-hydroxynaphthalene-2-carboxylic acid (R)-1-trifluoromethylheptyl ester obtained in the second stage of Example 9, 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 2 hours.

Further, the reaction was carried out at room temperature for 48 hours.

The reaction mixture was filtered, and the filtrate was concentrated. The concentrate obtained was separated by column chromatography to obtain 0.51 g of a compound as a colorless semisolid.

This compound had a M/e value in FD-mass spectrum of 694.

FIG. 8 shows $^1$H-NMR spectrum of this compound.

From these analytical results, this compound was identified as the title compound as desired.

EXAMPLE 12

Synthesis of 6-[4-(4-decyloxyphenyl)cyclohexylcarbonyloxy)-1,2,3,4-tetrahydro-2-naphthalenecarboxylic acid (R)-1-trifluoromethylheptyl ester [Compound (267)]

hydroxide, 3.0 g (20 mmol) of sodium iodide, 360 g of ethanol and 180 g of distilled water was heated under reflux at 100° C. for 9 hours. After 100 ml of 10% potassium hydroxide was added, the mixture was further heated under reflux for 20 hours. After allowing the reaction system to cool up to room temperature, the reaction system in cold water was acidified with 36% hydrochloric acid. The deposited product was separated by filtration and washed with hexane to obtain 67.4 g (0.187 mmol) of 4'-decyloxyphenylcyclohexane-4-carboxylic acid.

Second Stage

To a mixture of 0.36 g (1 mmol) of the 4'-decyloxyphenylcyclohexane-4-carboxylic acid obtained in the first stage, 0.36 g (1 mmol) of the 1,2,3,4-tetrahydro-6-hydroxynaphthalene-2-carboxylic acid (R)-1-trifluoromethylheptyl ester obtained in the second stage of Example 9, 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 2 hours.

Further, the reaction was carried out at room temperature for 19 hours.

The reaction mixture was filtered, and the filtrate was concentrated. The concentrate obtained was separated by column chromatography to obtain 0.58 g of a compound as a colorless semisolid.

This compound had a M/e value in FD-mass spectrum of 700.

FIG. 9 shows $^1$H-NMR spectrum of this compound.

From these analytical results, this compound was identified as the title compound as desired.

EXAMPLE 13

Synthesis of 4-[6-(6-heptyloxy-2-naphthoyloxy)-1,2,3,4-tetrahydro-2-naphthoyloxy]benzoic acid (R)-1-trifluoromethylheptyl ester [Compound (288)]

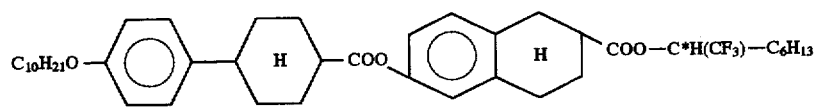

[267]

First Stage

A mixture of 44 g (0.2 mol) of 4'-hydroxyphenylcyclohexane-4-carboxylic acid, 66.4 g (0.3 mol) of n-decyl bromide, 26.4 g (0.4 mol) of 85% potassium

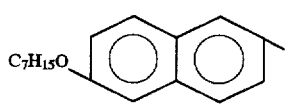 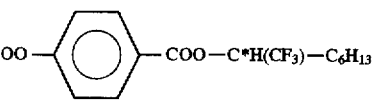

[288]

First Stage

To a mixture of 0.24 g (0.84 mmol) of 6-heptyloxynaphthalene-2-carboxylic acid synthesized by conventional means, 0.56 g (0.84 mmol) of the 4-(1',2',3', 4'-tetrahydro-6'-hydroxy-2'-naphthoyloxy)benzoic acid (R)-1-trifluoromethylheptyl ester obtained in the fifth stage of Example 8, 0.012 g (0.1 mmol) of 4-N,N-dimethylaminopyridine and 20 ml of methylene chloride was added dropwise 2 ml of a methylene chloride solution containing 0.20 g (1 mmol) of N,N'-dicyclohexylcarbodiimide with stirring at room temperature over a period of 1 hour.

Further, the reaction was carried out at room temperature for 14 hours.

The reaction mixture was filtered, and the filtrate was concentrated. The concentrate obtained was separated by column chromatography to obtain 0.05 g of a compound as a colorless semisolid.

This compound had a M/e value in FD-mass spectrum of 746.

From the analytical result, this compound was identified as the title compound as desired.

EXAMPLE 14

Synthesis of 6-(6-heptyloxy-2-naphthoyloxy)-1,2,3,4-tetrahydro-2-naphthalenecarboxylic acid (R)-1-trifluoromethylheptyl ester [Compound (296)]

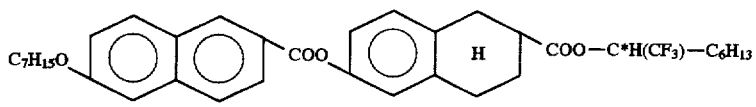

[296]

First Stage

To a mixture of 0.24 g (0.84 mmol) of 6-heptyloxynaphthalene-2-carboxylic acid synthesized by conventional means, 0.69 g (0.84 mmol) of the 1,2,3,4-tetrahydro-6-hydroxynaphthalene-2-carboxylic acid (R)-1-trifluoromethylheptyl ester obtained in the second stage of Example 9, 0.012 g (0.1 mmol) of 4-N,N-dimethylaminopyridine and 20 ml of methylene chloride was added dropwise 2 ml of a methylene chloride solution containing 0.17 g (0.84 mmol) of N,N'-dicyclohexylcarbodiimide with stirring at room temperature over a period of 1 hour.

Further, the reaction was carried out at room temperature for 14 hours.

The reaction mixture was filtered, and the filtrate was concentrated. The concentrate obtained was separated by column chromatography to obtain 0.27 g of a compound as a colorless semisolid.

This compound had a M/e value in FD-mass spectrum of 626.

FIG. 10 shows $^1$H-NMR spectrum of this compound.

From these analytical results, this compound was identified as the title compound as desired.

EXAMPLE 15

Synthesis of 6-(6-decyloxy-2-naphthoyloxy)-1,2,3,4-tetrahydro-2-naphthalenecarboxylic acid (R)-1-trifluoromethylheptyl ester (Compound (299)]

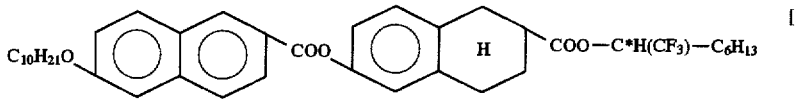

[299]

First Stage

The reaction was conducted in the same manner as in Example 14 except that 6-decyloxynaphthalene-2-carboxylic acid was used instead of 6-heptyloxynaphthalene-2-carboxylic acid, to thereby obtain 0.64 g of a compound as a colorless semisolid.

This compound had a M/e value in FD-mass spectrum of 668.

FIG. 11 shows $^1$H-NMR spectrum of this compound.

From these analytical results, this compound was identified as the title compound as desired.

EXAMPLE 16

Synthesis of 6-[4-(5-decyl-2-pyrimidinyl)benzoyloxy]-1, 2,3,4-tetrahydro-2-naphthalenecarboxylic acid (R)-1-trifluoromethyl heptyl ester [Compound (331)]

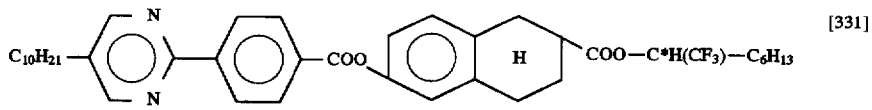

[331]

159

First Stage

To a mixture of 0.358 g (1 mmol) of the 1,2,3,4-tetrahydro-6-hydroxynaphthalene-2-carboxylic acid (R)-1-trifluoromethylheptyl ester obtained in the second stage of Example 9, 0.33 g (1 mmol) of 4-(5'-decyl-2'-pyrimidinyl) benzoic acid (manufactured by Kojima Kagaku Kabusiki Kaisha), 0.01 g (0.1 mmol) of 4-N,N-dimethylaminopyridine and 10 ml of methylene chloride was added dropwise 3 ml of a methylene chloride solution containing 0.23 g (1.1 mmol) of N,N'-dicyclohexylcarbodiimide with stirring at room temperature over a period of 1.5 hours.

Further, the reaction was carried out at room temperature for 5 hours.

The reaction mixture was filtered, and the filtrate was concentrated. The concentrate obtained was separated by column chromatography to obtain 0.74 g of a compound as a colorless semisolid.

This compound had a M/e value in FD-mass spectrum of 680.

FIG. 12 shows $^1$H-NMR spectrum of this compound.

From these analytical results, this compound was identified as the title compound as desired.

EXAMPLE 17

Synthesis of 6-(4-decyloxybenzoyloxy)-1,2,3,4-tetrahydro-2-naphthalenecarboxylic acid (R)-1-trifluoromethylheptyl ester [Compound (235)]

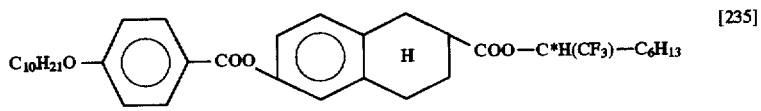

[235]

First Stage

To a mixture of 0.28 g (1.0 mmol) of the 4-decyloxybenzoic acid synthesized separately by conventional means, 0.36 g (1.0 mmol) of 1,2,3,4-tetrahydro-6-hydroxynaphthalene-2-carboxylic acid R-1'-trifluoromethylheptyl ester obtained in the second stage of Example 9, 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 2 hours.

Further, the reaction was carried out at room temperature for 48 hours.

The reaction mixture was filtered, and the filtrate was concentrated. The concentrate obtained was separated by column chromatography to obtain 0.50 g of a compound as a white solid.

This compound had a M/e value in FD-mass spectrum of 618.

160

From the analytical result, this compound was identified as the title compound as desired.

EXAMPLE 18

The compound (204) represented by the following formula [204] obtained in Example 8 was mixed with compound (A) represented by the following formula [A] in the weight ratio of 50:50 to obtain a liquid crystal composition of the present invention.

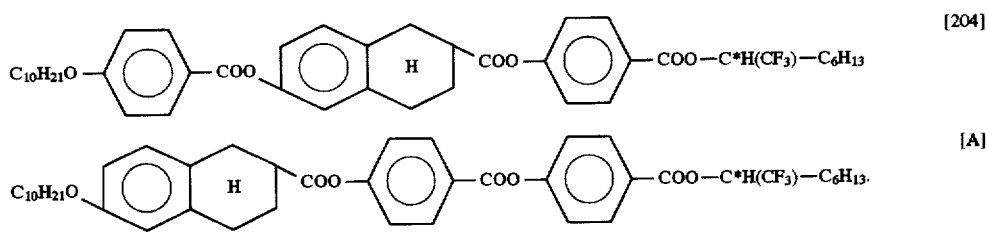

[204]

[A]

Phase transition temperatures of this composition measured are shown in Table 11.

TABLE 11

| Compound Number | Cry-SmC$_A$* | SmC$_A$*-SmA | SmA-Iso |
|---|---|---|---|
| (204) | −23° C. | 81° C. | 113° C. |
| (A) | 44° C. | 78° C. | 94° C. |
| (204) 50% + (A) 50% | <−° C. | 82° C. | 110° C. |

EXAMPLE 19

The compound (251) represented by the following formula [251] obtained in Example 11 was mixed with compound (B) represented by the following formula [B] in the weight ratio of 80:20 to obtain a liquid crystal composition of the present invention.

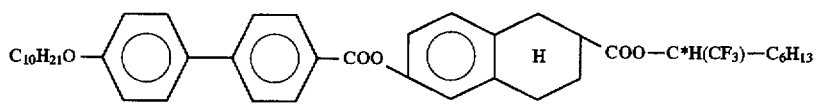
[251]

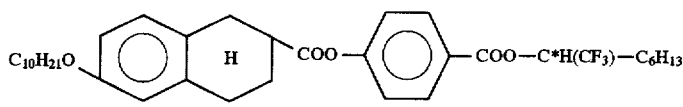
[B]

Phase transition temperatures of this composition measured are shown in Table 12.

TABLE 12

| Compound Number | Cry-SmC$_A$* or SmA | SmC$_A$*-SmA | SmA-Iso |
|---|---|---|---|
| (251) | 21° C. | 99° C. | 130° C. |
| (B) | <−30° C. | — | −14° C. |
| (251) 80% + (B) 20% | <−30° C. | 67° C. | 106° C. |

The compound (267) represented by the following formula [267] obtained in Example 12 was mixed with the compound (251) represented by the following formula [251] obtained in Example 11 in the weight ratio of 50:50 to obtain a liquid crystal composition of the present invention.

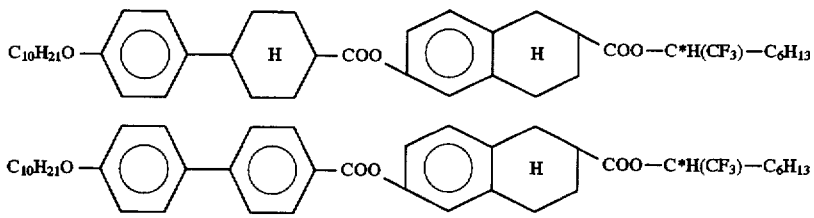
[267]

[251]

Phase transition temperatures of this composition measured are shown in Table 13.

EXAMPLE 21

The compound (296) represented by the following formula [296] obtained in Example 14 was mixed with compound (A) represented by the following formula [A] in the weight ratio of 50:50 to obtain a liquid crystal composition of the present invention.

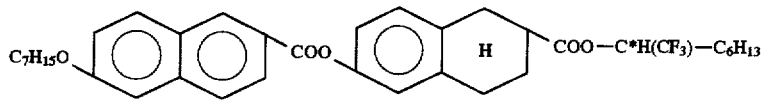
[296]

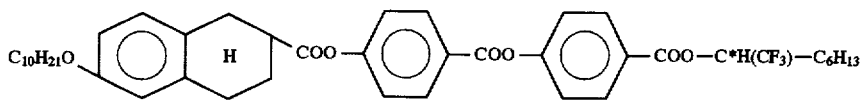
[A]

Phase transition temperatures of this composition measured are shown in Table 14.

TABLE 13

| Compound Number | Cry-SmC$_A$* | SmC$_A$*-SmC | SmC$_A$*-SmA or SmC* | SmA-Iso |
|---|---|---|---|---|
| (267) | −5° C. | — | 44° C. | 87° C. |
| (251) | 21° C. | — | 99° C. | 130° C. |
| (267) 50% + (251) 50% | 18° C. | 70° C. | 73° C. | 110° C. |

TABLE 14

| Compound Number | Cry-SmC$_A$* or SmA or Iso | SmC$_A$*-SmA | SmA-Iso |
|---|---|---|---|
| (296) | 80° C. | — | — |
| (A) | 44° C. | 78° C. | 94° C. |
| (296) 50% + (A) 50% | 16° C. | — | 81° C. |

EXAMPLE 22

The compound (331) represented by the following formula [331] obtained in Example 16 was mixed with the compound (251) represented by the following formula [251] obtained in Example 11 in the weight ratio of 10:90 to obtain a liquid crystal composition of the present invention.

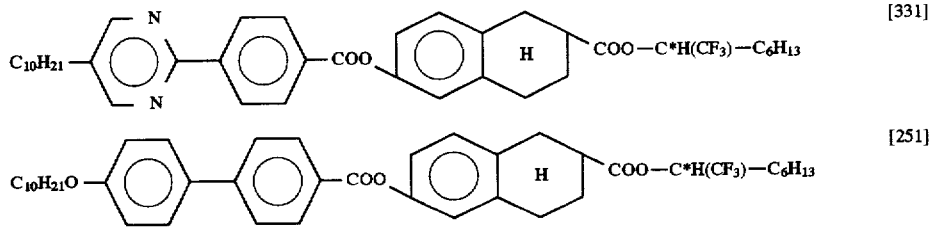

Phase transition temperatures of this composition measured are shown in Table 15.

TABLE 15

| Compound Number | Cry-SmC$_A$* | SmC$_A$*-SmC | SmC$_A$* or SmC*-SmA | SmA-Iso |
|---|---|---|---|---|
| (331) | 48° C. | — | — | 82° C. |
| (251) | 21° C. | — | 99° C. | 130° C. |
| (331) 10% + (251) 90% | 36° C. | 85° C. | 90° C. | 124° C. |

Synthesis of 6-[4-(4-decyloxybenzoyloxy)benzoyloxy]-1,2,3,4-tetrahydro-2-naphthalenecarboxylic acid (R)-1-trifluoromethylheptyl ester [Compound (604)]

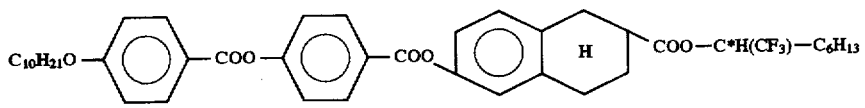

First Stage

To a mixture of 3.86 g (11.8 mmol) of 6-n-decyloxynaphthalene-2-carboxylic acid and 130 ml of 1,2-diethoxyethane was added 3.0 g (130 mg atom) of metallic sodium with stirring in a nitrogen atmosphere at 120° C., and the resulting mixture was further heated up to the reflux temperature.

To this mixture was added dropwise 10 g (114 mmol) of isoamyl alcohol over a period of 1 hour, and the resulting mixture was allowed to undergo reaction under reflux for 11 hours. After cooling the reaction system to room temperature, the remaining metallic sodium was converted to alcholate by the addition of ethanol, and the reaction mixture was acidified with 20% hydrochloric acid.

To the reaction mixture was added 100 ml of water, and then the organic phase was separated and washed with water.

The organic phase was concentrated under reduced pressure to obtain 4.25 g of a solid, which was recrystallized from toluene to obtain 2.95 g (8.89 mmol) of 1,2,3,4-tetrahydro-6-n-decyloxynaphthalene-2-carboxylic acid.

Second Stage

A mixture of 16.6 g (50 mmol) of the 1,2,3,4-tetrahydro-6-decyloxynaphthalene-2-carboxylic acid obtained in the first stage, 250 cc of acetic acid and 86.5 g (0.5 mol) of 47% hydrobromic acid was heated under reflux at 130° C. for 7 hours. To the reaction mixture was added distilled water, and then the resulting mixture was concentrated under reduced pressure to obtain 10.60 g (50 mmol) of 1,2,3,4-tetrahydro-6-hydroxynaphthalene-2-carboxylic acid.

Third Stage

A mixture of 10.60 g (50 mmol) of the 1,2,3,4-tetrahydro-6-hydroxynaphthalene-2-carboxylic acid obtained in the second stage, 12.85 g (75 mmol) of benzyl bromide, 6.6 g (100 mmol) of 85% potassium hydroxide, 0.525 g (3.5 mmol) of sodium iodide, 200 ml of ethanol and 25 ml of distilled water was heated under reflux at 100° C. for 12 hours. After 50 ml of 10% potassium hydroxide was added, the mixture was further heated under reflux for 2 hours. After allowing the reaction system to cool up to room temperature, the reaction mixture in cold water was acidified with 36% hydrochloric acid. The deposited product was separated by filtration and recrystallized from toluene to obtain 13.08 g (46.4 mmol) of 1,2,3,4-tetrahydro-6-benzyloxynaphthalene-2-carboxylic acid.

Fourth Stage

To a mixture of 5.64 g (20 mmol) of the 1,2,3,4-tetrahydro-6-benzyloxynaphthalene-2-carboxylic acid obtained in the third stage, 3.68 g (20 mmol) of R-1-trifluoromethylheptanol, 0.244 g (0.2 mmol) of 4-N,N-dimetylaminopyridine and 70 ml of methylene chloride was added dropwise 25 ml of a methylene chloride solution containing 4.53 g (22 mmol) of N,N'-dicyclohexylcarbodiimide with stirring at room temperature over a period of 2 hours.

Further, the reaction was carried out at room temperature for 2 hours.

The reaction mixture was filtered, and the filtrate was concentrated. The concentrate obtained was separated by column chromatography to obtain 8.19 g (18.3 mmol) of 1,2,3,4-tetrahydro-6-benzyloxynaphthalene-2-carboxylic acid (R)-1-trifluoromethylheptyl ester as a colorless liquid.

Fifth Stage

Hydrogen gas was blown into a mixture of 8.19 g (18.3 mmol) of the 1,2,3,4-tetrahydro-6-benzyloxynaphthalene-2-carboxylic acid (R)-1-trifluoromethylheptyl ester obtained in the fourth stage, 3.6 g of 5% palladium/carbon as a catalyst and 50 ml of tetrahydrofuran with stirring at room temperature and ordinary pressure for 24 hours. The reaction mixture was filtered using Celite as a filter aid, and the filtrate obtained was concentrated to obtain 6.78 g (18.3 mmol) of 1,2,3,4-tetrahydro-6-hydroxynaphthalene-2-carboxylic acid (R)-1-trifluoromethylheptyl ester as a brown liquid.

Sixth Stage

To a mixture of 0.29 g (0.8 mmol) of the 1,2,3,4-tetrahydro-6-hydroxynaphthalene-2-carboxylic acid (R)-1-trifluoromethylheptyl ester obtained in the fifth stage, 0.32 g (0.8 mmol) of 4-(4'-decyloxybenzoyloxy)benzoic acid synthesized separately by conventional means, 0.01 g (0.08 mmol) of 4-N,N-dimethylaminopyridine and 10 ml of methylene chloride was added dropwise 5 ml of a methylene chloride solution containing 0.20 g (0.96 mmol) of N,N'-dicyclohexylcarbodiimide with stirring at room temperature over a period of 40 minutes.

Further, the reaction was carried out at room temperature for 3.5 hours.

The reaction mixture was filtered, and the filtrate was concentrated. The concentrate obtained was separated by column chromatography to obtain 0.38 g of a compound as a white solid.

This compound had a M/e value in FD-mass spectrum of 738.

FIG. 13 shows $^1$H-NMR spectrum of this compound.

From these analytical results, this compound was identified as the title compound as desired.

EXAMPLE 24

Synthesis of 6-{4-[4-((R)-1-methylheptyloxy)benzoyloxy]benzoyloxy}-1,2,3,4-tetrahydro-2-naphthalenecarboxylic acid (R)-1-trifluoromethylheptyl ester [Compound (745)]

benzoic acid] benzyl ester obtained in the first stage, 0.16 g of 5% palladium/carbon as a catalyst and 10 ml of tetrahydrofuran with stirring at room temperature and ordinary pressure for 16 hours. The reaction mixture was filtered using Celite as a filter aid, and the filtrate obtained was concentrated to obtain 0.66 g (1.74 mmol) of 4-[4'-((R)-1"-methylheptyloxy)benzoyloxy] benzoic acid as a white solid.

Third Stage

To a mixture of 0.30 g (0.8 mmol) of the 4-[4'-((R)-1"-methylheptyloxy)benzoyloxy] benzoic acid obtained in the second stage, 0.29 g (0.8 mmol) of the 1,2,3,4-tetrahydro-6-hydroxynaphthalene-2-carboxylic acid (R)-1-trifluoromethylheptyl ester obtained in the fifth stage of Example 23, 0.01 g (0.08 mmol) of 4-N,N-dimethylaminopyridine and 10 ml of methylene chloride was added dropwise 5 ml of a methylene chloride solution containing 0.18 g (0.88 mmol) of N,N'-dicyclohexylcarbodiimide with stirring at room temperature over a period of 1 hour.

Further, the reaction was carried out at room temperature for 3 hours.

The reaction mixture was filtered, and the filtrate was concentrated. The concentrate obtained was separated by column chromatography to obtain 0.48 g of a compound as a white solid.

This compound had a M/e value in FD-mass spectrum of 710.

FIG. 14 shows $^1$H-NMR spectrum of this compound.

From these analytical results, this compound was identified as the title compound as desired.

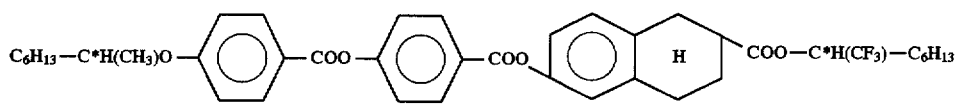

[745]

First Stage

To a mixture of 0.50 g (2 mmol) of 4-((R)-1'-methylheptyloxy)benzoic acid (manufactured by Arakawa Kagaku Kogyo K.K.), 0.46 g (2 mmol) of 4-hydroxybenzoic acid benzyl ester synthesized separately by conventional means, 0.02 g (0.2 mmol) of 4-N,N-dimethylaminopyridine and 20 ml of methylene chloride was added dropwise 8 ml of a methylene chloride solution containing 0.45 g (2.2 mmol) of N,N'-dicyclohexylcarbodiimide with stirring at room temperature over a period of 1 hour.

Further, the reaction was carried out at room temperature for 3 hours.

The reaction mixture was filtered, and the filtrate was concentrated. The concentrate obtained was separated by column chromatography to obtain 0.8 g (1.74 mmol) of 4-[4'-((R)-1"-methylheptyloxy)benzoyloxy)benzoic acid] benzyl ester as a white solid.

Second Stage

Hydrogen gas was blown into a mixture of 0.8 g (1.74 mmol) of the 4-[4'-((R)-1"-methylheptyloxy)benzoyloxy)

EXAMPLE 25

Synthesis of 6-[4-(4-decyloxybenzoyloxy)benzoyloxy]-5,6,7,8-tetrahydro-2-naphthalenecarboxylic acid (R)-1-trifluoromethylheptyl ester [Compound (795)]

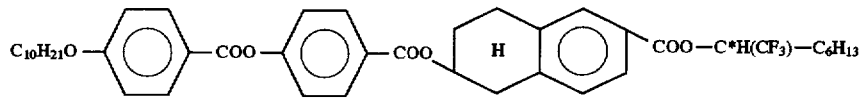

[795]

First Stage

In a 1-liter autoclave, 30 g (160 mmol) of 6-hydroxynaphthalene-2-carboxylic acid, 5 g of 5% palladium/carbon as a catalyst and 500 ml of tetrahydrofuran were mixed together, and the mixture was heated in a nitrogen atmosphere up to 105° C.

The mixture was allowed to undergo reaction in the autoclave maintained at a hydrogen pressure of 20 kg/cm$^2$ G and a temperature of 105° C. with stirring for 3 hours.

After a three-hour reaction, the reaction system was allowed to cool to room temperature, the hydrogen gas was released, the reaction mixture obtained was filtered using Celite as a filter aid, and the filtrate obtained was concentrated.

The mixture obtained was recrystallized from toluene to obtain 16.1 g of a compound as a white crystal.

This compound had a M/e value in FD-mass spectrum of 192.

EXAMPLE 26

Synthesis of 6-{4-[4-((R)-1-methylheptyloxy) benzoyloxy]benzoyloxy}-5,6,7,8-tetrahydro-2-naphthalenecarboxylic acid (R)-1-trifluoromethylheptyl ester [Compound (936)]

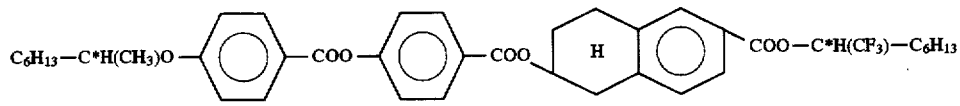

[936]

From this analytical result, this compound was identified as 5,6,7,8-tetrahydro-6-hydroxynaphthalene-2-carboxylic acid.

Second Stage

To a mixture of 2.88 g (15 mmol) of the 5,6,7,8-tetrahydro-6-hydroxynaphthalene-2-carboxylic acid obtained in the first stage, 2.76 g (15 mmol) of R-1-trifluoromethylheptanol, 0.183 g (1.5 mmol) of 4-N,N-dimethylaminopyridine and 50 ml of methylene chloride was added dropwise 20 ml of a methylene chloride solution containing 3.40 g (16.5 mmol) of N,N'-dicyclohexylcarbodiimide with stirring at room temperature over a period of 24 hours.

Further, 2 ml of a methylene chloride solution containing 0.41 g (2.0 mmol) of N,N'-dicyclohexylcarbodiimide was added thereto, and allowed to undergo reaction at room temperature for 72 hours.

The reaction mixture was filtered, and the filtrate was concentrated. The concentrate obtained was separated by column chromatography to obtain 3.11 g (8.69 mmol) of 5,6,7,8-tetrahydro-6-hydroxynaphthalene-2-carboxylic acid (R)-1-trifluoromethylheptyl ester as a white solid.

Third Stage

To a mixture of 0.29 g (0.8 mmol) of the 5,6,7,8-tetrahydro-6-hydroxynaphthalene-2-carboxylic acid (R)-1-trifluoromethylheptyl ester obtained in the second stage, 0.32 g (0.8 mmol) of the 4-(4'-decyloxybenzoyloxy)benzoic acid synthesized separately by conventional means, 0.01 g (0.08 mmol) of 4-N,N-dimethylaminopyridine and 10 ml of methylene chloride was added dropwise 5 ml of a methylene chloride solution containing 0.20 g (0.96 mmol) of N,N'-dicyclohexylcarbodiimide with stirring at room temperature over a period of 1 hour.

Further, the reaction was carried out at room temperature for 4 hours.

The reaction mixture was filtered, and the filtrate was concentrated. The concentrate obtained was separated by column chromatography to obtain 0.23 g of a compound as a viscous semisolid.

This compound had a M/e value in FD-mass spectrum of 738.

FIG. 15 shows 1H-NMR spectrum of this compound.

From these analytical results, this compound was identified as the title compound as desired.

First Stage

To a mixture of 0.30 g (0.8 mmol) of 4-[4'-(R)-1-methylheptyloxy)benzoyloxy]benzoic acid obtained in the second stage of Example 24, 0.29 g (0.8 mmol) of the 5,6,7,8-tetrahydro-6-hydroxynaphthalene-2-carboxylic acid (R)-1-trifluoromethylheptyl ester obtained in the second stage of Example 25, 0.01 g (0.08 mmol) of 4-N,N-dimethylaminopyridine and 10 ml of methylene chloride was added dropwise 5 ml of a methylene chloride solution containing 0.18 g (0.88 mmol) of N,N'-dicyclohexylcarbodiimide with stirring at room temperature over a period of 1 hour.

Further, the reaction was carried out at room temperature for 14 hours.

The reaction mixture was filtered, and the filtrate was concentrated. The concentrate obtained was separated by column chromatography to obtain 0.34 g of a compound as a white solid.

This compound had a M/e value in FD-mass spectrum of 710.

FIG. 16 shows $^1$H-NMR spectrum of this compound.

From these analytical results, this compound was identified as the title compound as desired.

EXAMPLE 27

The compound (404) represented by the following formula [404] obtained in Example 23 was mixed with compound (A) represented by the following formula [A] in the weight ratio of 50:50 to obtain a liquid crystal composition of the present invention.

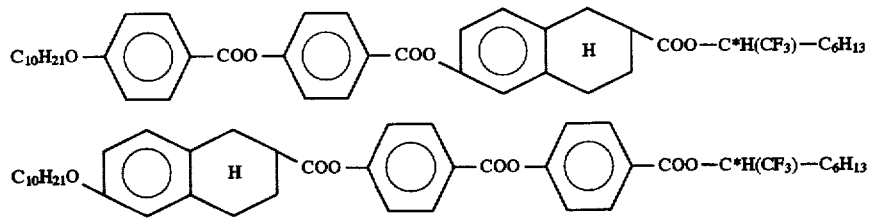

[604]

[A]

Phase transition temperatures of this composition were measured.

The results are shown in Table 16.

The phase transition temperature of the compound (404) and the compound (A) are also shown in Table 16.

TABLE 16

| Compound Number | Cry-SmC$_A$* | SmC$_A$*-SmC* | SmC$_A$* or SmC*-SmA | SmA-Iso |
|---|---|---|---|---|
| (404) | 50° C. | 77° C. | 85° C. | 122° C. |
| (A) | 44° C. | — | 78° C. | 94° C. |
| (404) 50% + (A) 50% | <−30° C. | — | 85° C. | 120° C. |

EXAMPLE 28

The compound (545) represented by the following formula [545] obtained in Example 24 was mixed with compound (A) represented by the following formula [A] in the weight ratio of 50:50 to obtain a liquid crystal composition of the present invention.

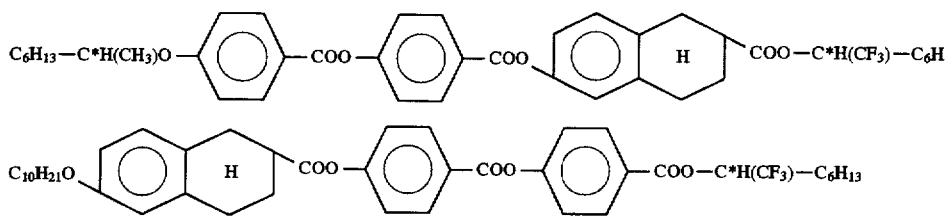

[759]

[A]

Phase transition temperatures of this composition were measured.

The results are shown in Table 17.

The phase transition temperature of the compound (545) and the compound (A) are also shown in Table 17.

TABLE 17

| Compound Number | Cry-SmC$_A$* or SmA or Iso | SmC$_A$*-SmA | SmA-Iso |
|---|---|---|---|
| (545) | 45° C. | — | — |
| (A) | 44° C. | 78° C. | 94° C. |
| (545) 50% + (A) 50% | <−30° C. | — | 88° C. |

EXAMPLE 29

The compound (575) represented by the following formula [575] obtained in Example 25 was mixed with compound (A) represented by the following formula [A] in the weight ratio of 25:75 to obtain a liquid crystal composition of the present invention.

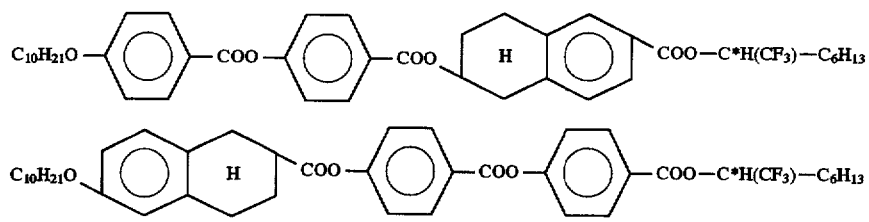

[575]

[A]

Phase transition temperatures of this composition were measured.

The results are shown in Table 18.

The phase transition temperature of the compound (575) and the compound (A) are also shown in Table 18.

TABLE 18

| Compound Number | Cry-SmC$_A$* | SmC$_A$*-SmA or Iso | SmA-Iso |
|---|---|---|---|
| (575) | 23° C. | 57° C. | — |
| (A) | 44° C. | 78° C. | 94° C. |
| (575) 75% + (A) 25% | <−30° C. | 66° C. | 72° C. |

EXAMPLE 30

Synthesis of 6-(4-decyloxybenzoyloxy)-1,2,3,4-tetrahydro-2-naphthalenecarboxylic acid (R)-1-trifluoromethylheptyl ester [Compound (235)]

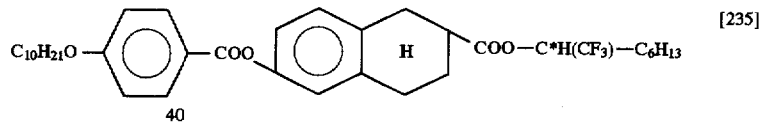

[235]

First Stage

To a mixture of 0.36 g (1 mmol) of 1,2,3,4-tetrahydro-6-hydroxynaphthalene-2-carboxylic acid (R)-1-trifluoromethylheptyl ester obtained in the fifth stage of Example 23, 0.28 g (1 mmol) of 4-decyloxybenzoic acid synthesized separately by conventional means, 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 2 hours.

Further, the reaction was carried out at room temperature for 48 hours.

The reaction mixture was filtered, and the filtrate was concentrated. The concentrate was separated by column chromatography to obtain 0.50 g of a white solid.

This compound had a M/e value in FD-mass spectrum of 618.

Figure 23:
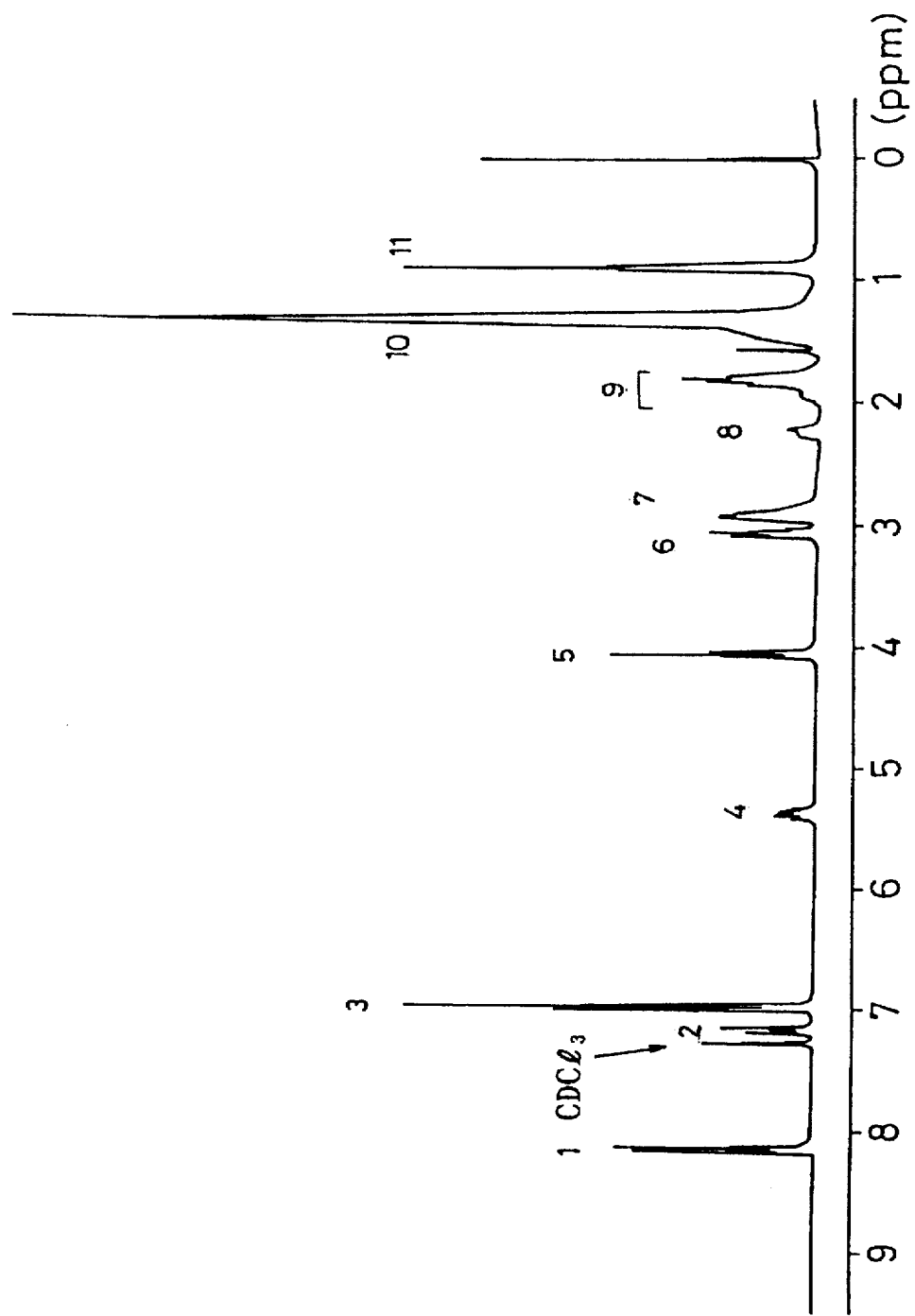
FIG. 23 shows $^1$H-NMR spectrum of 6-(4-decyloxybenzoyloxy)-1,2,3,4-tetrahydro-2-naphthalenecarboxylic acid (R)-1-trifluoromethylheptyl ester [Compound (235)].

FIG. 23 shows $^1$H-NMR spectrum of this compound.

From these analytical results, this compound was identified as the title compound as desired.

EXAMPLE 31

Synthesis of 6-(4'-undecyloxy-4-biphenylcarbonyloxy)-1,2,3,4-tetrahydro-2-naphthalenecarboxylic acid (R)-1-trifluoromethylheptyl ester [Compound (252)]

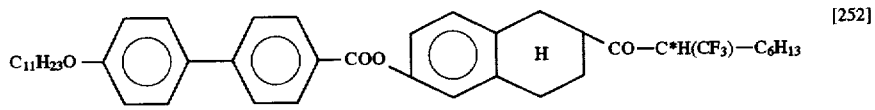

First Stage

To a mixture of 0.76 g (2 mmol) of 1,2,3,4-tetrahydro-6-hydroxynaphthalene-2-carboxylic acid (R)-1-trifluoromethylheptyl ester obtained in the fifth stage of Example 23, 0.773 g (2.1 mmol) of 4'-undecyloxybiphenyl-4-carboxylic acid prepared as in the first stage of Example 11, 0.024 g (0.2 mmol) of 4-N,N-dimethylaminopyridine and 20 ml of methylene chloride was added dropwise 10 ml of a methylene chloride solution containing 0.495 g (2.4 mmol) of N,N'-dicyclohexylcarbodiimide with stirring at room temperature over a period of 2 hours.

Further, the reaction was carried out at room temperature for 12 hours.

The reaction mixture was filtered, and the filtrate was concentrated. The concentrate was separated by column chromatography to obtain 1.06 g of a white solid.

This compound had a M/e value in FD-mass spectrum of 708.

Figure 24:
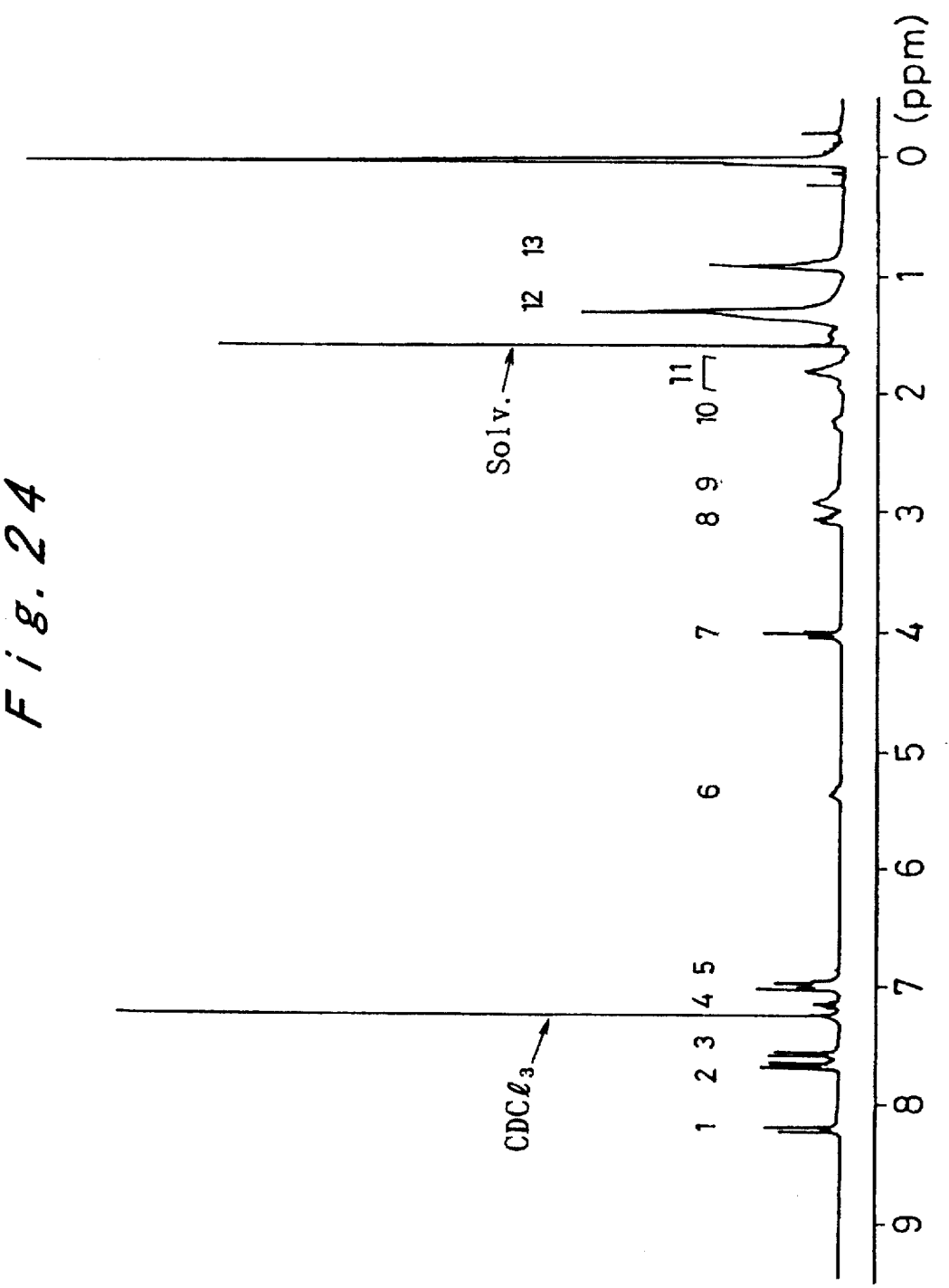
FIG. 24 shows $^1$H-NMR spectrum of 6-(4'-undecyloxy-4-biphenylcarbonyloxy)-1,2,3,4-tetrahydro-2-naphthalenecarboxylic acid (R)-1-trifluoromethylheptyl ester [Compound (252)].

FIG. 24 shows $^1$H-NMR spectrum of this compound.

From these analytical results, this compound was identified as the title compound as desired.

EXAMPLE 32

Synthesis of 6-(4'-dodecyloxy-4-biphenylcarbonyloxy)-1,2,3,4-tetrahydro-2-naphthalenecarboxylic acid (R)-1-trifluoromethylheptyl ester [Compound (253)]

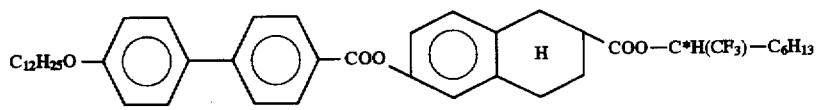

First Stage

To a mixture of 0.716 g (2 mmol) of 1,2,3,4-tetrahydro-6-hydroxynaphthalene-2-carboxylic acid (R)-1-trifluoromethylheptyl ester obtained in the fifth stage of Example 23, 0.802 g (2.1 mmol) of 4'-dodecyloxybiphenyl-4-carboxylic acid prepared as in the first stage of Example 11, 0.024 g (0.2 mmol) of 4-N,N-dimethylaminopyridine and 20 ml of methylene chloride was added dropwise 10 ml of a methylene chloride solution containing 0.495 g (2.4 mmol) of N,N'-dicyclohexylcarbodiimide with stirring at room temperature over a period of 2 hours.

Further, the reaction was carried out at room temperature for 12 hours.

The reaction mixture was filtered, and the filtrate was concentrated. The concentrate was separated by column chromatography to obtain 1.08 g of a white solid.

This compound had a M/e value in FD-mass spectrum of 722.

Figure 25:
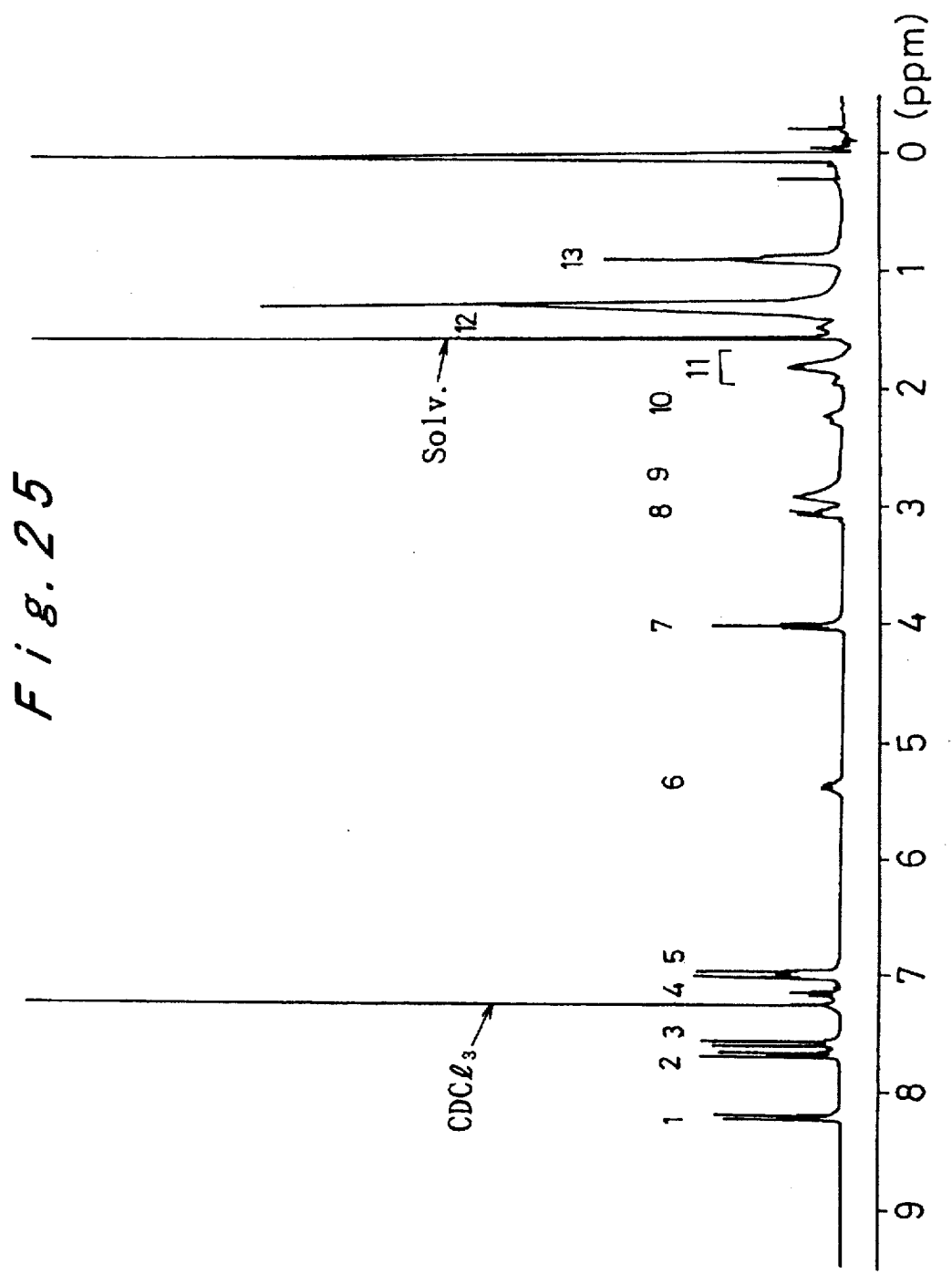
FIG. 25 shows $^1$H-NMR spectrum of 6-(4'-dodecyloxy-4-biphenylcarbonyloxy)-1,2,3,4-tetrahydro-2-naphthalenecarboxylic acid (R)-1-trifluoromethylheptyl ester [Compound (253)].

FIG. 25 shows $^1$H-NMR spectrum of this compound.

From these analytical results, this compound was identified as the title compound as desired.

EXAMPLE 33

Synthesis of 6-(4'-octyl-4-biphenylcarbonyloxy)-1,2,3,4-tetrahydro-2-naphthalenecarboxylic acid (R)-1-trifluoromethylheptyl ester [Compound (353)]

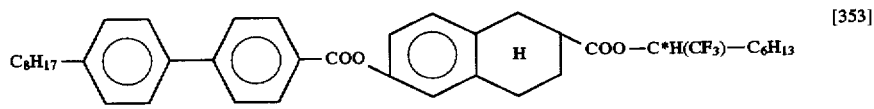

First Stage

To a mixture of 0.36 g (1 mmol) of 1,2,3,4-tetrahydro-6-hydroxynaphthalene-2-carboxylic acid (R)-1-trifluoromethylheptyl ester obtained in the fifth stage of Example 23, 0.31 g (1 mmol) of 4'-octylbiphenyl-4-carboxylic acid (FK-1124-8 from Teikoku Kagaku Sangyo K.K.), 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 2.5 hours.

Further, the reaction was carried out at room temperature for 36 hours.

The reaction mixture was filtered, and the filtrate was concentrated. The concentrate was separated by column chromatography to obtain 0.55 g of a colorless semisolid.

This compound had a M/e value in FD-mass spectrum of 650.

Figure 26:
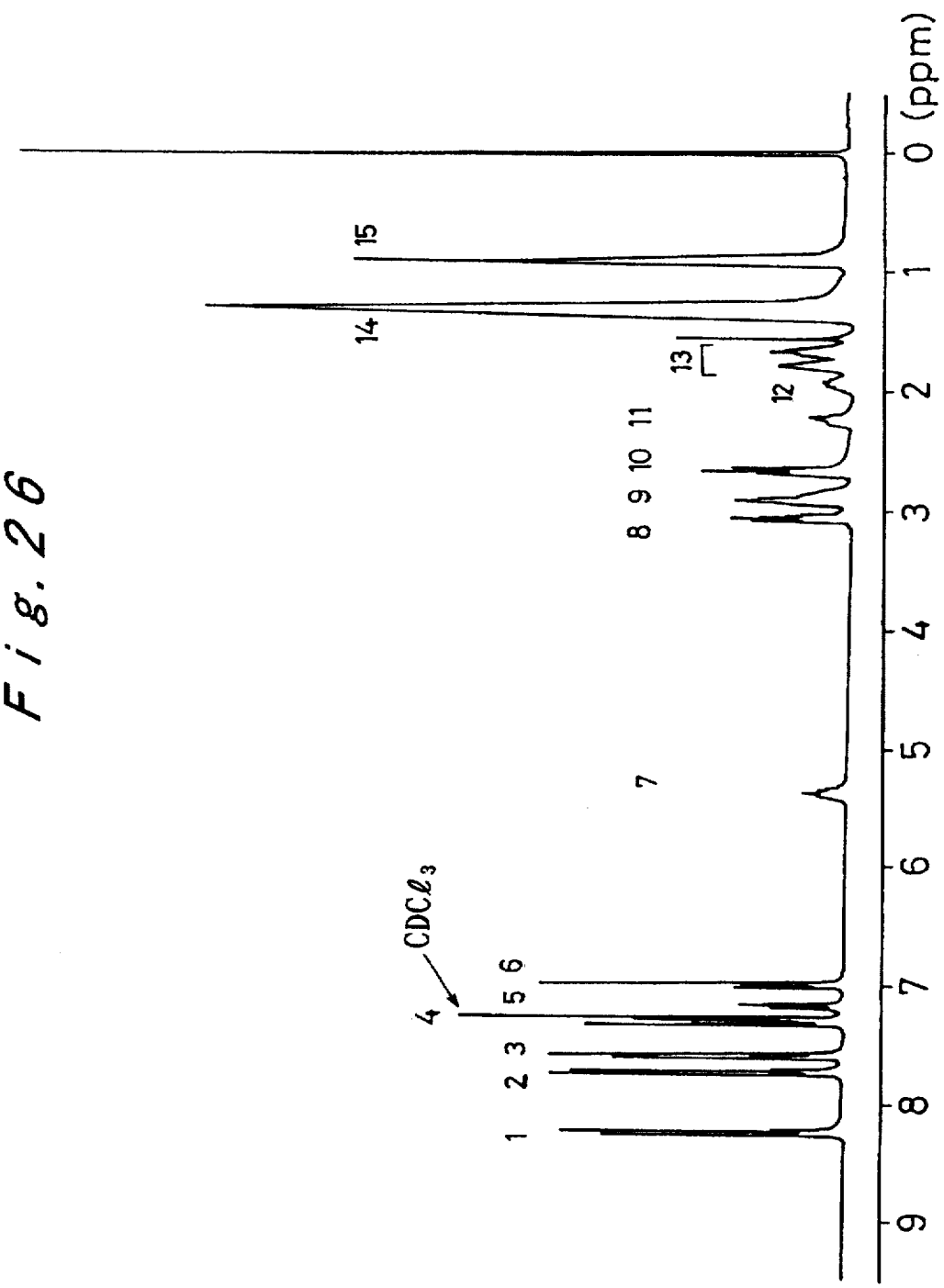
FIG. 26 shows $^1$H-NMR spectrum of 6-(4'-octyl-4-biphenylcarbonyloxy)-1,2,3,4-tetrahydro-2-naphthalenecarboxylic acid (R)-1-trifluoromethylheptyl ester [Compound (353)].

FIG. 26 shows $^1$H-NMR spectrum of this compound.

From these analytical results, this compound was identified as the title compound as desired.

EXAMPLE 34

Synthesis of 6-(4'-decyl-4-biphenylcarbonyloxy)-1,2,3,4-tetrahydro-2-naphthalenecarboxylic acid (R)-1-trifluoromethylheptyl ester [Compound (355)]

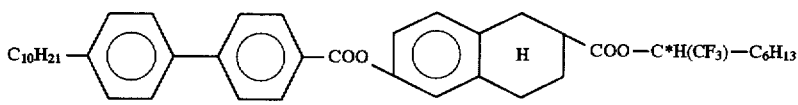

[355]

First Stage

To a mixture of 0.36 g (1 mmol) of 1,2,3,4-tetrahydro-6-hydroxynaphthalene-2-carboxylic acid (R)-1-trifluoromethylheptyl ester obtained in the fifth stage of Example 23, 0.34 g (1 mmol) of 4'-decylbiphenyl-4-carboxylic acid (FK-1124-10 from Teikoku Kagaku Sangyo K.K.), 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 2.5 hours.

Further, the reaction was carried out at room temperature for 20 hours.

The reaction mixture was filtered, and the filtrate was concentrated. The concentrate was separated by column chromatography to obtain 0.50 g of a colorless semisolid.

This compound had a M/e value in FD-mass spectrum of 678.

This compound had a M/e value in FD-mass spectrum of 706.

Figure 28:
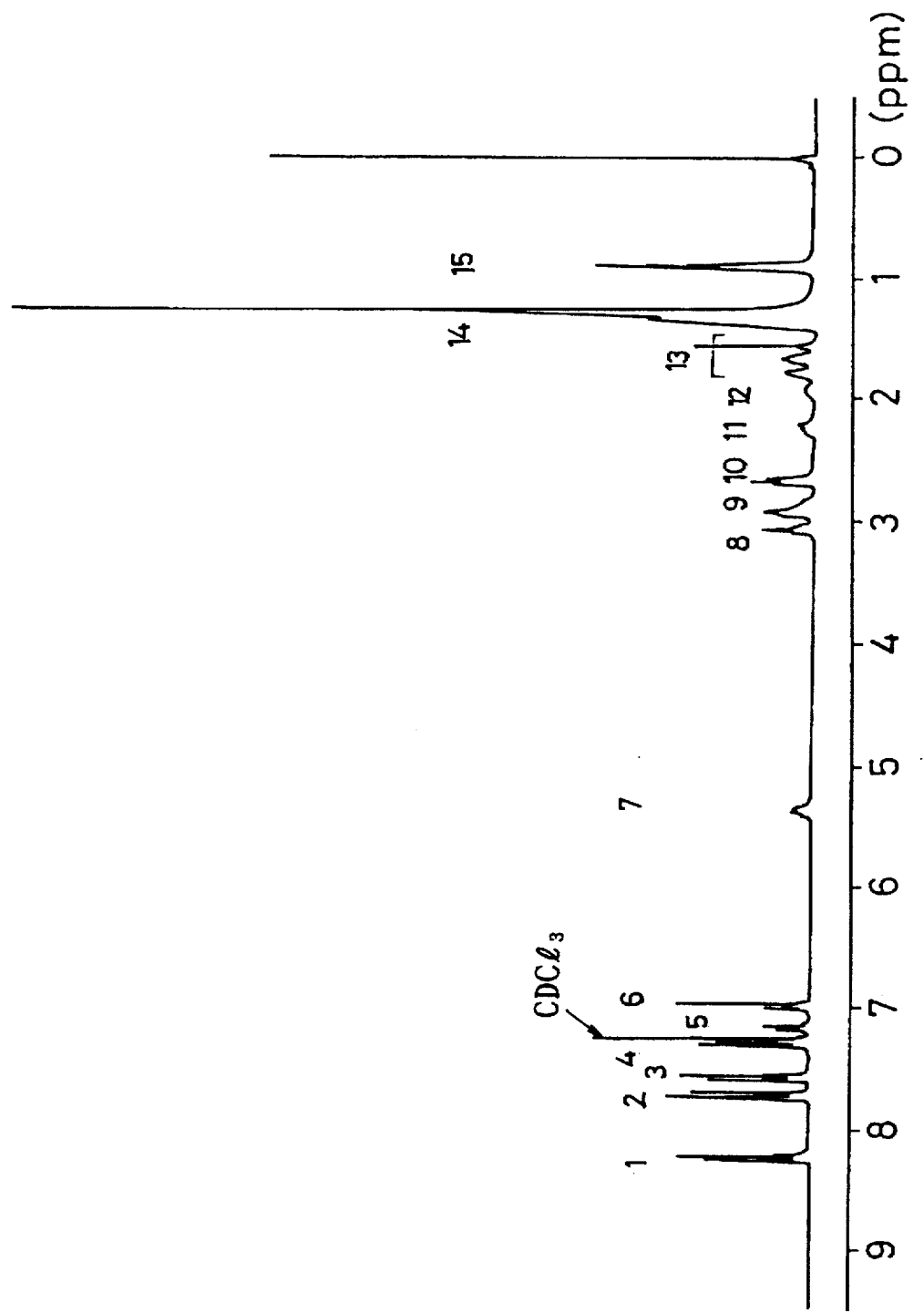
FIG. 28 shows $^1$H-NMR spectrum of 6-(4'-dodecyl-4-biphenylcarbonyloxy)-1,2,3,4-tetrahydro-2-naphthalenecarboxylic acid (R)-1-trifluoromethylheptyl ester [Compound (357)].

FIG. 28 shows $^1$H-NMR spectrum of this compound.

From these analytical results, this compound was identified as the title compound as desired.

EXAMPLE 36

Synthesis of 6-(4'-octylbiphenylcarbonyloxy)-1,2,3,4-tetrahydro-2-naphthalenecarboxylic acid (R)-1-methylheptyl ester [Compound (473)]

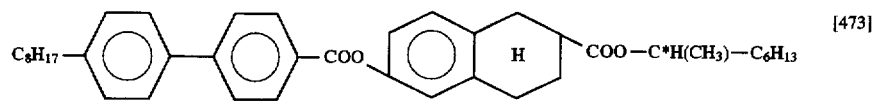

[473]

Figure 27:
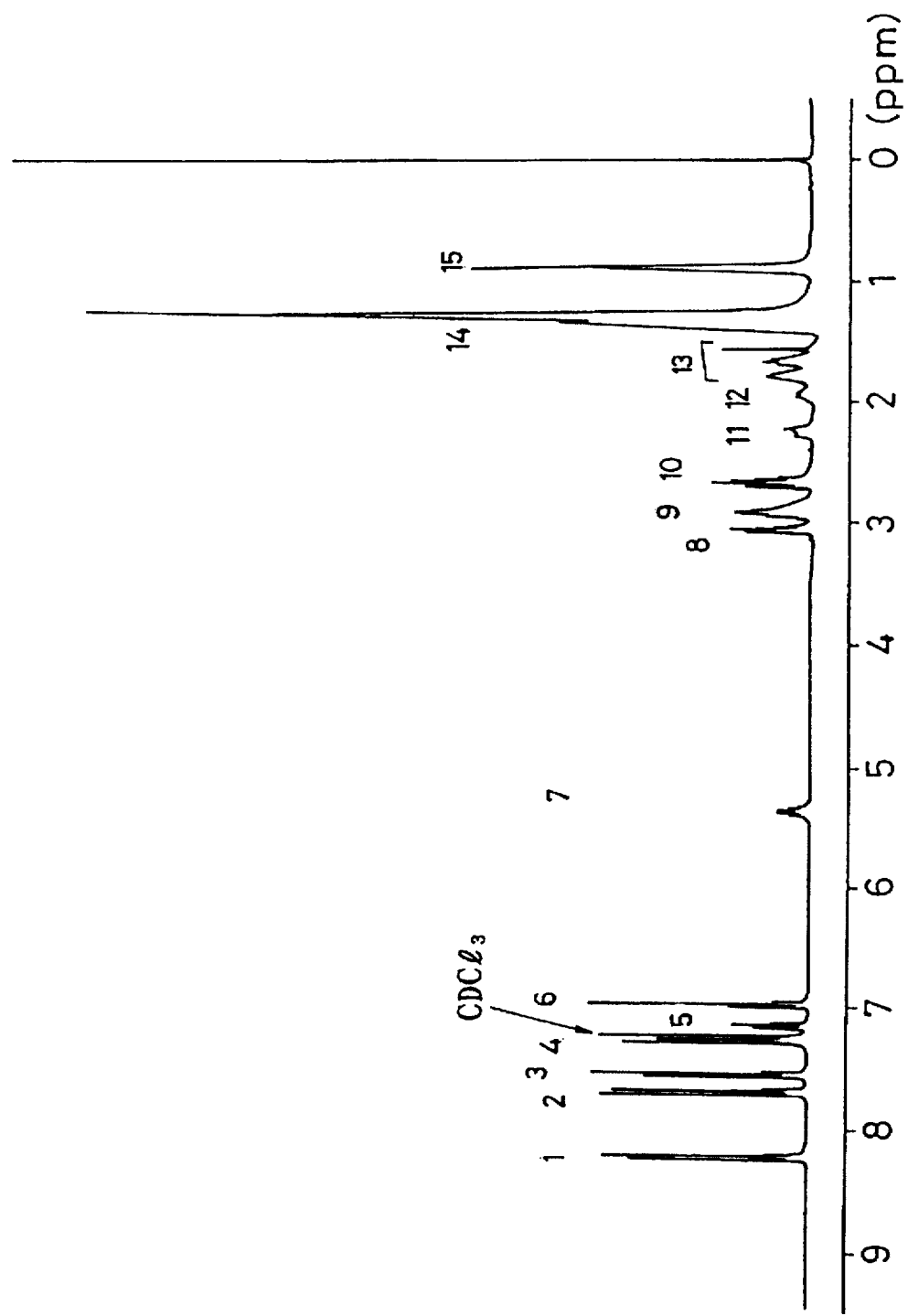
FIG. 27 shows $^1$H-NMR spectrum of 6-(4'-decyl-4-biphenylcarbonyloxy)-1,2,3,4-tetrahydro-2-naphthalenecarboxylic acid (R)-1-trifluoromethylheptyl ester [Compound (355)].

FIG. 27 shows $^1$H-NMR spectrum of this compound.

From these analytical results, this compound was identified as the title compound as desired.

EXAMPLE 35

Synthesis of 6-(4'-dodecylbiphenylcarbonyloxy)-1,2,3,4-tetrahydro-2-naphthalenecarboxylic acid (R)-1-trifluoromethylheptyl ester [Compound (357)]

First Stage

To a mixture of 0.31 g (1 mmol) of 1,2,3,4-tetrahydro-6-hydroxynaphthalene-2-carboxylic acid (R)-1-methylheptyl ester obtained as in the fourth stage of Example 23 where R-1-methyl heputanol was used in stead of (R)-1-trifluoromethylheptanol, 0.31 g (1 mmol) of 4'-octylbiphenyl-4-carboxylic acid (FK-1124-8 from Teikoku Kagaku Sangyo K.K.), 0.02 g (0.16 mmol) of 4-N,N-dimethylaminopyridine and 15 ml of methylene chloride was added dropwise 3 ml of a methylene chloride

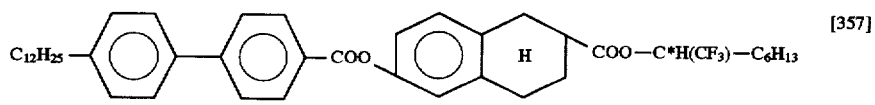

[357]

First Stage

To a mixture of 0.36 g (1 mmol) of 1,2,3,4-tetrahydro-6-hydroxynaphthalene-2-carboxylic acid (R)-1-trifluoromethylheptyl ester obtained in the fifth stage of Example 23, 0.37 g (1 mmol) of 4'-dodecylbiphenyl-4-carboxylic acid (FK-1124-12 from Teikoku Kagaku Sangyo K.K.), 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 2.5 hours.

Further, the reaction was carried out at room temperature for 20 hours.

The reaction mixture was filtered, and the filtrate was concentrated. The concentrate was separated by column chromatography to obtain 0.54 g of a colorless semisolid.

solution containing 0.27 g (1.3 mmol) of N,N'-dicyclohexylcarbodiimide with stirring at room temperature over a period of 3 hours.

Further, the reaction was carried out at room temperature for 20 hours.

The reaction mixture was filtered, and the filtrate was concentrated. The concentrate was separated by column chromatography to obtain 0.45 g of a colorless semisolid.

This compound had a M/e value in FD-mass spectrum of 596.

FIG. 29 shows $^1$H-NMR spectrum of this compound.

From these analytical results, this compound was identified as the title compound as desired.

EXAMPLE 37

Synthesis of 6-(4'-decylbiphenylcarbonyloxy)-1,2,3,4-tetrahydro-2-naphthalenecarboxylic acid (R)-1-methylheptyl ester [Compound (475)]

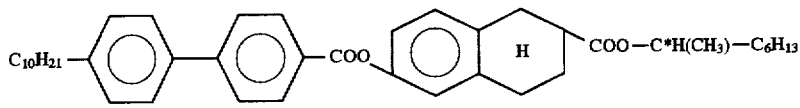

[475]

First Stage

To a mixture of 0.37 g (1.1 mmol) of 1,2,3,4-tetrahydro-6-hydroxynaphthalene-2-carboxylic acid (R)-1-methylheptyl ester obtained as in the fourth stage of Example 23 where (R)-1-methyl heputanol was used instead of (R)-1-trifluoromethylheptanol, 0.33 g (1.1 mmol) of 4'-decylbiphenyl-4-carboxylic acid (FK-1124-10 from Teikoku Kagaku Sangyo K.K.), 0.013 g (0.11 mmol) of 4-N,N-dimethylaminopyridine and 10 ml of methylene chloride was added dropwise 5 ml of a methylene chloride solution containing 0.27 g (1.3 mmol) of N,N'-dicyclohexylcarbodiimide with stirring at room temperature over a period of 2.5 hours.

Further, the reaction was carried out at room temperature for 60 hours.

The reaction mixture was filtered, and the filtrate was concentrated. The concentrate was separated by column chromatography to obtain 0.60 g of a colorless semisolid.

This compound had a M/e value in FD-mass spectrum of 624.

FIG. 30 shows $^1$H-NMR spectrum of this compound.

From these analytical results, this compound was identified as the title compound as desired.

EXAMPLE 38

Synthesis of 6-[4'-((S)-1-methylheptyloxy)biphenylcarbonyloxy]-1,2,3,4-tetrahydro-2-naphthalenecarboxylic acid (R)-1-trifluoromethylheptyl ester dicyclohexylcarbodiimide with stirring at room temperature over a period of 3 hours.

Further, the reaction was carried out at room temperature for 47 hours.

The reaction mixture was filtered, and the filtrate was concentrated. The concentrate was separated by column chromatography to obtain 0.54 g of a colorless semisolid.

This compound had a M/e value in FD-mass spectrum of 666.

FIG. 31 shows $^1$H-NMR spectrum of this compound.

From these analytical results, this compound was identified as the title compound as desired.

EXAMPLE 39

Synthesis of 6-[4-(4-octyloxyphenyl)cyclohexylcarbonyloxy]-1,2,3,4-tetrahydro-2-naphthalenecarboxylic acid (R)-1-trifluoromethylheptyl ester [Compound (265)]

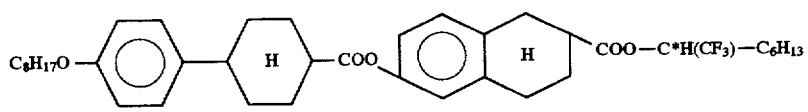

[265]

First Stage

To a mixture of 0.36 g (1 mmol) of 1,2,3,4-tetrahydro-6-hydroxynaphthalene-2-carboxylic acid (R)-1-trifluoromethylheptyl ester obtained in the fifth stage of Example 23, 0.33 g (1 mmol) of 4'-octyloxycyclohexane-4-carboxylic acid obtained as in the first stage of Example 12 where n-octyl bromide was used instead of n-decyl bromide, 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 4 hours.

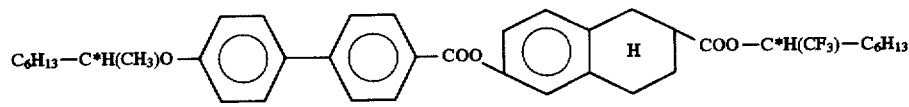

First Stage

To a mixture of 0.358 g (1 mmol) of 1,2,3,4-tetrahydro-6-hydroxynaphthalene-2-carboxylic acid (R)-1-trifluoromethylheptyl ester obtained in the fifth stage of Example 23, 0.326 g (1 mmol) of 4'-((S)-1''-methylheptyloxy)biphenyl-4-carboxylic acid (KB-502-8(S) from Arakawa Kagaku kogyo K.K.), 0.012 g (0.12 mmol) of 4-N,N-dimethylaminopyridine and 10 ml of methylene chloride was added dropwise 5 ml of a methylene chloride solution containing 0.25 g (1.2 mmol) of N,N'-

Further, the reaction was carried out at room temperature for 20 hours.

The reaction mixture was filtered, and the filtrate was concentrated. The concentrate was separated by column chromatography to obtain 0.35 g of a colorless semisolid.

This compound had a M/e value in FD-mass spectrum of 672.

Figure 32:
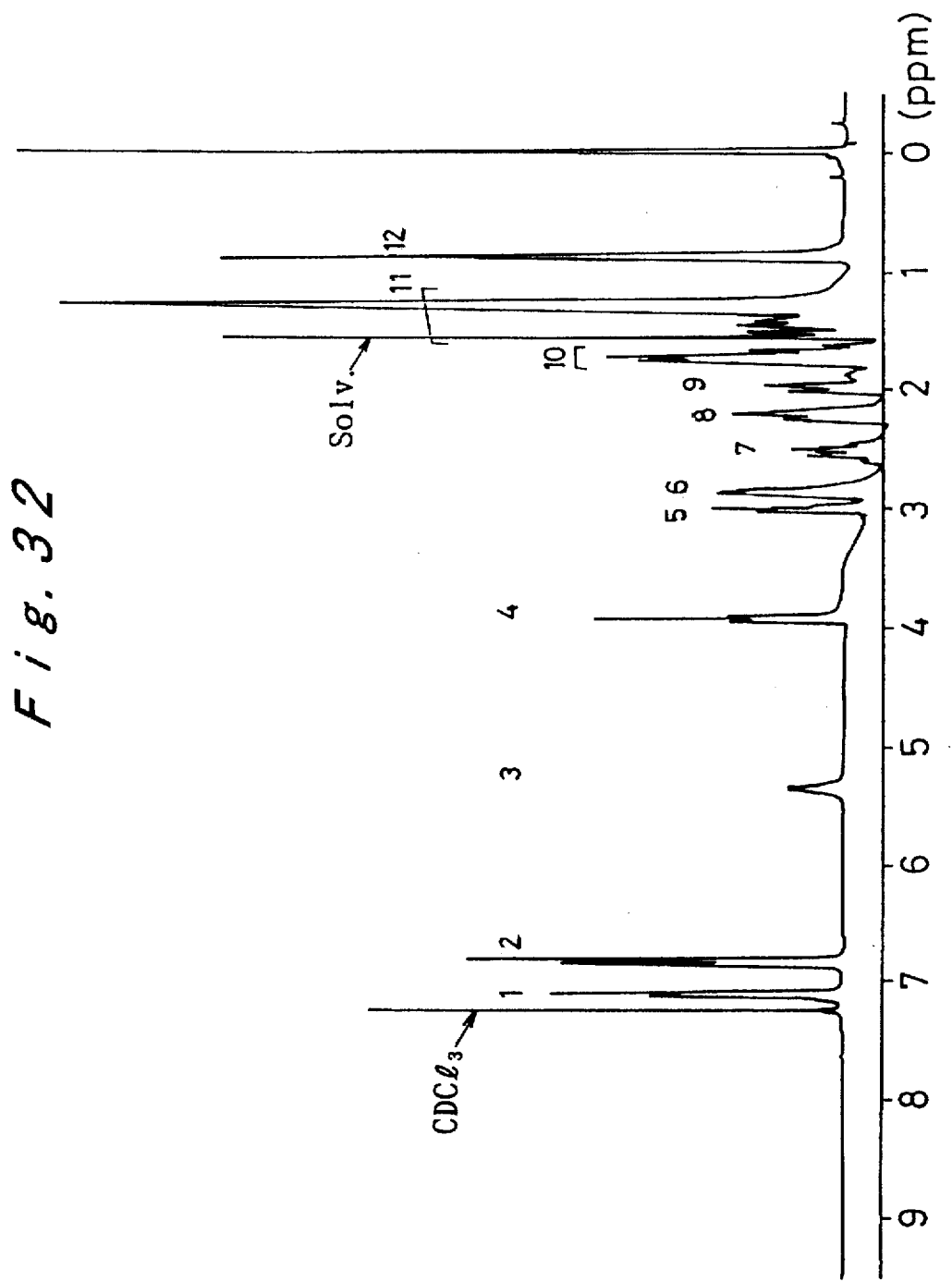
FIG. 32 shows $^1$H-NMR spectrum of 6-[4-(4-octyloxyphenyl)cyclohexylcarbonyloxy]-1,2,3,4-tetrahydro-2-naphthalenecarboxylic acid (R)-1-trifluoromethylheptyl ester [Compound (265)].

FIG. 32 shows $^1$H-NMR spectrum of this compound.

From these analytical results, this compound was identified as the title compound as desired.

EXAMPLE 40

Synthesis of 6-[4-(4-dodecyloxyphenyl)cyclohexylcarbonyloxy]-1,2,3,4-tetrahydro-2-naphthalenecarboxylic acid (R)-1-trifluoromethylheptyl ester [Compound (269)]

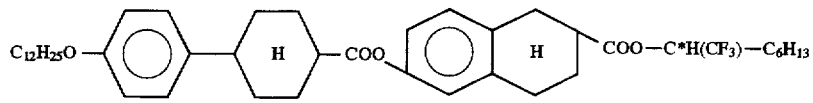
[269]

First Stage

To a mixture of 0.54 g (1.5 mmol) of 1,2,3,4-tetrahydro-6-hydroxynaphthalene-2-carboxylic acid (R)-1-trifluoromethylheptyl ester obtained in the fifth stage of Example 23, 0.61 g (1.7 mmol) of 4'-undecyloxyphenylcyclohexane-4-carboxylic acid obtained as in the first stage of Example 12 where n-undecyl bromide was used instead of n-decyl bromide, 0.018 g (0.15 mmol) of 4-N,N-dimethylaminopyridine and 20 ml of methylene chloride was added dropwise 10 ml of a methylene chloride solution containing 0.37 g (1.8 mmol) of N,N'-dicyclohexylcarbodiimide with stirring at room temperature over a period of 4 hours.

Further, the reaction was carried out at room temperature for 20 hours.

The reaction mixture was filtered, and the filtrate was concentrated. The concentrate was separated by column chromatography to obtain 0.53 g of a colorless semisolid.

This compound had a M/e value in FD-mass spectrum of 700.

Figure 33:
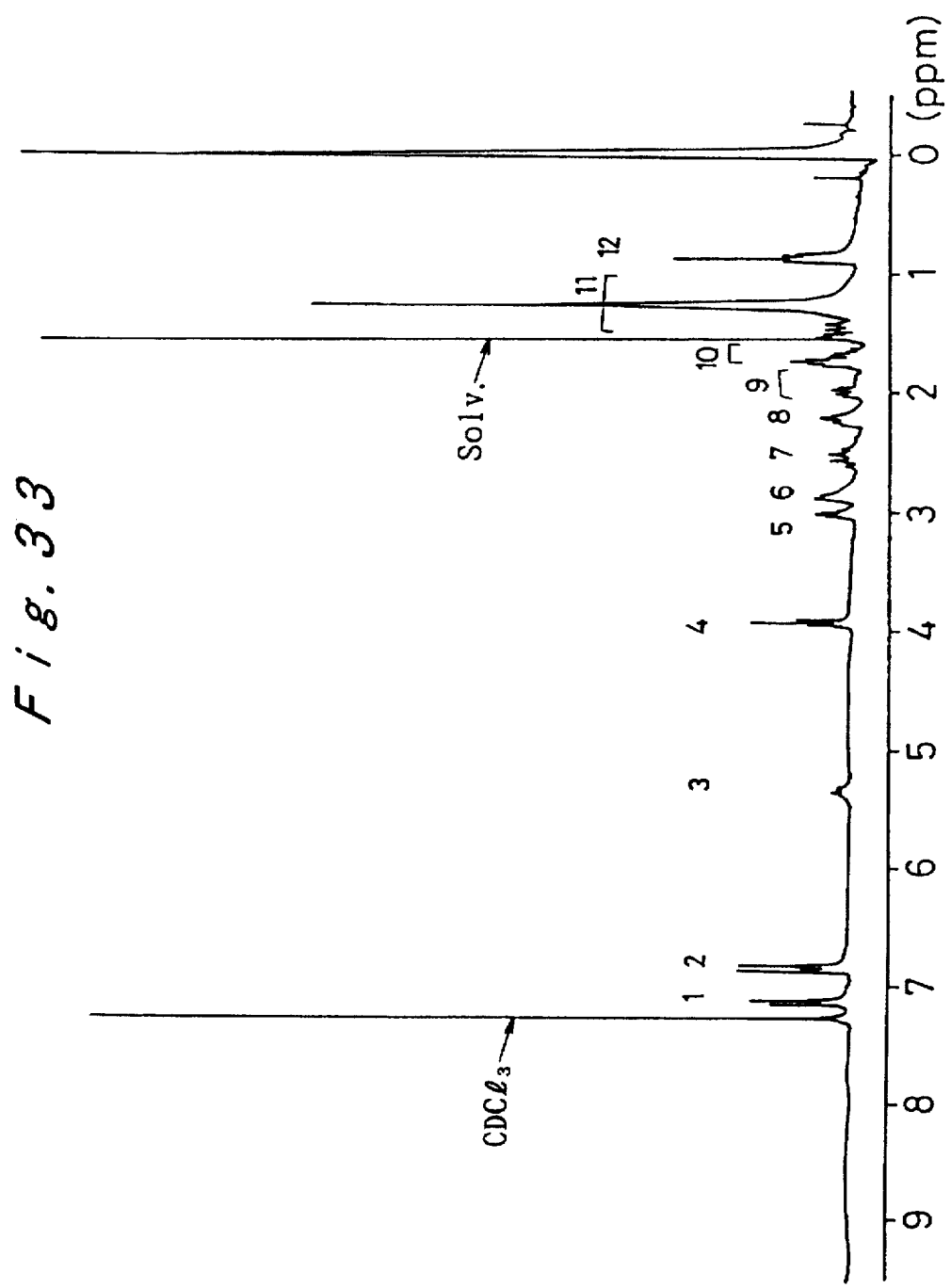
FIG. 33 shows $^1$H-NMR spectrum of 6-(4-(4-dodecyloxyphenyl)cyclohexylcarbonyloxy]-1,2,3,4-tetrahydro-2-naphthalenecarboxylic acid (R)-1-trifluoromethylheptyl ester [Compound (269)].

FIG. 33 shows $^1$H-NMR spectrum of this compound.

From these analytical results, this compound was identified as the title compound as desired.

EXAMPLE 41

Synthesis of 6-[4-(4-decylphenyl)cyclohexylcarbonyloxy]-1,2,3,4-tetrahydro-2-naphthalenecarboxylic acid (R)-1-trifluoromethylheptyl ester [Compound (363)]

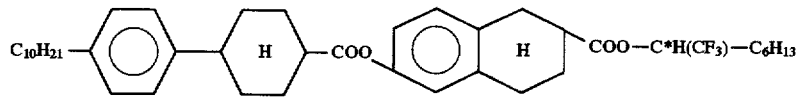
[363]

First Stage

A mixture of 5.07 g (15 mmol) of 4'-decylbiphenyl-4-carboxylic acid (FK-1124-10 from Teikoku Kagaku Sangyo K.K.), 4.49 g (0.195 mol) of metallic sodium and 200 ml of 1,2-diethoxyethane was heated at 150° C. for 4 hours while stirring. To the mixture was added dropwise 20 of isoamyl alcohol over a period of 8 hours under reflux at 150° C. and while stirring, followed by stirring for further 2 hours under reflux.

After cooling the reaction mixture, 80 ml of ethanol and 100 ml of distilled water were added to convert the remaining metallic sodium into alcholate. The aqueous phase separated was neutralized by the addition of hydrochloric acid to form a precipitate, which was then purified by column chromatography to separate into cis and trans isomers. Yield was 2.24 g of 4'-decylphenyltranscyclohexane-4-carboxylic acid as desired.

Second Stage

To a mixture of 0.36 g (1 mmol) of 1,2,3,4-tetrahydro-6-hydroxynaphthalene-2-carboxylic acid (R)-1-trifluoromethylheptyl ester obtained in the fifth stage of Example 23, 0.39 g (1.1 mmol) of 4'-decylphenyltranscyclohexane-4-carboxylic acid obtained in the first stage, 0.012 g (0.1 mmol) of 4-N,N-dimethylaminopyridine and 10 ml of methylene chloride was added dropwise 5 ml of a methylene chloride solution containing 0.25 g (1.2 mmol) of N,N'-dicyclohexylcarbodiimide with stirring at room temperature over a period of 4 hours.

Further, the reaction was carried out at room temperature for 19 hours.

The reaction mixture was filtered, and the filtrate was concentrated. The concentrate was separated by column chromatography to obtain 0.59 g of a colorless semisolid.

This compound had a M/e value in FD-mass spectrum of 684.

Figure 34:
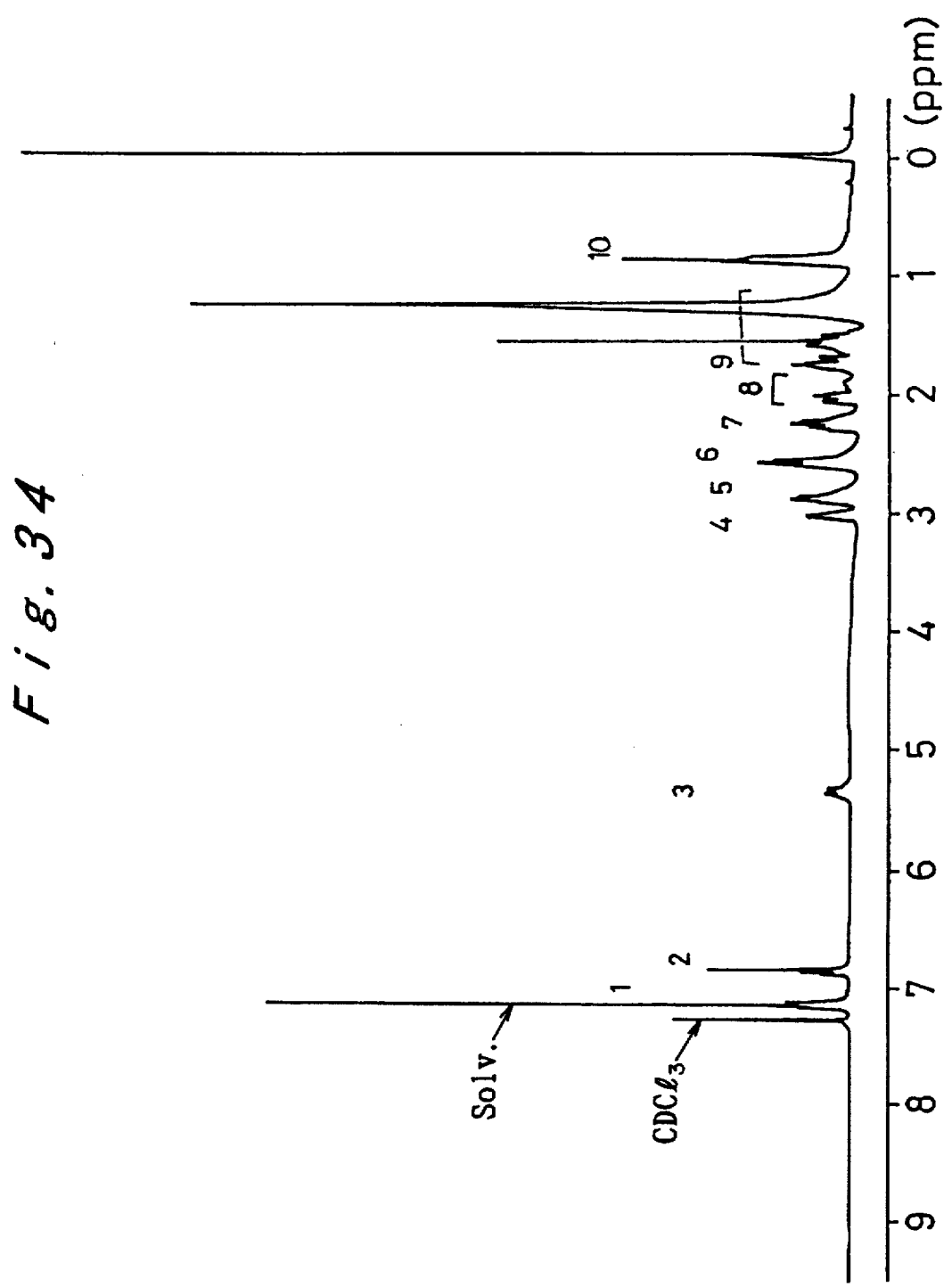
FIG. 34 shows ¹H-NMR spectrum of 6-[4-(4-decylphenyl)cyclohexylcarbonyloxy]-1,2,3,4-tetrahydro-2-naphthalenecarboxylic acid (R)-1-trifluoromethylheptyl ester [Compound (363)].

FIG. 34 shows $^1$H-NMR spectrum of this compound.

From these analytical results, this compound was identified as the title compound as desired.

EXAMPLE 42

Synthesis of 4-[6-(4-decylbenzoyloxy)-1,2,3,4-tetrahydro-2-naththoyloxy]benzoic acid (R)-1-trifluoromethylheptyl ester (Compound [212])

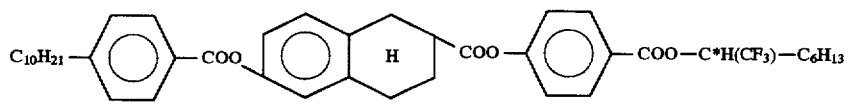
[212]

First Stage

To a mixture of 0.69 g (1.46 mmol) of 4-(1',2',3',4'-tetrahydro-6'-hydroxy-2'-naphthoyloxy)benzoic acid (R)-1"-trifluoromethylheptyl ester obtaind in the fifth stage of Example 8, 0.39 g (1.5 mmol) of 4-decylbenzoic acid synthesized separately by conventional means, 0.018 g (0.15 mmol) of 4-N,N-dimethylaminopyridine and 30 ml of methylene chloride was added dropwise 10 ml of a methylene chloride solution containing 0.37 g (1.8 mmol) of N,N'-dicyclohexylcarbodiimide with stirring at room temperature over a period of 4 hours.

Further, the reaction was carried out at room temperature for 20 hours.

The reaction mixture was filtered, and the filtrate was concentrated. The concentrate was separated by column chromatography to obtain 0.39 g of a colorless semisolid.

This compound had a M/e value in FD-mass spectrum of 718.

From the analytical result, this compound was identified as the title compound as desired.

EXAMPLE 43

Synthesis of 6-[4-(2-(4-decyloxyphenyl)ethyl)benzoyloxy]-1,2,3,4-tetrahydro-2-naphthalenecarboxylic acid (R)-1-trifluoromethylheptyl ester [Compound (651)]

collected by filtration, washed with water, and dried. Then, the obtained white fine powder was recrystallized from ethanol to obtain 18.1 g of 4-[2-(4-decyloxyphenyl)ethenyl]benzoic acid as a white-yellow scaly crystal (isolated yield: 60%, cis-trans mixture).

Fourth Stage 18.1 g of 4-[2-(4-decyloxyphenyl)ethenyl] benzoic acid (cis-trans mixture) was subjected to hydrogenation of olefin at room temperature and normal pressure while bubbling hydrogen using 1.6 g of 5% palladium/carbon and 1 ml of concentrated hydrochloric acid as a catalyst, and 160 ml of tetrahydrofuran as a solvent. The 5% palladium/carbon was removed using Celite as a filter aid. The resultant filtrate was concentrated and recrystallized from ethanol to obtain 15.1 g of 4-[2-(4-decyloxyphenyl)ethyl]benzoic acid as a white needle crystal (isolated yield: 84%).

Fifth Stage

To a mixture of 0.3 g (1 mmol) of 4-[2-(decyloxyphenyl)ethyl]benzoic acid, 0.18 g (0.5 mmol) of 1,2,3,4-tetrahydro-

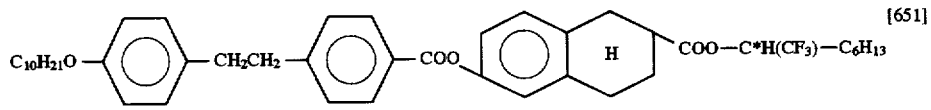

First Stage 39.7 g (287 mmmol) of p-toluylic acid, 51.2 g (287 mmmol) of N-bromosuccinimide and 2.8 g (11.5 mmol) of dibenzoyl peroxide were suspended in 350 ml of carbon tetrachloride. Then, the resultant mixture was heated with vigorously stirring to perform a reaction under reflux for 2 hours. After completion of the reaction, the reaction mixture was cooled in ice bath. The deposited crystalline product was collected by filtration, which was then washed with hexane and water, followed by drying. The resultant crystalline product was recrystallized from ethanol to obtain 40.3 g of 4-bromomethylbenzoic acid as a white needle crystal (isolated yield: 65%).

Second Stage 24.4 g (113 mmol) of 4-bromomethylbenzoic acid and 30.7 g (113 mmol) of triphenylphosphine were dissolved in 750 ml of acetone, and the resultant mixture was heated to the reflux temperature with stirring to conduct a reaction for 4 hours. After completion of the reaction, the reaction mixture was cooled in ice bath. The deposited crystal was collected by suction filtration, which was then washed with acetone and dried to obtain 47.4 g of phosphonium salt as a white powder (isolated yield: 88%).

Third Stage

To 1.6 L of absolute ethanol was added 9.2 g (400 mmol) of metallic sodium to prepare an alkoxide solution. To the resultant solution was added 38.2 g (80 mmol) of phosphonium salt obtained in the second stage at room temperature with stirring. Then, to the resultant mixture was dropwise added 22.1 g (80 mmol) of 4-decyloxybenzaldehyde at room temperature over a period of about 1 hour. After completion of the addition, the reaction was further carried out for 10 hours. The reaction mixture was neutralized with diluent hydrochloric acid. The resultant white fine powder was 6-hydroxy-2-naphthalenecarboxylic acid (R)-1-trifluoromethylheptyl ester and 10 ml of a dichloromethane solution containing 9 mg of dimethylaminopyridine as a reaction accelerator was dropwise added 5 ml of a dichloromethane solution containing 0.14 g (0.65 mmol) of dicyclohexylcarbodiimide with stirring at room temperature over a period of 4 hours.

Then, the reaction was further carried out overnight at room temperature. The reaction mixture was diluted with hexane and the deposited urea compound was removed. The resultant filtrate was concentrated to obtain a residue. The residue was purified twice by column chromatography (SiO$_2$/hexane-acetone/95-5) to obtain 0.25 g of a title compound (651) as a semisolid (isolated yield: 69%).

This semisolid compound had an M/e value in FD-mass spectrum of 722.

A $^1$H-NMR spectrum of this compound is shown in FIG. 35.

From these analytical results, this compound was identified as 6-[4-(2-(4-decyloxyphenyl)ethyl)benzoyloxy]-1,2,3,4-tetrahydro-2-naphthalenecarboxylic acid (R)-1-trifluoromethylheptyl ester [Compound (651)] as desired.

EXAMPLE 44

Synthesis of 6-[(4-(6-decyloxy-2-naphthoyloxy)benzoyloxy)]-1,2,3,4-tetrahydro-2-naphthalenecarboxylic acid (R)-1-trifluoromethylheptyl ester [Compound (691)]

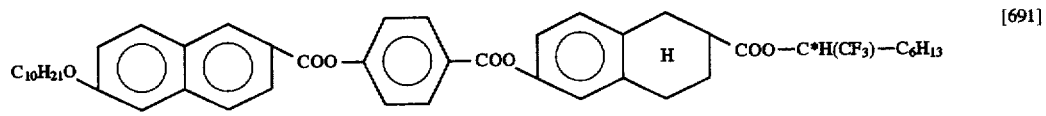

First Stage

To a mixture of 32.8 g (0.1 mol) of 6-decyloxy-2-naphthalenecarboxylic acid, 22.8 g (0.1 mol) of 4-hydroxyphenylbenzyl ester, 0.61 g (5 mmol) of 4-N,N-dimethylaminopyridine and 300 ml of methylene chloride was added 200 ml of a methylene chloride solution containing 22.7 g (0.11 mol) of N,N'-dicyclohexylcarbodiimide with stirring at room temperature over a period of 2 hours.

Then, the reaction mixture was filtered, and the filtrate was concentrated. The concentrate obtained was separated by column chromatography to obtain 35.6 g of 4-(6-decyloxy-2-naphthoyloxy)benzoic acid benzyl ester as a colorless semisolid.

Second Stage

To 37.6 g (0.07 mol) of the 4-(6-decyloxy-2-naphthoyloxy)benzoic acid benzyl ester obtained in the first stage was added 3.76 g of 5% palladium/carbon, and further added 188 g of THF. Then, hydrogen gas was blown into the mixture. The resultant mixture was stirred overnight and filtered to obtain 30.6 g of 4-(6-decyloxy-2-naphthoyloxy) benzoic acid.

Third Stage

To a mixture of 0.45 g (1 mmol) of the 4-(6-decyloxy-2-naphthoyloxy)benzoic acid obtained in the second stage, 0.36 g (1 mmol) of the 1,2,3,4-tetrahydro-6-hydroxy-2-naphthalenecarboxylic acid (R)-1-trifluoromethylheptyl ester obtained in the fifth stage of Example 23, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 19 hours.

The reaction mixture was filtered, and the filtrate was concentrated. The concentrate obtained was separated by column chromatography to obtain 0.62 g of a colorless semisolid.

This semisolid compound had an M/e value in FD-mass spectrum of 788.

$^1$H-NMR spectrum of this compound is shown in FIG. 36.

From these analytical results, this compound was identified as 6-[(4-(6-decyloxy-2-naphthoyloxy)benzoyloxy)]-1,2,3,4-tetrahydro-2-naphthalenecarboxylic acid (R)-1-trifluoromethylheptyl ester [Compound (691)] as desired.

EXAMPLE 45

Synthesis of 6-[4-((R)-1-trifluoromethylheptyloxycarbonyl)benzoyloxy]-1,2,3,4-tetrahydro-2-naphthalenecarboxylic acid 4-decyloxyphenyl ester [Compound (154)]

resultant filtrate was concentrated to obtain a residue. The residue was purified by column chromatography (SiO$_2$/hexane-dichlomethane/1-1) to obtain 0.36 g of 2-(4-decyloxyphenyloxycarbonyl)-1,2,3,4-tetrahydro-6-benzyloxynaphthalene as a white powder (isolated yield: 58%).

Then, 0.04 g of 5% palladium/carbon and 10 ml of a tetrahydrofuran solution containing 0.36 g of 2-(4-decyloxyphenyloxycarbonyl)- 1,2,3,4-tetrahydro-6-benzyloxynaphthalene were stirred overnight at room temperature in a stream of hydrogen to decompose a benzyl protective group by hydrogenation. 5% palladium/carbon was removed using Celite as a filter aid, and the filtrate was concentrated. The concentrate obtained was purified by column chromatography to obtain 0.29 g of 2-(4-decyloxyphenyloxycarbonyl)-1,2,3,4-tetrahydro-6-hydroxynaphthalene as a white crystal (isolated yield: 97%).

Second Stage

To a mixture of 4.93 g (32.8 mmol) of 4-formylbenzoic acid, 4.26 g (39.4 mmol) of benzyl alcohol and 250 ml of a dichloromethane solution containing 0.39 g (3.2 mmol) of dimethylaminopyridine as a reaction accelerator was dropwise added 100 ml of a dichloromethane solution containing 8.04 g (39.4 mmol) of dicyclohexylcarbodiimide with stirring at room temperature over a period of 12 hours.

Then, the reaction was further carried out overnight at room temperature. The reaction mixture was diluted with hexane and the deposited urea compound was removed. The resultant filtrate was concentrated to obtain a residue. The residue was purified by column chromatography (SiO$_2$/hexane-dichlomethane/1-1) to obtain 7.34 g of 4-formylbenzoic acid benzyl ester as a colorless liquid (isolated yield: 93%).

Third Stage

To 50 ml of an acetic acid solution containing 7.34 g (30.5 mmol) of 4-formylbenzoic acid benzyl ester were dropwise added 4.53 g (4.35 mmol) of chromic acid anhydride, 40 ml of acetic acid and 1.3 ml of water with stirring at room temperature for a period of 2 hours. The oxidation of a formyl group was further carried out overnight at room temperature. The reaction mixture was put into water, and the deposited black-green crystal was collected by filtration, followed by drying. The resultant crystal was recrystallized from acetone to obtain 4.08 g of 4-benzyloxycarbonylbenzoic acid as a white needle crystal (isolated yield: 49%).

Fourth Stage

To a mixture of 0.51 g (2 mmol) of 4-benzyloxycarbonylbenzoic acid, 0.28 g (1.5 mmol) of

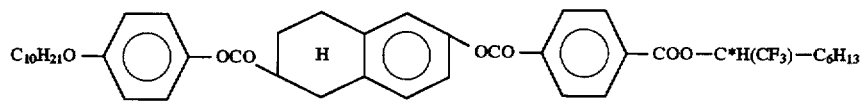

[154]

First Stage

To a mixture of 0.3 g (1.2 mmol) of 4-decyloxyphenol, 0.34 g (1.2 mmol) of 1,2,3,4-tetrahydro-6-benzyloxy-2-naphthalic acid and 12 ml of a dichloromethane solution containing 15 mg of dimethylaminopyridine as a reaction accelerator was dropwise added 6ml of a dichloromethane solution containing 0.3 g (1.5 mmol) of dicyclohexylcarbodiimide with stirring at room temperatue over a period of 4 hours.

Then, the reaction was further carried out overnight at room temperature. The reaction mixture was diluted with hexane and the deposited urea compound was removed. The (R)-1-trifluoromethyl-2-hepthanol, and 15 ml of a dichloromethane solution containing 18 mg (0.15 mmol) of dimethylaminopyridine as a reaction accelerator was dropwise added 7.5 ml of a dichloromethane solution containing 0.37 g (1.8 mmol) of dicyclohexylcarbodiimide with stirring at room temperature over a period of 4 hours.

Then, the reaction was further carried out overnight at room temperature. The reaction mixtre was diluted with hexane and the deposited urea compound was removed. The resultant filtrate was concentrated to obtain a residue.

The residue was purified by column chromatography (SiO$_2$/hexane-dichlomethane/1-1) to obtain 0.63 g of 4-((R)

-1-trifluoromethylheptyloxycarbonyl)benzoic acid benzyl ester as a colorless liquid (isolated yield: 99%).

Then, 0.07 g of 5% palladium/carbon and 10 ml of a tetrahydrofuran solution containing 0.63 g of 4-((R)-1-trifluoromethylheptyloxycarbonyl)benzoic acid benzyl ester were stirred overnight at room temperature in a stream of hydrogen to decompose a benzyl protective group by hydrogenation. 5% palladium/carbon was removed using Celite as a filter aid, and the filtrate was concentrated. The concentrate obtained was purified by column chromatography to obtain 0.49 g of 4-((R)-1-trifluoromethylheptyloxycarbonyl) benzoic acid as a colorless liquid (gradually crystallized) (isolated yield: 98%).

Fifth Stage

To a mixture of 0.17 g (0.4 mmol) of 2-(4-decyloxyphenyloxycarbonyl)-1,2,3,4-tetrahydro-6-hydroxynaphthalene, 0.13 g (0.4 mmol) of 4-((R)-1-trifluoromethyloxycarbonyl)benzoic acid and 10 ml of a dichloromethane solution containing 5 mg (0.04 mmol) of dimethylaminopyridine as a reaction accelerator was dropwise added 5 ml of a dichloromethane solution containing 0.11 g (0.5 mmol) of dicyclohexylcarbodiimide with stirring at room temperature over a period of 4 hours.

Then, the reaction was further carried out overnight at room temperature. The reaction mixture was diluted with hexane and the deposited urea compound was removed. The resultant filtrate was concentrated to obtain a residue. The residue was purified by column chromatography (SiO₂/hexane-dichlomethane/1-1) to obtain 0.18 g of 6-[4-((R)-1-trifluoromethylheptyloxycarbonyl) benzoyloxy]-1,2,3,4-tetrahydro-2-naphthalenecarboxylic acid 4-decyloxyphenyl ester as a semisolid (isolated yield: 61%).

This semisolid compound had an M/e value in FD-mass spectrum of 738.

A $^1$H-NMR spectrum of this compound is shown in FIG. 37.

From these analytical results, this compound was identified as 6-[4-((R)-1-trifluoromethylheptyloxycarbonyl)-benzoyloxy]-1,2,3,4-tetrahydro-2-naphthalenecarboxylic acid-4-decyloxyphenyl ester [Compound (154)] as desired.

EXAMPLE 46

Synthesis of 6-[4-(R)-1-methylheptyloxycarbonyl) benzoyloxy]-1,2,3,4-tetrahydro-2-naphthalenecarboxylic acid 4-decyloxyphenyl ester [Compound (162)]

Then, the reaction was further carried out overnight at room temperature. The reaction mixture was diluted with hexane and the deposited urea compound was removed. The resultant filtrate was concentrated to obtain a residue. The residue was purified by column chromatography (SiO₂/hexane-dichloromethane/1-l) to obtain 1.21 g of 4-((R)-1-methylheptyloxycarbonyl)benzoic acid benzyl ester as a colorless liquid (isolated yield: 82%).

Then, 0.12 g of 5% palladium/carbon and 30 ml of a tetrahydrofuran solution containing 1.21 g of 4-((R)-1-methylheptyloxycarbonyl)benzoic acid benzyl ester were stirred overnight at room temperature in a stream of hydrogen to decompose a benzyl protective group by hydrogenation. 5% palladium/carbon was removed using Celite as a filter aid, and the filtrate was concentrated. The concentrate obtained was purified by column chromatography to obtain 0.91 g of 4-((R)-1-methylheptyloxycarbonyl) benzoic acid as a colorless liquid (gradually crystallized) (isolated yield: 99%).

Second Stage

To a mixture of 0.09 g (0.21 mmol) of the 2-(4-decyloxyphenyloxycarbonyl)-1,2,3,4-tetrahydro-6-hydroxy-2-naphthalene obtained in first stage of Example 45, 0.08 g (0.28 mmol) of 4-((R)-1-methylheptyloxycarbonyl)benzoic acid and 10 ml of a dichloromethane solution containing 2 mg (0.02 mmol) of dimethylaminopyridine as a reaction accelerator was dropwise added 5 ml of a dichloromethane solution containing 0.06 g (0.28 mmol) of dicyclohexylcarbodiimide with stirring at room temperature over a period of 4 hours.

Then, the reaction was further carried out overnight at room temperature. The reaction mixture was diluted with hexane and the deposited urea compound was removed. The resultant filtrate was concentrated to obtain a residue. The residue was purified by column chromatography (SiO₂/hexane-dichloromethane/1-1) to obtain 0.14 g of 6-[4-((R)-1-methylheptyloxycarbonyl)benzoyloxy]-1,2,3,4-tetrahydro-2-naphthalenecarboxylic acid 4-decyloxyphenyl ester as a semisolid (isolated yield: 97%).

This semisolid compound had an M/e value in FD-mass spectrum of 684.

A $^1$H-NMR spectrum of this compound is shown in FIG. 38.

From these analytical results, this compound was identified as 6-[4-((R)-1-methylheptyloxycarbonyl)benzoyloxy]-1,2,3,4-tetrahydro-2-naphthalenecarboxylic acid 4-decyloxyphenyl ester [Compound (162)] as desired.

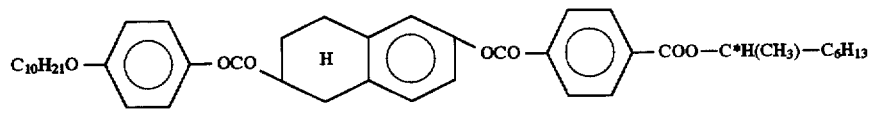

[162]

First Stage

To a mixture of 1.021 g (4 mmol) of the 4-benzyloxycarbonylbenzoic acid synthesized in the third stage of Example 45, 0.52 g (4 mmol) of (R)-2-octanol, and 40 ml of a dichloromethane solution cotaining 49 mg (0.4 mmol) of dimethylaminopyridine as a reaction accelerator was dropwise added 24 ml of a dichloromethane solution containing 0.99 g (4.8 mmol) of dicyclohexylcarbodiimide with stirring at room temperature over a period of 4 hours.

EXAMPLE 47

Synthesis of 6-[4-(4-dodecylphenyl) cyclohexylcarbonyloxy]-1,2,3,4-tetrahydro-2-naphthalenecarboxylic acid (R)-1-trifluoromethylheptyl ester [Compound (365)]

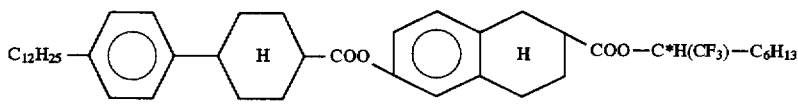

[365]

First Stage

To a mixture of 0.37 g (1 mmol) of 4-(4-dodecylphenyl)cyclohexanecarboxylic acid obtained in the same manner as in the first stage of Example 41, 0.36 g (1 mmol) of the 1,2,3,4-tetrahydro-6-hydroxy-2-naphthalenecarboxylic acid (R)-1-trifluoromethylheptyl ester obtained in the fifth stage of Example 23, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 19 hours. The reaction mixture was filtered, and the filtrate was concentrated. The concentrate obtained was separated by column chromatography to obtain 0.56 g of a colorless semisolid.

This semisolid compound had an M/e value in FD-mass spectrum of 712.

A $^1$H-NMR spectrum of this compound is shown in FIG. 39.

From these analytical results, this compound was identified as 6-[4-(4-dodecylphenyl)cyclohexylcarbonyloxy]-1,2,3,4-tetrahydro-2-naphthalenecarboxylic acid (R)-1-trifluoromethylheptyl ester [Compound (365)] as desired.

EXAMPLE 48

Synthesis of 6-[(4'-octyloxy-4-biphenyl)carbonyloxy]-1,2,3,4-tetrahydro-2-naphthalenecarboxylic acid (R)-1-trifluoromethylheptyl ester [Compound (249)]

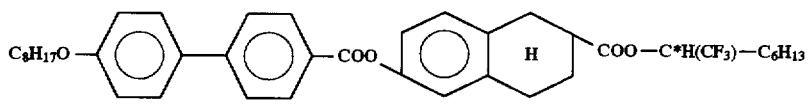

[249]

First Stage

To a mixture of 0.36 g (1.1 mmol) of 4'-octyloxy-4-biphenylcarboxylic acid obtained in the same manner as in the first stage of Example 11, 0.39 g (1.1 mmol) of the 1,2,3,4-tetrahydro-6-hydroxy-2-naphthalenecarboxylic acid (R)-1-trifluoromethylheptyl ester obtained in the fifth stage of Example 23, 0.013 g (0.11 mmol) of 4-N,N-dimethylaminopyridine and 10 ml of methylene chloride was dropwise added 5 ml of a methylene chloride solution containing 0.27 g (1.3 mmol) of N,N'-dicyclohexylcarbodiimide with stirring at room temperature over a period of 2 hours.

Then, the reaction was further carried out at room temperature for 48 hours. The reaction mixture was filtered, and the filtrate was concentrated. The concentrate obtained was separated by column chromatography to obtain 0.58 g of a semisolid.

This semisolid compound had an M/e value in FD-mass spectrum of 666.

A $^1$H-NMR spectrum of this compound is shown in FIG. 40.

From these analytical results, this compound was identified as 6-[(4'-octyloxy-4-biphenyl)carbonyloxy]-1,2,3,4-tetrahydro-2-naphthalenecarboxylic acid (R)-1-trifluoromethylheptyl ester [Compound (249)] as desired.

EXAMPLE 49

Synthesis of 6-[(4'-nonyloxy-4-biphenyl)carbonyloxy]-1,2,3,4-tetrahydro-2-naphthalenecarboxylic acid (R)-1-trifluoromethylheptyl ester [Compound (250)]

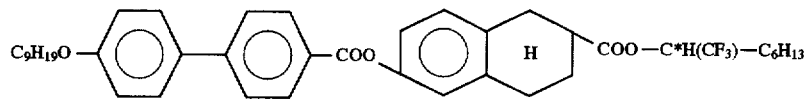

[250]

First Stage

To a mixture of 0.34 g (1 mmol) of 4'-nonyloxy-4-biphenylcarboxylic acid obtained in the same manner as in the first stage of Example 11, 0.36 g (1 mmol) of 1,2,3,4-tetrahydro-6-hydroxy-2-naphthalenecarboxylic acid (R)-1-trifluoromethylheptyl ester obtained in the fifth stage of Example 23, 0.02 g (0.1 mmol) of 4-N,N-dimethylaminopyridine and 10 ml of methylene chloride was dropwise added 5 ml of a methylene chloride solution containing 0.27 g (1.3 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.46 g of a colorless semisolid.

This semisolid compound had an M/e value in FD-mass spectrum of 680.

A $^1$H-NMR spectrum of this compound is shown in FIG. 41.

From these analytical results, this compound was identified as 6-[(4'-nonyloxy-4-biphenyl)carbonyloxy]-1,2,3,4-tetrahydro-2-naphthalenecarboxylic acid (R)-1-trifluoromethylheptyl ester [Compound (250)] as desired.

EXAMPLE 50

Synthesis of 6-[(4'-tetradecyloxy-4-biphenyl)carbonyloxy]-1,2,3,4-tetrahydro-2-naphthalenecarboxylic acid (R)-1-trifluoromethylheptyl ester [Compound (254)]

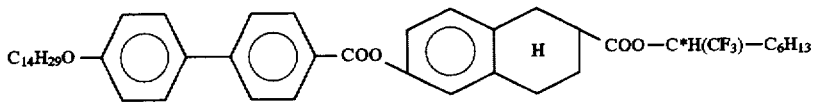

[254]

First Stage

To a mixture of 0.41 g (1 mmol) of 4'-tetradecyloxy-4-biphenylcarboxylic acid obtained in the same manner as in the first stage of Example 11, 0.36 g (1 mmol) of 1,2,3,4-tetrahydro-6-hydroxy-2-naphthalenecarboxylic acid (R)-1-trifluoromethylheptyl ester obtained in the fifth stage of Example 23, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours. The reaction mixture was filtered. The resultant filtrate was concentrated. The concentrate obtained was separated by column chromatography to obtain 0.47 g of a colorless semisolid.

This semisolid compound had an M/e value in FD-mass spectrum of 750.

A $^1$H-NMR spectrum of this compound is shown in FIG. 42.

From these analytical results, this compound was identified as 6-[(4'-tetradecyloxy-4-biphenyl)carbonyloxy]-1,2,3,4-tetrahydro-2-naphthalenecarboxylic acid (R)-1-trifluoromethylheptyl ester [Compound (254)] as desired.

EXAMPLE 51

Synthesis of 6-[(4'-nonyl-4-biphenyl)carbonyloxy]-1,2,3,4-tetrahydro-2-naphthalenecarboxylic acid (R)-1-trifluoromethylheptyl ester [Compound (354)]

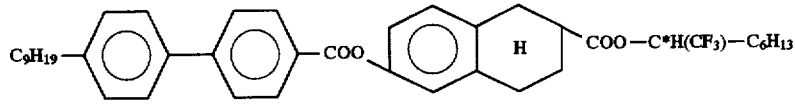

[354]

First Stage

To a mixture of 0.36 g (1.1 mmol) of 4'-nonyl-4-biphenylcarboxylic acid (manufactured by Teikoku Kagaku Sangyo, K.K.), 0.39 g (1.1 mmol) of the 1,2,3,4-tetrahydro-6-hydroxy-2-naphthalenecarboxylic acid (R)-1-trifluoromethylheptyl ester obtained in the fifth stage of Example 23, 0.013 g (0.11 mmol) of 4-N,N-dimethylaminopyridine and 10 ml of methylene chloride was dropwise added 5 ml of a methylene chloride solution containing 0.27 g (1.3 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.64 g of a colorless semisolid.

This semisolid compound had an M/e value in FD-mass spectrum of 664.

A $^1$H-NMR spectrum of this compound is shown in FIG. 43.

From these analytical results, this compound was identified as 6-[(4'-nonyl-4-biphenyl)carbonyloxy]-1,2,3,4-tetrahydro-2-naphthalenecarboxylic acid (R)-1-trifluoromethylheptyl ester [Compound (354)] as desired.

EXAMPLE 52

Synthesis of 6-[(4'-undecyl-4-biphenyl)carbonyloxy]-1,2,3,4-tetrahydro-2-naphthalenecarboxylic acid (R)-1-trifluoromethylheptyl ester [Compound (356)]

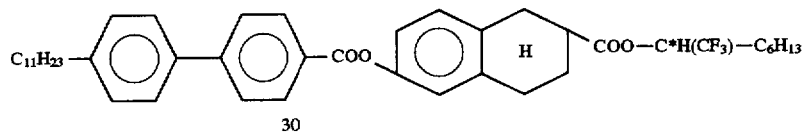

[356]

First Stage

To a mixture of 0.35 g (1 mmol) of 4'-undecyl-4-biphenylcarboxylic acid (manufactured by Teikoku Kagaku Sangyo, K.K.), 0.36 g (1 mmol) of the 1,2,3,4-tetrahydro-6-hydroxy-2-naphthalenecarboxylic acid (R)-1-trifluoromethylheptyl ester obtained in the fifth stage of Example 23, 0.02 g (0.1 mmol) of 4-N,N-dimethylaminopyridine and 10 ml of methylene chloride was dropwise added 5 ml of a methylene chloride solution containing 0.27 g (1.3 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.56 g of a colorless semisolid.

This semisolid compound had an M/e value in FD-mass spectrum of 692.

A $^1$H-NMR spectrum of this compound is shown in FIG. 44.

From these analytical results, this compound was identified as 6-[(4'-undecyl-4-biphenyl)carbonyloxy]-1,2,3,4-tetrahydro-2-naphthalenecarboxylic acid (R)-1-trifluoromethylheptyl ester [Compound (356)] as desired.

EXAMPLE 53

Synthesis of 6-[(4'-tetradecyl-4-biphenyl)carbonyloxy]-1,2,3,4-tetrahydro-2-naphthalenecarboxylic acid (R)-1-trifluoromethylheptyl ester [Compound (358)]

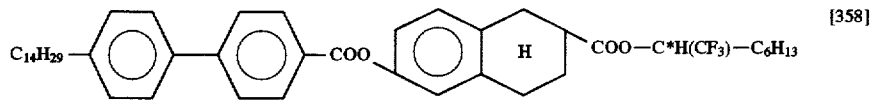

[358]

First Stage

To a mixture of 0.38 g (1 mmol) of 4'-tetradecyl-4-biphenylcarboxylic acid (manufactured by Teikoku Kagaku Sangyo, K.K.), 0.36 g (1 mmol) of the 1,2,3,4-tetrahydro-6-hydroxy-2-naphthalenecarboxylic acid (R)-1-trifluoromethylheptyl ester obtained in the fifth stage of Example 23, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.43 g of a colorless semisolid.

This semisolid compound had an M/e value in FD-mass spectrum of 734.

A $^1$H-NMR spectrum of this compound is shown in FIG. 45.

From these analytical results, this compound was identified as 6-[(4'-tetradecyl-4-biphenyl)carbonyloxy]-1,2,3,4-tetrahydro-2-naphthalenecarboxylic acid (R)-1-trifluoromethylheptyl ester [Compound (358)] as desired.

EXAMPLE 54

Synthesis of 6-[(4'-decyloxy-4-biphenyl)carbonyloxy]-1,2,3,4-tetrahydro-2-naphthalenecarboxylic acid (R)-1-trifluoromethylnonyl ester [Compound (371)]

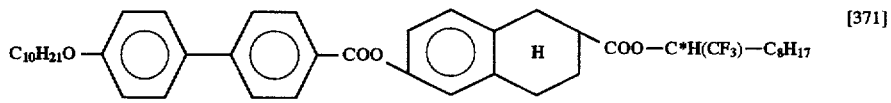

[371]

First Stage

To a mixture of 0.35 g (1 mmol) of the 4'-decyloxy-4-biphenylcarboxylic acid obtained in the first stage of Example 11, 0.39 g (1 mmol) of the 1,2,3,4-tetrahydro-6-hydroxy-2-naphthalenecarboxylic acid (R)-1-trifluoromethylnonyl ester obtained in the some manner as in the fourth stage of Example 23 except for using (R)-1-trifluoromethylnonanol in place of (R)-1-trifluoromethylheptanol, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.62 g of a colorless semisolid.

This semisolid compound had an M/e value in FD-mass spectrum of 722.

A $^1$H-NMR spectrum of this compound is shown in FIG. 46.

From these analytical results, this compound was identified as 6-[(4'-decyloxy-4-biphenyl)carbonyloxy]-1,2,3,4-tetrahydro-2-naphthalenecarboxylic acid (R)-1-trifluoromethylnonyl ester [Compound (371)] as desired.

EXAMPLE 55

Synthesis of 6-[(4'-decyloxy-4-biphenyl)carbonyloxy]-1,2,3,4-tetrahydro-2-naphthalenecarboxylic acid (R)-1-methylheptyl ester [Compound (467)]

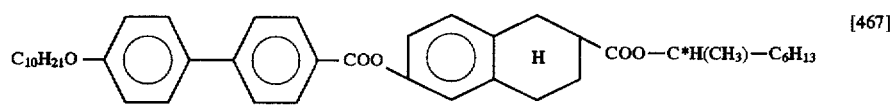

[467]

First Stage

To a mixture of the 0.35 g (1 mmol) of 4'-decyloxy-4-biphenylcarboxylic acid obtained in the first stage of Example 11, 0.30 g (1 mmol) of 1,2,3,4-tetrahydro-6-hydroxy- 2-naphthalenecarboxylic acid (R)-1-methylheptyl ester obtained in the same manner as in the fourth stage of Example 23 except for using (R)-1-methylheptanol in place of (R)-1-trifluoromethylheptanol, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.40 g of a colorless semisolid.

This semisolid compound had an M/e value in FD-mass spectrum of 641.

A ¹H-NMR spectrum of this compound is shown in FIG. 47.

From these analytical results, this compound was identified as 6-[(4'-decyloxy-4-biphenyl)carbonyloxy]-1,2,3,4-tetrahydro-2-naphthalenecarboxylic acid (R)-1-methylheptyl ester [Compound (467)] as desired.

EXAMPLE 56

Synthesis of 6-[(4'-decyloxy-4-biphenyl)carbonyloxy]-1,2,3,4-tetrahydro-2-naphthalenecarboxylic acid (R)-1-(trifluoromethyl)- 2-(ethoxycarbonyl)ethyl ester [Compound (483)]

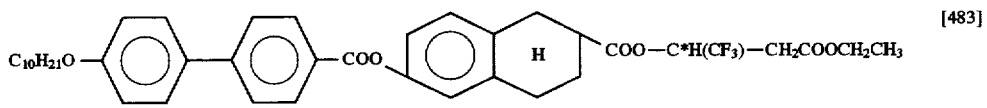

First Stage

To a mixture of 0.35 g (1 mmol) of the 4'-decyloxy-4-biphenylcarboxylic acid obtained in the first stage of Example 11, 0.36 g (1 mmol) of 1,2,3,4-tetrahydro-6-hydroxy-2-naphthalenecarboxylic acid (R)-1-(trifluoromethyl)-2-(ethoxycarbonyl)ethyl ester obtained in the same manner as in the fourth stage of Example 23 except for using (R)-1-trifluoromethyl-2-ethoxycarbonylethanol in place of (R)-1-trifluoromethylheptanol, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.51 g of a colorless semisolid.

This semisolid compound had an M/e value in FD-mass spectrum of 696.

A ¹H-NMR spectrum of this compound is shown in FIG. 48.

From these analytical results, this compound was identified as 6-[(4'-decyloxy-4-biphenyl)carbonyloxy]-1,2,3,4-tetrahydro-2-naphthalenecarboxylic acid (R)-1-(trifluoromethyl)-2-(ethoxycarbonyl)ethyl ester [Compound (483)] as desired.

EXAMPLE 57

Synthesis of 6-[(4'-decyl-4-biphenyl)carbonyloxy]-1,2,3,4-tetrahydro-2-naphthalenecarboxylic acid (R)-1-(trifluoromethyl)-2-(ethoxycarbonyl)ethyl ester [Compound (491)]

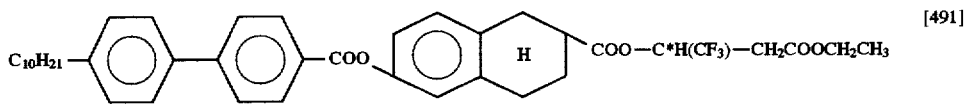

First Stage

To a mixture of 0.34 g (1 mmol) of 4'-decyl-4-biphenyl carboxylic acid (manufactured by Teikoku Kagaku Sangyo, K.K.), 0.36 g (1 mmol) of 1,2,3,4-tetrahydro-6-hydroxy-2-naphthalene-carboxylic acid (R)-1-(trifluoromethyl)-2-(ethoxycarbonyl) ethyl ester obtained in the same manner as in the fourth stage of Example 23 except for using (R)-1-trifluoromethyl-2-ethoxycarbonylethanol in place of (R)-1-trifluoromethylheptanol, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.52 g of a colorless semisolid.

This semisolid compound had an M/e value in FD-mass spectrum of 680.

A ¹H-NMR spectrum of this compound is shown in FIG. 49.

From these analytical results, this compound was identified as 6-[(4'-decyl-4-biphenyl)carbonyloxy]-1,2,3,4-tetrahydro-2-naphthalenecarboxylic acid (R)-1-(trifluoromethyl)-2-(ethoxycarbonyl)ethyl ester [Compound (491)] as desired.

EXAMPLE 58

Synthesis of 6-[(4'-decyloxy-4-biphenyl)methoxy]-1,2,3,4-tetrahydro-2-naphthalenecarboxylic acid (R)-1-trifluoromethylheptyl ester [Compound (419)]

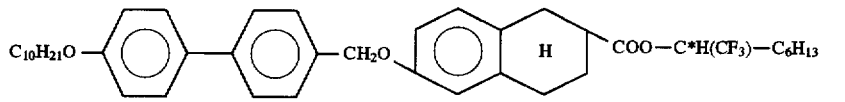
[419]

First Stage 0.81 g (21.34 mmol) of LiAlH$_4$ was introduced into 40 ml of diethyl ether and stirred. To the mixture was dropwise added a solution, prepared by introducing 1.71 g (5.06 mmol) of 4'-decyloxy-4-biphenylcarboxylic acid obtained in the first stage of Example 11 into 30 ml of diethyl ether, at room temperature over a period of 2 to 3 minutes, which was then continuously stirred for 5 days. After confirming the consumption of the raw material by TLC, to the resultant mixture was added 40 ml of water, and further added concentrated hydrochloric acid until the aqueous phase was approximately homogenized. The resultant solution was extracted with diethyl ether and dried, to obtain 4-hydroxymethyl-4'-decyloxybiphenyl.

Second Stage

To 0.81 g (2.51 mmol) of 4-hydroxymethyl-4'-decyloxybiphenyl was added 15 ml of an aqueous solution containing 47% HBr, and then heated at 115° C. for 3 hours. After completion of the reaction, the resultant mixture was extracted with ether and washed with water, which was further washed with an aqueous solution containing saturated NaHCO$_3$ and washed again with water. The reaction product was concentrated and, then, separated by colomun chromatography, to thereby obtain 0.92 g of 4'-bromomethyl-4-decyloxybiphenyl.

Third Stage

A mixture of 0.57 g (1 mmol) of the 4'-bromomethyl-4-decyloxybiphenyl obtained in the second stage, 0.36 g (1 mmol) of the 1,2,3,4-tetrahydro-6-hydroxy-2-naphthalenecarboxylic acid (R)-1-trifluoromethylheptyl ester obtained in the fifth stage of Example 23, 0.30 g (2.17 mmol) of K$_2$CO$_3$ and 10 ml of DMF was allowed to undergo reaction with stirring at 120° C. for 2 hours.

The reaction mixture was filtered, and to the filtrate was added 300 ml of water and the resulting mixture was extracted with diethyl ether. The resultant oil phase was concentrated. The concentrate obtained was separated by coloumn chromatography to obtain 0.41 g of a colorless semisolid.

This semisolid compound had an M/e value in FD-mass spectrum of 680.

A $^1$H-NMR spectrum of this compound is shown in FIG. 50.

From these analytical results, this compound was identified as 6-[(4'-decyloxy-4-biphenyl)methoxy]-1,2,3,4-tetrahydro-2-naphthalenecarboxylic acid (R)-1-trifluoromethylheptyl ester [Compound (419)] as desired.

EXAMPLE 59

Synthesis of 6-[(4'-dodecyloxy-4-biphenyl)methoxy]-1,2,3,4-tetrahydro-2-naphthalenecarboxylic acid (R)-1-trifluoromethylheptyl ester [Compound (421)]

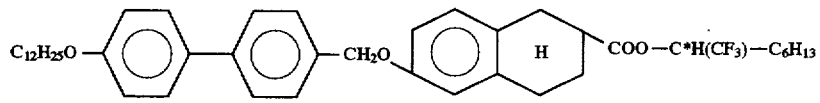
[421]

First Stage

A mixture of 0.46 g (1 mmol) of 4'-bromomethyl-4-dodecyloxybiphenyl obtained in the same manner as in the second stage of Example 58, 0.38 g (1 mmol) of the 1,2,3,4-tetrahydro-6-hydroxy-2-naphthalenecarboxylic acid (R)-1-trifluoromethylheptyl ester obtained in the fifth stage of Example 23, 0.21 g (1.5 mmol) of K$_2$CO$_3$ and 10 ml of DMF was allowed to undergo reaction with stirring at 110° C. over a period of 2 hours.

To the reaction mixture was added 50 ml of water, and then the resulting mixture was extracted with total amount of 150 ml of methylene chloride, which was then washed with water and concentrated. The concentrate obtained was separated by column chromatography to obtain 0.36 g of a colorless semisolid.

This semisolid compound had an M/e value in FD-mass spectrum of 708.

A $^1$H-NMR spectrum of this compound is shown in FIG. 51.

From these analytical results, this compound was identified as 6-[(4'-dodecyloxy-4-biphenyl)methoxy]-1,2,3,4-tetrahydro-2-naphthalenecarboxylic acid (R)-1-trifluoromethylheptyl ester [Compound (421)] as desired.

EXAMPLE 60

Synthesis of 6-[(4'-decyl-4-biphenyl)methoxy]-1,2,3,4-tetrahydro-2-naphthalenecarboxylic acid (R)-1-trifluoromethylheptyl ester [Compound (427)]

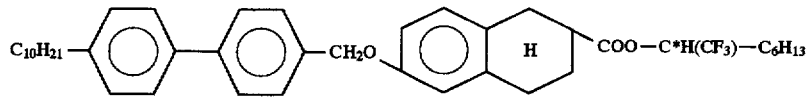
[427]

First Stage

A mixture of 0.53 g (1.37 mmol) of 4'-bromomethyl-4-decylbiphenyl obtained in the same manner as in the second stage of Example 58, 0.36 g (1 mmol) of the 1,2,3,4-tetrahydro-6-hydroxy-2-naphthalenecarboxylic acid (R)-1-trifluoromethylheptyl ester obtained in the fifth stage of Example 23, 0.3 g (2.17 mmol) of K$_2$CO$_3$ and 10 ml of DMF was allowed to undergo reaction with stirring at 90° C. over a period of 6 hours.

The reaction mixture was filtered, and the filtrate was concentrated. The concentrate obtained was separated by column chromatography to obtain 0.25 g of a colorless semisolid.

This semisolid compound had an M/e value in FD-mass spectrum of 664.

A $^1$H-NMR spectrum of this compound is shown in FIG. 52.

From these analytical results, this compound was identified as 6-[(4'-decyl-4-biphenyl)methoxy]-1,2,3,4-tetrahydro-2-naphthalenecarboxylic acid (R)-1-trifluoromethylheptyl ester [Compound (427)] as desired.

EXAMPLE 61

Synthesis of 6-[(4'-dodecyl-4-biphenyl)methoxy]-1,2,3,4-tetrahydro-2-naphthalenecarboxylic acid (R)-1-trifluoromethylheptyl ester [Compound (429)]

A $^1$H-NMR spectrum of this compound is shown in FIG. 53.

From these analytical results, this compound was identified as 6-[(4'-dodecyl-4-biphenyl)methoxy]-1,2,3,4-tetrahydro-2-naphthalenecarboxylic acid (R)-1-trifluoromethylheptyl ester [Compound (429)] as desired.

EXAMPLE 62

Synthesis of 6-[(4-dodecyloxy-4-biphenyl)methoxy]-1,2,3,4-tetrahydro-2-naphthalenecarboxylic acid (R)-1-trifluoromethylheptyl ester [Compound (437)]

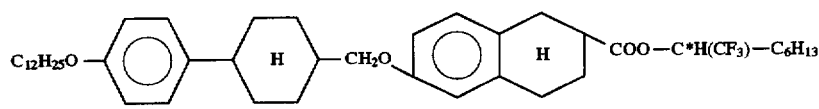

[437]

First Stage

A mixture of 0.51 g (1 mmol) of 4'-bromomethyl-4-dodecyloxyphenylcyclohexane obtained in the same manner as in the second stage of Example 58, 0.36 g (1 mmol) of the 1,2,3,4-tetrahydro-6-hydroxy-2-naphthalenecarboxylic acid (R)-1-trifluoromethylheptyl ester obtained in the fifth stage of Example 23, 0.21 g (1.5 mmol) of K$_2$CO$_3$ and 10 ml of DMF was allowed to undergo reaction with stirring at 110° C. over a period of 4 hours.

To the reaction mixture was added 30 ml of water, and then the resulting mixture was extracted with diethyl ether. The resultant oil phase was concentrated. The concentrate obtained was separated by column chromatography to obtain 0.18 g of a colorless semisolid.

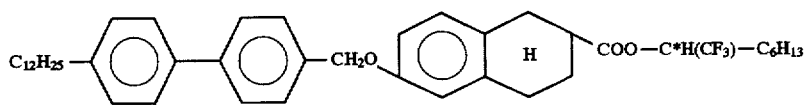

[429]

First Stage

A mixture of 0.46 g (1 mmol) of 4'-bromomethyl-4-dodecylbiphenyl obtained in the same manner as in the second stage of Example 58, 0.37 g (1 mmol) of the 1,2,3,4-tetrahydro-6-hydroxy-2-naphthalenecarboxylic acid (R)-1-trifluoromethylheptyl ester obtained in the fifth stage of Example 23, 0.15 g (1.1 mmol) of K$_2$CO$_3$ and 10 ml of DMF was allowed to undergo reaction with stirring at 110° C. over a period of 10 hours.

To the reaction mixture was added 10 ml of water, and then extracted with total amount of 200 ml of ethyl acetate. The resultant oil phase was concentrated. The concentrate obtained was separated by column chromatography to obtain 0.14 g of a colorless semisolid.

This semisolid compound had an M/e value in FD-mass spectrum of 692.

This semisolid compound had an M/e value in FD-mass spectrum of 714.

A $^1$H-NMR spectrum of this compound is shown in FIG. 54.

From these analytical results, this compound was identified as 6-[(4'-dodecyloxy-4-biphenyl)methoxy]-1,2,3,4-tetrahydro-2-naphthalenecarboxylic acid (R)-1-trifluoromethylheptyl ester [Compound (437)] as desired.

EXAMPLE 63

Synthesis of 6-[2-(4'-decyloxy-4-biphenyl)ethyl]-1,2,3,4-tetrahydro-2-naphthalenecarboxylic acid (R)-1-trifluoromethylheptyl ester [Compound (451)]

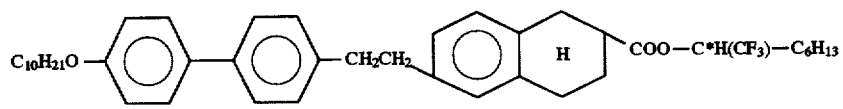

[451]

First Stage

A mixture of 6.60 g (18.6 mmol) of 4'-decyloxy-4-biphenylcarbocylic acid obtained in the first stage of Example 11, 10 ml of 36% hydrochloric acid and 350 ml of ethanol was heated under reflux for 8 hours in a nitrogen atmosphere. After cooling to room temperature, the deposited preciptate was filtered to obtain a white solid. The resultant filtrate was concentrated and the deposited precipitate was filtered. The filtrated precipitate was combined with the above white solid, which was then washed with water and dried, to obtain 6.10 g (16 mmol) of 4'-decyloxy-4-biphenylcarbocylic acid ethyl ester.

Second Stage

Litium aluminum hydride was suspended at 0° C. in a nitrogen atmospere in 200 ml of ethylether which was treated by dry distillation on sodium wire. To the resultant suspention was added a suspension of 6.10 g (16 mmol) of the 4'-decyloxy-4-biphenylcarboxylic acid ethyl ester obtained in the first stage in 200 ml of drying ethyl ether over a period of 15 minutes. Then, the temperature of the mixture was elevated to room temperature. After stirring at room temperature for 16 hours, the temperature was further elevated to the reflux temperature to continue the stirring for 1 hour. To the reaction mixture was added 100 ml of water while giving attention to the generating hydrogen.

Then, the thus produced aluminum hydroxide was dissolved by the addition of 36% hydrochloric acid. The aquious phase was separated, and then extracted with ether.

The resultant ether solution was combined with the above separated organic phase, and concentrated together and dried to obtain 5.61 g of a crude 4'-decyloxy-4-hydroxymetylbiphenyl.

Third Stage

A mixture of 5.61 g of the crude 4'-decyloxy-4-hydroxymetylbiphenyl obtained in the second stage and 150 ml of 48% hydrobromic acid was allowed to undergo reaction at reflux temperatuere for 1.5 hours in a nitrogen atmosphere. After cooling to room temperature, the deposited solid was filtered and separated by column chromatography to obtain 6.00 g (15 mmol) of 4'-decyloxy-4-bromomethylbiphenyl.

Fourth Stage

A mixture of 2.83 g (7 mmol) of 4'-decyloxy-4-bromomethylbiphenyl obtained in the third stage, 1.86 g (7 mmol) of triphenylphosphine and 30 ml of toluene was heated under reflux at reflux temperature for 7 hours. After cooling to room temperatrue, the deposited white solid was filtered and dried to obtain 2.05 g of (4'-decyloxy-4-biphenylmethyl)triphenylphosphoniumbromide.

Fifth Stage

To a mixture of 9.29 g (14 mmol) of (4'-decyloxy-4-biphenylmethyl)triphenylphosphoniumbromide obtained in the fourth stage, 2.89 g (13.5 mmol) of 6-formyl-2-naphthalenecarboxylic acid methyl ester and 130 ml of methylene chloride was dropwise added 5 ml of an aquious solution containing 1.0 g (15 mmol) of 85% potassium hydroxide with stirring at room temperature over a period of 20 minutes.

Then, the reaction was further carried out at room temperature for 15 hours.

The reaction mixture was filtered, and the filtrate was concentrated. The concentrate obtained was subjected to column chromatography for sparating and removing a high polar component to obtain 4.37 g of a light yellow solid.

Then, hydrogen was blown into a mixture of 4.37 g of the above-obtained light yellow solid, 2.0 g of 5% palladium/carbon and 50 ml of a tetrahydrofuran with stirring at room temperature and normal pressure for 6 hours. The reaction mixture was filtered using Celite as a filter aid, and the filtrate was concentrated to dryness. The thus obtained solid was recrystallized from tetrahydrofuran to obtain 2.35 g of 6-[2-(4'-decyloxy-4-bipheny)ethyl]-2-naphthalenecarboxylic acid methyl ester.

Sixth Stage

A mixture of 2.35 g (4.5 mmol) of 6-[2-(4'-decyloxy-4-bipheny)ethyl]-2-naphthalenecarboxylic acid methyl ester, 0.66 g (10 mmol) of 85%, potassium hydroxide, 100 ml of ethanol and 20 ml of water was allowed to undergo reaction at reflux temperature for 6.5 hours in a nitrogen atmosphere.

After cooling to room temperature, the deposited solid was filtered. The thus obtaiend solid, 100 ml of tetrahydrofuran and 36% hydrochloric acid were allowed to undergo reaction at reflux temperature for 6.5 hours. After cooling to room temperature, the reaction mixture was concentrated, and then 150 ml of water was added thereto. The deposited solid was filtered and dried to obtain 1.83 g (3.6 mmol) of 6-[2-(4'-decyloxy-4-bipheny)ethyl]-2-naphthalenecarboxylic acid as a white solid.

Seventh Stage 1.52 g (3.0 mmol) of 6-[2-(4'-decyloxy-4-bipheny)ethyl]-2-naphthalenecarboxylic acid obtained in the sixth stage and 0.90 g of metallic sodium were dissolved in 60 ml of 1,2-diethoxyethane to conduct reflux at 150° C. for 2 hours. Then, to the resultant mixture was dropwise added 2 ml of i-AmOH over a period of 3 hours, and further added 0.49 g of metallic sodium in addition to more 5.5 ml of the i-AmOH. The reflux of the resultant mixture was continued at 150° C. for 2 days.

After completion of the reaction, water was added to the reaction mixtuer, homogenized, and neutrallized with hydrochlorid acid. The deposited white preciptate was extracted with THF to obtain 0.81 g of 6-[2-(4'-decyloxy-4-bipheny)ethyl]-1,2,3,4-tetrahydro-2-naphthalenecarboxylic acid as desired.

Eighth Stage

To a mixture of 0.51 g (1 mmol) of 6-[2-(4'-decyloxy-4-bipheny)ethyl]-1,2,3,4-tetrahydro-2-naphthalenecarboxylic acid, 0.18 g (1 mmol) of (R)-1-trifluoromethylheptanol, 0.012 g (0.1 mmol) of 4-N,N'-dimethylaminopyridine and 15 ml of methylene chloride was dropwise added 3 ml of a methylene chloride solution containing 0.25 g (1.2 mmol) of N,N'-dicyclohexylcarbodiimide with stirring at room temperature for a period of 2 hours.

Then, the reaction was further carried out at room temperature for 18 hours.

The reaction mixture was filtered, and the filtrate was concentrated. The concentrate obtained was separated by column chromatography to obtain 0.23 g of a colorless semisolid. This semisolid compound had an M/e value in FD-mass spectrum of 678. $^1$H-NMR spectrum of this compound is shown in FIG. 55.

From these analytical results, this compound was identified as 6-[2-(4'-decyloxy-4-biphenyl)ethyl]-1,2,3,4-tetrahydro-2-naphthalenecarboxylic acid (R)-1-trifluoromethylheptyl ester [Compound (451)] as desired.

EXAMPLE 64

Synthesis of 6-[(4-(5-decyl-2-pyrimidinyl)phenylmethoxy]-1,2,3,4-tetrahydro-2-naphthalenecarboxylic acid (R)-1-trifluoromethylheptyl ester [Compound (507)]

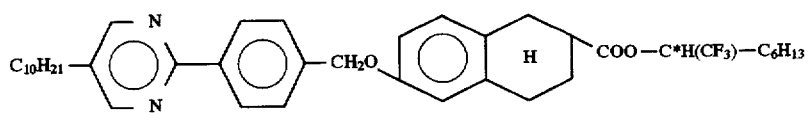

[507]

First Stage

A mixture of 0.35 g (0.9 mmol) of 2-(4-bromomethylphenyl)-5-decylpyrimidine obtained in the same manner as in the second stage of Example 58, 0.29 g (0.81 mmol) of the 1,2,3,4-tetrahydro-6-hydroxy-2-naphthalenecarboxylic acid (R)-1-trifluoromethylheptyl ester obtained in the fifth stage of Example 23, 0.24 g (1.74 mmol) of $K_2CO_3$ and 10 ml of DMF was allowed to undergo reaction with stirring at 80° C. over a period of 1.5 hours.

After cooling to room temperature, the reaction mixture was hydrorized, and then extracted with diethyl ether. The oil phase was concentrated. The concentrate obtained was separated by column chromatography to obtain 0.29 g of a colorless semisolid.

This semisolid compound had an M/e value in FD-mass spectrum of 666.

A $^1$H-NMR spectrum of this compound is shown in FIG. 56.

From these analytical results, this compound was identified as 6-[(4-(5-decyl-2-pyrimidinyl)phenylmethoxy]-1,2,3,4-tetrahydro-2-naphthalenecarboxylic acid (R)-1-trifluoromethylheptyl ester [Compound (507)] as desired.

EXAMPLE 65

Synthesis of 6-[4-(5-octyloxy-2-pyrimidinyl)benzoyloxy]-1,2,3,4-tetrahydro-2-naphthalenecarboxylic acid (R)-1-trifluoromethylheptyl ester [Compound (313)]

g (0.27 mmol) of the 1,2,3,4-tetrahydro-6-hydroxy-2-naphthalenecarboxylic acid (R)-1-trifluoromethylheptyl ester obtained in fifth stage of Example 23, 0.02 g (0.1 mmol) of 4-N,N-dimethylaminopyridine and 10 ml of methylene chloride was dropwise added 5 ml of a methylene chloride solution containing 0.07 g (0.34 mmol) of N,N'-dicyclohexylcarbodiimide with stirring at room temperature for a period of 2 hours.

Then, the reaction was further carried out at room temperature for 48 hours.

The reaction mixture was filtered, and the filtrate was concentrated. The concentrate obtained was separated by column chromatography to obtain 0.11 g of a colorless semisolid.

This semisolid compound had an M/e value in FD-mass spectrum of 668.

A $^1$H-NMR spectrum of this compound is shown in FIG. 57.

From these analytical results, this compound was identified as 6-[4-(5-octyloxy-2-pyrimidinyl)benzoyloxy]-1,2,3,4-tetrahydro-2-naphthalenecarboxylic acid (R)-1-trifluoromethylheptyl ester [Compound (313)] as desired.

EXAMPLE 66

Synthesis of 6-[(4'-decyloxy-4-biphenyl)carbonyloxy]-1,2,3,4-tetrahydro-2-naphthalenecarboxylic acid (R)-1-trifluoromethylhexyl ester [Compound (387)]

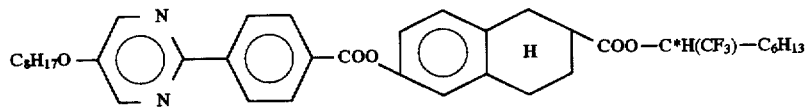

[313]

First Stage

To 20 ml of absolute ethanol was added 0.06 g (2.6 mg atom) of metallic sodium to prepare a sodium alkoxide. To

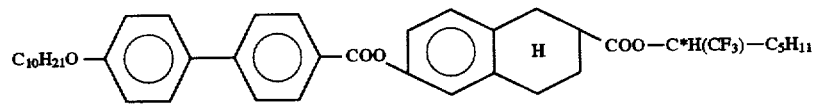

[387]

the mixture was added 0.37 g (2.0 mmol) of 4-amidinophenylcarboxylic acid ethyl ester and stirred, and further added 0.46 g (2.0 mmol) of α-octyloxy-β-dimethylaminoacrolein, and the mixture was heated at 95° C. for 4 hours. To the resultant mixture was added 4 ml of water and further heated at 95° C. for 2 hours. After completion of the reaction, to the reaction mixture was added 400 ml of water and, then, the resulting mixture was neutrallized with concentrated hydrochlorid acid. The deposit was filtered, which was then separated and purified by column chromatography to obtain 0.1 g of 4-(5-octyloxy-2-pyrimidinyl)benzoic acid as desired.

Second Stage

To a mixture of 0.09 g (0.27 mmol) of the 4-(5-octyloxy-2-pyrimidinyl)benzoic acid obtained in the first stage, 0.12

First Stage

To a mixture of 0.36 g (1 mmol) of 4'-decyloxy-4-biphenylcarboxylic acid obtained in the same manner as in the first stage of Example 11, 0.35 g (1 mmol) of 1,2,3,4-tetrahydro-6-hydroxy-2-naphthalenecarboxylic acid (R)-1-trifluoromethylhexyl ester obtained in the same manner as in the fourth stage of Example 23 except for using (R)-1-trifluoromethylhexanol in place of (R)-1-trifluoromethylheptanol, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.52 g of a colorless semisolid.

This semisolid compound had an M/e value in FD-mass spectrum of 680.

A $^1$H-NMR spectrum of this compound is shown in FIG. 58.

From these analytical results, this compound was identified as 6-[(4'-decyloxy-4-biphenyl)carbonyloxy]-1,2,3,4-tetrahydro-2-naphthalenecarboxylic acid (R)-1-trifluoromethylhexyl ester [Compound (387)] as desired.

EXAMPLE 67

Synthesis of 6-[(4'-undecyloxy-4-biphenyl)carbonyloxy]-1,2,3,4-tetrahydro-2-naphthalenecarboxylic acid (R)-1-trifluoromethylhexyl ester [Compound (388)]

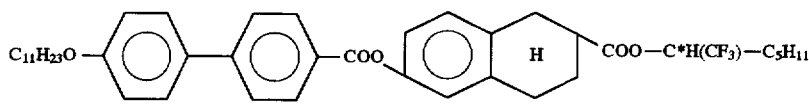

[388]

First Stage

To a mixture of 0.37 g (1 mmol) of 4'-undecyloxy-4-biphenylcarboxylic acid obtained in the same manner as in the first stage of Example 11, 0.35 g (1 mmol) of 1,2,3,4-tetrahydro-6-hydroxy-2-naphthalenecarboxylic acid (R)-1-trifluoromethylhexyl ester obtained in the same manner as in the fourth stage of Example 23 except for using (R)-1-trifluoromethylhexanol in place of (R)-1-trifluoromethylheptanol, 0.012 g (0.1 mmol) of 4-N,N-dimethylaminopyridine and 15 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated, followed by subjecting to columun chromatography to obtain 0.50 g of a colorless semisolid.

This semisolid compound had an M/e value in FD-mass spectrum of 694.

A $^1$H-NMR spectrum of this compound is shown in FIG. 59.

From these analytical results, this compound was identified as 6-[(4'-undecyloxy-4-biphenyl)carbonyloxy]-1,2,3,4-tetrahydro-2-naphthalenecarboxylic acid (R)-1-trifluoromethylhexyl ester [Compound (388)] as desired.

EXAMPLE 68

Synthesis of 6-[(4'-dodecyloxy-4-biphenyl)carbonyloxy]-1,2,3,4-tetrahydro-2-naphthalenecarboxylic acid (R)-1-trifluoromethylhexyl ester [Compound (389)]

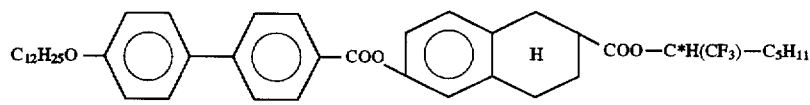

[389]

First Stage

To a mixture of 0.25 g (0.65 mmol) of 4'-dodecyloxy-4-biphenylcarboxylic acid obtained in the same manner as in the first stage of Example 11, 0.22 g (0.6 mmol) of 1,2,3,4-tetrahydro-6-hydroxy-2-naphthalenecarboxylic acid (R)-1-trifluoromethylhexyl ester obtained in the same manner as in the fourth stage of Example 23 except for using (R)-1-trifluoromethylhexanol in place of (R)-1-trifluoromethylheptanol, 0.007 g (0.06 mmol) of 4-N,N-dimethylaminopyridine and 10 ml of methylene chloride was dropwise added 5 ml of a methylene chloride solution containing 0.15 g (0.7 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.29 g of a colorless semisolid.

This semisolid compound had an M/e value in FD-mass spectrum of 708.

A $^1$H-NMR spectrum of this compound is shown in FIG. 60.

From these analytical results, this compound was identified as 6-[(4'-dodecyloxy-4-biphenyl)carbonyloxy]-1,2,3,4-tetrahydro-2-naphthalenecarboxylic acid (R)-1-trifluoromethylhexyl ester [Compound (389)] as desired.

EXAMPLE 69

Synthesis of 6-[(4'-dodecyl-4-biphenyl)carbonyloxy]-1,2,3,4-tetrahydro-2-naphthalenecarboxylic acid (R)-1-trifluoromethylhexyl ester [Compound (397)]

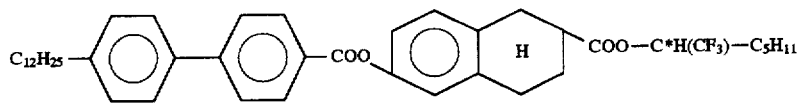

[397]

First Stage

To a mixture of 0.25 g (0.67 mmol) of 4'-dodecyl-4-biphenylcarboxylic acid (manufactured by Teikoku Kagaku Sangyo, K.K.), 0.34 g (1 mmol) of 1,2,3,4-tetrahydro-6-hydroxy-2-naphthalenecarboxylic acid (R)-1-trifluoromethylhexyl ester obtained in the fourth stage of Example 23 except for using (R)-1-trifluoromethylhexanol in place of (R)-1-trifluoromethylheptanol, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.40 g of a colorless semisolid.

This semisolid compound had an M/e value in FD-mass spectrum of 692.

A $^1$H-NMR spectrum of this compound is shown in FIG. 61.

From these analytical results, this compound was identified as 6-[(4'-dodecyl-4-biphenyl)carbonyloxy]-1,2,3,4-tetrahydro-2-naphthalenecarboxylic acid (R)-1-trifluoromethylhexyl ester [Compound (397)] as desired.

EXAMPLE 70

Synthesis of 6-[4'-decyloxy-4-biphenyl)carbonyloxy]-1,2,3,4-tetrahydro-2-naphthalenecarboxylic acid (R)-1-trifluoromethylpentyl ester [Compound (403)]

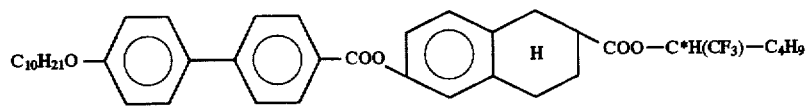

[403]

First Stage

To a mixture of 0.36 g (1 mmol) of 4'-decyloxy-4-biphenylcarboxylic acid obtained in the same manner as in the first stage of Example 11, 0.33 g (1 mmol) of 1,2,3,4-tetrahydro-6-hydroxy-2-naphthalenecarboxylic acid (R)-1-trifluoromethylpentyl ester obtained in the fourth stage of Example 23 except for using (R)-1-trifluoromethylpentanol in place of (R)-1-trifluoromethylheptanol, 0.01 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.51 g of a colorless semisolid.

This semisolid compound had an M/e value in FD-mass spectrum of 666.

A $^1$H-NMR spectrum of this compound is shown in FIG. 62.

From these analytical results, this compound was identified as 6-[(4'-decyloxy-4-biphenyl)carbonyloxy]-1,2,3,4-tetrahydro-2-naphthalenecarboxylic acid (R)-1-trifluoromethylpentyl ester [Compound (403)] as desired.

EXAMPLE 71

Synthesis of 6-[(4'-dodecyloxy-4-biphenyl)carbonyloxy]-1,2,3,4-tetrahydro-2-naphthalenecarboxylic acid (R)-1-trifluoromethylpentyl ester [Compound (405)]

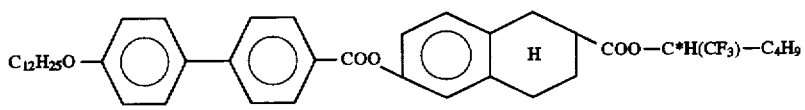

[405]

First Stage

To a mixture of 0.23 g (0.6 mmol) of 4'-dodecyloxy-4-biphenylcarboxylic acid obtained in the same manner as in the first stage of Example 11, 0.19 g (0.6 mmol) of 1,2,3,4-tetrahydro-6-hydroxy-2-naphthalenecarboxylic acid (R)-1-trifluoromethylpentyl ester obtained in the same manner as in the fourth stage of Example 23 except for using (R)-1-trifluoromethylpentanol in place of (R)-1-trifluoromethylheptanol, 0.007 g (0.06 mmol) of 4-N,N-dimethylaminopyridine and 10 ml of methylene chloride was dropwise added 5 ml of a methylene chloride solution containing 0.15 g (0.7 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.31 g of a colorless semisolid.

This semisolid compound had an M/e value in FD-mass spectrum of 694.

A $^1$H-NMR spectrum of this compound is shown in FIG. 63.

From these analytical results, this compound was identified as 6-[(4'-dodecyloxy-4-biphenyl)carbonyloxy]-1,2,3,4-tetrahydro-2-naphthalenecarboxylic acid (R)-1-trifluoromethylpentyl ester [Compound (405)] as desired.

EXAMPLE 72

Synthesis of 6-[(4'-dodecyl-4-biphenyl)carbonyloxy]-1,2,3,4-tetrahydro-2-naphthalenecarboxylic acid (R)-1-trifluoromethylpentyl ester [Compound (413)]

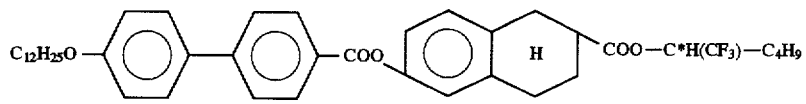

[413]

First Stage

To a mixture of 0.37 g (1 mmol) of 4'-dodecyl-4-biphenylcarboxylic acid (manufactured by Teikoku Kagaku Sangyo, K.K.), 0.33 g (1 mmol) of 1,2,3,4-tetrahydro-6-hydroxy-2-naphthalenecarboxylic acid (R)-1-trifluoromethylpentyl ester obtained in the same manner as in the fourth stage of Example 23 except for using (R)-1-trifluoromethylpentanol in place of (R)-1-trifluoromethylheptanol, 0.01 g (0.1 mmol) of 4-N,N-dimethylaminopyridine and 10 ml of methylene was added 10 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.54 g of a colorless semisolid.

This semisolid compound had an M/e value in FD-mass spectrum of 678.

A $^1$H-NMR spectrum of this compound is shown in FIG. 64.

From these analytical results, this compound was identified as 6-[(4'-dodecyl-4-biphenyl)carbonyloxy]-1,2,3,4-tetrahydro-2-naphthalenecarboxylic acid (R)-1-trifluoromethylpentyl ester [Compound (413)] as desired.

EXAMPLE 73

Synthesis of 6-[(4'-tetradecyl-4-biphenyl)carbonyloxy]-1,2,3,4-tetrahydro-2-naphthalenecarboxylic acid (R)-1-trifluoromethylpentyl ester [Compound (414]

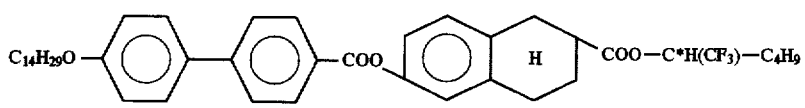

[414]

First Stage

To a mixture of 0.39 g (1 mmol) of 4'-tetradecyl-4-biphenylcarboxylic acid (manufactured by Teikoku Kagaku Sangyo K.K.), 0.33 g (1 mmol) of 1,2,3,4-tetrahydro-6-hydroxy-2-naphthalenecarboxylic acid (R)-1-trifluoromethylpentyl ester obtained in the fourth stage of Example 23 except for using (R)-1-trifluoromethylpentanol in place of (R)-1-trifluoromethylheptanol, 0.012 g (0.1 mmol) of 4-N,N-dimethylaminopyridine and 10 ml of methylene chloride was dropwise added 5 ml of a methylene chloride solution containing 0.25 g (1.2 mmol) of N,N'-dicyclohexylcarbodiimide with stirring at room temperature over a period of 2 hours.

Then, the reaction was further carried out at room temperature for 48 hours.

The reaction mixture was filtered, and the filtrate was concentrated. The concentrate obtained was separated by column chromatography to obtain 0.52 g of a colorless semisolid.

This semisolid compound had an M/e value in FD-mass spectrum of 706.

A $^1$H-NMR spectrum of this compound is shown in FIG. 65.

From these analytical results, this compound was identified as 6-[(4'-tetradecyl-4-biphenyl)carbonyloxy]-1,2,3,4-tetrahydro-2-naphthalenecarboxylic acid (R)-1-trifluoromethylpentyl ester [Compound (414)] as desired.

EXAMPLE 74

Synthesis of 6-[4'-((S)-2-methylbutyloxy)-4-biphenylcarbonyloxy]-1,2,3,4-tetrahydro-2-naphthalenecarboxylic acid (R)-1-trifluoromethylheptyl ester [Compound(774)]

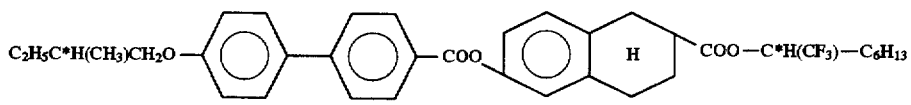

[774]

First Stage

To a mixture of 3.86 g (11.8 mmol) of 6-decyloxy-2-naphthalenecarbocylic acid and 130 ml of 1,2-diethoxyethane was added 3.0 g (130 mg atom) of metallic sodium with stirring at 120° C. in a nitrogen atmosphere, and then heated to reflux temperature.

To the resultant mixture was dropwise added 10 g (114 mmol) of iso-amylalcohol over a period of 1 hour and, then, the reaction was continued under reflux for more 11 hours. After cooling to room temperature, the remaining metallic sodium was dissolved by the addition of ethanol. Then, the reaction mixture was acidified using 20% hydrochloric acid.

To the resultant reaction mixture was added 100 ml of water, then the organic phase was separated from the mixture, and the organic phase was washed with water. The resultant organic phase was concentrated under a reduced pressure to obtain 4.25 g of a solid. The thus obtained solid was recrystallized with toluene to obtain 2.95 g (8.89 mmol) of 1,2,3,4-tetrahyro-6-decyloxy-2-naphthalenecarboxylic acid.

Second Stage

A mixture of 16.6 g (50 mmol) of the 6-decyloxy-2-naphthalenecarboxylic acid obtained in the first stage, 250 ml of acetic acid and 86.5 g (0.5 mol) of 47% hydrobromic acid was heated under reflux at 130° C. for 7 hours. After addition of distilled water, the mixture was concetrated under a reduced pressure to obtain 10.60 g (50 mmol) of 1,2,3,4-tetrahyro-6-hydroxy-2-naphthalenecarboxylic acid.

Third Stage

A mixture of 10.60 g (50 mmol) of the 1,2,3,4-tetrahyro-6-hydroxy-2-naphthalenecarboxylic acid obtained in the second stage, 12.85 g (75 mmol) of benzyl bromide, 6.6 g (100 ml) of 85% potassium hydroxide, 0.525 g (3.5 mmol) of sodium iodide, 200 ml of ethanol and 25 ml of distilled water was heated under reflux at 100° C. for 12 hours. To the resultant mixture was further added 50 ml of 10% potassium hydroxide, and they were heated under reflux for 2 hours.

After cooling to room temperature, the reaction mixture was added to cold water, and the reaction mixture was acidified using 36% hydrochloric acid. The resultant deposit was separated by filtration and recrystallized with toluene to obtain 13.08 g (46.4 mmol) of 1,2,3,4-tetrahydro-6-benzyloxy-2-naphathalenecarboxylic acid.

Fourth Stage

To a mixture of 8.46 g (30 mmol) of 1,2,3,4-tetrahydro-6-benzyloxy-2-naphathalenecarboxylic acid, 5.52 g (30 mmol) of (R)-1-trifluoromethylheptanol, 0.37 g (3 mmol) of 4-N,N-dimethylaminopyridine and 80 ml of methylene chloride was dropwise added 30 ml of a methylene chloride solution containing 6.80 g (33 mmol) of N,N'-dicyclohexylcarbodiimide with stirring at room temperature over a period of 2.5 hours.

Then, the reaction was further carried out at room temperature for 15 hours.

The reaction mixture was filtered, and the filtrate was concentrated. The concentrate obtained was separated by column chromatography to obtain 12.11 g (27.03 mmol) of 1,2,3,4-tetrahydro-6-benzyloxy-2-naphathalenecarboxylic acid (R)-1-trifluoromethylheptyl ester as a light yellow transparent liquid.

Fifth Stage

Hydrogen was blown into a mixture of 12.11 g (27.03 mmol) of the 1,2,3,4-tetrahydro-6-benzyloxy-2-naphathalenecarboxylic acid (R)-1-trifluoromethylheptyl ester obtained in the fourthe stage, 1.21 g of 5% palladium/carbon and 80 ml of a tetrahydrofuran with stirring at room temperature and normal pressure for 48 hours.

The reaction mixture was filtered using Celite as a filter aid, and the filtrate was concentrated to obtain 9.65 g (26.95 mmol) of 1,2,3,4-tetrahydro-6-hydroxy-2-naphathalenecarboxylic acid (R)-1-trifluoromethylheptyl ester as a light yellow liquid.

Sixth Stage

A mixture of 1.76 g (20 mmol) of (S)-2-methylbutanol, 3.82 g (20 mmol) of p-toluenesulfonyl chloride, 5 ml of pyridine and 30 ml of benzene was stirred at room temperature for 16 hours in a nitrogen atmosphere.

The reaction mixture was filtered, and the obtained filtrate was concentrated. The concentrate obtained was separated by column chromatography to obtain 4.0 g (16.5 mmol) of p-toluenesulfonic acid (S)-2-methylbutyl ester as a colorless transparent liquid.

Seventh Stage

A mixture of 4.0 g (16.5 mmol) of the p-toluenesulfonic acid (S)-2-methylbutyl ester obtained in the sixth stage, 5.0 g (16.5 mmol) of 4'-hydroxy-4-biphenycarboxylic acid benzyl ester, 2.76 g (20 mmol) of potassium carbonate and 50 ml of N,N-diethylformamide was heated under reflux for 5 hours. After cooling to room temperature, the resultant mixture was added to 50 ml of distilled water, and the obtained mixture was extracted using ether. The extracted ether solution was concentrated. The concentrate obtained was separated by column chromatography to obtain 4.74 g (12.7 mmol) of 4'-((S)-2-methylbutyloxy)-4-biphenylcarboxylic acid benzyl ester as a light yellow solid.

Eighth Stage

A mixture of 4.74 g (12.7 mmol) of the 4'-((S)-2-methylbutyloxy)-4-biphenylcarboxylic acid benzyl ester obtained in the seventh stage, 1.32 g (20 mmol) of 85% potassium hydroxide, 50 ml of ethanol and 10 ml of distilled water was heated under reflux for 12 hours.

After cooling to room temperature, the reaction mixture was added to cold water, and acidified using 36% hydrochloric acid. The resultant deposit was separated by filtration and recrystallized with tetrahydrofuran to obtain 3.17 g (11.2 mmol) of 4'-((S)-2-methylbutyloxy)-4-biphenylcarboxylic acid.

Ninth Stage

To a mixture of 0.36 g (1 mmol) of the 1,2,3,4-tetrahydro-6-hydroxy-2-naphathalenecarboxylic acid (R)-1-trifluoromethylheptyl ester obtained in the fifth stage, 0.28 g (1 mmol) of the 4'-((S)-2-methylbutyloxy)-4-biphenylcarboxylic acid obtained in the eighth stage, 0.02 g (0.16 mmol) of 4-N,N-dimethylaminopyridine and 15 ml of methylene chloride was dropwise added 3 ml of a methylene chloride solution containing 0.27 g (1.3 mmol) of N,N'-dicyclohexylcarbodiimide with stirring at room temperature over a period of 1 hour.

Then, the reaction was further carried out at room temperature for 5 hours.

The reaction mixture was filtered, and the filtrate was concentrated. The concentrate obtained was separated by column chromatography to obtain 0.60 g of a colorless semisolid.

This semisolid compound had an M/e value in FD-mass spectrum of 624.

A $^1$H-NMR spectrum of this compound is shown in FIG. 66.

From these analytical results, this compound as 6-[4'-((S)-2-methylbutyloxy)-4-biphenylcarbonyloxy]-1,2,3,4-tetrahydro-2-naphthalenecarboxylic acid (R)-1-trifluoromethylheptyl ester [Compound (774)] as desired.

EXAMPLE 75

Synthesis of 6-[4'-((S)-5-methylheptyloxy)-4-biphenylcarbonyloxy]-1,2,3,4-tetrahydro-2-naphthalenecarboxylic acid (R)-1-trifluoromethylheptyl ester [Compound(773)]

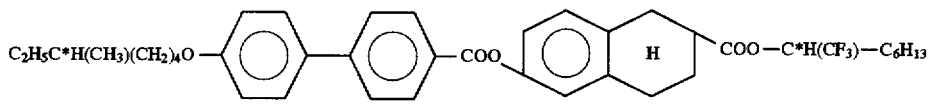

[773]

The same procedure as in the first stage to the ninth stage in Example 74 was repeated except for using (S)-5-methyl-1-heptanol in place of the (S)-2-methylbutanol used in the sixth stage to obtain 0.43 g of a colorless semisolid.

This semisolid compound had an M/e value in FD-mass spectrum of 666.

A $^1$H-NMR spectrum of this compound is shown in FIG. 67.

From these analytical results, this compound was identified as 6-[4'-((S)-5-methylheptyloxy)-4-biphenylcarbonyloxy]-1,2,3,4-tetrahydro-2-naphthalenecarboxylic acid (R)-1-trifluoromethylheptyl ester [Compound (773)]as desired.

EXAMPLE 76

Synthesis of 6-[4'-((S)-6-methyloctyloxy)-4-biphenylcarbonyloxy]-1,2,3,4-tetrahydro-2-naphthalenecarboxylic acid (R)-1-trifluoromethylheptyl ester [Compound (772)]

The same procedure as in first to ninth stage in Example 74 was repeated except for using (S)-1-trifuluoromethylheptanol in place of (R)-1-trifluoromethylheptanol used in the fourth stage and using (S)-6-methyl-1-octanol in place of (S)-2-methylbutanol used in the sixth stage to obtain 0.42 g of a colorless semisolid.

This semisolid compound had an M/e value in FD-mass spectrum of 680.

A $^1$H-NMR spectrum of this compound is shown in FIG. 69.

From these analytical results, this compound was identified as 6-[4'-((S)-6-methyloctyloxy)-4-biphenylcarbonyloxy]-1,2,3,4-tetrahydro-2-naphthalenecarboxylic acid (S)-1-trifluoromethylheptyl ester [Compound (772)] as desired.

EXAMPLE 78

Synthesis of 6-[4'-((S)-1-methylheptyloxy)-4-biphenylcarbonyloxy]-1,2,3,4-tetrahydro-2-

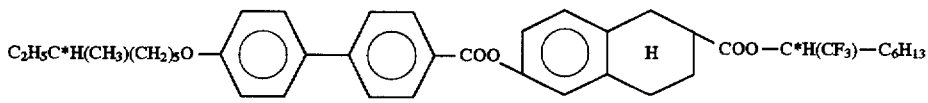

[772]

The same procedure as in the first stage to the ninth stage in Example 74 was repeated except for using (S)-6-methyl-1-octanol in place of the (S)-2-methylbutanol used in the sixth stage to obtain 0.52 g of a colorless semisolid.

This semisolid compound had an M/e value in FD-mass spectrum of 680.

naphthalenecarboxylic acid (R)-1-trifluoromethylheptyl ester [Compound (776)]

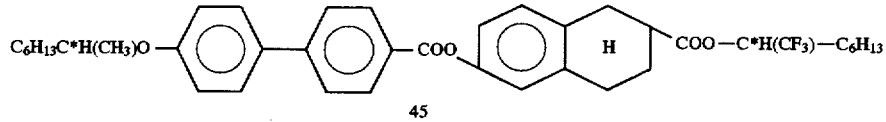

[776]

A $^1$H-NMR spectrum of this compound is shown in FIG. 68.

From these analytical results, this compound was identified as 6-[4'-((S)-6-methyloctyloxy)-4-biphenylcarbonyloxy]-1,2,3,4-tetrahydro-2-naphthalenecarboxylic acid (R)-1-trifluoromethylheptyl ester [Compound (772)] as desired.

EXAMPLE 77

Synthesis of 6-[4'-((S)-6-methyloctyloxy)-4-biphenylcarbonyloxy]-1,2,3,4-tetrahydro-2-naphthalenecarboxylic acid (S)-1-trifluoromethylheptyl ester [Compound (772)]

The same procedure as in the first stage to the ninth stage in Example 74 was repeated except for using 4'-((S)-1-methylheptyloxy)-4-biphenylcarboxylic acid in place of the 4'-((S)-2-methylbutyloxy)-4-biphenylcarboxylic acid used in the ninth stage to obtain 0.54 g of a colorless semisolid.

This semisolid compound had an M/e value in FD-mass spectrum of 666.

Figure 70:
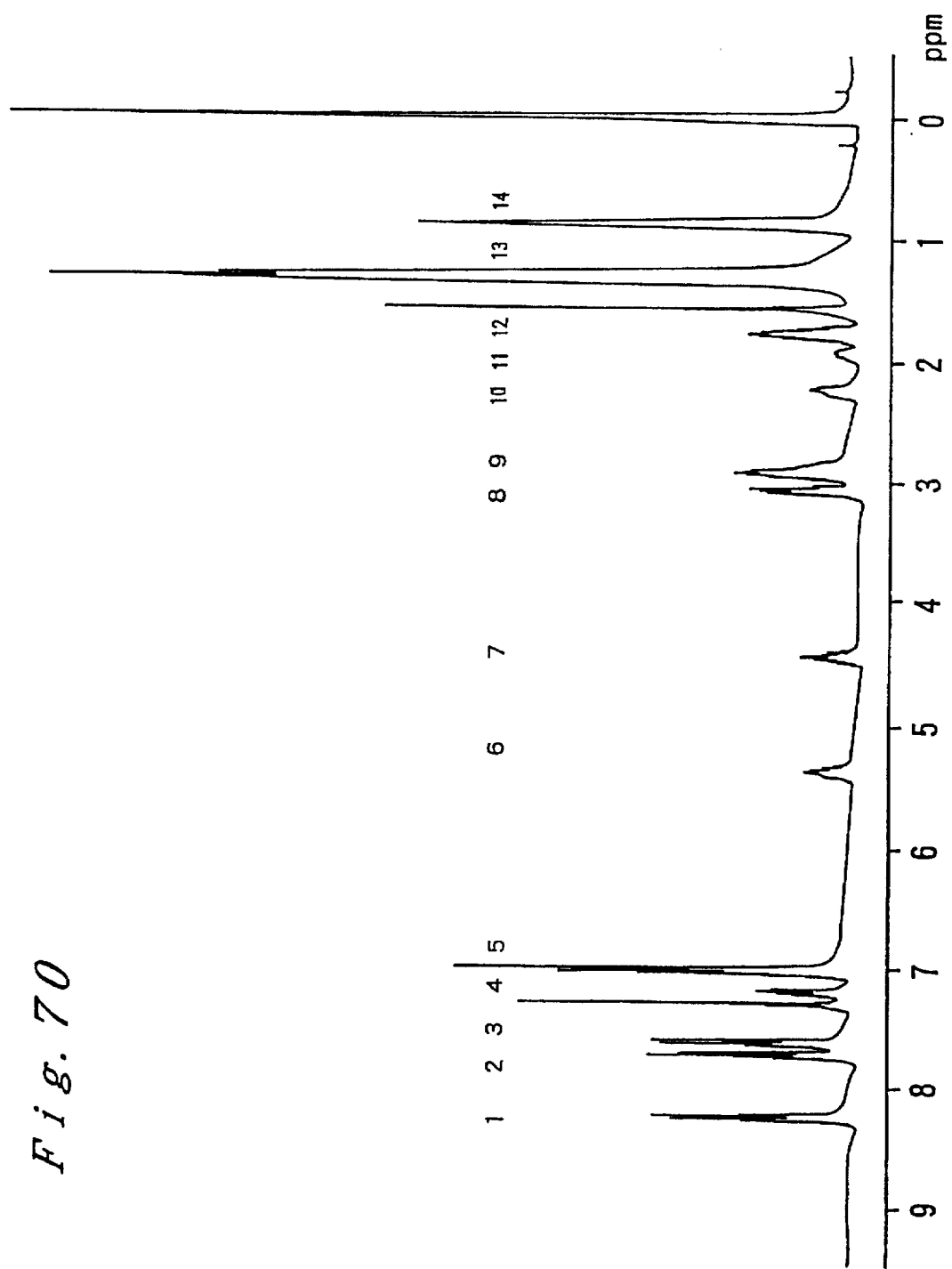
FIG. 70 shows $^1$H-NMR spectrum of 6-[4'-((S)-1-methylheptyloxy)-4-biphenylcarbonyloxy]-1,2,3,4-tetrahydro-2-naphthalenecarboxylic acid (R)-1-trifluoromethylhepthyl ester. [Examplified compound (776)]

A $^1$H-NMR spectrum of this compound is shown in FIG. 70.

From these analytical results, this compound was identified as 6-[4'-((S)-1-methylheptyloxy)-4-biphenylcarbonyloxy]-1,2,3,4-tetrahydro-2-naphthalenecarboxylic acid (R)-1-trifluoromethylheptyl ester [Compound (776)] as desired.

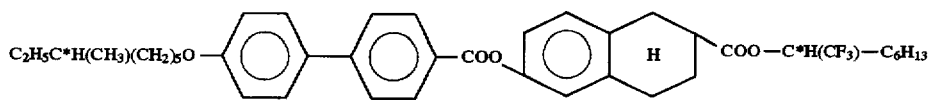

[772]

EXAMPLE 79

Synthesis of 6-[4'-((S)-2-methyloctyloxy)-4-biphenylcarbonyloxy]-1,2,3,4-tetrahydro-2-naphthalenecarboxylic acid (R)-1-trifluoromethylheptyl ester [Compound (775)]

Figure 71:
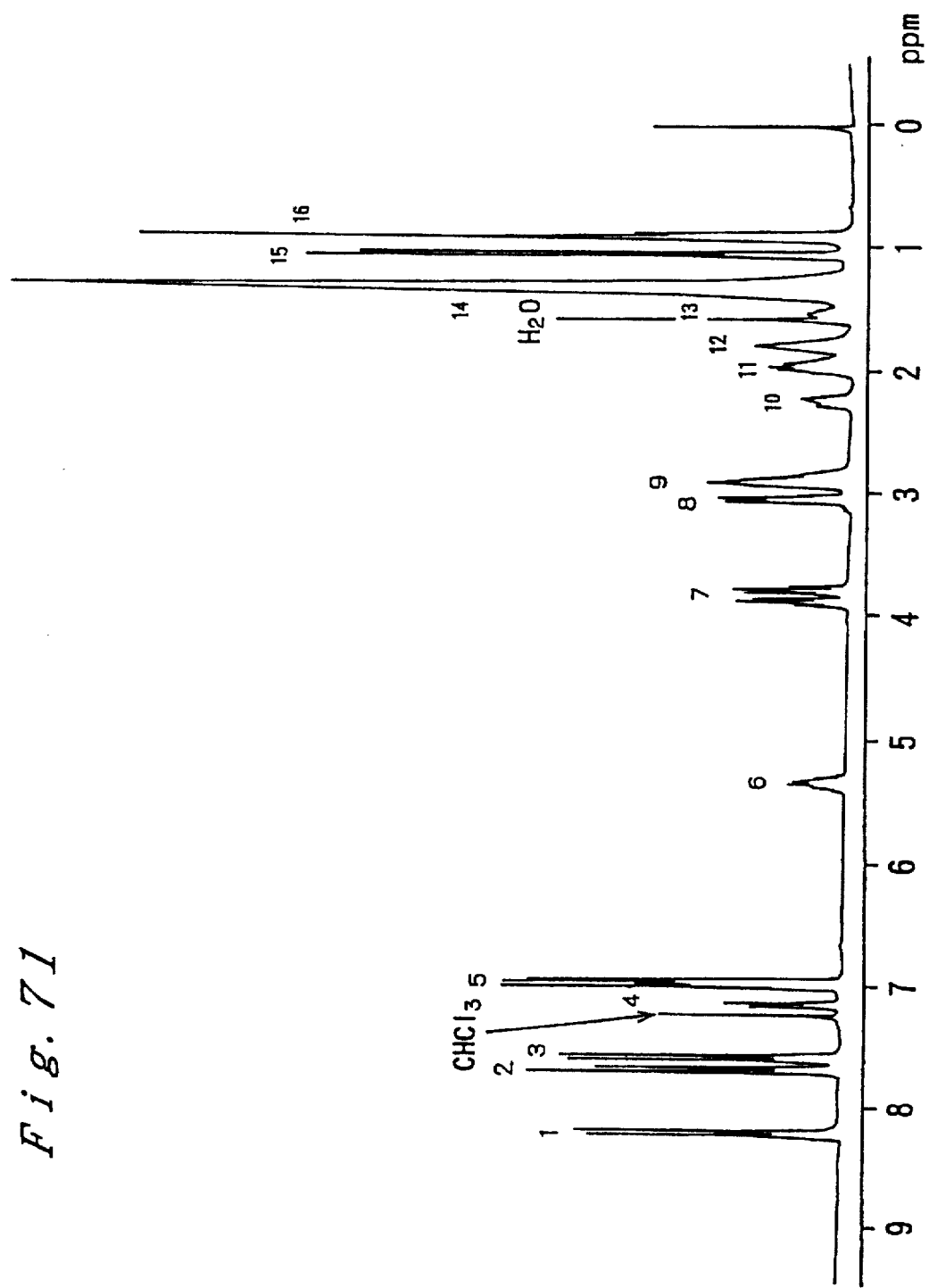
FIG. 71 shows $^1$H-NMR spectrum of 6-[4'-((S)-2-methyloctyloxy)-4-biphenylcarbonyloxy]-1,2,3,4-tetrahydro-2-naphthalenecarboxylic acid (R)-1-trifluoromethylheptyl ester. [Examplified compound (775)]

A ¹H-NMR spectrum of this compound is shown in FIG. 71.

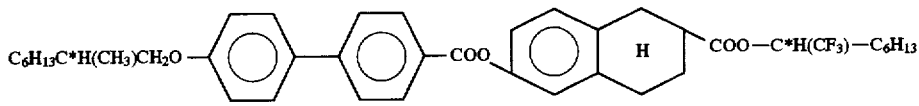

[775]

First Stage

Litium aluminum hydride was suspended at 0° C. in a nitrogen atmospere in 20 ml of diethyl ether which was treated by dry distillation on sodium wire. To the resultant suspention was added 5 ml of a dry diethyl ether solution containing 1.58 g (10 mmol) of S-2-methyl octanoic acid over a period 15 minutes, and the temperature of the mixture was elevated to room temperature. After stirring at room temperature for 6 hours, the temperature was further elevated to the reflux temperature, and the resultant mixture was further stirred for 1 hour. After cooling to room temperature, to the reaction mixture was added 10 ml of water while giving attention to the generated hydrogen. Then, the thus produced aluminum hydroxide was dissolved by the addition of 36% hydrochloric acid. The mixture was separated into an aqueous phase and an organic phase. The aqueous phase was extracted using ether. The resultant ether solution was combined with the above separated organic phase, dried, and concentrated to obtain 1.4 g (10 mmol) of (S)-2-methyloctanol as a colorless transparent liquid.

From these analytical results, this compound was identified as 6-[4'-((S)-2-methyloctyloxy)-4-biphenylcarbonyloxy]-1,2,3,4-tetrahydro-2-naphthalenecarboxylic acid (R)-1-trifluoromethylheptyl ester [Compound (775)] as desired.

EXAMPLE 80

The compound (651) represented by the following formula [651] obtained in Example 43 was mixed with the compound (253) represented by the following formula [253] obtained in Example 32 at the weight ratio of 50:50 to obtain a liquid crystal composition.

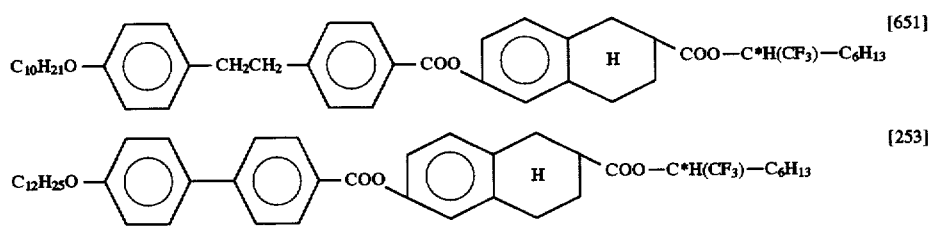

Phase transition temperatures of this composition measured are shown in Table 19.

Second Stage

The same procedure as in the first stage to the ninth stage in Example 74 was repeated except for using (S)-2-methyloctanol in place of the (S)-2-methylbutanol used in the ninth stage to obtain 0.60 g of a colorless semisolid.

This semisolid compound had an M/e value in FD-mass spectrum of 680.

TABLE 19

| Compound No. | Cryst. | | SmCA* | | SmC* | | SmA | | Iso |
|---|---|---|---|---|---|---|---|---|---|
| (651) | · | | 46 | · | 68 | — | | · | 78 | · |
| (253) | · | | 44 | · | 93 | · | 102 | · | 122 | · |
| (651) 50% + (253) 50% | · | | <–30 | · | 82 | — | | · | 100 | · |

EXAMPLE 81

The compound (254) represented by the following formula [254] obtained in Example 50 was mixed with the compound (C) represented by the following formula [C] at the weight ratio of 50:50 to obtain a liquid crystal composition.

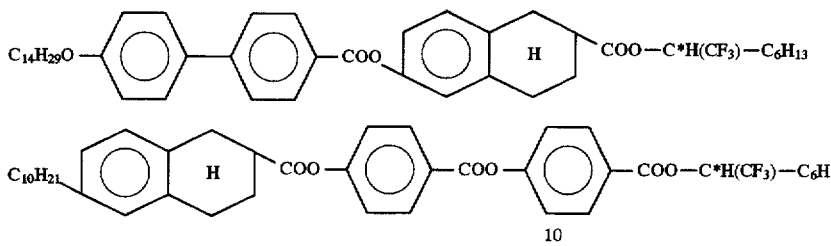

Phase transition temperatures of this composition measured are shown in Table 20.

TABLE 20

| Compound No. | Cryst. | | SmCA* | | SmC* | SmA | Iso |
|---|---|---|---|---|---|---|---|
| (254) | · | 47 | · | 89 | — | · 108 | · |
| (C) | · | 30 | · | 48 | — | · 66 | · |
| (254) 50% + (C) 50% | · | 48 | · | 80 | — | · 100 | · |

EXAMPLE 82

The compound (354) represented by the following formula [354] obtained in Example 51 was mixed with the compound (C) represented by the following formula [C] at the weight ratio of 50:50 to obtain a liquid crystal composition.

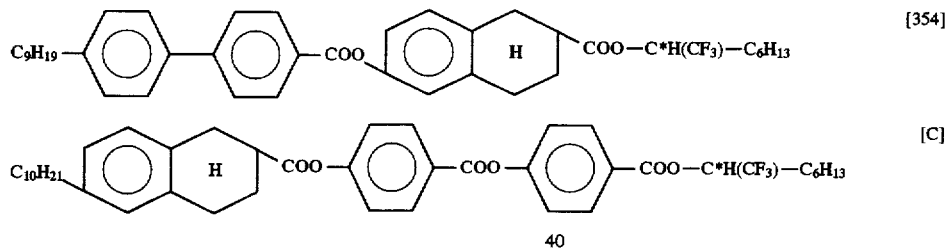

Phase transition temperatures of this composition measured are shown in Table 21.

TABLE 21

| Compound No. | Cryst. | | SmCA* | | SmC* | SmA | Iso |
|---|---|---|---|---|---|---|---|
| (354) | · | 40 | · | 66 | — | · 106 | · |
| (C) | · | 30 | · | 48 | — | · 66 | · |
| (651) 50% + (C) 50% | · | <−30 | · | 43 | — | · 83 | · |

EXAMPLE 83

The compound (356) represented by the following formula [356] obtained in Example 52 was mixed with the compound (C) represented by the following formula [C] at the weight ratio of 50:50 to obtain a liquid crystal composition.

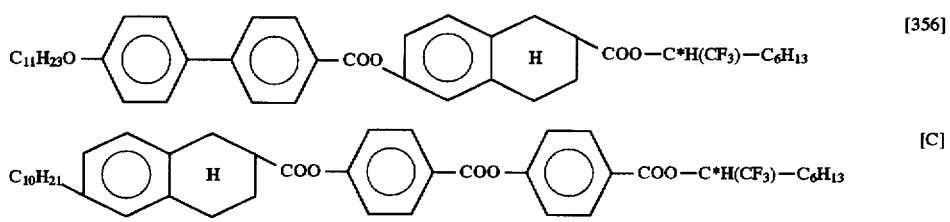

Phase transition temperatures of this composition measured are shown in Table 22.

TABLE 22

| Compound No. | Cryst. | | SmCA* | | SmC* | SmA | Iso |
|---|---|---|---|---|---|---|---|
| (356) | · | 38 | · | 71 | — | · 97 | · |
| (C) | · | 30 | · | 48 | — | · 66 | · |

TABLE 22-continued

| Compound No. | Cryst. | | SmCA* | | SmC* | SmA | | Iso |
|---|---|---|---|---|---|---|---|---|
| (356) 50% + (C) 50% | · | | <−30 | · | 48 | — | · | 79 · |

EXAMPLE 84

The compound (371) represented by the following formula [371] obtained in Example 54 was mixed with the compound (D) represented by the following formula [D] at the weight ratio of 50:50 to obtain a liquid crystal composition.

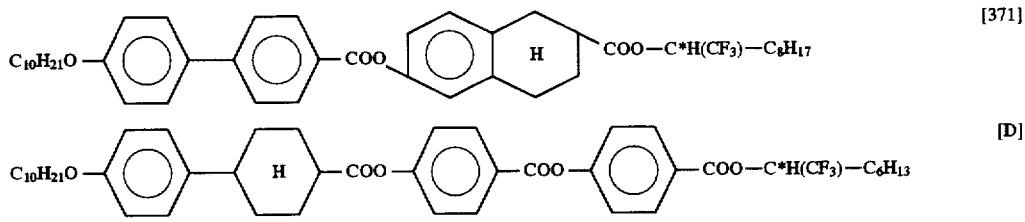

Phase transition temperatures of this composition measured are shown in Table 23.

TABLE 23

| Compound No. | Cryst. | | SmCA* | | SmC* | SmA | | Iso |
|---|---|---|---|---|---|---|---|---|
| (371) | · | | 50 | · | 91 | — | · | 122 · |
| (D) | · | | 26 | · | 38 | — | · | 40 · |
| (371) 50% + (D) 50% | · | | <−30 | · | 65 | — | · | 92 · |

EXAMPLE 85

The compound (483) represented by the following formula [483] obtained in Example 56 was mixed with the compound (358) represented by the following formula [358] obtained in Example 32 at the weight ratio of 20:80 to obtain a liquid crystal composition.

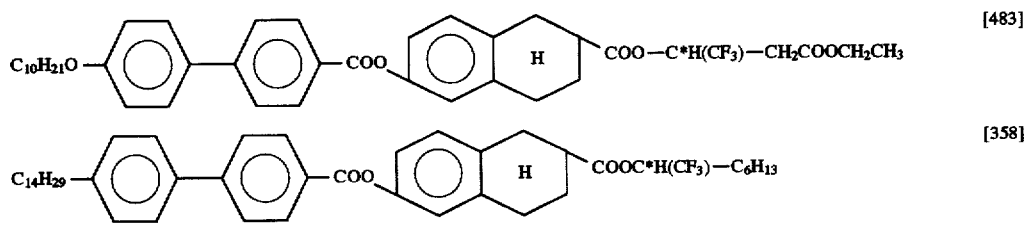

Phase transition temperatures of this composition measured are shown in Table 24.

TABLE 24

| Compound No. | Cryst. | | SmCA* | | SmC* | | SmA | | Iso |
|---|---|---|---|---|---|---|---|---|---|
| (483) | · | | 50 | | — | | · 104 | · | 129 · |
| | | | | | SmCγ* | | | | |
| (358) | · | | 28 | · | 59 | · | 71 | · | 89 · |
| (483) 20% + (358) 80% | · | | <−30 | · | 65 | · | | · | 95 · |

EXAMPLE 86

The compound (491) represented by the following formula [491] obtained in Example 57 was mixed with the compound (253) represented by the following formula [253] obtained in Example 32 at the weight ratio of 20:80 to obtain a liquid crystal composition.

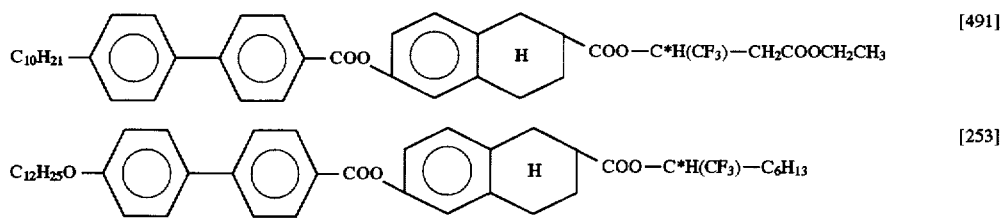

Phase transition temperatures of this composition measured are shown in Table 25.

TABLE 25

| Compound No. | Cryst. | | SmCA* | | SmC* | | SmA | | Iso |
|---|---|---|---|---|---|---|---|---|---|
| (491) | · | | 45 | | — | · | 76 | · | 103 · |
| (253) | · | | 44 | · | 93 | · | 102 | · | 122 · |
| (491) 20% + (253) 80% | · | | <−30 | · | 93 | — | | · | 116 · |

EXAMPLE 87

The compound (419) represented by the following formula [419] obtained in Example 56 was mixed with the compound (251) represented by the following formula [251] obtained in Example 11 at the weight ratio of 50:50 to obtain a liquid crystal composition.

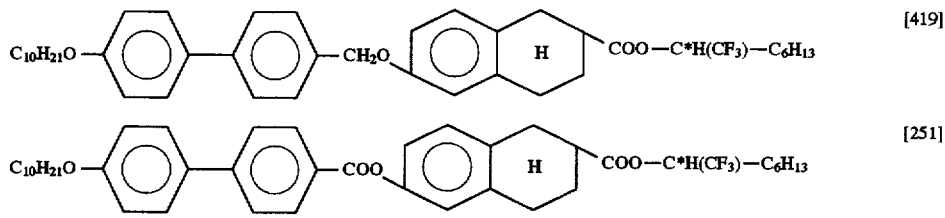

Phase transition temperatures of this composition measured are shown in Table 26.

TABLE 26

| Compound No. | Cryst. | | SmCA* | | SmC* | | SmA | | Iso |
|---|---|---|---|---|---|---|---|---|---|
| (419) | · | | 45 | – | 87 | · | 92 | · | 102 | · |
| (251) | · | | 21 | · | 96 | · | 99 | · | 132 | · |
| (419) 50% + (251) 50% | · | | <–30 | · | 93 | – | · | | 112 | · |

EXAMPLE 88

The compound (427) represented by the following formula [427] obtained in Example 60 was mixed with the compound (358) represented by the following formula [358] obtained in Example 32 at the weight ratio of 50:50 to obtain a liquid crystal composition.

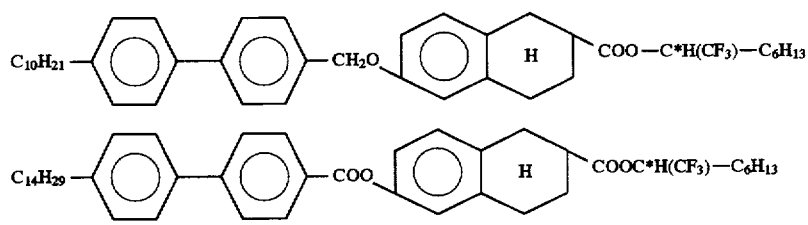

[427]

[358]

Phase transition temperatures of this composition measured are shown in Table 27.

TABLE 27

| Compound No. | Cryst. | | SmCA* | | SmC | | SmA | | Iso |
|---|---|---|---|---|---|---|---|---|---|
| (427) | · | | 38 | – | 61 | SmCγ* · | 66 | · | 76 | · |
| (358) | · | | 28 | · | 59 | SmCγ* · | 71 | · | 89 | · |
| (427) 50% + (358) 50% | · | | <–30 | · | 60 | – | · | | 77 | · |

EXAMPLE 89

The compound (451) represented by the following formula [451] obtained in Example 63 was mixed with the compound (251) represented by the following formula [251] obtained in Example 11 at the weight ratio of 50:50 to obtain a liquid crystal composition.

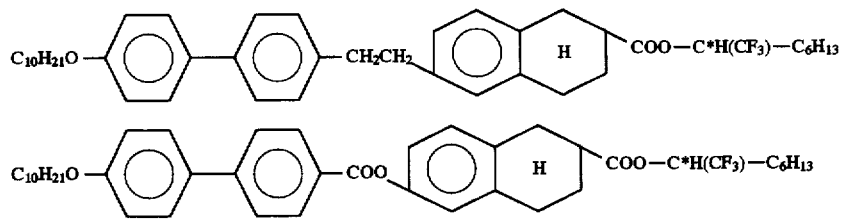

[451]

[251]

Phase transition temperatures of this composition measured are shown in Table 28.

TABLE 28

| Compound No. | Cryst. | | SmCA* | | SmC* | | SmA | | Iso |
|---|---|---|---|---|---|---|---|---|---|
| (451) | • | | 65 | — | 85 | — | • | 95 | • |
| (251) | • | | 21 | • | 96 | • 99 • | 132 | • |
| (451) 50% + (251) 50% | • | | <−30 | • | 91 | — | • | 111 | • |

EXAMPLE 90

The compound (507) represented by the following formula [507] obtained in Example 64 was mixed with the compound (251) represented by the following formula [251] obtained in Example 11 at the weight ratio of 40:60 to obtain a liquid crystal composition.

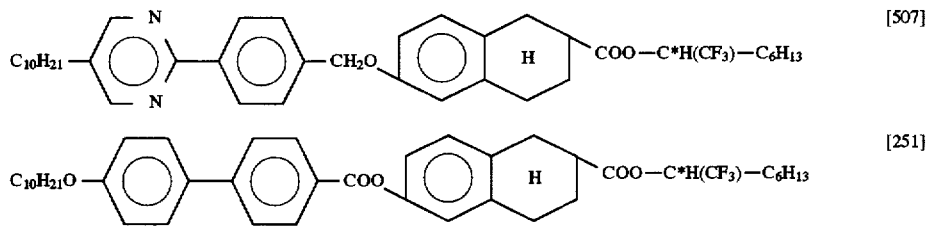

Phase transition temperatures of this composition measured are shown in Table 29.

TABLE 29

| Compound No. | Cryst. | | SmCA* | | SmC* | | SmA | | Iso |
|---|---|---|---|---|---|---|---|---|---|
| (507) | • | | 85 | — | — | — | (• | 72) | • |
| (251) | • | | 21 | • | 96 | • 99 • | 132 | • |
| (507) 40% + (251) 60% | • | | 45 | • | 75 | — | • | 99 | • |

EXAMPLE 91

The compound (313) represented by the following formula [313] obtained in Example 65 was mixed with the compound (251) represented by the following formula [251] obtained in Example 11 at the weight ratio of 20:80 to obtain a liquid crystal composition.

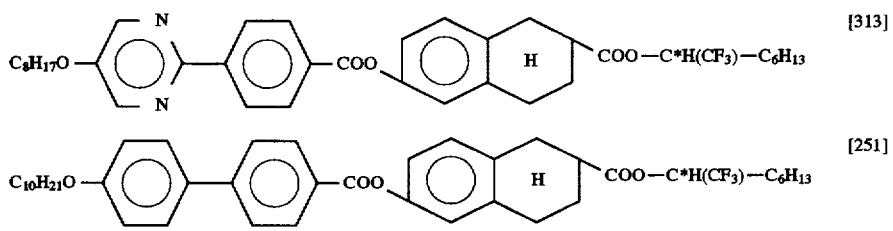

Phase transition temperatures of this composition measured are shown in Table 30.

TABLE 30

| Compound No. | Cryst. | | SmCA* | | SmC* | | SmA | | Iso |
|---|---|---|---|---|---|---|---|---|---|
| (313) | · | 82 | (· | 81) | · | 99 | · | 140 | · |
| (251) | · | 21 | · | 96 | · | 99 | · | 132 | · |
| (313) 20% + (251) 80% | · | <–30 | · | 97 | – | · | 127 | · | |

We claim:

1. A carboxylic acid ester compound represented by the following formula (I)

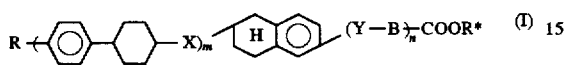

wherein

R is a group selected from the group consisting of an alkyl of 3–20 carbon atoms, an alkoxy of 3–20 carbon atoms, and a halogenated alkyl of 3–20 carbon atoms, X and Y are independently a group selected from the group consisting of —COO—, —OCO—, —CH$_2$CH$_2$—, —CH$_2$O—, —OCH$_2$—, —S—S—, —CO—CH$_2$— and —CH$_2$—CO—, or a single bond, B is a group selected from the group consisting of

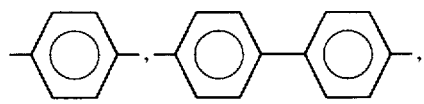

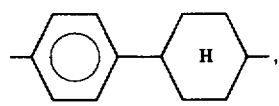

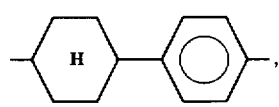

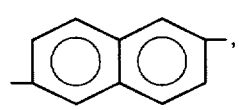

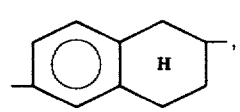

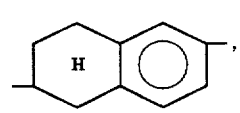

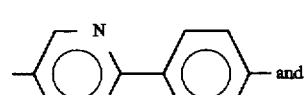

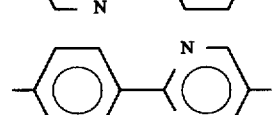

R* is an optically active group of 4–20 carbon atoms containing at least one asymmetric carbon atom where one or more hydrogen atoms attached to the carbon atoms constituting said optically active group may be substituted with a halogen atom, and m is 1 or 2 and n is an integer of 0–2.

2. A carboxylic acid ester compound represented by the formula (I) as claimed in claim 1 wherein R * is a group represented by the following formula (V)

wherein

Q$^1$ is —(CH$_2$)$_q$— in which q is an integer of 0–6, and

Q$^2$ and Q$^3$ are different from each other, and are each independently an alkyl of 1–10 carbon atoms, a fluoroalkyl of 1–10 carbon atoms or a halogen atom, and at least a part of the groups CH$_2$ or CF$_2$ in the Q$^1$, Q$^2$ and Q$^3$ may be replaced by at least one group selected from the group consisting of —O—, —S—, —CO—, —CHX— in which X is a halogen atom, —CHCN—, —O—CO—, —O—COO—, —CO—O— and —CH=CH— in such a manner that two hetero atoms do not bind directly.

3. A carboxylic acid ester compound represented by the formula (I) as claimed in claim 1 wherein R* is a group selected from the group consisting of —C*H(C$_2$H$_5$)—C$_5$H$_{11}$, —C*H(C$_2$H$_5$)—C$_6$H$_{13}$, —CH$_2$—C*H(CH$_3$)—C$_2$H$_5$, —(CH$_2$)$_3$—C*H(CH$_3$)—C$_2$H$_5$, and —C*H(CF$_3$)—CH$_2$—COO—C$_2$H$_5$.

4. A carboxylic acid ester compound represented by the formula (I) as claimed in claim 1 wherein X and Y are independently a group of —COO—, —OCO—, —CH$_2$O—, —CH$_2$CH$_2$— or a single bond.

5. A carboxylic acid ester compound represented by the formula (I) as claimed in claim 1 wherein R is a group selected from the group consisting of a straight chain alkyl of 3–20 carbon atoms, a straight chain alkoxy of 3–20 carbon atoms, and a halogenated straight chain alkyl of 3–20 carbon atoms.

6. A carboxylic acid ester compound represented by the formula (I) as claimed in claim 1 wherein R is a group selected from the group consisting of a branched alkyl of 3–20 carbon atoms, a branched alkoxy of 3–20 carbon atoms, and a halogenated branched alkyl of 3–20 carbon atoms.

7. A carboxylic acid ester compound represented by the formula (I) as claimed in claim 1 wherein B is a group selected from the group consisting of:

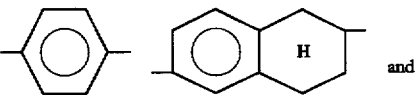

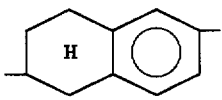

8. A carboxylic acid ester compound represented by the following formula (III) or (IV)

(III)

(IV)

wherein

R is a group selected from the group consisting of an alkyl of 3–20 carbon atoms, an alkoxy of 3–20 carbon atoms, a halogenated alkyl of 3–20 carbon atoms, a halogenated alkoxy of 3–20 carbon atoms and a hydrocarbon group, having —OCO— group wherein at least a part of hydrogen atoms constituting said hydrocarbon group may be substituted with halogen atoms, and R may have at least one asymmetric carbon atom, X and Y are independently a group selected from the group consisting of —COO—, —OCO—, —CH$_2$CH$_2$—, —CH$_2$O—, —OCH$_2$—, —S—S—, —CO—CH$_2$— and —CH$_2$—CO—, or a single bond, B' is a group selected from the group consisting of

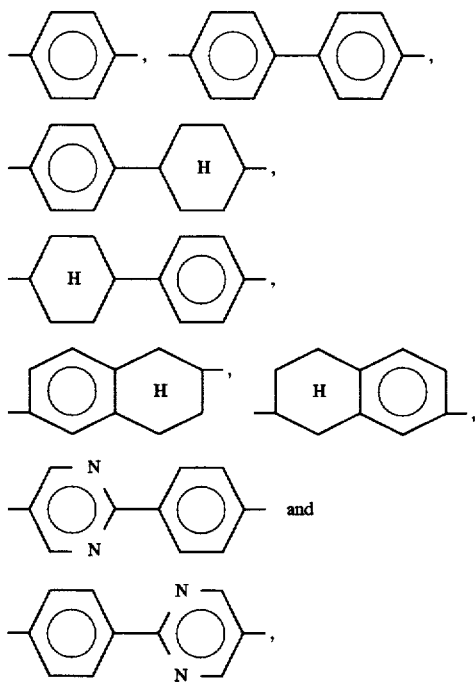

R* is an optically active group of 4–20 carbon atoms containing at least one asymmetric carbon atom where one or more hydrogen atoms attached to the carbon atoms constituting said optically active group may be substituted with a halogen atom, and m is 1 or 2, n is an integer of 0–2 and m+n≧2.

9. A carboxylic acid ester compound represented by the formula (III) or (IV) as claimed in claim 8 wherein R* is a group represented by the following formula (V)

—Q$^1$—C*H (Q$^2$)—Q$^3$ (V)

wherein

Q$^1$ is —(CH$_2$)$_q$— in which q is an integer of 0–6, and

Q$^2$ and Q$^3$ are different from each other, and are each independently an alkyl of 1–10 carbon atoms, a fluoroalkyl of 1–10 carbon atoms or a halogen atom, and at least a part of the groups CH$_2$ or CF$_2$ in the Q$^1$, Q$^2$ and Q$^3$ may be replaced by at least one group selected from the group consisting of —O—, —S—, —CO—, —CHX— in which X is a halogen atom, —CHCN—, —O—CO—, —O—COO—, —CO—O— and —CH=CH— in such a manner that two hetero atoms do not bind directly.

10. A carboxylic acid ester compound represented by the formula (III) or (IV) as claimed in claim 9 wherein R* is a group selected from the group consisting of —C*H(CF$_3$)—C$_6$H$_{13}$, —C*H(CH$_3$)—C$_6$H$_{13}$, —C*H(CH$_3$)—C$_5$H$_{11}$, —C*H(C$_2$H$_5$)—C$_5$H$_{11}$, —C*H(C$_2$H$_5$)—C$_6$H$_{13}$, —CH$_2$—C*H(CH$_3$)—C$_2$H$_5$, —(CH$_2$)$_3$—C*H (CH$_3$)—C$_2$H$_5$, and —C*H(CF$_3$)—CH$_2$—COO—C$_2$H$_5$.

11. A carboxylic acid ester compounds represented by the formula (III) or (IV) as claimed in claim 8 wherein X and Y are independently a group —COO—, —OCO—, —CH$_2$O—, —OCH$_2$—, CH$_2$CH$_2$— or a single bond.

12. A carboxylic acid ester compound represented by the formula (III) or (IV) as claimed in claim 8 wherein R is a group selected from the group consisting of a straight chain alkyl of 3–20 carbon atoms, a straight chain alkoxy of 3–20 carbon atoms, a halogenated straight chain alkyl of 3–20 carbon atoms and a halogenated straight chain alkoxy of 3–20 carbon atoms.

13. A carboxylic acid ester compound represented by the formula (III) or (IV) as claimed in claim 8 wherein R is a group selected from the group consisting of a branched alkyl of 3–20 carbon atoms, a branched alkoxy of 3–20 carbon atoms, a halogenated branched alkyl of 3–20 carbon atoms and a halogenated branched alkoxy of 3–20 carbon atoms.

14. A carboxylic acid ester compound represented by the formula (III) or (IV) as claimed in claim 13 wherein R is a group having an asymmetric carbon atom.

15. A carboxylic acid ester compound represented by the formula (III) or (IV) as claimed in claim 8 wherein R is a group selected from the group consisting of 2-methylbutyloxy, and 1-methylheptyloxy, and 5-methylheptyloxy.

16. A liquid crystal material comprising a carboxylic acid ester compound represented by the following formula (I)

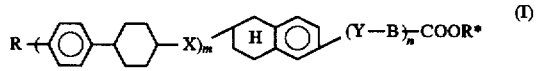
(I)

wherein

R is a group selected from the group consisting of a straight chain alkyl of 3–20 carbon atoms, a straight chain alkoxy of 3–20 carbon atoms, alkyl of 3–20 carbon atoms,, X and Y are independently a group selected from the group consisting of —COO—, —OCO—, —CH$_2$CH$_2$—, —CH$_2$O—, —OCH$_2$—, —S—S—, —CO—CH$_2$— and —CH$_2$—CO—, or a single bond, B is a group selected from the group consisting of

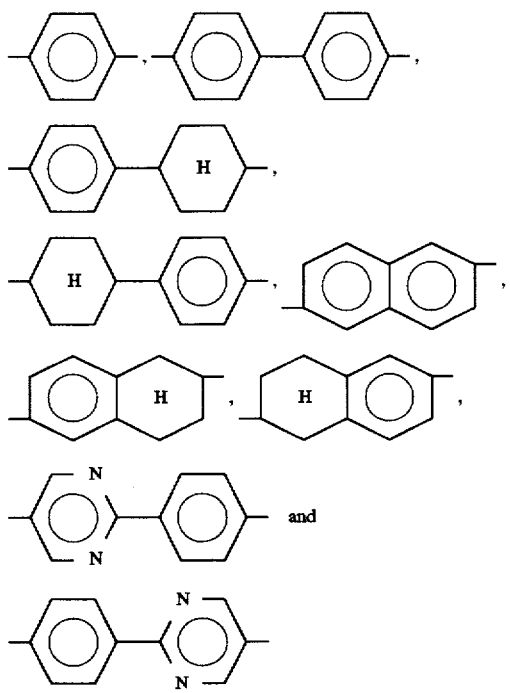

and

R* is an optically active group of 4–20 carbon atoms containing at least one asymmetric carbon atom where one or more hydrogen atoms attached to the carbon atoms constituting said optically active group may be substituted with a halogen atom, m is 1 or 2, and n is an integer of 0–1.

17. A liquid crystal material as claimed in claim 16 wherein R* is a group represented by the following formula (V)

$$-Q^1-C^*H(Q^2)-Q^3 \quad (V)$$

wherein $Q^1$ is —$(CH_2)_q$— in which q is an integer of 0–6, and $Q^2$ and $Q^3$ are different from each other, and are each independently an alkyl of 1–10 carbon atoms, a fluoroalkyl of 1–10 carbon atoms or a halogen atom, and at least a part of the groups $CH_2$ or $CF_2$ in the $Q^1$, $Q^2$ and $Q^3$ may be replaced by at least one group selected from the group consisting of —O—, —S—, —CO—, —CHX— in which X is a halogen atom, —CHCN—, —O—CO—, —O—COO—, —CO—O— and —CH=CH— in such a manner that two hetero atoms do not bind directly.

18. A liquid crystal material as claimed in claim 16 wherein R* is a group selected from the group consisting of —$C^*H(CF_3)$—$C_6H_{13}$, —$C^*H(CH_3)$—$C_6H_{13}$, —$C^*H(CH_3)$—$C_5H_{11}$, —$C^*H(C_2H_5)$—$C_5H_{11}$, —$C^*H(C_2H_5)$—$C_6H_{13}$, —$CH_2$—$C^*H(CH_3)$—$C_2H_5$, —$(CH_2)_3$—$C^*H(CH_3)$—$C_2H_5$, and —$CH(CF_3)$—$CH_2$—COO—$C_2H_5$.

19. A liquid crystal material as claimed in claim 16 wherein X and Y are independently a group —COO—, —OCO—, —$CH_2O$—, —$CH_2CH_2$— or a single bond.

20. A liquid crystal material as claimed in claim 16 wherein B is a group selected from the group consisting of;

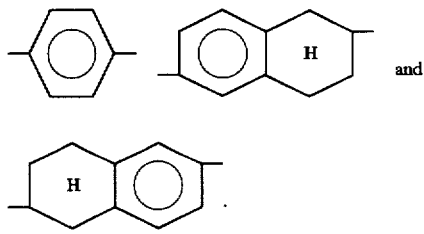

21. A liquid crystal material consisting of a carboxylic acid ester compound represented by the following formula (III) or (IV)

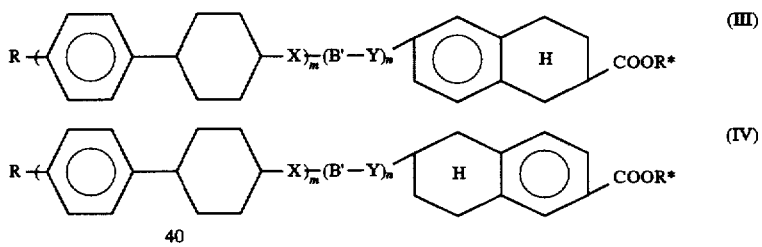

wherein

R is a group selected from the group consisting of a straight chain alkyl of 3–20 carbon atoms, a straight chain alkoxy of 3–20 carbon atom, an alkoxy of 3–20 carbon atoms having an asymmetric carbon atom, a halogenated straight chain alkoxy of 3–20 carbon atoms and a halogenated alkoxy of 3–20 carbon atoms having an asymmetric carbon atom, X and Y are independently a group selected from the group consisting of —COO—, —OCO—, —$CH_2CH_2$—, —$CH_2O$—, —$OCH_2$—, —S—S—, —CO—$CH_2$— and —$CH_2$—CO—, or a single bond, B' is a group selected from the group consisting of

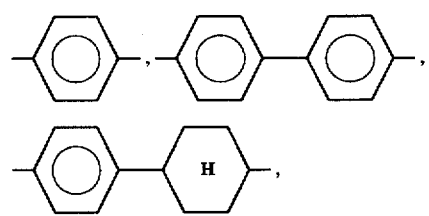

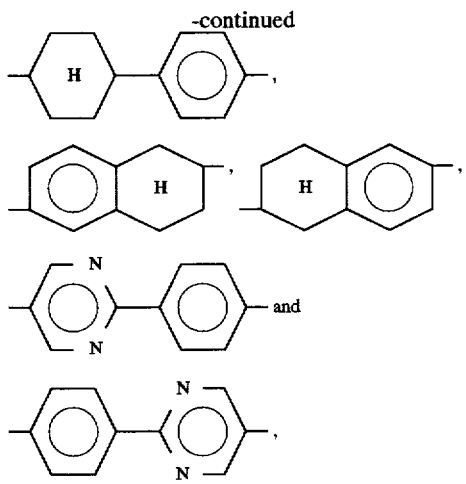

R* is an optically active group of 4–20 carbon atoms containing at least one asymmetric carbon atom where hydrogen atoms attached to the carbon atoms constituting said optically active group may be substituted with a halogen atom, and m is 1 or 2, n is an integer of 0–2 and m+n≧2.

22. A liquid crystal material as claimed in claim 21 wherein R* is a group represented by the following formula (V)

wherein $Q^1$ is —$(CH_2)_q$— in which q is an integer of 0–6, and $Q^2$ and $Q^3$ are different from each other, and are each independently an alkyl of 1–10 carbon atoms, a fluoroalkyl of 1–10 carbon atoms or a halogen atom, and at least a part of the groups $CH_2$ or $CF_2$ in the $Q^1$, $Q^2$ and $Q^3$ may be replaced by at least one group selected from the group consisting of —O—, —S—, —CO—, —CHX— in which X is a halogen atom, —CHCN—, —O—CO—, —O—COO—, —CO—O— and —CH=CH— in such a manner that two hetero atoms do not bind directly.

23. A liquid crystal material as claimed in claim 22 wherein R* is a group selected from the group consisting of C*H(CF$_3$)—C$_6$H$_{13}$, —C*H(CH$_3$) —C$_6$H$_{13}$, —C*H(CH$_3$) —C$_5$H$_{11}$, —C*H (C$_2$H$_5$)—C$_5$H$_{11}$, —C*H (C$_2$H$_5$)—C$_6$H$_{13}$, —CH$_2$—C*H(CH$_3$)—C$_2$H$_5$, —(CH$_2$)$_3$—C*H(CH$_3$)—C$_2$H$_5$, and C*H(CF$_3$)—CH$_2$—COO—C$_2$H$_5$.

24. A liquid crystal material as claimed in claim 21 wherein X and Y are independently a group —COO—, —OCO—, —CH$_2$O—, —OCH$_2$—, —CH$_2$CH$_2$— or a single bond.

25. A liquid crystal material as claimed in claim 21 wherein R is a group having an asymmetric carbon atom.

26. A liquid crystal material as claimed in claim 21 wherein R is a group selected from the group consisting of 4-methylhexyloxy, and 1-methylheptyloxy.

27. A liquid crystal composition comprising a mixture of two or more liquid crystal materials, at least one said materials being the liquid crystal material as claimed in claim 16.

28. The liquid crystal composition as claimed in claim 27 which comprises a mixture of two or more carboxylic acid ester compounds of said formula (I) and at least one other liquid crystal material.

29. The liquid crystal composition as claimed in claim 27 which comprises a mixture of at least one carboxylic acid ester compounds of said formula (I) and at least one other liquid crystal material.

30. A liquid crystal element comprising a cell composed of two substrates opposite to each other, a gap formed by said substrates and the liquid crystal composition as claimed in claim 27 filled in said gap.

31. A liquid crystal composition comprising a mixture of two or more liquid crystal materials, at least one of said materials consisting of the carboxylic acid ester compound liquid crystal material as claimed in claim 21.

32. The liquid crystal composition as claimed in claim 31 which comprises a mixture of two or more carboxylic acid ester compounds of said formulas (III) and (IV).

33. The liquid crystal composition as claimed in claim 31 which comprises a mixture of at least one carboxylic acid ester compounds of said formulas (III) and (IV) and at least one other liquid crystal material.

34. A liquid crystal element comprising a cell composed of two opposite to each other, a gap formed by said substrates and the liquid crystal composition as claimed in claim 31 filled in said gap.

35. The carboxylic acid ester compound according to claim 1 wherein R* is a group —C*H(CF$_3$)—C$_4$H$_9$, —C*H (CF$_3$)—C$_5$H$_{11}$, or —C*H(CF$_3$)—C$_8$H$_{17}$.

36. A carboxylic acid ester compound represented by the following formula (II)

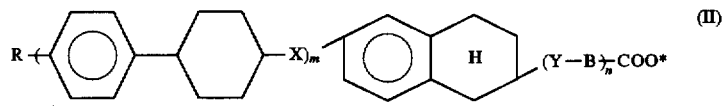

wherein

R is a group selected from the group consisting of an alkyl of 3–20 carbon atoms, an alkoxy of 3–20 carbon atoms, and a halogenated alkyl of 3–20 carbon atoms, X and Y are independently a group selected from the group consisting of —COO—, —OCO—, —CH$_2$CH$_2$—, —CH$_2$—, —OCH$_2$—, —S—S—, —CO—CH$_2$— and —CH$_2$—CO—, or a single bond, B is a group selected from the group consisting of

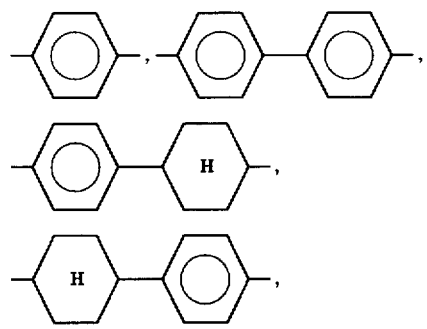

-continued

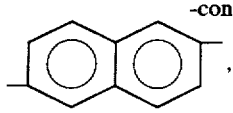

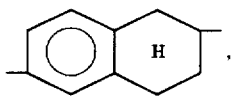

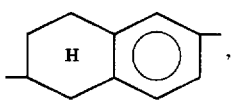

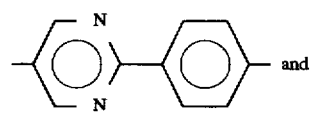 and

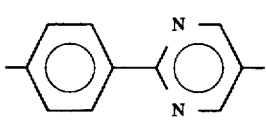

R* is an optically active group of 4–20 carbon atoms containing at least one asymmetric carbon atom where one or more hydrogen atoms attached to the carbon atoms constituting said optically active group may be substituted with a halogen atom, and m is 1 or 2 and n is an integer of 0–2.

37. A carboxylic acid ester compound according to claim 36 wherein R* is a group represented by the following formula (V)

—Q¹—C*H(Q²)—Q³ (V)

wherein

Q¹ is —(CH₂)$_q$— in which q is an integer of 0–6, and Q² and Q³ are different from each other, and are each independently an alkyl of 1–10 carbon atoms, a fluroalkyl of 1–10 carbon atoms or a halogen atom, and at least a part of the groups CH₂ or CH₃ in the Q¹, Q² and Q³ may be replaced by at least one group selected from the group consisting of —O—, —S—, —CO—, —CHX— in which X is a halogen atom, —CHCN—, —O—CO—, —O—COO—, —CO—O— and —CH=CH— in such a manner that two hetero atoms do not bind directly.

38. A carboxylic acid ester compound according to claim 36 wherein R* is a group selected from the group consisting of
—C*H(CF₃)—C₆H₁₃, —C*H(CH₃) —C₆H₁₃, —C*H (CH₃)—C₅H₁₁, —C*H(C₂H₅) —C₅H₁₁, —C*H (C₂H₅) —C₆H₁₃, —CH₂—C*H(CH₃) —C₂H₅, -(CH₂)₃—C*H(CH₃)—C₂H₅, and —C*H (CF₃) —CH₂—COO—C₂H₅.

39. A carboxylic acid ester compounds according to claim 36 wherein X and Y are independently a group of —COO—, —OCO—, —CH₂O—, —CH₂CH₂— or a single bond.

40. A carboxylic acid ester compound according to claim 36 wherein R is a group selected from the group consisting of a straight chain alkyl of 3–20 carbon atoms, a straight chain alkoxy of 3–20 carbon atoms, and a halogenated straight chain alkyl of 3–20 carbon atoms.

41. A carboxylic ester compound according to claim 36 wherein R is a group selected from the group consisting of a branched alkyl of 3–20 carbon atoms, a branched alkoxy of 3–20 carbon atoms, and a halogenated branched alkyl of 3–20 carbon atoms.

42. A carboxylic acid ester compound according to claim 36 wherein B is a group selected from the group consisting of:

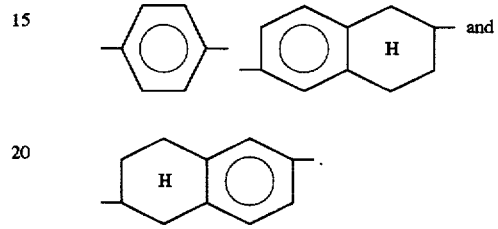

43. A liquid crystal material comprising a carboxylic acid ester compound represented by the following formula (II)

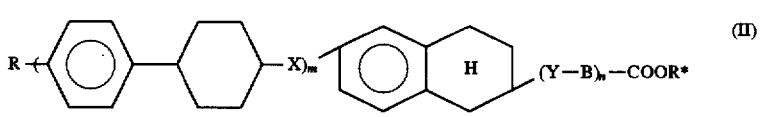

(II)

wherein

R is a group selected from the group consisting of an alkyl of 3–20 carbon atoms, an alkoxy of 3–20 carbon atoms, a halogenated alkyl of 3–20 carbon atoms, a halogenated alkoxy of 3–20 carbon atoms and a hydrocarbon group having —OCO— group wherein at least a part of hydrogen atoms constituting said hydrocarbon group may be substituted with halogen atoms, and R may have at least one asymmetric carbon atoms, X and Y are independently a group selected from the group consisting of —COO—, —OCO—, —CH₂CH₂—, —CH₂O—, —OCH₂—, —S—S, —CO—CH₂— and —CH₂—CO—, or a single bond, B' is a group selected from the group consisting of

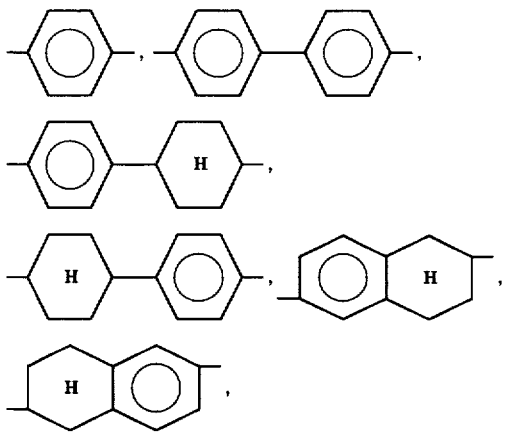

-continued

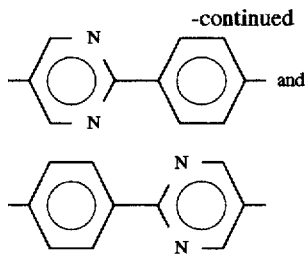

R* is an optically active group of 4–20 carbon atoms containing at least one asymmetric carbon atoms where one or more hydrogen atoms attached to the carbon atoms constituting said optically active group may be substituted with a halogen atom, and m is 1 or 2, n is an integer of 0–2 and m+n≧2.

44. A liquid crystal material according to claim 43 wherein R* is a group represented by the following formula (V)

—Q¹—C*H(Q²)—Q³ (V)

wherein

Q¹ is —(CH₂)_q— in which q is an integer of 0–6, and

Q² and Q³ are different from each other, and are each independently an alkyl of 1–10 carbon atoms, a fluoroalkyl of 1–10 carbon atoms or a halogen atom, and at least a part of the groups CH₂ or CF₂ in the Q¹, Q² and Q³ may be replaced by at least one group selected from the group consisting of —O—, —S—, —CO—, —CHX— in which X is a halogen atom, —CHCN—, —O—CO—, —O—COO—, —CO—O— and —CH=CH— in such a manner that two hetero atoms do not bind directly.

45. A liquid crystal material according to claim 43 wherein R* is a group selected from the group consisting of —C*H(CF₃)—C₆H₁₃, —C*H(CH₃)—C₆H₁₃, —C*H(CH₃)—C₅H₁₁, —C*H(C₂H₅)—C₅H, —C*H(C₂H₅)—C₆H₁₃, —CH₂—C*H(CH₃)—C₂H₅, —(CH₂)₃—C*H(CH₃)—C₂H₅, and —C*H(CF₃)—CH₂—COO—C₂H₅.

46. A liquid crystal material according to claim 45 wherein X and Y are independently a group —COO—, —OCO—, —CH₂O—, —CH₂CH₂— a single bond.

47. A liquid crystal material according to claim 43 wherein B is a group selected from the group consisting of

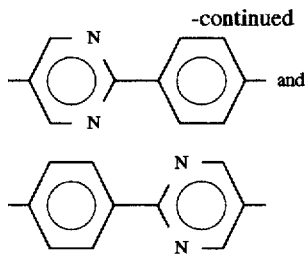

48. A liquid crystal composition comprising a mixture of two or more liquid crystal materials, at least one said materials being the liquid crystal material according to claim 43.

49. The liquid crystal composition as claimed in claim 48 which comprises a mixture of two or more carboxylic acid ester compounds of said formula (II) and at least one other liquid crystal material.

50. The liquid crystal composition as claimed in claim 48 which comprises a mixture of at least one carboxylic acid ester compounds of said formula (II) and at least one other liquid crystal material.

51. A liquid crystal element comprising a cell composed of two substrates opposite to each other, a gap formed by said substrates and the liquid crystal composition as claimed in claim 48 filled in said gap.

52. The carboxylic acid ester compound according to claim 32 wherein R* is a group —C*H(CF₃)—C₄H₉, —C*H(CF₃)—C₅H₁₁, or —C*H (CF₃) —C₈H₁₇.

53. The carboxylic acid ester compound according to claim 36 wherein R* is a group —C*H(CF₃)—C₄H₉, —C*H(CF₃)—C₅H₁₁, or —C*H (CF₃) —C₈H₁₇.

54. The liquid crystal material according to claim 33 wherein R* is a group —C*H(CF₃)—C₄H₉, —C*H(CF₃)—C₅H₁₁, or —C*H (CF₃) —C₈H₁₇.

55. The liquid crystal material according to claim 34 wherein R* is a group —C*H(CF₃)—C₄H₉, —C*H(CF₃)—C₅H₁₁, or —C*H (CF₃) —C₈H₁₇.

56. The liquid crystal material according to claim 43 wherein R* is a group —C*H(CF₃)—C₄H₉, —C*H(CF₃)—C₅H₁₁, or —C*H (CF₃)—C₈H₁₇.

57. The carboxylic acid ester compound according to claim 32 wherein R is an asymmetric group selected from the group consisting of 5-methylheptyloxy, 2-methyloctyloxy and 6-methyloctyloxy.

58. The liquid crystal material according to claim 34 wherein R is an asymmetric group selected from the group consisting of 5-methylheptyloxy, 2-methyloctyloxy, and 6-methyloctyloxy.

59. A carboxylic acid ester compound represented by the following formula (I) or (II)

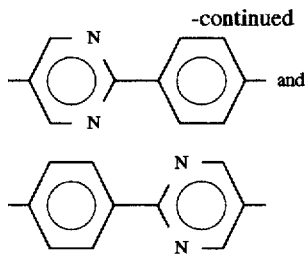 (I)

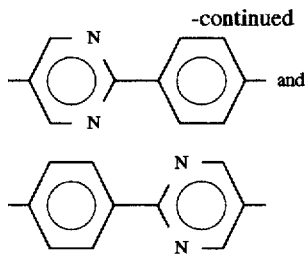 (II)

wherein

R represents a halogenated straight chain alkoxy of 3–20 carbon atoms,

X and Y are independently a group selected from the group consisting of —COO—, —OCO—, —CH$_2$CH$_2$—, —CH$_2$O—, —OCH$_2$—, —S—S—, —CO—CH$_2$— and —CH$_2$—CO—, or a single bond, B is a group selected from the group consisting of

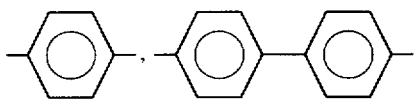

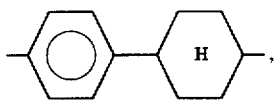

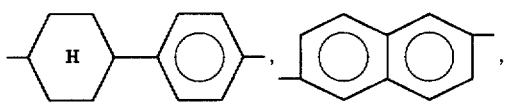

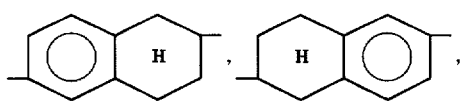

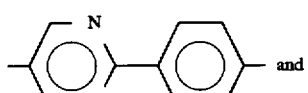

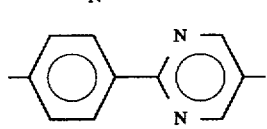

R* is an optically active group of 4–20 carbon atoms containing at least one asymmetric carbon atom where one or more hydrogen atoms attached to the carbon atoms constituting said optically active group may be substituted with a halogen atom, and m is 1 or 2 and n is an integer of 0–2.

60. A liquid crystal material comprising a carboxylic acid ester compound represented by the following formula (I) or (II)

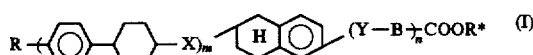

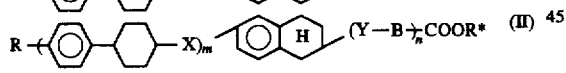

wherein

R is a halogenated straight chain alkoxy of 3–20 carbon atoms,

X and Y are independently a group selected from the group consisting of —COO—, —OCO—, —CH$_2$CH$_2$—, —CH$_2$O—, —OCH$_2$—, —S—S—, —CO—CH$_2$— and —CH$_2$—CO—, or a single bond, B is a group selected from the group consisting of

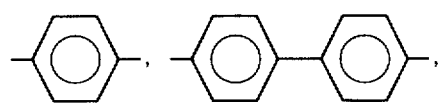

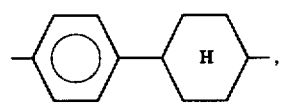

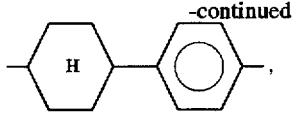

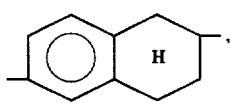

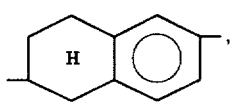

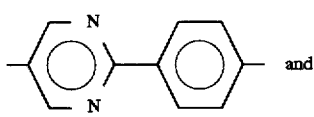

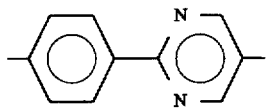

R* is an optically active group of 4–20 carbon atoms containing at least one asymmetric carbon atom where one or more hydrogen atoms attached to the carbon atoms constituting said optically active group may be substituted with a halogen atom, and m is 1 or 2 and n is an integer of 0–1.

61. A carboxylic acid ester compound represented by the following formula (I) or (II)

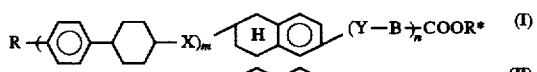

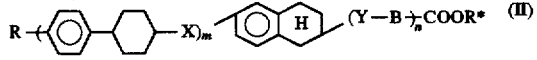

wherein

R represents a halogenated branched chain alkoxy of 3–20 carbon atoms,

X and Y are independently a group selected from the group consisting of —COO—, —OCO—, —CH$_2$CH$_2$—, —CH$_2$O—, —OCH$_2$—, —S—S—, —CO—CH$_2$— and —CH$_2$—CO—, or a single bond, B is a group selected from the group consisting of

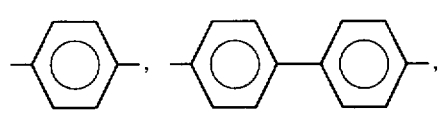

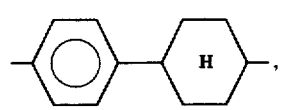

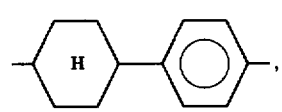

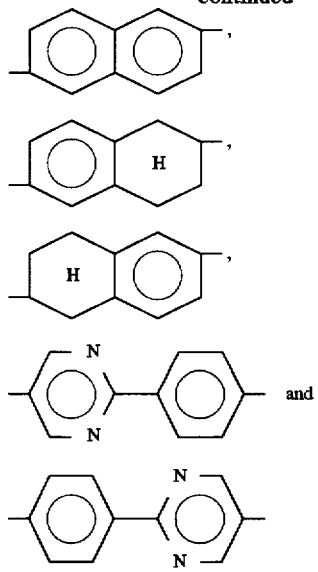

R* is an optically active group of 4–20 carbon atoms containing at least one asymmetric carbon atom where one or more hydrogen atoms attached to the carbon atoms constituting said optically active group may be substituted with a halogen atom, and m is 1 or 2 and n is an integer of 0–2.

62. A liquid crystal material comprising a carboxylic acid ester compound represented by the following formula (I) or (II)

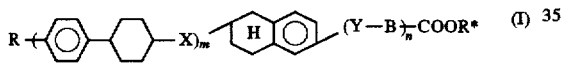

wherein

R is a halogenated alkoxy of 3–20 carbon atoms having an asymmetric carbon atom, X and Y are independently a group selected from the group consisting of —COO—, —OCO—, —CH$_2$CH$_2$—, —CH$_2$O—, —OCH$_2$—, —S—S—, —CO—CH$_2$— and —CH$_2$—CO—, or a single bond, B is a group selected from the group consisting of

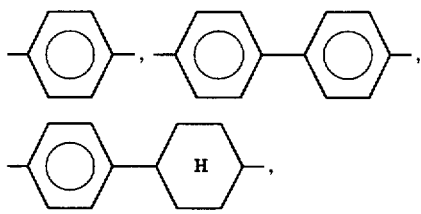

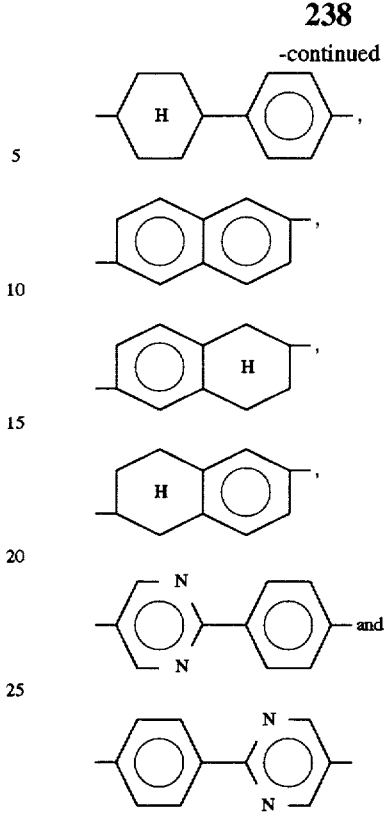

R* is an optically active group of 4–20 carbon atoms containing at least one asymmetric carbon atom where one or more hydrogen atoms attached to the carbon atoms constituting said optically active group may be substituted with a halogen atom, and m is 1 or 2 and n is an integer of 0–1.

63. The carboxylic acid ester compound according to claim 61 wherein R is a group having an asymmetric carbon atom.

64. The carboxylic acid ester compound according to claim 63 wherein R is an asymmetric group selected from the group consisting of 1-methylhexyloxy, 4-methylhexyloxy, 1-ethylhexyloxy, 1-methylheptyloy, 2-methylheptyloxy, 5-methylheptyloxy, 1-ethylheptyloxy, 1-methylheptyloxy, 2-methyloctyloxy, 6-methyloctyloxy and 1-trifluoromethylheptyloxy.

65. The liquid crystal material according to claim 62 wherein R is an asymmetric group selected from the group consisting of 1-methylhexyloxy, 4-methylhexyloxy, 1-ethylhexyloxy, 1-methylheptyloy, 2-methylheptyloxy, 5-methylheptyloxy, 1-ethylheptyloxy, 1-methylheptyloxy, 2-methyloctyloxy, 6-methyloctyloxy and 1-trifluoromethylheptyloxy.

* * * * *